(12) United States Patent
Pivonka et al.

(10) Patent No.: US 10,898,719 B2
(45) Date of Patent: Jan. 26, 2021

(54) APPARATUS FOR PERIPHERAL OR SPINAL STIMULATION

(71) Applicant: Nalu Medical, Inc., Carlsbad, CA (US)

(72) Inventors: Daniel Pivonka, Palo Alto, CA (US); Anatoly Yakovlev, Santa Clara, CA (US); Michael J. Partsch, San Mateo, CA (US); Lee Fason Hartley, Carlsbad, CA (US); James C. Makous, Woodland Hills, CA (US); Brett Daniel Schleicher, San Francisco, CA (US); Lakshmi Narayan Mishra, Carlsbad, CA (US)

(73) Assignee: Nalu Medical, Inc., Carlsbad, CA (US)

( * ) Notice: Subject to any disclaimer, the term of this patent is extended or adjusted under 35 U.S.C. 154(b) by 0 days.

(21) Appl. No.: 15/916,023

(22) Filed: Mar. 8, 2018

(65) Prior Publication Data
US 2018/0256906 A1    Sep. 13, 2018

Related U.S. Application Data

(63) Continuation of application No. PCT/US2016/051177, filed on Sep. 9, 2016.
(Continued)

(51) Int. Cl.
*A61N 1/36* (2006.01)
*A61N 1/05* (2006.01)
(Continued)

(52) U.S. Cl.
CPC ........... *A61N 1/36142* (2013.01); *A61N 1/00* (2013.01); *A61N 1/05* (2013.01); *A61N 1/0553* (2013.01);
(Continued)

(58) Field of Classification Search
CPC ... A61N 1/37; A61N 1/36; A61N 1/05; A61N 1/37229; A61N 1/0553; A61N 1/0551;
(Continued)

(56) References Cited

U.S. PATENT DOCUMENTS

| 1,023,887 A1 | 3/2019 | Pivonka et al. |
| 1,033,559 A1 | 7/2019 | Yakovlev et al. |

(Continued)

FOREIGN PATENT DOCUMENTS

| WO | WO-2014153124 A1 | 9/2014 |
| WO | WO-2014153228 A1 | 9/2014 |

(Continued)

OTHER PUBLICATIONS

"International Search Report for PCT/US2016/051177 dated Mar. 16, 2017".
(Continued)

*Primary Examiner* — Paula J Stice
(74) *Attorney, Agent, or Firm* — Wilson Sonsini Goodrich and Rosati, P.C.

(57) ABSTRACT

Provided herein are methods of treating a patient comprising providing a medical apparatus comprising an external system and an implantable system, implanting the implantable system, and delivering at least one of power or data to the implantable system with the external system. The external system comprises: at least one external antenna configured to transmit a first transmission signal to the implantable system; an external transmitter configured to drive the at least one external antenna; an external power supply; and an external controller. The implantable system comprises: at least one implantable antenna configured to receive the first transmission signal from the first external device; an implantable receiver; at least one implantable functional element configured to interface with the patient; an implant- (Continued)

able controller; an implantable energy storage assembly; and an implantable housing surrounding at least the implantable controller and the implantable receiver. Medical apparatus are also provided.

25 Claims, 24 Drawing Sheets

Related U.S. Application Data

(60) Provisional application No. 62/217,356, filed on Sep. 11, 2015.

(51) Int. Cl.

| | |
|---|---|
| *A61N 2/00* | (2006.01) |
| *A61N 1/37* | (2006.01) |
| *A61N 1/00* | (2006.01) |
| *A61N 1/372* | (2006.01) |
| *A61N 1/378* | (2006.01) |
| *A61N 5/06* | (2006.01) |
| *G16H 40/67* | (2018.01) |
| *G16H 40/63* | (2018.01) |
| *A61N 1/375* | (2006.01) |
| *A61N 2/02* | (2006.01) |
| *H01Q 1/27* | (2006.01) |

(52) U.S. Cl.
CPC ......... *A61N 1/36071* (2013.01); *A61N 1/372* (2013.01); *A61N 1/3708* (2013.01); *A61N 1/378* (2013.01); *A61N 1/3727* (2013.01); *A61N 1/3787* (2013.01); *A61N 1/37229* (2013.01); *A61N 1/37241* (2013.01); *A61N 1/37247* (2013.01); *A61N 1/37258* (2013.01); *A61N 1/37518* (2017.08); *A61N 2/006* (2013.01); *A61N 2/02* (2013.01); *A61N 5/0622* (2013.01); *G16H 40/63* (2018.01); *G16H 40/67* (2018.01); *A61N 1/36002* (2017.08); *A61N 1/36128* (2013.01); *H01Q 1/273* (2013.01)

(58) Field of Classification Search
CPC ............ A61N 1/36071; A61N 1/36128; A61N 1/36062
See application file for complete search history.

(56) References Cited

U.S. PATENT DOCUMENTS

| | | | |
|---|---|---|---|
| 2005/0278000 A1 | 12/2005 | Strother et al. | |
| 2012/0283800 A1* | 11/2012 | Perryman | A61N 1/36142 607/60 |
| 2014/0088664 A1* | 3/2014 | Sharma | A61N 1/36071 607/48 |
| 2014/0172047 A1* | 6/2014 | Spitaels | A61N 1/36125 607/60 |
| 2015/0012071 A1* | 1/2015 | Bradley | A61N 1/36153 607/72 |
| 2016/0127130 A1 | 5/2016 | Hazay et al. | |
| 2016/0331956 A1 | 11/2016 | Yakovlev et al. | |
| 2018/0028824 A1 | 2/2018 | Pivonka et al. | |
| 2018/0368875 A1 | 12/2018 | Castillo et al. | |
| 2019/0001139 A1 | 1/2019 | Mishra et al. | |
| 2019/0009097 A1 | 1/2019 | Hartley et al. | |
| 2019/0151659 A1 | 5/2019 | Mishra et al. | |
| 2019/0269913 A1 | 9/2019 | Pivonka et al. | |
| 2019/0374776 A1 | 12/2019 | Mishra et al. | |
| 2020/0101291 A1 | 4/2020 | Yakovlev et al. | |
| 2020/0139138 A1 | 5/2020 | Sit et al. | |

FOREIGN PATENT DOCUMENTS

| | | |
|---|---|---|
| WO | WO-2014089299 A3 | 10/2014 |
| WO | WO-2014205129 A1 | 12/2014 |
| WO | WO-2015139053 A1 | 9/2015 |
| WO | WO-2015196164 | 12/2015 |
| WO | WO-2016127130 A1 | 8/2016 |
| WO | WO-2017044904 A1 | 3/2017 |
| WO | WO-2017142948 A1 | 8/2017 |
| WO | WO-2017165410 A1 | 9/2017 |
| WO | WO-2017205675 A1 | 11/2017 |
| WO | WO-2018017463 A1 | 1/2018 |
| WO | WO-2018126062 A1 | 7/2018 |
| WO | WO-2018156953 A1 | 8/2018 |
| WO | WO-2018208992 A1 | 11/2018 |

OTHER PUBLICATIONS

"IPRP for PCT/US2016/051177 Mar. 13, 2018".
EP16845235.7 European Search Report dated Apr. 24, 2019.

* cited by examiner

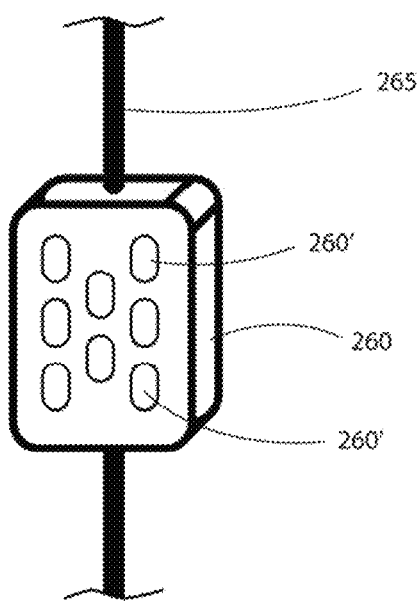
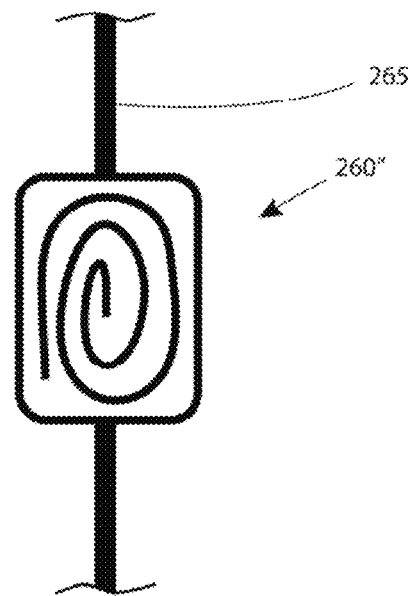
FIG 20A
FIG 20B
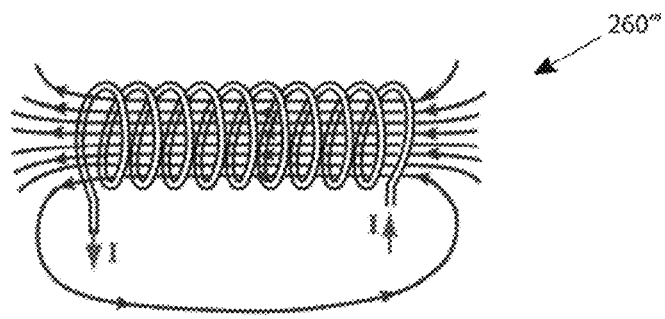
FIG 20C
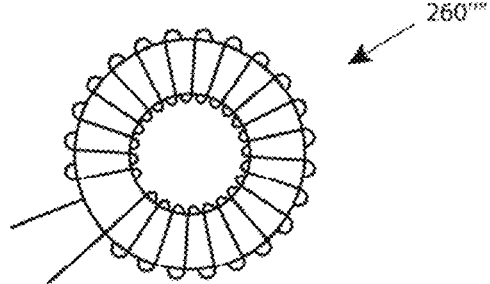
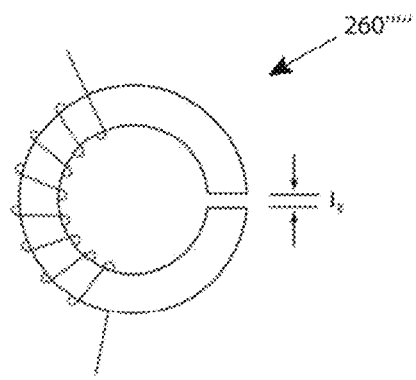
FIG 20D
FIG 20E

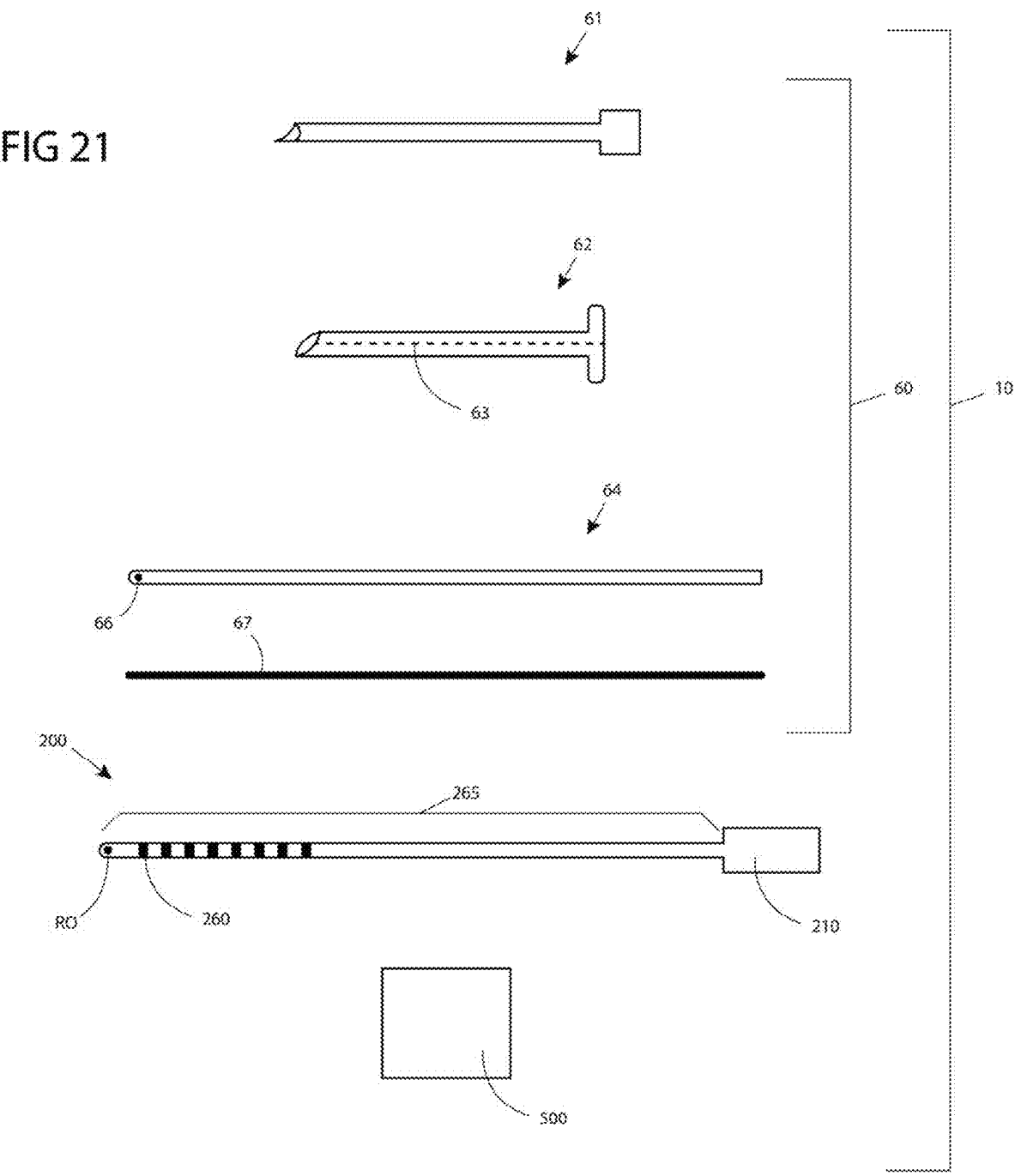

APPARATUS FOR PERIPHERAL OR SPINAL STIMULATION

CROSS-REFERENCE

This application is a continuation of PCT Application No. PCT/US2016/051177, filed on Sep. 9, 2016, which claims priority to U.S. Provisional Patent Application No. 62/217,356, filed on Sep. 11, 2015, the contents of which are incorporated herein by reference in its entirety for all purposes.

DESCRIPTION OF THE INVENTION

Related Applications

This application is related to International PCT Patent Application Serial Number PCT/US2014/043023, titled "Method and Apparatus for Minimally Invasive Implantable Modulators", filed Jun. 18, 2014; International PCT Patent Application Serial Number PCT/US2015/002080, titled "Method and Apparatus for Versatile Minimally Invasive Neuromodulators", filed Mar. 16, 2015; U.S. Provisional Patent Application Ser. No. 62/015,392, titled "Method and Apparatus for Neuromodulation Treatments of Pain and other Conditions", filed Jun. 21, 2014; U.S. Provisional Patent Application Ser. No. 62/530,085, titled "Method and Apparatus for Operation with Minimally Invasive Neuromodulators", filed Sep. 19, 2014; and U.S. Provisional Patent Application Ser. No. 62/077,181, titled "Method and Apparatus for Implantable Neuromodulation Systems", filed Nov. 8, 2014; U.S. Provisional Patent Application Ser. No. 62/112,858, titled "Medical Apparatus including an Implantable System and an External System", filed Feb. 6, 2015; the content of each of which is incorporated herein by reference in its entirety.

Field of the Invention

The present invention relates generally to medical apparatus for a patient, and in particular, apparatus that include portions implanted in a patient and portions external to the patient where power and/or data is transmitted to an implanted portion from an external portion.

BACKGROUND OF THE INVENTION

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g. to treat pain). Most implants are relatively large devices with batteries and long conduits, such as implantable leads configured to deliver electrical energy or implantable tubes (i.e. catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices and methods that provide one or more implantable devices and are designed for simplicity of implantation and use, as well as enhanced flexibility and capability in treating patients and/or recording patient data.

SUMMARY

Described herein are apparatus, systems, devices and methods for treating patient and/or recording patient data. According to one aspect of the present inventive concepts, A medical apparatus comprises an external system configured to transmit one or more transmission signals, each transmission signal comprising at least power or data; and an implantable system configured to receive the one or more transmission signals from the external system. The external system comprises a first external device comprising: at least one external antenna configured to transmit a first transmission signal to the implantable system, the first transmission signal comprising at least power or data; an external transmitter configured to drive the at least one external antenna; an external power supply configured to provide power to at least the external transmitter; and an external controller configured to control the external transmitter. The implantable system comprises a first implantable device comprising: at least one implantable antenna configured to receive the first transmission signal from the first external device; an implantable receiver configured to receive the first transmission signal from the at least one implantable antenna; at least one implantable functional element configured to interface with the patient; an implantable controller configured to control the at least one implantable functional element; an implantable energy storage assembly configured to provide power to an element selected from the group consisting of: the at least one implantable functional element; the implantable controller; the implantable receiver; and combinations thereof; and an implantable housing surrounding at least the implantable controller and the implantable receiver.

According to one aspect of the inventive concepts, a method of treating a patient comprises providing a medical apparatus, such as a medical apparatus comprising an external system and an implantable system as described herein. The method can comprise implanting a first implantable device in the patient; and delivering at least one of power or data to the first implantable device with a first external device.

In some embodiments, the medical apparatus is configured to stimulate tissue of the peripheral nervous system.

In some embodiments, the medical apparatus is configured to stimulate tissue with at least a magnetic field.

In some embodiments, the medical apparatus is configured to stimulate tissue to treat at least one of neuropathy, neuralgia or overactive bladder.

In some embodiments, the medical apparatus is configured to stimulate tissue to treat occipital neuralgia.

In some embodiments, the medical apparatus is configured to stimulate tissue to treat post-herpetic neuralgia.

In some embodiments, the medical apparatus is configured to stimulate tissue to treat diabetic neuropathy.

In some embodiments, the medical apparatus is configured to stimulate tissue to treat complex regional pain syndrome.

In some embodiments, the medical apparatus is configured to stimulate tissue to treat pain related to at least one of hernia or hernia repair.

In some embodiments, the medical apparatus is configured to stimulate tissue to treat post-amputation pain.

In some embodiments, the medical apparatus is configured to stimulate tissue to treat overactive bladder.

In some embodiments, the medical apparatus is configured to stimulate tissue to treat fecal incontinence.

In some embodiments, the medical apparatus is configured to stimulate tissue to treat pelvic pain.

In some embodiments, the medical apparatus is configured to stimulate tissue to treat subcutaneous pain.

In some embodiments, the medical apparatus is configured to stimulate tissue to treat visceral pain.

In some embodiments, the medical apparatus is configured to stimulate tissue to treat at least one of peripheral vascular disease, diabetic neuropathy or other diabetic condition.

In some embodiments, the medical apparatus is configured to stimulate tissue to treat at least one of occipital pain or headache pain.

In some embodiments, the medical apparatus is configured to stimulate tissue to treat at least one of bladder dysfunction or bowel dysfunction.

In some embodiments, the medical apparatus is configured to stimulate the nervous tissue associated with the multifidus muscle to rehabilitate function of the multifidus muscle and/or improve spinal stability.

In some embodiments, the medical apparatus is configured to transvascularly stimulate tissue.

In some embodiments, the method comprises stimulating tissue of the central nervous system.

In some embodiments, the medical apparatus is configured to deliver stimulation energy to tissue, and wherein the stimulation energy is selected from the group consisting of: electrical energy; magnetic energy; electromagnetic energy; light energy; infrared light energy; visible light energy; ultraviolet light energy; mechanical energy; thermal energy; heat energy; cryogenic energy; sound energy; ultrasonic sound energy; high intensity focused ultrasound energy; low intensity focused ultrasound energy; subsonic sound energy; chemical energy; and combinations thereof.

In some embodiments, the medical apparatus is configured to perform a function selected from the group consisting of: deliver electric energy; deliver controlled electrical current and/or voltage to tissue; deliver magnetic energy; deliver magnetic field energy; deliver controlled current or voltage to a coil or other magnetic field generating element positioned proximate tissue; deliver electromagnetic energy; deliver both current to tissue and a magnetic field to tissue; and combinations thereof.

In some embodiments, the method comprises stimulating at least one set of multifidus muscle fascicles.

In some embodiments, the method comprises stimulating at least three sets of multifidus muscle fascicles.

In some embodiments, the method comprises stimulating tissue selected from the group consisting of: one or more muscle motor points and/or the deep fibers of lumbar multifidus; quadratus lumborum; the erector spinae; psoas major; transverse abdominis; connective tissue such as the annulus or facet capsule; ligaments coupling bony structures of the spine; and combinations thereof.

In some embodiments, the method comprises stimulating tissue selected from the group consisting of: multifidus tissue; transverse abdominus tissue; quadratus lumborum tissue; psoas major tissue; internus abdominus tissue; obliquus externus abdominus tissue; erector spinae tissue; and combinations thereof.

In some embodiments, wherein the method is configured to at least one of depolarize, hyperpolarize or block innervated sections of the muscle to perform a function selected from the group consisting of: propagate an activating stimulus along nerve fibers recruiting muscle tissue remote from the site of stimulation; propagate an inhibiting stimulus along the nerve fibers recruiting muscle tissue remote from the site of stimulation; modulate nerve activity; inhibit nerve conduction; improve nerve conduction; improve muscle activity; and combinations thereof.

In some embodiments, the method comprises stimulating tissue selected from the group consisting of: dorsal ramus nerve; medial branch of dorsal ramus nerve; nervous tissue associated with multifidus muscle; and combinations thereof.

In some embodiments, the method comprises delivering stimulation energy to contract the multifidus muscle.

In some embodiments, the method comprises stimulating tissue by providing episodic electrical stimulation.

In some embodiments, the medical apparatus further comprises a tool configured to diagnose a defect in at least one of a spinal muscle or the motor control system.

In some embodiments, the medical apparatus further comprises a tool configured to test function of the multifidus muscle. The tool can comprise a tool selected from the group consisting of: MRI; ultrasound imager; electromyogram; tissue biopsy device; a device configured to test displacement as a function of load for a spine; and combinations thereof.

In some embodiments, the medical apparatus is configured to deliver high frequency energy comprising electrical energy at or above 1 kHz, and the method can comprise providing paresthesia-enhanced pain management. The medical apparatus can be further configured to provide low frequency electrical energy at a frequency at or below 1 kHz. The method can comprise delivering the low frequency electrical energy during a trialing procedure.

In some embodiments, the medical apparatus is configured to provide paresthesia during a trialing procedure.

In some embodiments, the medical apparatus is configured to deliver low frequency stimulation energy to stimulate motor nerve tissue. The medical apparatus can be further configured to deliver high frequency stimulation to treat pain.

In some embodiments, the method is configured to treat a disease or disorder selected from the group consisting of: neuropathy; neuralgia; overactive bladder; and combinations thereof. The method can comprise delivering stimulation energy to tissue of at least one of the central nervous system or the peripheral nervous system.

In some embodiments, the method is configured to treat neuralgia. The method can be configured to treat neuralgia resulting from at least one of: surgery; trauma or phantom pain. The neuralgia can comprise neuralgia resulting from groin surgery, and the at least one implantable functional element can be positioned to stimulate nerve tissue selected from the group consisting of: ilioinguinal; genitofemoral; iliohypogastric; and combinations thereof. The neuralgia can comprise neuralgia resulting from shoulder surgery, and the at least one implantable functional element can be positioned to stimulate axial nerve tissue. The first implantable device can comprise a lead comprising the at least one implantable functional element, and the lead can be implanted in a suprascapular location. The neuralgia can comprise neuralgia resulting from lung surgery, and the at least one implantable functional element can be positioned to stimulate intercostal nerve tissue. The neuralgia can comprise neuralgia associated with carpal tunnel syndrome, and the at least one implantable functional element can be positioned to stimulate median nerve tissue. The neuralgia can comprise neuralgia associated with temporomandibular joint disorder, and the at least one implantable functional element can be positioned to stimulate V2 of trigeminal nerve tissue. The neuralgia can comprise facial neuralgia, and the at least one implantable functional element can be positioned to stimulate trigeminal nerve tissue. The neuralgia can comprise leg neuralgia, and the at least one implantable functional element can be positioned to stimulate nerve tissue proximal a contributing lesion.

In some embodiments, the method is configured to treat diabetic neuropathy. The diabetic neuropathy can comprise painful diabetic neuropathy. The at least one implantable functional element can be positioned proximate the lower spinal cord. The method can comprise stimulating the tibial nerve. The method can comprise stimulating dorsal root ganglia. The diabetic neuropathy can comprise diabetic neuropathy of at least one of the hand or foot. The method can comprises transvascularly stimulating nerve tissue.

In some embodiments, method is configured to treat a disease or disorder selected from the group consisting of: visceral pain; angina; and combinations thereof. The method can comprise stimulating the vagus nerve. The method can be configured to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations thereof.

In some embodiments, the method is configured to treat a disease or disorder selected from the group consisting of: post-surgical neuralgia; post-surgical neuralgia following hernia repair; headache; headache due to occipital neuralgia; post-herpetic neuralgia; chronic pelvic pain; chronic hip pain; knee pain; and combinations thereof.

In some embodiments, the method is configured to treat pain associated with at least one of hernia or hernia repair by stimulating a location selected from the group consisting of: cutaneous branch of the ilioinguinal and/or inguinal nerves; the genital branch of the genitofemoral nerves; corresponding branches of spinal nerves correlating to one or more dermatomes related to pain associated with at least one of hernia or hernia repair; and combinations thereof. The nerve tissue to be stimulated can be localized using an imaging device. The method can comprise transvascularly stimulating the genitofemoral and/or ilioinguinal nerves. The method can transvascularly stimulate nerve tissue, such as via a blood vessel selected from the group consisting of: femoral vein; femoral artery; superficial external pudendal vein; superficial external pudendal artery; deep external pudendal vein; deep external pudendal artery; superficial epigastric vein; superficial epigastric artery; and combinations thereof. The method can be configured to treat painful areas innervated by at least one of: ilioinguinal nerve, genitofemoral nerve or iliohypogastric nerves. The method can deliver stimulation energy to the spinal cord in the L1-L5 region. The method can comprise delivering stimulation energy to the L1-L2 dorsal root ganglia. The at least one implantable functional element can be positioned at a location selected from the group consisting of: over a dorsal column; over a dorsal root; in the dorsal root entry zone; and combinations thereof. The at least one implantable functional element can comprise at least two implantable functional elements positioned in a configuration selected from the group consisting of: unilateral; bilateral; midline; and combinations thereof.

In some embodiments, the method is configured to treat occipital neuralgia. The at least one implantable functional element can be positioned to stimulate peripheral nerve tissue to reduce pain. The at least one implantable functional element can be positioned to stimulate a cervical nerve. The at least one implantable functional element is positioned unilaterally or bilaterally. The method can be configured to treat a disease or disorder selected from the group consisting of: migraine headache; headache; cluster headache; and combinations thereof. The method can comprise stimulating nerve tissue selected from the group consisting of: occipital; supraorbital; infraorbital; greater occipital nerve (GON); lesser occipital nerve (LON); both supraorbital and GON; supratroclear; sphenopalantine (SPG); and combinations thereof.

In some embodiments, the method is configured to treat a disease or disorder selected from the group consisting of: occipital pain; headache; and combinations thereof. The method can be configured to treat a disease or disorder selected from the group consisting of: occipital neuralgia; cervicogenic headache; tension headache; chronic and episodic migraine headache; tension headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations thereof. The method can comprise stimulating one or more nerves in the head. The method can comprise stimulating one or more nerves selected from the group consisting of: greater and/or lesser occipital nerve; the greater and/or lesser auricular nerves; the third occipital nerve; and combinations thereof. The method can comprise stimulating one or more nerves selected from the group consisting of: auriculotemporal nerve; supratrochlear nerve; sub-occipital nerve; and combinations thereof. The implantable housing can be positioned at a location selected from the group consisting of: in the head; behind the ear; in the back of the head; in the neck; in the face; and combinations thereof. The at least one external device can be positioned in a device selected from the group consisting of: hat; headband; glasses; goggles; earpiece; necklace; patch; and combinations thereof. The method can comprise stimulating spinal cord tissue proximate C2-C3. The at least one implantable functional element can be positioned at a location selected from the group consisting of: over a dorsal columns; in the gutter; over a dorsal root entry zone; in the foramen at the dorsal root ganglion; and combinations thereof.

In some embodiments, the method is configured to treat post-herpetic neuralgia. The at least one implantable functional element can be positioned to stimulate corresponding branches of spinal nerves correlating to one or more dermatomes related to the post-herpetic neuralgia. The method can be configured to treat a disease or disorder selected from the group consisting of: shingles; herpes zoster; zoster; zona; varicella zoster virus infection; zoster sine herpete; fever blisters; herpes zoster blisters; herpes zoster rash; and combinations thereof. The method can comprise delivering a high frequency alternating current block. The method can comprise stimulating nerve tissue from a location selected from the group consisting of: leg; arm; torso; sacrum; spinal cord; and combinations thereof. The method can comprise transvascularly stimulating nerve tissue from a location selected from the group consisting of: leg; arm; torso; sacrum; and combinations thereof.

In some embodiments, the method is configured to treat a disease or disorder selected from the group consisting of: pelvic disorder; bladder disorder; and combinations thereof, and wherein the method comprises stimulating a nerve selected from the group consisting of: sacral; pudendal; tibial; and combinations thereof.

In some embodiments, the method is configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations thereof.

In some embodiments, the method is configured to treat a pelvic or other disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations thereof.

In some embodiments, the method is configured to treat a disease or disorder selected from the group consisting of: pelvic disorder; bladder dysfunction; bowel dysfunction; and combinations thereof. The method can comprise stimulating the sacral nerves S2, S3 and/or S4. The first implantable device can comprise at least one implantable lead comprising the at least one implantable functional element, and the method can comprise passing the at least one implantable lead through the foramen to the anterior side of the sacrum and/or positioning the at least one implantable lead inside the foramen. The first implantable device can comprise at least one implantable lead comprising the at least one implantable functional element, and the method can comprise inserting the at least one implantable lead rostrally toward the sacral roots. The first implantable device can comprise at least one implantable lead comprising the at least one implantable functional element, and the method can comprise positioning the at least one implantable lead along the sacral canal. The first implantable device can comprise at least one implantable lead comprising the at least one implantable functional element, and the method can comprise positioning the at least one implantable lead in a manner selected from the group consisting of: threaded from the spinal canal into a sacral foramen in an anterior trajectory; inserted into the sacral canal in a caudal trajectory; inserted into the sacral canal via the sacral hiatus in an anterograde trajectory; and combinations thereof. The method can comprise accessing the sacral nerves as they enter the spinal cord at the cauda equina. The method can comprise transvascularly stimulating the sacral nerves. The method can comprise stimulating the pudendal nerve. The method can comprise positioning the at least one implantable functional element proximate the ischial spine. The first implantable device can further comprise at least one implantable lead comprising the at least one implantable functional element, and the method can comprise inserting the at least one implantable lead through the vaginal wall toward the ischial spine. The first implantable device can further comprise at least one implantable lead comprising the at least one implantable functional element, and the method can comprise inserting the at least one implantable lead to a position just medial to the ischial tuberosity and toward the ischial spine. The method can comprise transvascularly stimulating the pudendal nerve. The method can comprise stimulating pudendal afferents. The method can comprise stimulating pudendal afferents by stimulating the dorsal genital nerve. The first implantable device can further comprise at least one implantable lead comprising the at least one implantable functional element, and the method can comprise inserting the at least one implantable lead periurethrally. The method can comprise stimulating tibial nerve tissue.

In some embodiments, the method is configured to treat pelvic pain. The method can be configured to treat at least one of interstitial cystitis or bladder pain. The method can comprise positioning the at least one implantable functional element to stimulate peripheral nervous system tissue and/or central nervous system tissue. The method can comprise stimulating peripheral nervous system tissue by positioning the at least one implantable functional element proximate tissue selected from the group consisting of: pudendal tissue; S-2 root; S-3 root; S-4 root; and combinations thereof. The method can comprise stimulating central nervous system tissue by positioning the at least one implantable functional element proximate tissue selected from the group consisting of: lower spinal cord tissue; s3 neural foramen; and combinations thereof. The method can be configured to treat anal pain, and the method can comprise positioning the at least one implantable functional element to stimulate nerve tissue selected from the group consisting of: pudendal tissue; S-2 root; S-3 root; S-4 root; and combinations thereof. The method can be configured to stimulate tibial nerve tissue.

In some embodiments, the method is configured to treat overactive bladder. The method can be configured to treat urinary incontinence. The method can be configured to reduce the effect of overactive bladder and/or decrease use of an overactive bladder medication. The method can comprise stimulating tissue selected from the group consisting of: central nervous system tissue; peripheral nervous system tissue; and combinations thereof. The method can comprise stimulating one or more nerves that control and/or relate to bladder function. The method can be configured to provide a therapeutic benefit selected from the group consisting of: to increase bladder capacity; improve bladder emptying; reduce urge incontinence; reduce stress incontinence; and combinations thereof. The method can comprise stimulating at least one of tibial nerve tissue or sacral nerve tissue. The method can comprise modulating transmission of excitatory nerve signals to the bladder muscles. The method can comprise providing temporary stimulation of tissue to treat overactive bladder. The method can comprise stimulating at least one sphincter muscle, such as by stimulating multiple sphincter muscles. The at least one implantable functional element can comprise a first implantable functional element and a second implantable functional element, and the method can comprise positioning the first implantable functional element on one side of the urethral orifice and positioning the second implantable functional element on the opposite side of the urethral orifice. The method can comprise positioning the implantable housing in a location selected from the group consisting of: suprapubic region; perineum; and combinations thereof.

In some embodiments, the method is configured to treat fecal incontinence. The method can comprise stimulating tissue selected from the group consisting of: sacral nerve tissue; tissue whose stimulation strengthens muscles of the bowel and/or rectum; and combinations thereof. The first implantable device can comprise at least one implantable lead comprising the at least one implantable functional element, and the method can comprise positioning the at least one implantable lead in a location selected from the group consisting of: the pelvic girdle; the sacral foramina; the lower back; the upper buttock; and combinations thereof. The method can be further configured to treat a bladder disorder.

In some embodiments, the method is configured to treat subcutaneous pain.

In some embodiments, the method is configured to treat post-amputation pain. The method can be configured to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations thereof. The method can comprise delivering a high frequency alternating current block. The method can comprise stimulating a nerve from a location selected from the group consisting of: leg; arm; sacrum; spinal cord; and combinations thereof. The method can comprise transvascularly stimulating a nerve from a location selected from the group consisting of: leg; arm; and combinations thereof.

In some embodiments, the method is configured to treat carpal tunnel syndrome. The method can be configured to treat a disease or disorder selected from the group consisting of: median nerve entrapment; tingling and/or numbness in fingers or hand; median nerve irritation or compression; narrowing of the carpal tunnel; and combinations thereof.

In some embodiments, the method is configured to treat erectile dysfunction. The method can be configured to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED; and combinations thereof.

In some embodiments, the method is configured to treat complex regional pain syndrome. The method can be configured to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations thereof.

In some embodiments, the method is configured to treat a condition of diabetes. The method can be configured to treat a disease or disorder selected from the group consisting of: peripheral vascular disease; diabetic neuropathy; and combinations thereof. The method can be configured to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations thereof. The method can comprise positioning the at least one implantable functional element proximate nerve tissue in a location selected from the group consisting of: foot; leg; arm; sacrum; and combinations thereof. The method can comprise stimulating the spinal cord. The method can comprise transvascularly stimulating tissue. The method can comprise stimulating tibial nerve tissue. The method can be configured to treat a diabetic malady of the foot.

In some embodiments, the method comprises stimulating the tibial nerve. The method can be configured to treat a disease or disorder selected from the group consisting of: overactive bladder; bowel disorder; diabetic disorder; diabetic malady of the foot; and combinations thereof. The first implantable device comprises at least one implantable lead comprising the at least one implantable functional element, and the method can comprise placing the at least one implantable lead in the popliteal fossa behind the knee. The method can comprise transvascularly stimulated the tibial nerve tissue.

In some embodiments, the method comprises stimulating the posterior tibial nerve. The method can be configured to treat bladder voiding dysfunction.

In some embodiments, the method comprises positioning the at least one implantable functional element to perform retrograde stimulation of the sacral nerve plexus. The method can be configured to restore the balance between bladder inhibitory and excitatory control systems.

In some embodiments, the method comprises stimulating a region of the pelvic floor. The method can be configured to perform a function selected from the group consisting of: change the reflex thresholds of the bladder muscles responsible for bladder emptying; strengthen and/or otherwise improve the condition of the muscles that maintain closure on the bladder outlet; change the state of the neural pathways, musculature and/or bladder during and beyond the period stimulation; decrease the severity of urinary incontinence; and combinations thereof.

In some embodiments, the method comprises stimulating periurethral muscles. The method can comprise stimulating pudendal afferents.

In some embodiments, the method comprises stimulating tissue of at least one of the vagina or the anus.

In some embodiments, the method comprises stimulating the vagus nerve. The method can be configured to treat at least one of visceral pain or angina.

In some embodiments, the method comprises stimulating a nerve selected from the group consisting of: peroneal nerve; saphenous nerve; and combinations thereof.

In some embodiments, the method comprises stimulating a nerve selected from the group consisting of: median nerve; ulnar nerve; radial nerve; and combinations thereof.

In some embodiments, the method comprises stimulating the spinal cord. The method can comprise positioning the at least one implantable functional element between T5-S5. The method can be configured to treat pain and/or reduced circulation of the leg and/or foot. The method can comprise positioning the at least one implantable functional element between C2 and T8. The method can be configured to treat pain and/or reduced circulation of the arm and/or hand. The first implantable device can comprise at least one implantable lead comprising the at least one implantable functional element, and the method can comprise positioning the at least one implantable lead along the midline. The method can comprise positioning the at least one implantable lead bilaterally. The method can comprise positioning the at least one implantable lead unilaterally. The method can comprise positioning the at least one implantable lead at a location selected from the group consisting of: over the dorsal columns; in the gutter; in the dorsal root entry zone; and combinations thereof. The method can comprise positioning the at least one implantable functional element to span multiple vertebral levels. The method can comprise positioning the at least one implantable functional element to span a single vertebral level. The method can comprise positioning the at least one functional element to stimulate dorsal root ganglia that supply nerve tissue selected from the group consisting of: common peroneal; tibial; femoral; and combinations thereof. The method can be configured to treat the leg and/or the foot. The method can further comprise positioning the at least one functional element to stimulate dorsal root ganglia that supply nerve tissue selected from the group consisting of: radial; median; ulnar; and combinations thereof. The method can be configured to treat the arm and/or the hand. The first implantable device can comprise at least one implantable lead comprising the at least one implantable functional element, and the method can comprise passing the at least one implantable lead through the intervertebral foramina. The method can comprise stimulating tissue between T9 and T12. The method can be configured to treat back pain. The method can comprise stimulating tissue between L5 and T5. The method can comprise stimulating peripheral nerve tissue. The method can comprise stimulating tissue between C5 and T1 and/or C3 and T5. The method can comprise treating upper limb pain. The method can comprise stimulating tissue between T9 and T1 and/or T5 and L5. The method can comprise treating lower limb pain. The method can comprise stimulating tissue between C7 and T1 and/or C5 and T5. The method can comprise treating angina. The method can further comprise visualizing the patient's anatomy to place the at least one implantable functional element.

In some embodiments, the method comprises stimulating the dorsal root ganglion. The method can be configured to treat pain at a location selected from the group consisting of: leg; torso; arm; and combinations thereof.

In some embodiments, the method comprises transvascularly stimulating tissue. The first implantable device can further comprise at least one implantable lead comprising the at least one functional element, and the method can comprise positioning the at least one implantable lead in a blood vessel selected from the group consisting of: internal pudendal vein and/or artery; common iliac vein and/or artery; inferior and/or superior gluteal vein and/or artery; middle rectal, pudendal plexus and/or internal iliac vein and/or artery; medial and/or lateral sacral vein and/or artery; uterine and/or obturator vein and/or artery; and combinations thereof.

The method can comprise transvascularly stimulating a nerve at a location selected from the group consisting of: leg; foot; arm; hand; and combinations thereof.

The method can comprise transvascularly stimulating a leg nerve selected from the group consisting of: tibial nerve; sacral root; deep fibular nerve; and combinations thereof.

The method can comprise transvascularly stimulating an arm nerve selected from the group consisting of: median nerve; ulnar nerve; superior ulnar nerve; medial cutaneous nerve; radial nerve; and combinations thereof.

The method can comprise transvascularly stimulating at least one of a median nerve, an ulnar nerve or a radial nerve, the at least one implantable functional element can comprise one or more electrodes, and the method can further comprise positioning the one or more electrodes in a blood vessel selected from the group consisting of: brachial vein; brachial artery; basilic vein; basilic artery; deep vein of the arm; deep artery of the arm; and combinations thereof.

The method can comprise transvascularly stimulating at least one of a median nerve or an ulnar nerve, the at least one implantable functional element can comprise one or more electrodes, and the method can further comprise positioning the one or more electrodes in a blood vessel selected from the group consisting of: brachial vein; brachial artery; and combinations thereof.

The method can comprise transvascularly stimulating the radial nerve, the at least one implantable functional element can comprise one or more electrodes, and the method can further comprise positioning the one or more electrodes in a blood vessel selected from the group consisting of: deep vein of arm; deep artery of arm; basilic vein; radial collateral vein; radial collateral artery; medial collateral vein; medial collateral artery; radial vein; radial artery; and combinations thereof.

The method can comprise transvascularly stimulating the medial cutaneous nerve, the at least one implantable functional element can comprise one or more electrodes, and the method can further comprise positioning the one or more electrodes in the basilic vein.

The method can comprise transvascularly stimulating the ulnar nerve, the at least one implantable functional element can comprise one or more electrodes, and the method can further comprise positioning the one or more electrodes in a blood vessel selected from the group consisting of: ulnar collateral vein; ulnar collateral artery; ulnar vein; ulnar artery; and combinations thereof.

The method can comprise transvascularly stimulating the median nerve, the at least one implantable functional element can comprise one or more electrodes, and the method can further comprise positioning the one or more electrodes in a blood vessel selected from the group consisting of: brachial vein; brachial artery; ulnar vein; ulnar artery; and combinations thereof.

The method can comprise transvascularly stimulating the tibial nerve. The at least one implantable functional element can comprise one or more electrodes, and the method can comprise positioning the one or more electrodes in a blood vessel selected from the group consisting of: popliteal artery; popliteal vein; saphenous vein; posterior tibial artery; posterior tibial vein; and combinations thereof. The first implantable device can further comprise at least one implantable lead comprising the one or more electrodes, and the method can comprise positioning the at least one implantable lead in at least one of the femoral artery or the femoral vein.

The method can comprise transvascularly stimulating the deep fibial nerve.

The method can comprise transvascularly stimulating an arm nerve selected from the group consisting of: median nerve; ulnar nerve; superior ulnar nerve; medial cutaneous nerve; radial nerve; and combinations thereof. The method can comprise transvascularly stimulating at least one of a median nerve, an ulnar nerve or a radial nerve, the at least one implantable functional element can comprise one or more electrodes, and the method can further comprise positioning the one or more electrodes in a blood vessel selected from the group consisting of: brachial vein; brachial artery; basilic vein; basilic artery; deep vein of the arm; deep artery of the arm; and combinations thereof. The method can comprise transvascularly stimulating at least one of a median nerve or an ulnar nerve, the at least one implantable functional element can comprise one or more electrodes, and the method can further comprise positioning the one or more electrodes in a blood vessel selected from the group consisting of: brachial vein; brachial artery; and combinations thereof. The method can comprise transvascularly stimulating the radial nerve, the at least one implantable functional element can comprise one or more electrodes, and the method can further comprise positioning the one or more electrodes in a blood vessel selected from the group consisting of: deep vein of arm; deep artery of arm; basilic vein; radial collateral vein; radial collateral artery; medial collateral vein; medial collateral artery; radial vein; radial artery; and combinations thereof. The method can comprise transvascularly stimulating the medial cutaneous nerve, the at least one implantable functional element can comprise one or more electrodes, and the method can further comprise positioning the one or more electrodes in the basilic vein. The method can comprise transvascularly stimulating the ulnar nerve, the at least one implantable functional element can comprise one or more electrodes, and the method can further comprise positioning the one or more electrodes in a blood vessel selected from the group consisting of: ulnar collateral vein; ulnar collateral artery; ulnar vein; ulnar artery; and combinations thereof. The method can comprise transvascularly stimulating the median nerve, the at least one implantable functional element can comprise one or more electrodes, and the method can further comprise positioning the one or more electrodes in a blood vessel selected from the group consisting of: brachial vein; brachial artery; ulnar vein; ulnar artery; and combinations thereof.

The method can comprise transvascularly stimulating the tibial nerve. The at least one implantable functional element can comprise one or more electrodes, and the method can comprise positioning the one or more electrodes in a blood vessel selected from the group consisting of: popliteal artery; popliteal vein; saphenous vein; posterior tibial artery; posterior tibial vein; and combinations thereof. The first implantable device can further comprise at least one implantable lead comprising the one or more electrodes, and the method can comprise positioning the at least one implantable lead in at least one of the femoral artery or the femoral vein.

The method can comprise transvascularly stimulating the deep fibial nerve. The at least one implantable functional element can comprise one or more electrodes, and the method can comprise positioning the one or more electrodes in a blood vessel selected from the group consisting of: anterior tibial vein; anterior tibial artery; and combinations thereof.

The method can comprise transvascularly stimulating the saphenous nerve. The at least one implantable functional element can comprise one or more electrodes, and the method can comprise positioning the one or more electrodes in a blood vessel selected from the group consisting of: femoral vein; femoral artery; and combinations thereof.

The method can comprise transvascularly stimulating the sural nerve. The at least one implantable functional element can comprise one or more electrodes, and the method can comprise positioning the one or more electrodes in a small saphenous vein.

In some embodiments, the method comprises delivering one or more of: electrical stimulation energy at a frequency of approximately between 10 Hz and 15 Hz; electrical stimulation energy at a frequency of between 5 Hz and 25 Hz; electrical stimulation energy with a pulse width of approximately between 180 μsec and 240 μsec; electrical stimulation energy with a pulse width of approximately between 10 μsec and 200 μsec; electrical stimulation energy with an amplitude of approximately 0.1V to 8.5V; electrical stimulation energy with a current between 0.1 mA to 10 mA; electrical stimulation energy with an amplitude between 0.4V and 2.0V; continuous electrical stimulation energy; intermittent electrical stimulation energy; intermittent electrical stimulation energy with a period between 8 seconds and 24 seconds; intermittent electrical stimulation energy with an on time between 8 seconds and 16 seconds; monopolar electrical stimulation energy; bipolar electrical stimulation energy; and combinations thereof. The method can be configured to treat a disease or disorder selected from the group consisting of: fecal incontinence; overactive bladder; urinary incontinence; a pelvic disorder; and combinations thereof. The at least one implantable functional element can comprise between two and six implantable functional elements.

In some embodiments, the first implantable device is configured to adjust the amount of stimulation energy delivered by varying a parameter selected from the group consisting of: at least one implantable functional element size and/or configuration; at least one implantable functional element shape; shape of a generated electric field; shape of a generated magnetic field; stimulation signal parameters; and combinations thereof.

In some embodiments, the first implantable device is configured to provide electrical stimulation energy at a current between 0.1 mA and 15 mA. The first implantable device can be configured to provide electrical stimulation energy at a current between 0.1 mA and 12 mA. The first implantable device can be configured to provide electrical stimulation energy at a current between 0.1 mA and 10 mA.

In some embodiments, the first implantable device is configured to perform magnetic field modulation. The first implantable device can be configured to perform a magnetic field modulation selected from the group consisting of: targeted magnetic field neuromodulation (TMFN), electromagnetic field neuromodulation, such as targeted electromagnetic field neuromodulation (TEMFN), transcutaneous magnetic field stimulation (TMS), and combinations thereof.

In some embodiments, the first implantable device is configured to provide at least one of localized magnetic stimulation or localized electrical stimulation. The first implantable device can be configured to provide by localized magnetic stimulation and localized electrical stimulation via superposition.

In some embodiments, the first implantable device is configured to provide a stimulation signal comprising a waveform selected from the group consisting of: square wave; sine wave; sawtooth; triangle wave; trapezoidal; ramp; waveform with exponential increase; waveform with exponential decrease; pulse shape which minimizes power consumption; Gaussian pulse shape; pulse train; root-raised cosine; bipolar pulses; and combinations thereof.

In some embodiments, the first implantable device is configured to provide a stimulation signal comprising a high frequency signal modulated with a low frequency signal. The stimulation signal can comprise one or more high frequency signals that are frequency modulated, amplitude modulated, phase modulated and/or pulse width modulated.

In some embodiments, the first implantable device comprises an implantable sensor. The implantable sensor can comprise a sensor selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations thereof.

In some embodiments, the medical apparatus further comprises a second implantable device comprising: at least one implantable functional element configured to interface with the patient. The medical apparatus can further comprise a connecting filament operatively connecting the first implantable device to the second implantable device. The method can further comprise operatively connecting the first implantable device to the second implantable device with the connecting filament.

In some embodiments, the at least one implantable functional element is configured to deliver electrical energy to a location selected from the group consisting of: spinal cord tissue; spinal canal tissue; epidural space; spinal root tissue; dorsal spinal root tissue; ventral spinal root tissue; dorsal root ganglion; nerve tissue; peripheral nerve tissue; spinal nerve tissue; brain tissue, ganglia; sympathetic ganglia; parasympathetic ganglia; a plexus; and combinations thereof.

In some embodiments, the at least one implantable functional element is positioned in a location selected from the group consisting of: epidural space; intrathecal space; outside of the dura in the epidural space but proximate the spine; a blood vessel; and combinations thereof.

In some embodiments, the first implantable functional element comprises a magnetic field generating element. The at least one implantable functional element can comprise a coil. The at least one implantable functional element can be implanted to at least partially surround tissue to be stimulated. The at least one implantable functional element can be configured to produce a magnetic field to induce application of mechanical energy. The at least one implantable functional element can be positioned to stimulate DRG tissue while avoiding stimulating ventral root tissue.

In some embodiments, the implantable housing comprises a shape selected from the group consisting of: disc; pill; cylinder; sphere; oblate spheroid; tombstone or elongated "D" shape; dish-like shape; bowl-like shape; cone; rectangular prism; trapezoidal prism; a portion of a toroid; and combinations thereof.

In some embodiments, the implantable housing comprises a material selected from the group consisting of: glass; ceramic; stainless steel; titanium; polyurethane; an organic compound; liquid crystal polymer (LCP); gold; platinum; tungsten; epoxy; a thermoplastic; a thermoset plastic; and combinations thereof.

In some embodiments, the at least one implantable antenna is positioned within the implantable housing.

In some embodiments, the at least one implantable antenna is positioned outside the implantable housing.

In some embodiments, the first implantable device further comprises a second implantable housing. The first implantable device can further comprise a connecting filament operatively connecting the first implantable housing to the second implantable housing.

In some embodiments, the first implantable device further comprises at least one implantable lead comprising the at least one functional element. The at least one implantable lead can comprise a first implantable lead comprising a functional element and a second implantable lead comprising a functional element, and the first implantable lead and the second implantable lead can each be operatively connected to the implantable housing.

In some embodiments, the first implantable device further comprises at least one flange attached to the implantable housing. The at least one flange can comprise at least a flexible portion. The at least one flange can comprise at least a rigid portion. The at least one flange can comprise an anchor element. The at least one flange can comprise an element selected from the group consisting of: antenna; conductive sheet; conductive surface; conductive element; capacitor; supercapacitor; energy storage element; and combinations thereof. The at least one flange comprises a conductive element can be configured to improve transmission of power and/or data between the first implantable device and the first external device. The at least one flange can comprise an electrically isolated component.

In some embodiments, the implantable housing comprises at least a first housing portion and a second housing portion. The implantable housing can comprise at least a third housing portion. The first housing portion can be attached to the second housing portion with a fixation selected from the group consisting of: adhesive; solvent; welding process; mechanical fixation; and combinations thereof. The implantable housing can further comprise a gap filling material constructed and arranged to fill gaps between the first housing portion and the second housing portion. The implantable housing can further comprise feedthroughs. The feedthroughs can be configured to electrically attach to the at least one implantable functional element. The feedthroughs can electrically attach to the at least one functional element using an attachment selected from the group consisting of: soldering; crimping; wire bonding; welding; laser welding; ultrasonic welding; tab bonding; applying a conductive adhesive; applying a conductive epoxy; tab welding; welding a folded flap with mating metal pads; brazing; and combinations thereof. The first implantable device can further comprise a conductive ribbon, and the feedthroughs can electrically attach to the conductive ribbon. The feedthroughs can be positioned away from the at least one implantable antenna. The implantable housing can comprise a material selected from the group consisting of: glass; ceramic; plastic; urethane; metal; titanium; and combinations thereof.

In some embodiments, the implantable housing comprises a major axis less than or equal to 20 mm in length. The implantable housing major axis can comprise a length less than or equal to a length selected from the group consisting of: 50 mm, 25 mm; 15 mm; 12 mm and 10 mm.

In some embodiments, the implantable housing comprises a minor axis with a length less than or equal to 8 mm. The implantable housing can comprise a minor axis with a length less than or equal to 6 mm.

In some embodiments, the implantable housing can comprise a wall thickness between 0.2 mm and 2.0 mm, such as between 0.2 mm and 1.0 mm. The implantable housing can comprise a wall thickness between 0.2 mm and 1.5 mm, such as between 0.2 mm and 0.5 mm. The implantable housing can comprise a wall thickness of approximately 1.3 mm or alternatively 0.3 mm.

In some embodiments, the implantable housing comprises a surface, and the first implantable device can comprise an implantable component positioned on the implantable housing surface. The implantable component can comprise a component selected from the group consisting of: passive electrical component; capacitor; the at least one implantable antenna; and combinations thereof. The surface can comprise an interior surface of the implantable housing. The surface can comprise an exterior surface of the implantable housing. The at least one implantable antenna can comprise an antenna electrically patterned on the surface. The antenna patterned on the surface can comprise meandering lines positioned on the surface. The antenna patterned on the surface can comprise insulated wires attached to the surface. The antenna patterned on the surface can comprise an antenna selected from the group consisting of: loop antenna; electric dipole antenna; patch antenna; and combinations thereof. The surface can comprise a first surface and a second surface, and the antenna patterned on the surface can comprise a first antenna patterned on the first surface and a second antenna patterned on the second surface. The first surface can be relatively orthogonal to the second surface.

In some embodiments, the first implantable device further comprises a desiccant positioned within the implantable housing.

In some embodiments, the first implantable device further comprises a potting material positioned within the implantable housing. The potting material can comprise RF-transparent potting material.

In some embodiments, the first implantable device further comprises a covering surrounding at least a portion of the housing. The covering can comprise a covering applied via at least one of a dipping or overmolding process.

In some embodiments, the implantable energy storage assembly is configured to provide stimulation energy when power provided by the first external device is interrupted. The method can be configured to provide cardiac resynchronization therapy.

In some embodiments, the implantable controller is configured to control a parameter selected from the group consisting of: a direct current (DC) parameter such as amplitude of voltage and/or current; amplitude; frequency; pulse width; inter-pulse interval (e.g. random, varied or constant); an amplitude modulation parameter; a frequency modulation parameter; anode/cathode configuration; voltage; current; pulse shape; a duty cycle parameter such as frequency, pulse width or off time; polarity; drive impedance; energy storage capacity; and combinations thereof.

In some embodiments, the first external device further comprises a magnetic field generating element. The first implantable device can further comprise a focusing component configured to focus the magnetic field generated by the first external device. The magnetic field generating element can be configured to induce application of mechanical energy. The magnetic field generating element can comprise a configuration selected from the group consisting of: wrist band; wrist watch; arm band; leg band; ankle band; and combinations thereof.

In some embodiments, the first external device comprises an external sensor configured to record a patient parameter selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity; skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations thereof.

In some embodiments, the first external device is constructed and arranged to mechanically adjust the position of the at least one external antenna. The first external device can comprise a mechanical adjustment assembly comprising a component selected from the group consisting of: motorized positioner; pulleys; gears; tensioners; fluid reservoir; and combinations thereof.

In some embodiments, the at least one external antenna comprises at least two external antennas configured to perform electrical beam steering.

In some embodiments, the first transmission signal comprises a frequency between 0.01 GHz and 10.6 GHz, such as between 0.01 GHz and 0.1 GHz, 0.01 GHz and 3.0 GHz, 0.1 GHz and 3.0 GHz, 0.1 GHz and 10.6 GHz, 0.4 GHz and 1.5 GHz, 0.902 GHz and 0.928 GHz, 10 MHz and 100 MHz, 40.66 MHz and 40.70 MHz or in a frequency range proximate to 866 MHz, or approximately between 863 MHz and 870 MHz. In some embodiments, the first implantable device further comprises a first implantable lead comprising one or more of the functional elements. The medical apparatus can further comprise a second implantable lead comprising one or more of the functional elements. The method can comprise bilaterally positioning the first implantable lead and the second implantable lead about the spine. The first implantable lead and the second implantable can be attached to the implantable housing. The implantable system can further comprise a second implantable housing, and the first implantable lead can be operatively attached to the first implantable housing and the second implantable lead can be operatively attached to the second implantable housing. The implantable system can further comprise a second implantable antenna, and the first implantable lead can be operatively attached to the first implantable antenna and the second implantable lead can be operatively attached to the second implantable antenna. The external antenna can transmit power and/or data to both the first implantable antenna and the second implantable antenna. The method can comprise positioning the first and second implantable leads such that their functional elements are in a staggered configuration. The method can comprise bilaterally positioning the first and second implantable leads about the spine. The at least one functional element can comprise one or more functional elements laterally deployable from the implantable lead. The implantable device can further comprise a second implantable lead, a third implantable lead and a fourth implantable lead, each comprising one or more functional elements. The method can comprise positioning four implantable leads in a diamond configuration. The method can comprise positioning four implantable leads in an X-shaped configuration.

In some embodiments, the medical apparatus further comprises a connecting filament operatively connecting two or more components of the first implantable device. The method can further comprise operatively connecting the connecting filament to one of the components. The connecting filament can operatively connect to one or more of: a lead of the first implantable device; the implantable housing; the at least one implantable antenna; and combinations thereof. The connecting filament can be constructed and arranged to allow an operator to operatively connect the connecting filament to at least one component of the first implantable device.

In some embodiments, the medical apparatus further comprises an implantation tool. The first implantable device can comprise at least one implantable lead comprising the at least one implantable functional element, and the method can further comprise implanting the at least one implantable lead into the patient. The at least one implantable lead can be implanted in the patient with the implantable housing attached to the at least one implantable lead. The implantation tool can comprise a cannula configured to surround the at least one implantable lead and penetrate through tissue of the patient while surrounding the at least one implantable lead. The cannula can comprise a peel-away cannula, and the method can further comprise removing the cannula from the at least one implantable lead by peeling apart the cannula. The cannula can comprise a first portion comprising a first opening and a second portion comprising a second opening, the first portion can surround the second portion, and the method can further comprise laterally removing the cannula from the at least one implantable lead after rotating the first portion relative to the second portion to align the first opening with the second opening. The first portion can comprise a larger radius of curvature than the second portion. The cannula can comprise a first portion and a second portion configured to mechanically engage the first portion, and the method can further comprise laterally removing the cannula from the at least one implantable lead after mechanically disengaging the first portion from the second portion. The first portion can comprise a similar radius of curvature as the second portion. The implantation tool can comprise a component selected from the group consisting of: penetrating element; cannula; stiffening element; stylet; and combinations thereof. The implantation tool can comprise a penetrating element comprising a Touhy needle. The first implantable device can comprise an implantable lead comprising the at least one implantable functional element, and the implantation tool can comprise a stiffening element configured to provide a pathway for advancing an elongate device through tissue. The stiffening element can comprise a marker selected from the group consisting of: radiopaque marker; ultrasonically reflective marker; magnetic marker; and combinations thereof.

In some embodiments, the medical apparatus further comprises a patient attachment device. The patient attachment device can comprise a device selected from the group consisting of: belt; belt with pockets; belt with adhesive, adhesive; strap; strap with pockets; strap with adhesive shoulder strap; shoulder band; shirt; shirt with pockets; clothing; clothing with pockets; epidural electronics packaging; clip; bracelet; wrist band; wrist watch; anklet; ankle bracelet; knee strap; knee band; thigh strap; thigh band; necklace; hat; headband; collar; glasses; goggles; earpiece; behind-the-earpiece; and combinations thereof.

In some embodiments, the medical apparatus further comprises a diagnostic assembly. The diagnostic assembly can be configured to assess the link between the at least one implantable antenna and the at least one external antenna. The diagnostic assembly can be configured to detect the presence and/or operation of the first implantable device. The diagnostic assembly can be configured to assess the charge and/or discharge rate of the implantable energy storage assembly. The diagnostic assembly can be configured to assess the frequency of a voltage-controller oscillator that is driven by an unregulated voltage of a power converter of the implantable energy storage assembly. The diagnostic assembly can be configured to assess the impedance of at least one of the at least one external antenna or the at least one implantable antenna. The diagnostic assembly can be configured to assess the impedance by performing a function selected from the group consisting of: performing a frequency sweep; performing an impulse response; comparing voltage and current of a waveform; and combinations thereof. The diagnostic assembly can be configured to adjust a matching network based on the assessed impedance of the at least one external antenna or the at least one implantable antenna.

In some embodiments, the first implantable device at least one implantable functional element comprises at least one electrode. The at least one electrode can comprise one or more electrodes selected from the group consisting of: microelectrode; cuff electrode; array of electrodes; linear array of electrodes; circular array of electrodes; paddle-shaped array of electrodes; bifurcated electrodes; and combinations thereof.

In another aspect of the present invention, medical apparatus is provided comprising:
an external system configured to transmit one or more transmission signals, each transmission signal comprising at least power or data; and an implantable system configured to receive the one or more transmission signals from the external system, wherein the implantable system includes at least one implantable functional element configured to interface with the patient and an implantable controller configured to control the at least one implantable functional element, wherein the medical apparatus is configured to perform a function selected from the group consisting of:
stimulate tissue of a peripheral nervous system,
stimulate tissue with at least a magnetic field,
stimulate tissue to treat at least one of neuropathy, neuralgia or overactive bladder,
stimulate tissue to treat occipital neuralgia,
stimulate tissue to treat post-herpetic neuralgia
stimulate tissue to treat diabetic neuropathy
stimulate tissue to treat complex regional pain syndrome,
stimulate tissue to treat pain related to at least one of hernia or hernia repair,
stimulate tissue to treat post-amputation pain,
stimulate tissue to treat overactive bladder,
stimulate tissue to treat fecal incontinence,
stimulate tissue to treat pelvic pain,
stimulate tissue to treat subcutaneous pain,
stimulate tissue to treat visceral pain,
stimulate tissue to treat at least one of peripheral vascular disease, diabetic neuropathy or other diabetic condition,
stimulate tissue to treat at least one of occipital pain or headache pain,
stimulate tissue to treat at least one of bladder dysfunction or bowel dysfunction,
stimulate nervous tissue associated with a multifidus muscle to rehabilitate function of the multifidus muscle and/or improve spinal stability,
stimulate tissue transvascularly,
and combinations of one or more of these.

In some embodiments, the external system comprises a first external device comprising: at least one external antenna configured to transmit the one or more transmission signals to the implantable system; an external transmitter configured to drive the at least one external antenna; an external power supply configured to provide power to at least the external transmitter; and an external controller configured to control the external transmitter.

In some embodiments, the implantable system comprises a first implantable device comprising: at least one implantable antenna configured to receive the one or more transmission signals; an implantable receiver configured to receive the one or more transmission signals from the at least one implantable antenna; and an implantable energy storage assembly configured to provide power to an element selected from the group consisting of: the at least one implantable functional element, the implantable controller, the implantable receiver, and combinations of these.

In some embodiments, the apparatus is configured to deliver stimulation energy to tissue, and wherein the stimulation energy is selected from the group consisting of: electrical energy, magnetic energy, electromagnetic energy, light energy, infrared light energy, visible light energy, ultraviolet light energy, mechanical energy, thermal energy, heat energy, cryogenic energy, sound energy, ultrasonic sound energy, high intensity focused ultrasound energy, low intensity focused ultrasound energy, subsonic sound energy, chemical energy, and combinations thereof.

In some embodiments, the apparatus is configured to perform a function selected from the group consisting of: deliver electric energy, deliver controlled electrical current and/or voltage to tissue, deliver magnetic energy, deliver magnetic field energy, deliver controlled current or voltage to a coil or other magnetic field generating element positioned proximate tissue, deliver electromagnetic energy, deliver both current to tissue and a magnetic field to tissue, and combinations thereof.

In some embodiments, the apparatus is configured to stimulate at least one set of multifidus muscle fascicles.

In some embodiments, the apparatus is configured to at least one of depolarize, hyperpolarize or block innervated sections of a muscle to perform a function selected from the group consisting of: propagate an activating stimulus along nerve fibers recruiting muscle tissue remote from a site of stimulation; propagate an inhibiting stimulus along nerve fibers recruiting muscle tissue remote from a site of stimulation, modulate nerve activity, inhibit nerve conduction, improve nerve conduction, improve muscle activity, and combinations thereof.

In some embodiments, the apparatus is configured to stimulate tissue by providing episodic electrical stimulation.

In some embodiments, the apparatus further comprises a tool configured to diagnose a defect in at least one of a spinal muscle or a motor control system.

In some embodiments, the apparatus further comprises a tool configured to test function of a multifidus muscle. In some instances, the tool is selected from the group consisting of: magnetic resonance imager, ultrasound imager, electromyogram, tissue biopsy device, a device configured to test displacement as a function of load for a spine, and combinations thereof.

In some embodiments, the apparatus is configured to deliver high frequency energy comprising electrical energy at or above 1 kHz. In other embodiments, the apparatus is configured to deliver low frequency electrical energy at a frequency at or below 1 kHz.

In some embodiments, the apparatus further comprising a lead having the at least one implantable functional element, and wherein the lead is configured for implantation in a suprascapular location.

In some embodiments, the apparatus is configured to stimulate tissue to treat neuralgia, wherein
  the neuralgia results from at least one of: surgery, trauma or pain,
  the neuralgia results from groin surgery and wherein the at least one implantable functional element is positioned to stimulate nerve tissue selected from the group consisting of: ilioinguinal, genitofemoral, iliohypogastric, and combinations thereof,
  the neuralgia results from shoulder surgery, wherein the at least one implantable functional element is positionable to stimulate axial nerve tissue, and further comprising a lead comprising the at least one implantable functional element wherein the lead is implantable in a suprascapular location,
  the neuralgia results from lung surgery and wherein the at least one implantable functional element is positionable to stimulate intercostal nerve tissue,
  the neuralgia is associated with carpal tunnel syndrome and wherein the at least one implantable functional element is positionable to stimulate median nerve tissue,
  the neuralgia is associated with temporomandibular joint disorder and wherein the at least one implantable functional element is positionable to stimulate V2 of trigeminal nerve tissue,
  the neuralgia comprises facial neuralgia and wherein the at least one implantable functional element is positionable to stimulate trigeminal nerve tissue, or
  the neuralgia comprises leg neuralgia and wherein the at least one implantable functional element is positionable to stimulate nerve tissue proximal a contributing lesion.

In some embodiments, the medical apparatus is configured to stimulate tissue to treat diabetic neuropathy, wherein
  the at least one implantable functional element is positionable proximate a lower spinal cord,
  the at least one implantable functional element is positionable to stimulating a tibial nerve,
  the at least one implantable functional element is configured to stimulate a dorsal root ganglion,
  the at least one implantable functional element is configured to treat diabetic neuropathy of at least one of a hand or foot, or
  the at least one implantable functional element is configured to transvascularly stimulate nerve tissue.

In some embodiments, the medical apparatus is configured to treat a disease or disorder selected from the group consisting of: visceral pain; angina; and combinations thereof.

In some embodiments, the medical apparatus is configured to treat a disease or disorder selected from the group consisting of: post-surgical neuralgia; post-surgical neuralgia following hernia repair; headache; headache due to occipital neuralgia; post-herpetic neuralgia; chronic pelvic pain; chronic hip pain; knee pain; and combinations thereof.

In some embodiments, the medical apparatus is configured to treat knee pain, wherein the at least one implantable functional element is configured to be positioned
  along a medial femoral cutaneous or infrapatellar cutaneous branch of a saphenous nerve to target a medial portion of a knee, along a constant articular branch of a common peroneal, lateral retinacular nerve to target a lateral portion of a knee, along a lateral, medial, or anterior cutaneous femoral nerve, infrapatellar branch of a saphenous nerve, a medial or lateral retinacular nerve or an articular branch of a peroneal nerve to target an anterior portion of a knee, or along an obturator, posterior tibial or sciatic nerve to target a posterior portion of a knee.

along a superior, middle or inferior genicular nerve arising from a tibial nerve, along a superior lateral, inferior lateral, or recurrent genicular nerve arising from a common peroneal nerve, along a genicular branch of an obturator arising from an obturator nerve, or along a saphenous nerve arising from a femoral nerve.

In some embodiments, the medical apparatus is configured to treat pain associated with at least one of hernia or hernia repair by stimulating a location selected from the group consisting of: cutaneous branch of the ilioinguinal and/or inguinal nerves; genital branch of the genitofemoral nerves; corresponding branches of spinal nerves correlating to one or more dermatomes related to pain associated with at least one of hernia or hernia repair; and combinations thereof. In some embodiments, the apparatus further comprising an imaging device for localizing the nerve tissue to be stimulated. Optionally, the medical apparatus is configured to:

transvascularly stimulate the genitofemoral and/or ilioinguinal nerves, transvascularly stimulate nerve tissue via a blood vessel selected from the group consisting of: femoral vein; femoral artery; superficial external pudendal vein; superficial external pudendal artery; deep external pudendal vein; deep external pudendal artery; superficial epigastric vein; superficial epigastric artery; and combinations thereof, treat painful areas innervated by at least one of: ilioinguinal nerve, genitofemoral nerve or iliohypogastric nerves wherein the apparatus delivers stimulation energy to the spinal cord in the L1-L5 region, deliver stimulation energy to the L1-L2 dorsal root ganglia, or position the at least one implantable functional element at a location selected from the group consisting of: over a dorsal column; over a dorsal root; in the dorsal root entry zone; and combinations thereof.

In some embodiments, the medical apparatus is configured to treat occipital neuralgia, and wherein the at least one implantable functional element is positionable to stimulate peripheral nerve tissue to reduce pain, positionable to stimulate a cervical nerve, configured to treat a disease or disorder selected from the group consisting of: migraine headache; headache; cluster headache; and combinations thereof, or configured to stimulate nerve tissue selected from the group consisting of: occipital; supraorbital; infraorbital; greater occipital nerve (GON); lesser occipital nerve (LON); both supraorbital and GON; supratroclear; sphenopalantine (SPG); and combinations thereof.

In some embodiments, the apparatus is configured to treat a disease or disorder selected from the group consisting of: occipital pain; headache; and combinations thereof.

In some embodiments, the apparatus is configured to treat a disease or disorder selected from the group consisting of: occipital neuralgia; cervicogenic headache; tension headache; chronic and episodic migraine headache; tension headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations thereof.

In some embodiments, the apparatus is configured to stimulate one or more nerves in the head.

In some embodiments, the apparatus is configured to stimulate one or more nerves selected from the group consisting of: greater and/or lesser occipital nerve; the greater and/or lesser auricular nerves; the third occipital nerve; and combinations thereof, to stimulate one or more nerves selected from the group consisting of: auriculotemporal nerve; supratrochlear nerve; sub-occipital nerve; and combinations thereof, to stimulate spinal cord tissue proximate C2-C3, or so that at least one implantable functional element is positionable at a location selected from the group consisting of: over a portion of a dorsal column; in the gutter; over a dorsal root entry zone; in the foramen at the dorsal root ganglion; and combinations thereof.

In some embodiments, the apparatus is configured to treat post-herpetic neuralgia, wherein the at least one implantable functional element is positionable to stimulate corresponding branches of spinal nerves correlating to one or more dermatomes related to the post-herpetic neuralgia, the apparatus is configured to treat a disease or disorder selected from the group consisting of: shingles; herpes zoster; zoster; zona; varicella zoster virus infection; zoster sine herpete; fever blisters; herpes zoster blisters; herpes zoster rash; and combinations thereof, the apparatus is configured to deliver a high frequency alternating current block, the apparatus is configured to stimulate nerve tissue from a location selected from the group consisting of: leg; arm; torso; sacrum; spinal cord; and combinations thereof, or the apparatus is configured to transvascularly stimulate nerve tissue from a location selected from the group consisting of: leg; arm; torso; sacrum; and combinations thereof.

In some embodiments, wherein the apparatus is configured to treat a disease or disorder selected from the group consisting of: pelvic disorder; bladder disorder; and combinations thereof, and wherein the apparatus is configured to stimulate a nerve selected from the group consisting of: sacral; pudendal; tibial; and combinations thereof.

In some embodiments, the apparatus is configured to treat at least one of a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations thereof.

In some embodiments, the apparatus is configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations thereof.

In some embodiments, the device is configured to treat a disease or disorder selected from the group consisting of: pelvic disorder; bladder dysfunction; bowel dysfunction; and combinations thereof.

In some embodiments, the apparatus is configured to stimulate the sacral nerves S2, S3 and/or S4.

In some embodiments, the implantable system comprises at least one implantable lead comprising the at least one implantable functional element, wherein
  the lead is configured to be passed through a foramen to an anterior side of a sacrum and/or positioned inside the foramen,
  the lead is configured to be inserted rostrally toward at least one sacral root,
  the lead is configured to be positioned along a sacral canal or
  the lead is configured to be comprises positioned in a manner selected from the group consisting of: threaded from a spinal canal into a sacral foramen in an anterior trajectory; inserted into the sacral canal in a caudal trajectory; inserted into the sacral canal via a sacral hiatus in an anterograde trajectory; and combinations thereof.

In some embodiments, the apparatus is configured to access at least one sacral nerve as it enters a spinal cord at a cauda equina.

In some embodiments, the apparatus is configured to transvascularly stimulate at least one sacral nerve.

In some embodiments, the apparatus is configured to stimulate the pudendal nerve, wherein
  the apparatus is configured to position the at least one implantable functional element proximate an ischial spine,
  the implantable system further comprises at least one implantable lead comprising the at least one implantable functional element, and wherein the lead is configured to be inserted through a vaginal wall toward the ischial spine,
  the implantable system further comprises at least one implantable lead comprising the at least one implantable functional element, and wherein the lead is configured to be inserted to a position just medial to an ischial tuberosity and toward the ischial spine, or
  the apparatus is configured to transvascularly stimulate the pudendal nerve.

In some embodiments, the apparatus is configured to stimulate pudendal afferents, wherein
  the apparatus is configured to stimulate pudendal afferents by stimulating a dorsal genital nerve, or
  the implantable system further comprises at least one implantable lead comprising the at least one implantable functional element, and wherein the lead is configured to be inserted periurethrally.

In some embodiments, the apparatus is configured to treat pelvic pain, wherein the apparatus
  is configured to treat at least one of interstitial cystitis or bladder pain,
  is configured to position the at least one implantable functional element to stimulate at least one of peripheral nervous system tissue or central nervous system tissue,
  is configured to position the at least one implantable functional element to stimulate peripheral nervous system tissue by positioning the at least one implantable functional element proximate tissue selected from the group consisting of: pudendal tissue; S-2 root; S-3 root; S-4 root; and combinations thereof,
  is configured to position the at least one implantable functional element to stimulate central nervous system tissue by positioning the at least one implantable functional element proximate tissue selected from the group consisting of: lower spinal cord tissue; s3 neural foramen; and combinations thereof,
  is configured to treat anal pain, and wherein the apparatus is configured to position the at least one implantable functional element to stimulate nerve tissue selected from the group consisting of: pudendal tissue; S-2 root; S-3 root; S-4 root; and combinations thereof, or
  is configured to stimulate tibial nerve tissue.

In some embodiments, the apparatus is configured to treat overactive bladder, wherein the apparatus
  is configured to treat urinary incontinence,
  is configured to the effect of overactive bladder or decrease use of an overactive bladder medication,
  is configured to stimulate tissue selected from the group consisting of: central nervous system tissue; peripheral nervous system tissue; and combinations thereof,
  is configured to stimulate one or more nerves that at least one of control or relate to bladder function,
  is configured to provide a therapeutic benefit selected from the group consisting of: to increase bladder capacity; improve bladder emptying; reduce urge incontinence; reduce stress incontinence; and combinations thereof,
  is configured to stimulate at least one of tibial nerve tissue or sacral nerve tissue,
  is configured to modulate transmission of excitatory nerve signals to the bladder muscles,
  is configured to provide temporary stimulation of tissue to treat overactive bladder,
  is configured to stimulate at least one sphincter muscle,
  is configured to stimulate multiple sphincter muscles,
  includes the at least one implantable functional element which further comprises a first implantable functional element and a second implantable functional element, wherein the first implantable functional element is configured to be positioned on one side of the urethral orifice and the second implantable functional element is configured to be positioned on the opposite side of the urethral orifice, or
  includes an implantable housing which is positionable in a location selected from the group consisting of: suprapubic region; perineum; and combinations thereof.

In some embodiments, the apparatus is configured to treat fecal incontinence, and wherein
  the apparatus is configured to stimulate tissue selected from the group consisting of: sacral nerve tissue; tissue whose stimulation strengthens muscles of the bowel and/or rectum; and combinations thereof, the implantable device comprises at least one implantable lead comprising the at least one implantable functional element, and wherein the apparatus comprises positioning the at least one implantable lead in a location selected from the group consisting of: the pelvic girdle; the sacral foramina; the lower back; the upper buttock; and combinations thereof, or the apparatus is further configured to treat a bladder disorder.

In some embodiments, the apparatus is configured to treat a disease or disorder selected from the group consisting of: post-amputation pain, phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations thereof, and wherein the apparatus comprises the capability of at least one of: delivering a high frequency alternating current block or stimulating a nerve from a location selected from the group consisting of: leg; arm; sacrum; spinal cord; and combinations thereof, or comprises the capability of transvascularly stimulating a nerve from a location selected from the group consisting of: leg; arm; and combinations thereof.

In some embodiments, the apparatus is configured to treat carpal tunnel syndrome, and wherein the apparatus is configured to treat a disease or disorder selected from the group consisting of: median nerve entrapment; tingling and/or numbness in fingers or hand; median nerve irritation or compression; narrowing of the carpal tunnel; and combinations thereof.

In some embodiments, the apparatus is configured to treat erectile dysfunction, impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED, complex regional pain syndrome, CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations thereof.

In some embodiments, the apparatus is configured to treat a condition of diabetes, and wherein the apparatus is configured to treat a disease or disorder selected from the group consisting of: peripheral vascular disease; diabetic neuropathy; and combinations thereof, to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations thereof, to position the at least one implantable functional element proximate nerve tissue in a location selected from the group consisting of: foot; leg; arm; sacrum; and combinations thereof, to stimulate a spinal cord, to transvascularly stimulate tissue, to stimulate tibial nerve tissue.

to treat a diabetic malady of a foot, to stimulate a tibial nerve, to treat a disease or disorder selected from the group consisting of: overactive bladder; bowel disorder; diabetic disorder; diabetic malady of the foot; and combinations thereof, to comprise at least one implantable lead comprising the at least one implantable functional element, and wherein the at least one implantable lead is positionable in a popliteal fossa behind a knee, or to transvascularly stimulate a tibial nerve tissue.

In some embodiments, wherein the apparatus is configured to stimulate a posterior tibial nerve and/or treat bladder voiding dysfunction.

In some embodiments, the apparatus is positionable so that the at least one implantable functional element is able to perform retrograde stimulation of the sacral nerve plexus. Optionally, the apparatus is configured to restore balance between bladder inhibitory and excitatory control systems.

In some embodiments, the apparatus is configured to stimulate a region of the pelvic floor and perform a function selected from the group consisting of: change the reflex thresholds of the bladder muscles responsible for bladder emptying; strengthen and/or otherwise improve the condition of the muscles that maintain closure on the bladder outlet; change the state of the neural pathways, musculature and/or bladder during and beyond the period stimulation; decrease the severity of urinary incontinence; and combinations thereof.

In some embodiments, the apparatus is configured for stimulating periurethral muscles and/or pudendal afferents.

In some embodiments, the apparatus comprises stimulating tissue of at least one of a vagina or an anus.

In some embodiments, the apparatus comprises stimulating a vagus nerve, peroneal nerve; saphenous nerve; median nerve; ulnar nerve; radial nerve; and combinations thereof.

In some embodiments, the apparatus comprises stimulating a spinal cord, and wherein the apparatus is configured to position the at least one implantable functional element between T5-S5, treat pain or reduced circulation of at least one of a leg or a foot, position the at least one implantable functional element between C2 and T8, treat pain or reduced circulation of at least one of an arm or a hand, position an at least one implantable lead having the at least one implantable functional element along a midline of the spinal cord, position an at least one implantable lead having the at least one implantable functional element at a location selected from the group consisting of: over a dorsal column; in a gutter; in a dorsal root entry zone; and combinations thereof, position the at least one implantable functional element to span multiple vertebral levels, position the at least one implantable functional element to span a single vertebral level, position the at least one functional element to stimulate dorsal root ganglia that supply nerve tissue selected from the group consisting of: common peroneal; tibial; femoral; and combinations thereof, treat at least one of a leg or a foot, position the at least one functional element to stimulate dorsal root ganglia that supply nerve tissue selected from the group consisting of: radial; median; ulnar; and combinations thereof, treat at least one of an arm or a hand, pass at least one implantable lead having the at least one implantable functional element through an intervertebral foramina,
stimulate tissue between T9 and T12,
treat back pain,
stimulate peripheral nerve tissue,
stimulate tissue between L5 and T5,
stimulate tissue between C5 and T1 and/or C3 and T5,
treat upper limb pain,
stimulate tissue between T9 and T1 and/or T5 and L5,
treat lower limb pain,
stimulate tissue between C7 and T1 and/or C5 and T5,
treat angina, or
visualize the patient's anatomy to place the at least one implantable functional element.

In some embodiments, the apparatus is configured to stimulate a dorsal root ganglion.

In some embodiments, the apparatus is configured for transvascularly stimulating tissue, and
further comprising at least one implantable lead comprising the at least one functional element, and the at least one implantable lead is positionable in a blood vessel selected from the group consisting of: internal pudendal vein and/or artery; common iliac vein and/or artery; inferior and/or superior gluteal vein and/or artery; middle rectal, pudendal plexus and/or internal iliac vein and/or artery; medial and/or lateral sacral vein and/or artery; uterine and/or obturator vein and/or artery; and combinations thereof,
transvascularly stimulating a nerve at a location selected from the group consisting of: leg; foot; arm; hand; and combinations thereof,
transvascularly stimulating a leg nerve selected from the group consisting of: tibial nerve; sacral root; deep fibular nerve; and combinations thereof,
transvascularly stimulating an arm nerve selected from the group consisting of: median nerve; ulnar nerve; superior ulnar nerve; medial cutaneous nerve; radial nerve; and combinations thereof,
transvascularly stimulating at least one of a median nerve, an ulnar nerve or a radial nerve, wherein the at least one implantable functional element comprises one or more electrodes, and wherein the method further comprises positioning the one or more electrodes in a blood vessel selected from the group consisting of: brachial vein; brachial artery; basilic vein; basilic artery; deep vein of the arm; deep artery of the arm; and combinations thereof,
transvascularly stimulating at least one of a median nerve or an ulnar nerve, wherein the at least one implantable functional element comprises one or more electrodes, and the one or more electrodes is positionable in a blood vessel selected from the group consisting of: brachial vein; brachial artery; and combinations thereof,
transvascularly stimulating a radial nerve, wherein the at least one implantable functional element comprises one or more electrodes, and the one or more electrodes are positionable in a blood vessel selected from the group consisting of: deep vein of arm; deep artery of arm; basilic vein; radial collateral vein; radial collateral artery; medial collateral vein; medial collateral artery; radial vein; radial artery; and combinations thereof,
transvascularly stimulating a medial cutaneous nerve, wherein the at least one implantable functional element comprises one or more electrodes, and wherein the one or more electrodes are positionable in a basilic vein,
transvascularly stimulating an ulnar nerve, wherein the at least one implantable functional element comprises one or more electrodes, and wherein the one or more electrodes are positionable in a blood vessel selected from the group consisting of: ulnar collateral vein; ulnar collateral artery; ulnar vein; ulnar artery; and combinations thereof,
transvascularly stimulating a median nerve, wherein the at least one implantable functional element comprises one or more electrodes, and wherein the one or more electrodes are positionable in a blood vessel selected from the group consisting of: brachial vein; brachial artery; ulnar vein; ulnar artery; and combinations thereof,
transvascularly stimulating a tibial nerve,
the at least one implantable functional element comprises one or more electrodes, and wherein the one or more electrodes are positionable in a blood vessel selected from the group consisting of: popliteal artery; popliteal vein; saphenous vein; posterior tibial artery; posterior tibial vein; and combinations thereof,
further comprising at least one implantable lead comprising one or more electrodes, and the at least one implantable lead is positionable in at least one of a femoral artery or a femoral vein,
transvascularly stimulating a deep fibial nerve,
the at least one implantable functional element comprises one or more electrodes, and wherein the one or more electrodes are positionable in a blood vessel selected from the group consisting of: anterior tibial vein; anterior tibial artery; and combinations thereof,
transvascularly stimulating a saphenous nerve,
the at least one implantable functional element comprises one or more electrodes, and wherein the one or more electrodes is positionable in a blood vessel selected from the group consisting of: femoral vein; femoral artery; and combinations thereof,
transvascularly stimulating a sural nerve, or
the at least one implantable functional element comprises one or more electrodes, and wherein the one or more electrodes is positionable in a small saphenous vein.

In some embodiments, the apparatus is configured to deliver one or more of:
electrical stimulation energy at a frequency of approximately between 10 Hz and 15 Hz;
electrical stimulation energy at a frequency of between 5 Hz and 25 Hz;
electrical stimulation energy with a pulse width of approximately between 180 μsec and 240 μsec;
electrical stimulation energy with a pulse width of approximately between 10 μsec and 200 μsec;
electrical stimulation energy with an amplitude of approximately 0.1V to 8.5V;
electrical stimulation energy with a current between 0.1 mA to 10 mA;
electrical stimulation energy with an amplitude between 0.4V and 2.0V;
continuous electrical stimulation energy;
intermittent electrical stimulation energy;
intermittent electrical stimulation energy with a period between 8 seconds and 24 seconds;
intermittent electrical stimulation energy with an on time between 8 seconds and 16 seconds;
monopolar electrical stimulation energy;
bipolar electrical stimulation energy; and combinations thereof.

In some embodiments, the apparatus is configured to treat a disease or disorder selected from the group consisting of: fecal incontinence; overactive bladder; urinary incontinence; a pelvic disorder; and combinations thereof. Optionally, the at least one implantable functional element comprises between two and six implantable functional elements.

In some embodiments, the first implantable system is configured to adjust an amount of stimulation energy delivered by varying a parameter selected from the group consisting of: at least one implantable functional element size and/or configuration; at least one implantable functional element shape; shape of a generated electric field; shape of a generated magnetic field; stimulation signal parameters; and combinations thereof.

In some embodiments, the implantable system is configured to
- provide electrical stimulation energy at a current between 0.1 mA and 15 mA,
- provide electrical stimulation energy at a current between 0.1 mA and 12 mA,
- provide electrical stimulation energy at a current between 0.1 mA and 10 mA,
- perform magnetic field modulation,
- perform a magnetic field modulation selected from the group consisting of: targeted magnetic field neuromodulation (TMFN), electro-magnetic field neuromodulation, such as targeted electro-magnetic field neuromodulation (TEMFN), transcutaneous magnetic field stimulation (TMS), and combinations thereof,
- provide at least one of localized magnetic stimulation or localized electrical stimulation,
- provide by localized magnetic stimulation and localized electrical stimulation via superposition,
- provide a stimulation signal comprising a waveform selected from the group consisting of: square wave; sine wave; sawtooth; triangle wave; trapezoidal; ramp; waveform with exponential increase; waveform with exponential decrease; pulse shape which minimizes power consumption; Gaussian pulse shape; pulse train; root-raised cosine; bipolar pulses; and combinations thereof,
- provide a stimulation signal comprising a high frequency signal modulated with a low frequency signal, or
- provide a stimulation signal wherein the stimulation signal comprises one or more high frequency signals that are frequency modulated, amplitude modulated, phase modulated and/or pulse width modulated.

In some embodiments, the implantable system comprises an implantable sensor. Optionally, the implantable sensor comprises a sensor selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations thereof.

In some embodiments, the at least one implantable functional element is configured to deliver electrical energy to a location selected from the group consisting of: spinal cord tissue; spinal canal tissue; epidural space; spinal root tissue; dorsal spinal root tissue; ventral spinal root tissue; dorsal root ganglion; nerve tissue; peripheral nerve tissue; spinal nerve tissue; brain tissue, ganglia; sympathetic ganglia; parasympathetic ganglia; a plexus; and combinations thereof.

In some embodiments, the at least one implantable functional element is positionable in a location selected from the group consisting of: epidural space; intrathecal space; outside of the dura in the epidural space but proximate the spine; a blood vessel; and combinations thereof.

In some embodiments, the implantable functional element comprises a magnetic field generating element. In some instances, the at least one implantable functional element
- comprises a coil,
- is implantable to at least partially surround tissue to be stimulated,
- is configured to produce a magnetic field to induce application of mechanical energy, or
- is positionable to stimulate DRG tissue while avoiding stimulating ventral root tissue.

In some embodiments, the apparatus includes an implantable housing, wherein
- the housing comprises a shape selected from the group consisting of: disc; pill; cylinder; sphere; oblate spheroid; tombstone or elongated "D" shape; dish-like shape; bowl-like shape; cone; rectangular prism; trapezoidal prism; a portion of a toroid; and combinations thereof,
- the housing comprises a material selected from the group consisting of: glass; ceramic; stainless steel; titanium; polyurethane; an organic compound; liquid crystal polymer (LCP); gold; platinum; tungsten; epoxy; a thermoplastic; a thermoset plastic; and combinations thereof.
- at least one implantable antenna is positionable within the implantable housing, or
- at least one implantable antenna is positionable outside the implantable housing.

In some embodiments, the implantable system further comprises at least one flange attached to an implantable housing, wherein
- the at least one flange comprises at least a flexible portion,
- the at least one flange comprises at least a rigid portion,
- the at least one flange comprises an anchor element.
- the at least one flange comprises an element selected from the group consisting of: antenna; conductive sheet; conductive surface; conductive element; capacitor; supercapacitor; energy storage element; and combinations thereof,
- the at least one flange comprises a conductive element configured to improve transmission of at least one of power or data between the first implantable device and the first external device, or
- the at least one flange comprises an electrically isolated component.

In some embodiments, wherein the implantable system comprises an implantable energy storage assembly configured to provide stimulation energy when power provided by the external system is interrupted.

In some embodiments, the implantable system is configured to provide cardiac resynchronization therapy.

In some embodiments, the implantable system comprises an implantable controller configured to control a parameter selected from the group consisting of: a direct current (DC) parameter such as amplitude of voltage and/or current; amplitude; frequency; pulse width; inter-pulse interval (e.g. random, varied or constant); an amplitude modulation parameter; a frequency modulation parameter; anode/cathode configuration; voltage; current; pulse shape; a duty cycle parameter such as frequency, pulse width or off time; polarity; drive impedance; energy storage capacity; and combinations thereof.

In some embodiments, the external system comprises an external sensor configured to record a patient parameter selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity; skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations thereof.

In some embodiments, the one or more transmission signals comprises a signal having a frequency
between 0.01 GHz and 10.6 GHz,
between 0.01 GHz and 0.1 GHz,
between 0.1 GHz and 3.0 GHz,
between 0.1 GHz and 10.6 GHz,
between 0.4 GHz and 1.5 GHz,
between 0.902 GHz and 0.928 GHz,
between 40.66 MHz and 40.7 MHz,
of approximately 866 MHz or
between 863 MHz and 870 MHz.

In some embodiments, the medical apparatus further comprises an implantation tool.

In some embodiments, the implantation tool comprises a cannula configured to surround at least one implantable lead having the at least one function element and penetrate through tissue of the patient while surrounding the at least one implantable lead.

In some embodiments, the cannula comprises a peel-away cannula, and wherein the cannula is removable from the at least one implantable lead by peeling apart the cannula.

In some embodiments, the cannula comprises a first portion comprising a first opening and a second portion comprising a second opening, wherein the first portion surrounds the second portion, and wherein the cannula is laterally removable from the at least one implantable lead after rotating the first portion relative to the second portion to align the first opening with the second opening. Optionally, the first portion comprises a larger radius of curvature than the second portion. In some embodiments, the cannula comprises a first portion and a second portion configured to mechanically engage the first portion, and the cannula is laterally removable from the at least one implantable lead after mechanically disengaging the first portion from the second portion. In some embodiments, the first portion comprises a similar radius of curvature as the second portion. In some embodiments, the implantation tool comprises a component selected from the group consisting of: penetrating element; cannula; stiffening element; stylet; and combinations thereof.

In some embodiments, the medical apparatus further comprises a patient attachment device. Optionally, the patient attachment device comprises a device selected from the group consisting of: belt; belt with pockets; belt with adhesive, adhesive; strap; strap with pockets; strap with adhesive shoulder strap; shoulder band; shirt; shirt with pockets; clothing; clothing with pockets; epidural electronics packaging; clip; bracelet; wrist band; wrist watch; anklet; ankle bracelet; knee strap; knee band; thigh strap; thigh band; necklace; hat; headband; collar; glasses; goggles; earpiece; behind-the-earpiece; and combinations thereof.

In some embodiments, wherein the medical apparatus further comprises a diagnostic assembly. In some instances, the diagnostic assembly is configured to assess the link between at least one implantable antenna and at least one external antenna.

In some embodiments, the diagnostic assembly is configured to
  detect the presence and/or operation of the implantable system,
  assess at least one of a charge or discharge rate of an implantable energy storage assembly,
  assess the frequency of a voltage-controller oscillator that is driven by an unregulated voltage of a power converter of the implantable energy storage assembly,
  assess impedance of at least one of at least one external antenna or at least one implantable antenna,
  assess impedance by performing a function selected from the group consisting of: performing a frequency sweep; performing an impulse response; comparing voltage and current of a waveform; and combinations thereof, or
  adjust a matching network based on the assessed impedance of the at least one external antenna or the at least one implantable antenna.

In some embodiments, the at least one implantable functional element comprises at least one electrode. In some instances, the at least one electrode comprises one or more electrodes selected from the group consisting of: microelectrode; cuff electrode; array of electrodes; linear array of electrodes; circular array of electrodes; paddle-shaped array of electrodes; bifurcated electrodes; and combinations thereof.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIG. 20A is a perspective view of a functional element comprising an array of electrodes, consistent with the present inventive concepts.

FIG. 20B is a side view of a functional element comprising a coil, consistent with the present inventive concepts.

FIG. 20C is side view of a functional element comprising a solenoid coil, consistent with the present inventive concepts.

FIG. 20D is a side view of a functional element comprising a toroid coil, consistent with the present inventive concepts.

FIG. 20E is a side view of a functional element comprising a broken toroid coil, consistent with the present inventive concepts.

FIG. 21 is a schematic view of an apparatus comprising an external device, an implantable device and a tool for implanting the implantable device, consistent with the present inventive concepts.

DETAILED DESCRIPTION OF THE DRAWINGS

Figure 1:
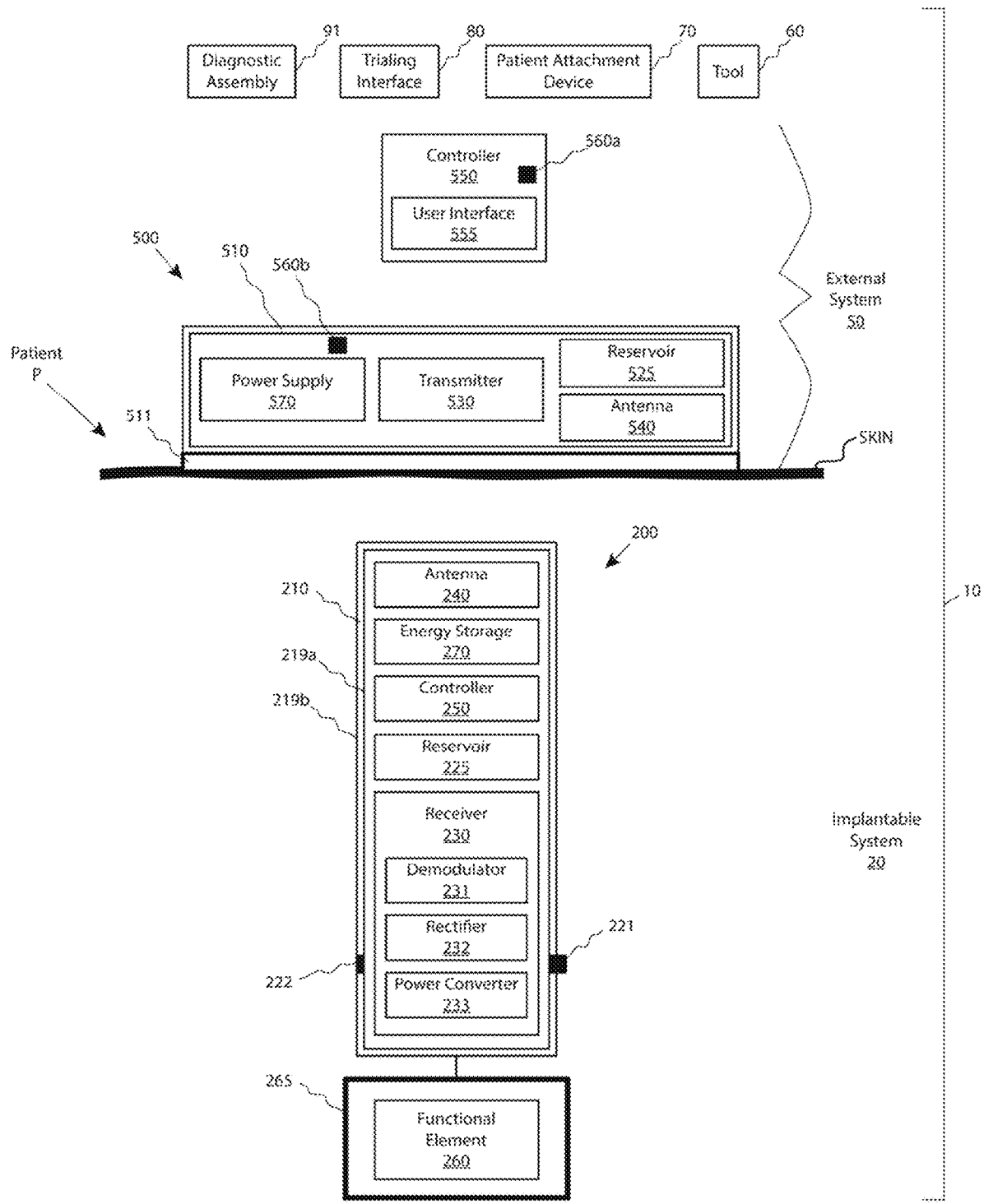
FIG. 1 is a schematic anatomical view of a medical apparatus comprising an external system and an implantable system, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.). A first component (e.g. a device, assembly, housing or other component) can be "attached", "connected" or "coupled" to another component via a connecting filament (as defined below). In some embodiments, an assembly comprising multiple components connected by one or more connecting filaments is created during a manufacturing process (e.g. pre-connected at the time of an implantation procedure of the system of the present inventive concepts). Alternatively or additionally, a connecting filament can comprise one or more connectors (e.g. a connectorized filament comprising a connector on one or both ends), and a similar assembly can be created by a user (e.g. a clinician) operably attaching the one or more connectors of the connecting filament to one or more mating connectors of one or more components of the assembly.

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

The term "transmission signal" where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include a signal transmitted using body conduction. Alternatively or additionally, a transmission signal can comprise reflected energy, such as energy reflected from any power and/or data signal.

The term "data signal" where used herein is to be taken to include a transmission signal including at least data. For example, a data signal can comprise a transmission signal including data and sent from a component external to the patient and one or more components implanted in the patient. Alternatively, a data signal can comprise a transmission signal including data sent from an implanted component to one or more components external to the patient. A data signal can comprise a radiofrequency signal including data (e.g. a radiofrequency signal including both power and data) and/or a data signal sent using body conduction.

The term "implantable" where used herein is to be taken to define a component which is constructed and arranged to be fully or partially implanted in a patient's body and/or a component that has been fully or partially implanted in a patient. The term "external" where used herein is to be taken to define a component which is constructed and arranged to be positioned outside of the patient's body.

The terms "connection", "connected", "connecting" and the like, where used herein, are to be taken to include any type of connection between two or more components. The connection can include an operable connection which allows multiple connected components to operate together such as to transfer information, power and/or material (e.g. an agent to be delivered) between the components. An operable connection can include a physical connection, such as a physical connection including one or more wires, optical fibers, wave guides, tubes such as fluid transport tubes and/or linkages such as translatable rods or other mechanical linkages. Alternatively or additionally, an operable connection can include a non-physical or "wireless" connection, such as a wireless connection in which information and/or power is transmitted between components using electromagnetic energy. A connection can include a connection selected from the group consisting of: a wired connection; a wireless connection; an electrical connection; a mechanical connection; an optical connection; a sound propagating connection; a fluid connection; and combinations of one or more of these.

The term "connecting filament" where used herein is to be taken to define a filament connecting a first component to a second component. The connecting filament can include a connector on one or both ends, such as to allow a user to operably attach at least one end of the filament to a component. A connecting filament can comprise one or more elements selected from the group consisting of: wires; optical fibers; fluid transport tubes; mechanical linkages; wave guides; flexible circuits; and combinations of one or more of these. A connecting filament can comprise rigid filament, a flexible filament or it can comprise one or more flexible portions and one or more rigid portions.

The term "connectorized" where used herein is to be taken to refer to a filament, housing or other component that includes one or more connectors (e.g. clinician or other user-attachable connectors) for operably connecting that component to a mating connector (e.g. of the same or different component).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts include a medical apparatus and clinical methods for treating a patient, and/or recording patient information. The patient can comprise a human or other mammalian patient. The medical apparatus can comprise a stimulation apparatus. The medical apparatus comprises an implantable system and an external system. The implantable system can comprise one or more similar and/or dissimilar implantable devices. Each implantable device can comprise one or more implantable antennas configured to receive power and/or data. Each implantable device can comprise an implantable receiver configured to receive the power and/or data from the one or more implantable antennas. Each implantable device can comprise one or more implantable functional elements. An implantable functional element can be configured to interface with the patient (e.g. interface with tissue or the patient or any patient location). Alternatively or additionally, an implantable functional element can interface with a portion of an implantable device. In some embodiments, the one or more implantable functional elements can comprise one or more transducers, electrodes, and/or other elements configured to deliver energy to tissue. Alternatively or additionally, the one or more implantable functional elements can comprise one or more sensors, such as a sensor configured to record a physiologic parameter of the patient. In some embodiments, one or more implantable functional elements are configured to record device information and/or patient information (e.g. patient physiologic or patient environment information).

Each implantable device can comprise an implantable controller configured to control (e.g. modulate power to, send a signal to and/or receive a signal from) the one or more implantable functional elements. In some embodiments, an implantable controller of a first implantable device is configured to control one or more other implantable devices. Each implantable device can comprise an implantable energy storage assembly configured to provide power to the implantable controller, the implantable receiver and/or the one or more implantable functional elements. In some embodiments, an implantable energy storage assembly is further configured to provide power to an implantable antenna (e.g. when the implantable device is further configured to transmit data to one or more external devices). Each implantable device can comprise an implantable housing surrounding at least the implantable controller and the implantable receiver. In some embodiments, one or more implantable antennas are positioned within the implantable housing. Alternatively or additionally, one or more implantable antennas and/or implantable functional elements can be tethered (e.g. electrically tethered) to the implantable housing. In some embodiments, one or more implantable functional elements are positioned on an implantable lead, such as a flexible lead mechanically fixed or attachable to the implantable housing and operably connected (e.g. electrically, fluidly, optically and/or mechanically) to one or more components internal to the implantable housing. The implantable lead can be inserted (e.g. tunneled) through tissue of the patient, such that its one or more functional elements are positioned proximate tissue to be treated and/or positioned at an area in which data is to be recorded.

The external system of the medical apparatus of the present inventive concepts can comprise one or more similar and/or dissimilar external devices. Each external device can comprise one or more external antennas configured to transmit power and/or data to one or more implanted components of the implantable system. Each external device can comprise an external transmitter configured to drive the one or more external antennas. Each external device can comprise an external power supply configured to provide power to at least the external transmitter. Each external device can comprise an external controller configured to control the external transmitter. Each external device can comprise an external housing surround at least the external transmitter. In some embodiments, the external housing surrounds the one or more external antennas, the external power supply and/or the external controller.

The external controller can comprise a discrete controller separate from the one or more external devices, and/or a controller integrated into one or more external devices. The external controller can comprise a user interface, such as a user interface configured to set and/or modify one or more treatment and/or data recording settings of the medical apparatus of the present inventive concepts. In some embodiments, the external controller can be configured to collect and/or diagnose recorded patient information, such as to provide the information and/or diagnosis to a clinician of the patient, to a patient family member and/or to the patient themselves. The collected information and/or diagnosis can be used to adjust treatment or other operating parameters of the medical apparatus.

In some embodiments, a medical apparatus comprises a stimulation apparatus for activating, blocking, affecting or otherwise stimulating (hereinafter "stimulate" or "stimulating") tissue of a patient, such as nerve tissue or nerve root tissue (hereinafter "nerve", "nerves", "nerve tissue" or "nervous system tissue"). The stimulation apparatus comprises an external system configured to transmit power, and an implanted system configured to receive the power from the external system and to deliver stimulation energy to tissue. The stimulation signal (also referred to as "stimulation energy") delivered by the implanted system can be independent of the power received from the external system, such as to be independent of one or more of: the position of one or more components of the external system; the changing position of one or more components of the external system; the frequency of the power received from the external system; the amplitude of the power received from the external system; changes in amplitude of the power received from the external system; duty cycle of the power received from the external system; envelope of the power received from the external system; and combinations of one or more of these.

Referring now to FIG. 1, a schematic anatomical view of a medical apparatus for treating and/or diagnosing a patient is illustrated, consistent with the present inventive concepts. Apparatus 10 comprises implantable system 20 and external system 50. Implantable system 20 comprises implantable device 200 shown implanted beneath the skin of patient P. In some embodiments, implantable system 20 comprises multiple implantable devices 200 (singly or collectively implantable device 200), such as is described herebelow in reference to FIG. 2. External system 50 comprises external device 500 which includes housing 510. In some embodiments, external system 50 comprises multiple external devices 500 (singly or collectively external device 500), also as is described herebelow in reference to FIG. 2. External system 50 can further comprise controller 550, which can comprise a user interface, such as user interface 555. Controller 550 is configured to control one or more external devices 500.

Apparatus 10 can comprise a patient treatment apparatus, such as a stimulation apparatus configured to stimulate tissue (e.g. stimulate nerve tissue such as tissue of the central nervous system or tissue of the peripheral nervous system, such as to neuromodulate nerve tissue), such as by having one or more implantable devices 200 deliver and/or provide energy (hereinafter "deliver energy") and/or deliver an agent (e.g. a pharmaceutical compound or other agent) to one or more tissue locations, while receiving power and/or data from one or more external devices 500. Alternatively or additionally, apparatus 10 can comprise a patient diagnostic apparatus, such as by having one or more implantable devices 200 record a patient parameter (e.g. a patient physiologic parameter) from one or more tissue locations, while receiving power and/or data from one or more external devices 500. In some embodiments, during its use, one or more implantable devices 200 at least receives power from one or more external devices 500. Alternatively or additionally, apparatus 10 can comprise a patient information recording apparatus, such as by having one or more implantable devices 200 and/or one or more external devices 500 record patient information (e.g. patient physiologic information and/or patient environment information). In some embodiments, one or more implantable devices 200 and/or one or more external devices 500 further collect information (e.g. status information or configuration settings) of one or more of the components of apparatus 10.

In some embodiments, apparatus 10 is configured to deliver stimulation energy to tissue (e.g. nerve tissue). The delivered energy can comprise energy selected from the group consisting of: electrical energy; magnetic energy; electromagnetic energy; light energy such as infrared light energy; visible light energy and/or ultraviolet light energy; mechanical energy; thermal energy such as heat energy and/or cryogenic energy; sound energy such as ultrasonic sound energy (e.g. high intensity focused ultrasound and/or low intensity focused ultrasound) and/or subsonic sound energy; chemical energy; and combinations of one or more of these. In some embodiments, apparatus 10 is configured to deliver to tissue one or more of: electrical energy such as by providing a controlled (e.g. constant or otherwise controlled) electrical current and/or voltage to tissue; magnetic energy (e.g. magnetic field energy) such as by applying controlled current or voltage to a coil or other magnetic field generating element positioned proximate tissue; and/or electromagnetic energy such as by providing both current to tissue and a magnetic field to tissue. The coil or other magnetic field generating element can surround (e.g. at least partially surround) the target nerve and/or it can be incorporated as part of an anchoring system to the target tissue. Alternatively or additionally, the magnetic energy can be applied externally and focused to specific target tissue via an implant comprising a coil and/or ferromagnetic materials. In some embodiments, the magnetic energy is configured to induce the application of mechanical energy.

In some embodiments, apparatus 10 is configured as a stimulation apparatus in which external system 50 transmits a power signal to implantable system 20, and implantable system 20 delivers stimulation energy to tissue with a stimulation signal, with the power signal and the stimulation signal having one or more different characteristics. The power signal can further be modulated with data (e.g. configuration or other data to be sent to one or more implantable devices 200). In these embodiments, the characteristics of the stimulation signal (delivered e.g. amplitude, frequency, duty cycle and/or pulse width), can be independent (e.g. partially or completely independent) of the characteristics of the power signal (e.g. amplitude, frequency, phase, envelope, duty cycle and/or modulation). For example, the frequency and modulation of the power signal can change without affecting the stimulation signal, or the stimulation signal can be changed (e.g. via controller 550), without requiring the power signal to change. In some embodiments, implantable system 20 can be configured to rectify the power signal, and produce a stimulation waveform with entirely different characteristics (e.g. amplitude, frequency and/or duty cycle) from the rectified power signal. Implantable system 20 can comprise an oscillator and/or controller configured to produce the stimulation signal. In some embodiments, implantable system 20 can be configured to perform frequency multiplication, in which multiple signals are multiplexed, mixed, added, and/or combined in other ways to produce a broadband stimulation signal.

In some embodiments, apparatus 10 is configured such that external system 50 transmits data (e.g. data and power) to implantable system 20, and implantable system 20 recovers (e.g. decodes, demodulates or otherwise recovers) the transmitted data without synchronizing to the carrier and/or data symbol rate of the transmitted signal from external system 50. In some embodiments, the transmitted signal comprises a power signal, and a clock and/or data is recovered without synchronizing to the power signal. In some embodiments, the transmitted signal comprises a clock and/or data signal, and a clock and/or data is recovered without synchronizing to the transmitted clock and/or data signal. In some embodiments, the recovered signal comprises a clock and/or data and a clock and/or data is recovered from the transmission signal without synchronizing to the recovered clock and/or data. Avoiding synchronization reduces power consumption of each implantable device 200, such as by obviating the need for (and avoiding the power consumed by) a frequency locked loop (FLL), phase locked loop (PLL); high frequency clock; and/or crystal oscillator needed to perform the synchronization. Avoiding these components can also be correlated to reduced package size of each implantable device 200 (e.g. avoidance of a relatively large sized crystal oscillator). Asynchronous data transfer between external system 50 and implantable system 20 is also advantageous as it relates to: increased communication data rate; power transfer efficiency; operation with more than one implantable device 200; and combinations of one or more of these. In some embodiments, one or more components of apparatus 10 are of similar construction and arrangement as similar components described in U.S. patent application Ser. No. 13/591,188, titled "Method of Making and Using an Apparatus for a Locomotive Micro-Implant using Active Electromagnetic Propulsion", filed Aug. 21, 2012, the content of which is incorporated herein by reference in its entirety. In some embodiments, external system 50 and implantable system 20 provide asynchronous data transfer or are otherwise configured as described in U.S. patent application Ser. No. 13/734,772, titled "Method and Apparatus for Efficient Communication with Implantable Devices", filed Jan. 4, 2013, the content of which is incorporated herein by reference in its entirety.

Apparatus 10 can be configured to treat a patient disease or disorder and/or it can be configured to record patient information. Apparatus 10 can be configured to treat pain, such as back pain. In some embodiments, apparatus 10 is configured to treat pain type from the group consisting of: back pain; joint pain; neuropathic pain; tennis elbow; muscle pain; shoulder pain; chronic, intractable pain of the back and/or lower limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations of one or more of these. In some embodiments, apparatus 10 is configured to treat a patient disease or disorder selected from the group consisting of: chronic pain; acute pain; migraine; cluster headaches; urge incontinence; fecal incontinence; bowel disorders; tremor; obsessive compulsive disorder; depression; epilepsy; inflammation; tinnitus; high blood pressure; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations of one or more of these.

Apparatus 10 can be configured to treat heart disease, such as heart failure of a patient. In these embodiments, stimulation of spinal cord can be performed. In canine and porcine animals with failing hearts, spinal cord stimulation has been shown to reverse left ventricular dilation and improve cardiac function, while suppressing the prevalence of cardiac arrhythmias. In canines, coronary artery occlusion has been associated with increased intracardiac nerve firing, and stimulation at spinal segment T1 has been shown to suppress that nerve firing. Stimulation via apparatus 10 at one or more spinal cord locations can be used to suppress undesired cardiac nerve firing in humans and other mammalian patients. In some embodiments, stimulation via apparatus 10 at multiple spinal cord locations is used to enhance a cardiac treatment. For example, one or more functional elements 260 of one or more implantable devices 200 can be implanted at one or more spinal locations. Power and/or data can be transmitted to the one or more implantable devices 200 via one or more external devices 500 of external system 50. One or more stimulation signals can be delivered to spinal cord tissue, such as to treat heart failure or other cardiac disease or disorder. In some embodiments, one or more functional elements 260 are configured to deliver energy (e.g. electrical energy) to tissue to treat heart failure, such as tissue selected from the group consisting of: spinal canal; nerves in the spinal canal; nerves in the epidural space; peripheral nerves; posterior spinal nerve root; dorsal root; dorsal root ganglion; pre-ganglionic tissue on posterior spinal nerve root; post-ganglionic tissue on posterior nerve root; dorsal ramus; grey ramus communicans; white ramus communicans; ventral ramus; and combinations of one or more of these. In some embodiments, one or more functional elements of apparatus 10 (e.g. one or more functional elements 260 of implantable system 20) are used to record a patient parameter, such as a patient heart or spine parameter, and the information recorded is used to adjust the delivered stimulation signals. The at least one heart parameter can comprise a parameter selected from the group consisting of: EKG; blood oxygen; blood pressure; heart rate; ejection fraction; wedge pressure; cardiac output; and combinations thereof.

Apparatus 10 can be configured to pace and/or defibrillate the heart of a patient. One or more functional elements 260 can be positioned proximate cardiac tissue and deliver a stimulation signal as described herein (e.g. based on power and/or data received by implantable system 20 from external system 50). The stimulation signal can be used to pace, defibrillate and/or otherwise stimulate the heart. Alternatively or additionally, apparatus 10 can be configured to record cardiac activity (e.g. by recording EKG, blood oxygen, blood pressure, heart rate, ejection fraction, wedge pressure, cardiac output and/or other properties or functions of the cardiovascular system), such as to determine an onset of cardiac activity dysfunction or other undesired cardiac state. In some embodiments, apparatus 10 is configured to both record cardiac information and deliver a stimulation signal to cardiac tissue. For example, apparatus 10 can be configured such that external system 50 transmits power and/or data to implantable system 20. Implantable system 20 monitors cardiac activity, and upon detection of an undesired cardiovascular state, implantable system 20 deliver a pacing and/or defibrillation signal to the tissue that is adjacent to one or more functional elements 260 configured to deliver a cardiac stimulation signal.

Apparatus 10 can be configured to perform a diagnostic procedure including measuring of one or more patient parameters (e.g. patient physiologic or other patient parameters), such as are described in detail herebelow. In some embodiments, apparatus 10 is configured to measure a physiologic parameter that can be sensed from one or more sensor-based functional elements 260 positioned in subcutaneous tissue. In these embodiments, external system 50 can comprise an external device 500 configured for placement proximate an implantable device 200 implanted in a position to record data from subcutaneous tissue (e.g. blood glucose data). The external device 500 can comprise a wrist band, a wrist watch or an arm band configuration such as when the implantable device 200 is positioned in subcutaneous tissue proximate the patient's wrist or upper arm. The external device 500 can comprise a leg or ankle band configuration, such as when one or more implantable devices 200 are positioned in subcutaneous tissue proximate the patient's ankle, knee or thigh. Power and/or data can be sent to the implantable device 200 from the external device 500, and data (e.g. blood glucose data) can be sent to external device 500 (or another component of external system 50) by implantable device 200, such as using a communication configuration described in detail herebelow. In some embodiments, external device 500 comprises a functional element 560 configured to deliver an agent (e.g. insulin or glucose delivered by a needle-based functional element 560), based on the information received from implantable device 200. Alternatively or additionally, implantable device 200 comprises a functional element 260 configured to deliver an agent (e.g. insulin or glucose delivered by a needle-based functional element 260), based on the information recorded by implantable device 200. Various closed loop sensing and agent delivery combinations and configurations should be considered within the spirit and scope of the present inventive concepts, including but not limited to: sensing a blood parameter such as white blood cell count and delivering a chemotherapeutic or other agent based on the blood parameter; sensing a hormone level and delivering a hormone or a hormone affecting agent; sensing blood pressure and delivering stimulation energy and/or a blood pressure affecting agent; sensing neural activity and delivering stimulation energy and/or a neural affecting agent or other agent based on the neural activity, such as for treating epilepsy; and combinations of one or more of these.

External system 50 can be configured to transmit power and/or data (e.g. implantable system 20 configuration data) to one or more implantable devices 200 of implantable system 20. Configuration data provided by external system 50 (e.g. via one or more antennas 540 of one or more external devices 500) can include a stimulation parameter such as an energy delivery stimulation parameter selected from the group consisting of: initiation of energy delivery; cessation of energy delivery; amount of energy to be delivered; rate of energy delivery; amplitude of energy delivery; power of energy delivery; frequency of energy delivery; waveform shape of energy delivery; duration of energy delivery; time of energy delivery initiation; and combinations of one or more of these. The configuration data can include a stimulation parameter such as an agent (e.g. a pharmaceutical agent) delivery stimulation parameter selected from the group consisting of: initiation of agent delivery; cessation of agent delivery; amount of agent to be delivered; volume of agent to be delivered; rate of agent delivery; duration of agent delivery; time of agent delivery initiation; and combinations of one or more of these. The configuration data can include a sensing parameter, such as a sensing parameter selected from the group consisting of: initiation of sensor recording; cessation of sensor recording; frequency of sensor recording; resolution of sensor recording; thresholds of sensor recording; sampling frequency of sensor recording; dynamic range of sensor recording; initiation of calibration of sensor recording; and combinations of one or more of these.

External system 50 can comprise one or more external devices 500. External system 50 can comprise one or more antennas 540, such as when a single external device 500 comprises one or more antennas 540 or when multiple external devices 500 each comprise one or more antennas 540. The one or more antennas 540 can transmit power and/or data to one or more antennas 240 of implantable system 20, such as when a single implantable device 200 comprises one or more antennas 240 or when multiple implantable devices 200 each comprise one or more antennas 240. In some embodiments, one or more antennas 540 define a radiation footprint (e.g. a footprint defining a volume, such as a volume of tissue, in which electromagnetic transmissions radiated by antennas 540 can be properly received by antennas 240), such as is described in applicant's co-pending U.S. Provisional Patent Application Ser. No. 62/112,858, titled "Medical Apparatus including an Implantable System and an External System", filed Feb. 6, 2015; the content of which is incorporated herein by reference in its entirety.

External system 50 transmits power and/or data with a transmission signal comprising at least one wavelength, $\lambda$. This wavelength will be designed based on the tissue absorption, antenna size, and the requirements of the intended use. External system 50 and/or implantable system 20 can be configured such that the distance between an external antenna 540 transmitting the power and/or data and one or more implantable antennas 240 receiving the power and/or data transmission signal is equal to between $0.001\lambda$ and $1000.0\lambda$, such as between $0.01\lambda$ and $100.0\mu$, $0.1\lambda$ and $10.0\lambda$, and $0.2\lambda$ and $2.0\lambda$. In some embodiments, one or more transmission signals are delivered at a frequency range between 0.01 GHz and 10.6 GHz, such as between 0.01 GHz and 0.1 GHz, 0.01 GHz and 3.0 GHz, 0.1 GHz and 3.0 GHz, 0.1 GHz and 10.6 GHz, 0.4 GHz and 1.5 GHz, 0.902 GHz and 0.928 GHz, 40.66 MHz and 40.70 MHz or in a frequency range proximate to 866 MHz, or approximately between 863 MHz and 870 MHz.

In addition to transmitting power and/or data to implantable system 20, external system 50 can be further configured to provide information (e.g. apparatus 10 performance information and/or patient information) to one or more other devices, such as tool 60 shown in FIG. 1 and described in detail herebelow.

One or more external devices 500 (singly or collectively external device 500) can be configured to transmit power and/or data (e.g. implantable system 20 configuration data) to one or more implantable devices 200. In some embodiments, one or more external devices 500 are configured to transmit both power and data (e.g. simultaneously and/or sequentially) to one or more implantable devices 200. In some embodiments, one or more external devices 500 are further configured to receive data from one or more implantable devices 200 (e.g. via data transmitted by one or more antennas 240 of one or more implantable devices 200). Each external device 500 can comprise housing 510, power supply 570, a transmitter 530, and/or one or more antennas 540, each described in detail herebelow. Each external device 500 can further comprise one or more functional elements 560, such as a functional element comprising a sensor, electrode, energy delivery element, a magnetic-field generating transducer, and/or any transducer, also described in detail herebelow. In some embodiments, a functional element 560 comprises one or more sensors configured to monitor performance of external device 500 (e.g. to monitor voltage of power supply 570, quality of transmission of power and/or data to implantable system 20, temperature of a portion of an external device 500, and the like).

One or more housings 510 (singly or collectively housing 510) of each external device 500 can comprise one or more rigid and/or flexible materials which surround various components of external device 500 such as antenna 540, transmitter 530 and/or power supply 570 shown in FIG. 1. In some embodiments, a housing 510 further surrounds a controller 550 and/or a power supply 570. In some embodiments, housing 510 comprises both a rigid material and a flexible material. In some embodiments, housing 510 comprises a material selected from the group consisting of: plastic; injection-molded plastic; an elastomer; metal; and combinations of one or more of these. In some embodiments, housing 510 comprises a shielded portion (e.g. shielded to prevent transmission of electromagnetic waves), and an unshielded portion, such as an unshielded portion surrounding antenna 540.

Housing 510 can comprise an adhesive element, such as an adhesive element configured to temporarily attach an external device 500 to the patient's skin. Housing 510 can be constructed and arranged to engage (e.g. fit in the pocket of) a patient attachment device, such as patient attachment device 70 described herebelow.

One or more antennas 540 (singly or collectively antenna 540) can each comprise one or more external antennas. Antenna 540 can comprise one or more polarizable antennas, such as one or more antennas with adjustable polarization. Antenna 540 can comprise an array of antennas, such as an array of antennas configured to: support beam shaping and/or focusing; allow adjustment of the amplitude and/or phase of the transmission signal; increase the radiation footprint; and combinations of one or more of these. An array of antennas 540 can be configured to be selectively activated, such as to improve coupling with one or more implanted antennas 240, such as to adjust for movement of the array of the antennas 540 relative to the implanted antennas 240. Antenna 540 can comprise an array of selectable conductors configured to adjust a radiation pattern and/or an electromagnetic field of a resultant antenna. Antenna 540 can comprise a surface and shield material positioned on the surface, such as when the shield material is positioned on the side facing away from the patient's skin. The shield material can comprise radio-absorptive shield material and/or radio-reflective shield material.

In some embodiments, a spacer 511 is positioned between antenna 540 and the patient's skin, such as a spacer comprising a thickened portion of housing 510 or a discrete spacer 511 placed on a side of housing 510 (as shown) or on a side of antenna 540. Spacer 511 can comprise one or more materials that match the impedance of antenna 540 to the impedance of the patient's tissue. Spacer 511 can comprise a thickness of between 0.1 cm to 3 cm, such as a thickness between 0.2 cm and 1.5 cm. Spacer 511 can comprise materials which isolate heat (e.g. a spacer 511 comprising thermally insulating material). Spacer 511 can comprise a soft or otherwise compressible material (e.g. foam) for patient comfort. Spacer 511 can be inflatable, such as to control the separation distance of an external antenna 540 from the patient's skin. An inflatable spacer 511 can be compartmentalized into several sections with independently controlled air pressure or volume to adjust the separation distance of an external antenna 540 and the patient's skin and/or its angle (e.g. tilt) with respect to the tissue surface.

In some embodiments, antenna 540 comprises a multi-feed point antenna, such as a multi-feed point antenna configured to: support beam shaping and/or focusing; allow adjustment of amplitude and/or phase of a transmission signal; increase the radiation footprint; or combinations of one or more of these.

In some embodiments, antenna 540 comprises one or more antennas selected from the group consisting of: patch antenna; slot antenna; array of antennas; concentric loop antenna; antenna loaded with reactive elements; dipole antenna; polarizable antenna; selectable conductors that form an antenna; and combinations of one or more of these.

Antenna 540 can comprise a major axis between 1 cm and 25 cm, such as 1 cm and 10 cm, 2 cm and 5 cm or 3 cm and 15 cm. Antenna 540 can be further configured to receive a signal, such as when an antenna 240 is configured to transmit data to an external device 500. Antenna 540 can be positioned on (e.g. fabricated onto) a substrate, such as a flexible printed circuit board or other printed circuit board (e.g. a single or multiple layer printed circuit board comprising electrical traces connecting components).

A single external antenna 540 can be configured to transmit power and/or data to multiple implantable devices 200 (e.g. each containing one or more antennas 240). In some embodiments, a single external device 500, comprising one or more antennas 540 can be configured to transmit power and/or data to multiple implantable devices 200.

One or more antennas 540 can comprise a multi-turn spiral loop antenna, such as a multi-turn spiral loop antenna configured to desensitize coupling sensitivity and/or boost input voltage. In some embodiments, one or more antennas 540 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

In some embodiments, one or more external devices 500 comprise a first antenna 540 and a second antenna 540. In these embodiments, the first antenna 540 can be similar or dissimilar to the second antenna 540. In some embodiments, a first antenna 540 and a dissimilar second antenna 540 are positioned within a single external device 500 (e.g. within housing 510). In other embodiments, a first antenna 540 is positioned in a first external device 500, and a dissimilar second antenna 540 is positioned in a second external device 500. The similarity or dissimilarity of the antennas can be configured to enhance one or more design and/or performance parameters selected from the group consisting of: implantable device 200 operation depth; polarization; power efficiency; radiation footprint $F_1$ (described herein); directional gain; beam shaping and/or focusing; sensitivity to implantable device 200 placement; patient comfort; patient usability; data transfer; and combinations of one or more of these. In some embodiments, the first antenna 540 can be optimized for a different design parameter than the second antenna 540, and each antenna 540 can be activated independently or simultaneously to realize both benefits. In some embodiments, the first antenna 540 can be similar to the second antenna 540 and placed in an array to increase the radiation footprint $F_1$ (described herein) or placed in different external locations to operate with multiple implants 200 implanted at different sites.

In some embodiments, a first external antenna 540 and a second external antenna 540 transmit power and/or data to a single implantable antenna 240. In some embodiments, a first antenna 540 and a second antenna 540 can transmit power and/or data to the one or more antennas 240 simultaneously or sequentially. In sequential power and/or data transfers, a first external device 500 comprising a first one or more antennas 540 can be replaced (e.g. swapped) with a second external device 500 comprising a second one or more antennas 540. Alternatively or additionally, sequential power and/or data transfer can be initiated by one or more of the following conditions: when the first external antenna 540 moves (e.g. moves relative to the implanted antenna 240); when a second external device 500 comprising the second antenna 540 is turned on or otherwise activated; when the second antenna 540 provides improved power and/or data transfer to the antenna 240 than is provided by the first antenna 540; and/or when power received from the first antenna 540 decreases (e.g. decreases below a threshold). In some embodiments, an antenna 240 receives power from a first antenna 540 and a second antenna 540, but only receives data from the first antenna 540.

One or more transmitters 530 (singly or collectively external transmitter 530) can each comprise one or more external transmitters that drive one or more antennas 540 (e.g. one or more antennas 540 positioned in a single external device 500 or multiple external devices 500). Transmitter 530 is operably attached to antenna 540 and is configured to provide one or more drive signals to antenna 540, such as one or more power signals and/or data signals transmitted to one or more implantable devices 200 of implantable system 20. In some embodiments, transmitter 530 comprises a transmitter that operates in a frequency range between 0.01 GHz and 10.6 GHz, such as a transmitter that operates in a frequency range between 0.01 GHz and 0.1 GHz, 0.1 GHz and 3.0 GHz, between 0.4 GHz and 1.5 GHz, between approximately 0.902 GHz and 0.928 GHz, 40.66 MHz and 40.70 MHz, or in a frequency range proximate to 866 MHz, or approximately between 863 MHz and 870 MHz. Transmitter 530 can comprise a transmitter that produces a transmission signal with a power level between 0.1 W and 4.0 W, such as a transmission signal with a power level between 0.05 W and 2.0 W, 0.1 W and 2.0 W, 0.2 W and 1.0 W, or between 0.05 W and 0.330 W.

As described hereabove, one or more external devices 500 can be configured to transmit data (e.g. configuration data) to one or more implantable devices 200, such as via a data transmission produced by transmitter 530 and sent to one or more antennas 540. In some embodiments, a transmitter 530 is configured to perform data modulation comprising amplitude shift keying with pulse-width modulation. In these embodiments, the transmitter can be configured to perform multi-level amplitude shift keying. The amplitude shift-keying can be configured to provide adjustable-depth modulation between 0-100% depth, such as between 0-75% depth, 0-50% depth, 5-30% depth, 5-75% depth, or such as between 10-50% depth. In some embodiments, one or more external devices 500 transmit data to one or more implantable devices 200 using time division multiple access (TDMA). In some embodiments, one or implantable devices 200 are independently addressable through unique identification (ID) codes. Alternatively or additionally, transmitter 530 can be configured to transmit one or more data signals with a bandwidth between 0.01 MHz and 100 MHz, 0.1 MHz and 10 MHz, 0.25 MHz and 1 MHz, 0.1 MHz and 100 MHz, or between 1 MHz and 26 MHz.

As described hereabove, one or more external devices 500 can be configured to transmit power to one or more implantable devices 200, such as via a power transmission produced by transmitter 530 and set to one or more antennas 540. One or more transmitters 530 can deliver power to one or more implantable devices 200 simultaneously or sequentially. In some embodiments, one or more transmitters 530 are configured to adjust the level of power transmitted to one or more implantable devices 200, such as by adjusting one or more duty cycling parameters. In these embodiments, power transmitted can be adjusted to: set a power transfer based on a stimulation level produced by implantable system 20; prevent oversaturation; to reduce interference with implantable system 20 data transmissions (e.g. when one or more implantable devices 200 are further configured to transmit data to external system 50); set a power transfer based on charge information and/or discharge information related to an implantable device 200 (e.g. charge rate and/or discharge rate of an implantable energy storage assembly 270); and combinations of one or more of these. In some embodiments, implantable system 20 comprises a first receiver 230 (e.g. of a first implantable device 200) and a second receiver 230 (e.g. of a second implantable device 200). One or more transmitters 530 can be configured to transmit a first power transmission to the first receiver 230, and a second power transmission to the second receiver 230. The first power transmission and the second power transmission can be adjusted or otherwise be different, such as to prevent oversaturation.

In some embodiments, transmitter 530 (and/or another component of external system 50) is further configured as a receiver, such as to receive data from implantable system 20. For example, a transmitter 530 can be configured to receive data via one or more antennas 240 of one or more implantable devices 200. Data received can include patient information (e.g. patient physiologic information, patient environment information or other patient information) and/or information related to an implantable system 20 parameter (e.g. an implantable device 200 configuration parameter as described herein).

In some embodiments, transmitter 530 comprises a first transmitter to transmit power and/or data to one or more implantable devices 200, and a second transmitter to transmit data to a different device, as described herebelow. In these embodiments, a second transmitter of transmitter 530 can be configured to transmit data to tool 60 or another device such as a controller 550, a cell phone; computer; tablet; a computer network such as the internet or a LAN; and combinations of one or more of these. In some embodiments, the second transmitter of transmitter 530 comprises a wireless transmitter; a Bluetooth transmitter; a cellular transmitter; and combinations of one or more of these. In some embodiments, a functional element 560 comprises a transmitter such as a Bluetooth transmitter.

Each power supply 570 (singly or collectively power supply 570) can be operably attached to a transmitter 530, and one or more other electrical components of each external device 500. Power supply 570 can comprise a power supplying and/or energy storage element selected from the group consisting of: battery; rechargeable battery; AC power converter; capacitor; and combinations of one or more of these. In some embodiments, power supply 570 comprises two or more batteries, such as two or more rechargeable batteries, such as to allow the first battery to be replaced (e.g. serially replaced) by the second battery. In some embodiments, power supply 570 is configured to provide a voltage of at least 3V. In some embodiments, power supply 570 is configured to provide a capacity between 1 Watt-hour and 75 Watt-hours, such as a battery or capacitor with a capacity of approximately 5 Watt-hours. In some embodiments, power supply 570 comprises an AC power source.

Each controller 550 (singly or collectively controller 550) comprises an external controller configured to control one or more components of apparatus 10. Controller 550 can comprise a user interface 555. Controller 550 can send and/or receive commands to and/or from one or more external devices 500 via a wireless or wired connection (wired connection not shown but such as one or more insulated conductive wires). In some embodiments, one or more external devices 500 comprise controller 550, such as when user interface 555 is integrated into housing 510 of external device 500. In some embodiments, apparatus 10 comprises multiple external controllers 550.

Controller 550 can be configured to adjust one or more parameters of apparatus 10, such as a stimulation parameter; a sensing parameter; a therapy parameter; a data recording parameter (e.g. a patient data recording parameter and/or an implantable device 200 data recording parameter); power transfer; data rate; activity of one or more external transmitters 530; activity of one or more external antennas 540; a functional element 260 parameter; a functional element 560 parameter; and combinations of one or more of these, such as is described hereabove. Controller 550 can be further configured to provide information, such as patient physiologic information recorded by one or more implantable devices 200, or apparatus 10 information, such as performance and/or configuration information (singly or collectively "status information") of one or more external devices 500 and/or implantable devices 200. In some embodiments, the controller 550 uses information recorded by one or more implantable devices 200, apparatus 10 information, and/or information from external devices 500 to adapt configuration parameters of one or more components of apparatus 10.

In some embodiments, controller 550 can be configured to confirm that an adequate power transmission and/or an adequate data transmission has occurred between one or more external devices 500 and one or more implantable devices 200. In these embodiments, controller 550 can comprise diagnostic assembly 91 described herebelow, or otherwise be configured to detect one or more of: power transmission to the implantable system 20 (e.g. to detect power transmission to implantable system 20 below a threshold); power transmission to the implantable system 20 trending in an undesired direction; improper and/or inadequate data transfer to the implantable system 20; and combinations of one or more of these. In some embodiments, the controller 550 monitors power transfer in real-time and adjusts power transmission accordingly to optimize the rectifier 232 efficiency of one or more implantable devices 200.

In some embodiments, controller 550 and/or another component of apparatus 10 comprises a matching network configured to match the impedance of one or more antennas 540 to one or more transmitters 530. The matching network can comprise an adjustable matching network. The matching network can comprise a directional coupler configured to measure a reflection coefficient. A transmitter 530 can comprise an output, and a controller 550 can be configured to monitor a standing wave pattern at the output of the transmitter 530.

In some embodiments, controller 550 can comprise a temperature sensor, such as a functional element 560 described herein configured as a temperature sensor and positioned proximate a portion of controller 550, housing 510 and/or one or more antennas 540 (e.g. to measure the temperature of one or more portions of an external device 500). In these embodiments, the temperature data recorded by the functional element 560 is used to adjust one or more of: matching network; stimulation level (e.g. stimulation energy delivered by one or more implantable devices 200); power transmission level (e.g. level of power transmitted between one or more external devices 500 and one or more implantable devices 200); and combinations of one or more of these. In some embodiments, the temperature sensor-based functional element 560 is a part of a safety mechanism that deactivates controller 550 and/or another component of apparatus 10 if the recorded temperature exceeds a threshold. Alternatively or additionally, a temperature sensor-based functional element 560 can be configured to measure temperature of the patient, such as when placed on housing 510, such as to adjust energy or agent delivery performed by implantable device 200 based on the recorded patient temperature.

In some embodiments, controller 550 comprises a lookup table of stimulation signal waveform patterns, such as to allow a clinician, patient and/or other operator of apparatus 10 to select a predetermined stimulation pattern. In some embodiments, controller 550 comprises a set of adjustable stimulation signal parameters configured to be varied to allow an operator to construct customized waveforms, the adjustable stimulation signal parameters selected from the group consisting of: frequency; amplitude; duty cycle; duration of pulse and/or amplitude level; duration of stimulation waveform; repetition of stimulation waveform; pulse shape; and combinations of one or more of these. In some embodiments, the controller 550 is configured to allow an operator to create a customized waveform by specifying an amplitude at one or more discrete steps of a stimulation signal.

In some embodiments, controller 550 comprises a transmitter configured to transmit data to tool 60 or another device such as a cell phone; computer; tablet; a computer network such as the internet or a LAN; and combinations of one or more of these. In these embodiments, controller 550 can comprise a wireless transmitter; a Bluetooth transmitter; a cellular transmitter; and combinations of one or more of these.

User interface 555 of each controller 550 can comprise one or more user input components and/or user output components, such as a component selected from the group consisting of: keyboard; mouse; keypad; switch; membrane switch; touchscreen; display; audio transducer such as a speaker or buzzer; vibrational transducer; light such as an LED; and combinations of one or more of these.

In some embodiments, one or more components of external system 50 and/or other external component of apparatus 10, comprises one or more functional elements 560, such as functional elements 560*a* and/or 560*b* (singly or collectively functional element 560), shown positioned in controller 550 and in external device 500, respectively. Each functional element 560 can comprise a sensor, an electrode, an energy delivery element, an agent delivery element, a magnetic field generating transducer, and/or any transducer. In some embodiments, one or more functional elements 560 comprise a transducer selected from the group consisting of: light; light emitting diode; wireless transmitter; Bluetooth device; mechanical transducer; piezoelectric transducer; pressure transducer; temperature transducer; humidity transducer; vibrational transducer; audio transducer; speaker; and combinations of one or more of these. In some embodiments, functional element 560 comprises a needle, a catheter (e.g. a distal portion of a catheter), an iontophoretic element or a porous membrane, such as an agent delivery element configured to deliver one or more agents contained (e.g. one or more agents in a reservoir, such as reservoir 525 described herebelow) within an external device 500 and delivered into the patient (e.g. into subcutaneous tissue, into muscle tissue and/or into a blood vessel such as a vein). In some embodiments, the functional element 560 can comprise an electrode for sensing electrical activity and/or delivering electrical energy. In some embodiments, apparatus 10 is configured to cause stochastic resonance, and the addition of white noise can enhance the sensitivity of nerves to be stimulated and/or boosts weak signals to be recorded.

In some embodiments, one or more functional elements 560 comprise a sensor, such as a sensor configured to record data related to a patient parameter (e.g. a patient physiologic parameter), an external system 50 parameter and/or an implantable system 20 parameter. In some embodiments, operation of one or more implantable devices 200 (e.g. stimulation energy delivered by one or more implantable devices 200) is configured to be delivered based on the data recorded by one or more sensor-based functional elements 560, such as in a closed-loop energy delivery mode.

Functional element 560 can comprise one or more sensors selected from the group consisting of: electrode; sensor configured to record electrical activity of tissue; blood glucose sensor such as an optical blood glucose sensor; pressure sensor; blood pressure sensor; heart rate sensor; inflammation sensor; neural activity sensor; muscular activity sensor; pH sensor; strain gauge; accelerometer; gyroscope; GPS; respiration sensor; respiration rate sensor; temperature sensor; magnetic sensor; optical sensor; MEMs sensor; chemical sensor; hormone sensor; impedance sensor; tissue impedance sensor; body position sensor; body motion sensor; physical activity level sensor; perspiration sensor; patient hydration sensor; breath monitoring sensor; sleep monitoring sensor; food intake monitoring sensor; urine movement sensor; bowel movement sensor; tremor sensor; pain level sensor; and combinations of one or more of these.

Functional element 560 can comprise one or more sensors configured to record data regarding a patient parameter selected from the group consisting of: blood glucose; blood pressure; EKG; heart rate; cardiac output; oxygen level; pH level; pH of blood; pH of a bodily fluid; tissue temperature; inflammation level; bacteria level; type of bacteria present; gas level; blood gas level; neural activity; neural spikes; neural spike shape; action potential; local field potential (LFP); EEG; muscular activity; electrical activity produced by skeletal muscles (e.g. as measured using electromyography, EMG); gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

Functional element 560 can comprise one or more sensors configured to record data representing a parameter of external system 50 or any component of apparatus 10. Functional element 560 can comprise one or more sensors selected from the group consisting of: an energy sensor; a voltage sensor; a current sensor; a temperature sensor (e.g. a temperature of one or more components of external device 500 or controller 550); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via controller 250) the data recorded by functional element 560 to assess one or more of: power transfer; link gain; power use; energy within power supply 570; performance of power supply 570; expected life of power supply 570; discharge rate of power supply 570; ripple or other variations of power supply 570; matching of antenna 240 and 540; communication error rate between implantable device 200 and external device 500; integrity of transmission between implantable device 200 and external device 500; and combinations of one or more of these.

In some embodiments, one or more functional elements 560 are positioned on a housing 510. A functional element 560 can comprise a body conduction sensor, such as a body conduction sensor configured to record and/or receive data via skin conduction. A functional element 560 can be configured to record data associated with stimulation delivered by one or more implantable devices 200 (e.g. record data associated with stimulation energy delivered by one or more functional elements 260), such as to provide closed loop or semi-closed loop stimulation. A functional element 560 can be configured to record temperature, such as when apparatus 10 is configured to deactivate or otherwise modify the performance of an external device 500 when the recorded temperature (e.g. patient temperature and/or external device 500 temperature) exceeds a threshold.

Implantable system 20 comprises one or more implantable devices 200, such as one or more implantable devices 200 provided sterile or configured to be sterilized for implantation into the patient. A first implantable device 200 can be of similar or dissimilar construction and arrangement to a second implantable device 200. Each implantable device 200 can be configured to treat a patient and/or record patient information, such as by delivering energy and/or an agent to tissue and/or by recording one or more physiologic parameters of tissue.

One or more portions of an implantable device 200 or other component of implantable system 20 can be configured to be visualized or contain a visualizable portion or other visualizable element, such as visualizable element 222 shown. Visualizable element 222 can comprise a material selected from the group consisting of: radiopaque material; ultrasonically reflective material; magnetic material; and combinations of one or more of these. In these embodiments, each implantable device 200 can be visualized (e.g. during and/or after implantation) via an imaging device such as a CT, X-ray, fluoroscope, ultrasound imager and/or MRI.

In some embodiments, implantable system 20 comprises multiple implantable devices 200 and implantable system 20 comprises a "multi-point ready" system, in which the operation (e.g. energy delivery, agent deliver, data recording and/or other function) of the multiple implantable devices 200 is performed simultaneously, asynchronously, and/or sequentially. The implantable devices 200 can be part of network with one or more external devices 500 in which the treating of a patient and/or the recording of patient information relies on operation of the implantable devices 200 at one or more implantation sites in a synchronized, asynchronized, and/or otherwise coordinated way. The synchronization or otherwise coordination can be controlled by a single or multiple external devices 500, which can further be synchronized to a single clock. Each implantable device 200 of implantable system 20 can receive a power signal and/or a data signal from one or more external devices 500. In some embodiments of the multi-point ready implantable system 20, each implantable device 200 comprises a unique ID, such that each implantable device 200 can be individually addressed (e.g. receive unique signals from external system 50). In some embodiments, external system 50 transmits high-bandwidth signals to implantable system 20, such that time-domain multiple access communication can be performed while operating in near real time. In some embodiments, implantable system 20 is configured as a multi-point ready system such that stimulation energy delivered by implantable system 20 is independent of power received by implantable system 20 from external system 50.

Two implantable device 200s, or two discrete components of a single implantable device 200 (e.g. two components comprising or positioned in different housings), can be attached to each other by a connecting filament as defined hereabove. In some embodiments, a connecting filament comprises a user-attachable (e.g. clinician-attachable) connector on at least one end. The filament connector is configured to operably attach to a mating connector on a component (e.g. a housing 210) of an implantable device 200, such as filament connectors 243 or 268 described herebelow in reference to FIG. 2, each of which can be attached by a user (e.g. a clinician) to a connector of housing 210 (e.g. connector 203 described herebelow in reference to FIG. 2).

Each implantable device 200 is configured to receive power and/or data (e.g. implantable system 20 configuration data) from one or more external devices 500. In some embodiments, one or more implantable devices 200 are configured to receive both power and data (e.g. simultaneously and/or sequentially) from one or more external devices 500. In some embodiments, a single external device 500 sends power and/or data to multiple implantable devices 200. Alternatively or additionally, a single implantable device 200 can receive power and/or data from multiple external devices 500. In some embodiments, a first external device 500 is positioned on or near the patient's skin at a location proximate an implanted first implantable device 200, and a second external device 500 is positioned on or near the patient's skin (hereinafter "on" the patient's skin) at a location proximate an implanted second implantable device 200. In these embodiments, the first external device 500 transmits data and/or power to at least the first implantable device 200 and the second external device 500 transmits data and/or power to at least the second implantable device 200.

Each implantable device 200 can comprise one or more functional elements 260, configured to stimulate, deliver energy to, deliver an agent to, record information from and/or otherwise interface with the patient. Alternatively or additionally, the one or more functional elements 260 can be configured to record patient information. Each implantable device 200 can comprise housing 210, receiver 230, controller 250, energy storage assembly 270 and/or one or more antennas 240, each described in detail herebelow. Each functional element 260 can comprise a sensor and/or any transducer, as described in detail herebelow. One or more functional elements 260 can be positioned on a lead 265, such as is described herebelow in reference to FIG. 2. Each implantable device 200 can further comprise anchor element 221, as described in detail herebelow. Each implantable device 200 can comprise one or more leads 265, such as two leads attached to a single housing 210, or a first lead 265 attached to a first housing 210 and a second lead 265 attached to a second housing 265.

In some embodiments, one or more implantable devices 200 are further configured to transmit data to one or more external devices 500, such as via one or more antennas 240 transmitting a signal to one or more antennas 540, or otherwise. Data transmitted by an implantable device 200 can comprise patient information (e.g. patient physiologic information recorded by one or more functional elements 260 configured as a physiologic sensor), or implantable device 200 information (e.g. data recorded by one or more functional elements 260 configured as a sensor and positioned in implantable device 200, or other implantable device 200 configuration and/or performance data).

Housing 210 of each implantable device 200 can comprise one or more rigid and/or flexible materials which surround various components, such as antenna 240, energy storage assembly 270, controller 250 and/or receiver 230 as shown in FIG. 1. In some embodiments, one or more functional elements 260 are positioned in, on and/or within housing 210. In some embodiments, housing 210 surrounds a substrate, such as a flexible and/or foldable printed circuit board, such as multiple discrete or continuous printed circuit boards positioned in different planes (e.g. a flexible or foldable printed circuit board).

Housing 210 can comprise one or more shapes or combination of shapes, such as one or more shapes selected from the group consisting of: disc; pill; cylinder; sphere; oblate spheroid; dish-like shape; bowl-like shape; cone; rectangular prism; trapezoidal prism; a portion of a toroid; and combinations of one or more of these.

Housing 210 can comprise a major axis and a minor axis, defined hereabove. In some embodiments, housing 210 comprises a major axis less than or equal to 50 mm, such as a major axis less than or equal to 25 mm, 20 mm, 15 mm, 12 mm or 10 mm. In some embodiments, housing 210 comprises a minor axis less than or equal to 20 mm, such as a minor axis less than or equal to 10 mm, 8 mm, 6 mm, or less than or equal to 5 mm. Housing 210 can comprise a wall thickness between 0.2 mm and 2.0 mm, such as a wall thickness between 0.2 mm and 0.5 mm, 0.2 mm and 1.0 mm, such as a wall thickness of approximately 1.3 mm or 0.3 mm. Housing 210 can comprise a displacement volume less than or equal to 2000 mm$^3$, such as less than or equal to 1000 mm$^3$, 600 mm$^3$, or 500 mm$^3$.

Housing 210 can comprise one or more portions that are transmissive to radiofrequency (RF) signals. In some embodiments, housing 210 comprises glass. In some embodiments, housing 210 comprises a material selected from the group consisting of: glass; ceramic; stainless steel; titanium; polyurethane; an organic compound; liquid crystal polymer (LCP); gold; platinum; tungsten; epoxy; a thermoplastic; a thermoset plastic; and combinations of one or more of these. In some embodiments, one or more portions of housing 210 comprises one or more coatings, such as one or more coatings configured to cause or prevent a physiologic reaction and/or a coating configured to block (e.g. shield) an electromagnetic transmission.

Housing 210 can comprise one or more passageways or other feedthroughs, such as for the passage of a lead, wire, optical fiber, fluid delivery tube, mechanical linkage and/or other conduit through a wall of housing 210, such as is described in applicant's co-pending U.S. Provisional Patent Application Ser. No. 62/112,858, titled "Medical Apparatus including an Implantable System and an External System", filed Feb. 6, 2015; the content of which is incorporated herein by reference in its entirety.

In some embodiments, one or more inner or outer surfaces (or portions of surfaces) of housing 210 includes an insulating and/or shielding layer (e.g. a conductive electromagnetic shielding layer), such as inner coating 219a and/or outer coating 219b shown (singly or collectively coating 219). Coating 219 can comprise an electrically insulating and/or a thermally insulating layer or other coating. In some embodiments, one or more portions of housing 210 comprise an electrically shielding coating 219, while other portions are transmissive to electromagnetic signals such as radiofrequency signals.

Figure 14A:
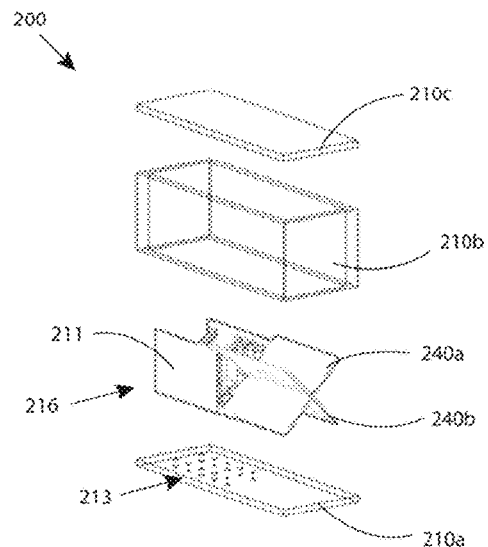
FIGS. 14A and 14B are an exploded view and an assembled view of an implantable device comprising an implantable housing surrounding multiple antennas and various electrical components, consistent with the present inventive concepts.
Figure 14B:
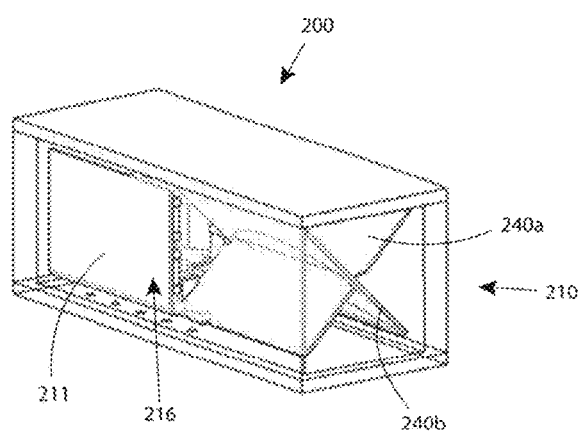
Figure 14C:
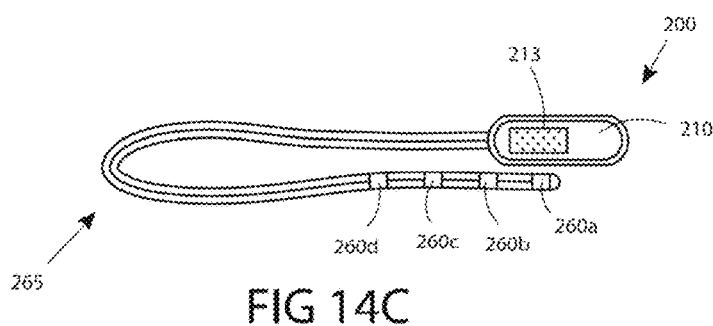
FIG. 14C is a perspective view of the implantable device 200 of FIGS. 14A and 14B, further comprising a lead 265, consistent with the present inventive concepts.

In some embodiments, housing 210 comprises an array of feedthroughs, such as feedthroughs 213 described herebelow in reference to FIGS. 14A-C. In some embodiments, housing 210 is surrounded by a covering, such as covering 218 described herebelow in reference to FIG. 15. The covering can comprise a flexible and/or non-conductive covering, such as a covering made of an elastomer.

In some embodiments, one or more implantable devices 200 comprises one or more anchor elements configured to secure one or more portions of implantable device 200 to tissue, such as anchor element 221 shown positioned on housing 210. Anchor element 221 can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these.

One or more antennas 240 (singly or collectively antenna 240) can be configured to receive power and/or data, and receiver 230 can receive the power and/or data from the one or more antennas 240. Each antenna 240 can comprise one or more implantable antennas, such as one or more antennas positioned within housing 210, and/or one or more antennas electrically attached to a connecting filament (e.g. connecting filament 242 described herebelow in reference to FIG. 2). In some embodiments, one or more implantable devices 200 comprise at least two antennas 240, or at least three antennas 240. Antenna 240 can be configured to receive power and/or data from one or more external devices 500, such that an attached receiver 230 receives the power and/or data. In some embodiments, implantable system 20 comprises at least two implantable devices 200, each of which comprise one or more (e.g. two or three) antennas 240 which are positioned within a housing 210 and/or electrically tethered to a housing 210. In some embodiments, an implantable device 200 comprises a first antenna 240 positioned in a first plane and a second antenna 240 positioned in a second plane. The first plane and second plane can be relatively orthogonal planes, or planes oriented between 30° and 90° relative to each other, such as between 40° and 90°, approximately 30°, approximately 45° and/or approximately 60° relative to each other. In some embodiments, an implantable device 200 comprises a first antenna 240 positioned in a first plane, a second antenna 240 positioned in a second plane, and a third antenna 240 positioned in a third plane.

In some embodiments, implantable device 200 comprises one or more antennas 240 positioned on a substrate, such as a printed circuit board (PCB), a flexible printed circuit board and/or a foldable substrate (e.g. a substrate comprising rigid portions and hinged portions). In some embodiments, the substrate can be folded or otherwise pivoted to position the various antennas 240 on differently oriented planes, such as multiple planes oriented between 5° and 90° relative to each other, such as two antennas 240 positioned on two planes oriented between 30° and 90° or between 40° and 90° relative to each other, or three antennas 240 positioned on three planes oriented between 5° and 60° relative to each other. Two or more antennas 240 can be positioned on two or more different planes that are approximately 45° relative to each other, or approximately 60° or approximately 90° relative to each other.

Implantable device 200 can comprise three antennas 240. In some embodiments, a first antenna 240 can comprise an electrical dipole antenna, and the second and third antennas 240 can be positioned in different planes than the first antenna 240. In some embodiments, the three antennas 240 each comprise a loop antenna, such as when each loop antenna is positioned on a different plane. In some embodiments, a first antenna 240 comprises an electrical dipole antenna, and a second antenna 240 and a third antenna 240 each comprise a loop antenna. In these embodiments, the second antenna 240 and the third antenna 240 can be positioned relatively orthogonal to each other (e.g. positioned on two relatively orthogonal planes). In some embodiments, a first antenna (e.g. an electrical dipole antenna) is positioned outside of housing 210, while a second antenna (e.g. a loop antenna) and a third antenna (e.g. a loop antenna) are each positioned on, in and/or within housing 210. In some embodiments, implantable device 200 can comprise one or more antennas 240 in which any combination of antenna types (as described herein) are used in combination.

One or more antennas 240 can comprise an antenna selected from the group consisting of: loop antenna; multiple-turn loop antenna; planar loop antenna; coil antenna; dipole antenna; electric dipole antenna; magnetic dipole antenna; patch antenna; loaded dipole antenna; concentric loop antenna; loop antenna with ferrite core; and combinations of one or more of these. One or more antennas 240 can comprise a loop antenna, such as an elongated loop antenna or a multiple-turn loop antenna.

One or more antennas 240 can comprise a multi-turn spiral loop antenna, such as a multi-turn spiral loop antenna configured to desensitize coupling sensitivity and/or boost input voltage. In some embodiments, one or more antennas 240 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

One or more antennas 240 can comprise a minor axis and a major axis. In some embodiments, one or more antennas 240 comprise a minor axis between 1 mm and 15 mm, such as between 1 mm and 8 mm, 2 mm and 5 mm or between 2 mm and 10 mm. In some embodiments, one or more antennas 240 comprise a major axis between 1 mm and 25 mm, such as between 3 mm and 15 mm or between 4 mm and 8 mm. In some embodiments, one or more antennas 240 comprise a major axis above 3 mm, such as between 1 mm and 40 mm, such as 3 mm and 15 mm, such as when the antenna 240 is positioned outside of housing 210.

One or more antennas 240 can comprise a foldable and/or unfoldable antenna, such as is described in applicant's co-pending International PCT Application PCT/US2014/043023, titled "Method and Apparatus for Minimally Invasive Implantable Modulators", filed Jun. 18, 2014, the content of which is incorporated herein by reference in its entirety.

One or more antennas 240 can be positioned inside of housing 210. Alternatively or additionally, one or antennas 240 can be positioned outside of housing 210.

Implantable system 20, one or more implantable devices 200 and/or one or more antennas 240 can be configured to be positioned at a desired depth beneath the patient's skin, such as at a depth between 0.5 cm and 7.0 cm, such as a depth of between 1.0 cm and 3.0 cm.

One or more energy storage assemblies 270 (singly or collectively energy storage assembly 270) can comprise one or more implantable energy storage components, such as one or more batteries (e.g. rechargeable batteries) and/or capacitors (e.g. a supercapacitor). Energy storage assembly 270 can be configured to provide power to one or more of: one or more functional elements 260; controller 250; receiver 230; and combinations of one or more of these. In some embodiments, energy storage assembly 270 further provides power to one or more antennas 240. In some embodiments, energy storage assembly 270 can include digital control for charge/discharge rates, voltage outputs, current outputs, and/or system power distribution and/or management.

Energy storage assembly 270 can comprise one or more capacitors with a single or collective capacitance between 0.01 µF and 10 F, such as a capacitance between 1 µF and 1.0 mF, or between 1 µF and 10 µF. The energy storage assembly 270 can comprise one or more capacitors with capacitance between 1 mF and 10 F, such as when energy storage assembly 270 comprises super-capacitors and/or ultra-capacitors. Such large capacitance can be used to store sufficient charge to maintain operation (e.g. maintain delivery of stimulation energy and/or delivery of an agent) without the use (e.g. sufficient proximity) of an associated external device 500. A capacitor or other energy storage element (e.g. a battery) can be chosen to provide sufficient energy to maintain operation for at least 30 seconds, at least 2 minutes, at least 5 minutes, at least 30 minutes, and up to several hours or more (e.g. during showering, swimming or other physical activity). Energy storage assembly 270 can comprise one or more capacitors with a breakdown voltage above 1.0V, such as a breakdown voltage above 1.5V, 4.0V, 10V, or 15V. In some embodiments, energy storage assembly 270 can comprise capacitors distributed outside of housing 210, such as when one or more capacitors are distributed along lead 265. Energy storage assembly 270 can comprise one or more capacitors with low self-leakage, such as to maintain stored energy for longer periods of time.

In some embodiments, energy storage assembly 270 comprises a temporary energy storage component, such as a super-capacitor, configured to store a sufficient quantity of energy to provide uninterrupted stimulation, such as during time periods in which the link gain may be of poor quality or it may be temporarily unavailable (e.g. an external device 500 not being in place such as during a shower, swimming, and the like). An energy storage assembly 270 comprising an ultra-capacitor, super-capacitor or flexible battery can be charged via the wireless power transmission of the present inventive concepts, such as to store a sufficient amount of energy for one or more functional elements 260 to delivery stimulation energy during subsequent (intended or unintended) unavailability of one or more external devices 500 (e.g. an external device 500 is intentionally removed or unintentionally falls off or otherwise loses its position sufficiently proximate one or more implantable devices 200). An energy storage assembly 270 comprising one or more high capacity energy storage components can be beneficial in applications where therapy interruption provides a significant risk or is otherwise relatively unacceptable, such as for life support therapies, cardiac resynchronization therapies, and the like. The high capacity energy storage components of energy storage assembly 270 can be positioned in an assembly positioned within housing 210, on an inner or outer surface of housing 210, within a separate housing, and/or within lead 265.

One or more controllers 250 (singly or collectively controller 250) can be configured to control one or more functional elements 260, such as a functional element 260 comprising a stimulation-based transducer (e.g. an electrode or other energy delivery element) and/or a sensor (e.g. a physiologic sensor and/or a sensor configured to monitor an implantable device 200 parameter). In some embodiments, controller 250 is configured to transmit a stimulation signal (e.g. transmit stimulation energy) to one or more functional elements 260 (e.g. one or more functional elements 260 comprising an electrode and/or other energy delivery element), independent of the power signal received by one or more antennas 240 (e.g. independent of power transmitted by external system 50), such as by using energy stored in energy storage assembly 270. In these embodiments, the power signal and/or the RF path for the power signal can be adjusted to optimize power efficiency (e.g. by tuning matching network on transmitter 530 and/or receiver 230; configuring antennas 540 and/or 240 in an array; tuning operating frequency; duty cycling the power signal; adjusting antenna 540 and/or 240 position; and the like), and a stimulation signal can be precisely delivered (e.g. by using energy stored on energy storage assembly 270 and generating stimulation signal locally on the implantable device 200) to ensure clinical efficacy. Also, if the power signal transmission (also referred to as "power link") is perturbed unexpectedly, the stimulation signal can be configured so that it is not significantly affected (e.g. unaffected). In some configurations, the stimulation signal being delivered by one or more implantable devices 200 can be insensitive to interference that may be present. In these embodiments, a power transmission signal and stimulation signal can vary in one or more of: amplitude; changes in amplitude; average amplitude; frequency; changes in frequency; average frequency; phase; changes in phase; average phase; waveform shape; pulse shape; duty cycle; polarity; and combinations of one or more of these.

Controller 250 can receive commands from receiver 230, such as one or more commands related to one or more implantable device 200 configuration parameters selected from the group consisting of: stimulation parameter; data rate of receiver; data rate of data transmitted by the first implantable device 200 at least one implantable antenna 240; functional element 260 configuration; state of controller 250; antenna 240 impedance; clock frequency; sensor configuration; electrode configuration; power management parameter; energy storage assembly parameter; agent delivery parameter; sensor configuration parameter; and combinations of one or more of these.

In some embodiments, one or more functional elements 260 comprise a stimulation element configured to deliver energy (e.g. electrical energy) to tissue, and controller 250 is configured to control the energy delivery, such as to control one or more of: a direct current (DC) parameter such as amplitude of voltage and/or current; amplitude; frequency; pulse width; inter-pulse interval (e.g. random, varied or constant); an amplitude modulation parameter; a frequency modulation parameter; anode/cathode configuration; voltage; current; pulse shape; a duty cycle parameter such as frequency, pulse width or off time; polarity; drive impedance; energy storage capacity; and combinations of one or more of these. In some embodiments, one or more functional elements 260 comprise a stimulation element configured to stimulate a target (e.g. nerve tissue such as spinal nerve tissue and/or peripheral nerve tissue). The amount of stimulation delivered to the target can be controlled by varying a parameter selected from the group consisting of: functional element 260 size and/or configuration (e.g. electrode size and/or configuration); functional element 260 shape (e.g. electrode shape, magnetic field generating transducer shape or agent delivering element shape); shape of a generated electric field; shape of a generated magnetic field; stimulation signal parameters; and combinations of one or more of these.

In some embodiments, one or more functional elements 260 comprise an element configured to deliver electrical energy to tissue (e.g. an electrode), and controller 260 is configured to control charge balance, such as to actively control charge balance. Charge balance can be essential for patient safety in electrical stimulation of nerves or other tissue. Imbalanced stimulation waveforms can cause electrode corrosion and/or dissolution which can lead to deposition of toxic materials in tissue, implant rejection, and nerve damage. The stimulation waveform can be balanced such that net outflow charge approximately equals net inflow charge. With stimulation waveform amplitudes that can vary between 0.1 mA to 15 mA (such as between 0.1 mA and 12 mA, or between 0.1 mA and 10 mA), depending on the treatment, the error in charge balance can be on the order of 0.001% to 0.01%. Controller 250 can comprise AC coupling capacitors that are configured to balance stimulation waveforms passively. The AC coupling capacitance can be fairly large (e.g. greater than 10 µF), in order to pass the stimulation waveform with minimal filtering. In some embodiments, apparatus 10 can be configured to perform active charge balancing. In some embodiments, an implantable device 200 can comprise a precise resistor in series with a stimulation electrode-based functional element 260. The precise resistor can be used to measure outflow and inflow currents, such as when controller 250 comprises an analog to digital converter (ADC). Controller 250 can integrate current over time during a first phase in which stimulation energy is delivered, and during a second phase in which a reverse current is applied (e.g. a reverse current used to balance charge). Controller 250 can be configured to balance the total charge in the two phases, to ensure that the net DC current is approximately zero. The integration can be achieved using an analog integrator and/or a digital summer of controller 250, with controller 250 keeping track of the pulse duration. Implantable device 200 can comprise a precise series resistance comprising an on-chip trimmed resistor or an off chip resistor. In some embodiments, implantable device 200 comprises a bank of trimmed resistors that are used to control the net series resistance, such as to adjust resistance based on stimulation amplitude requirements (e.g. to take advantage of the full dynamic range of an ADC of controller 250). In some embodiments, controller 250 comprises a shunt path with an RC-based low pass filter used for both outflow and inflow of current. RC elements of controller 250 can be chosen such that the shunt current is only a fraction of the stimulation current. Since the same RC elements can be used for both outflow and inflow current, the precision required for the RC components can be lower. An ADC can be used to sense the voltage on the capacitor at the end of a stimulation pulse. After the stimulation pulse, the capacitor can be discharged and the polarity of the stimulation current can be reversed and set to any amplitude, until the capacitor is charged to approximately the same voltage (according to the ADC precision) as it was charged during the stimulation pulse. The ADC resolution can be high enough to ensure the residual error is less than what would cause an undesired charge accumulation. ADC resolution requirements can be further be reduced by reducing the net capacitance in a shunt RC circuit, to cause accelerated charging of the capacitor. The capacitor can be discharged every time the voltage exceeds a certain predefined threshold, while controller 250 keeps track of the number of times the capacitor has been charged and reset. By resetting the capacitor through a low resistance path, the discharge time can be insignificant compared to the charge time, reducing the error due to discharge period. Since the net charge equivalent to full scale voltage on the ADC can be divided into multiple cycles, the required resolution of the ADC to achieve the same residual error can be divided by the number of cycles.

In some embodiments, controller 250 is configured to produce a stimulation signal comprising a waveform or a waveform pattern (hereinafter stimulation waveform), for one or more functional elements 260 configured as a stimulation element (e.g. such that one or more functional elements 260 deliver stimulation energy comprising or at least resembling that stimulation waveform). Controller 250 can produce a stimulation signal comprising a waveform selected from the group consisting of: square wave; sine wave; sawtooth; triangle wave (e.g. symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to produce a stimulation signal comprising a waveform including a combination of two or more waveforms selected from the group consisting of: square wave; sine wave; triangle wave; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to construct a custom waveform (e.g. an operator customized waveform), such as by adjusting amplitude at specified time steps.

In some embodiments, controller 250 is configured to provide a stimulation signal comprising waveforms and/or pulses repeated at a frequency (e.g. includes a frequency component) between 1.0 Hz and 50 KHz, such as between 10 Hz and 500 Hz, between 40 Hz and 160 Hz and/or between 5 KHz and 15 KHz. In some embodiments, controller 250 is configured to produce a stimulation signal comprising a frequency between 1 Hz and 1000 Hz, such as a stimulation signal with a frequency between 10 Hz and 500 Hz. In some embodiments, controller 250 is configured to produce a stimulation signal comprising a duty cycle between 0.1% and 25%, such as a duty cycle between 1% and 10%. In some embodiments, controller 250 is configured to produce a stimulation signal comprising a frequency modulated stimulation waveform, such as a stimulation waveform comprising a frequency component between 1 KHz and 20 KHz. In some embodiments, controller 250 is configured to produce a stimulation signal comprising a mix and/or modulation of low frequency and high frequency signals, which can be of any of the waveform shapes described herein. In these embodiments, the stimulation signal can comprise low frequency signals between 1 Hz and 1000 Hz, and high frequency signals between 1 KHz and 50 KHz, or between 1 KHz and 20 KHz. Alternatively or additionally, the stimulation signal can comprise a train of high frequency signals and bursts of low frequency signals, and/or a train of low frequency signals and bursts of high frequency signals. Alternatively or additionally, the stimulation signal can comprise one or more high frequency signals modulated with one or more low frequency signals, such as one or more high frequency signals frequency modulated (FM), amplitude modulated (AM), phase modulated (PM) and/or pulse width modulated (PWM) with one or more low frequency signals. The stimulation signal can cycle among different waveforms shapes at specified time intervals. The stimulation signal can comprise a pseudo random binary sequence (PRBS) non-return-to-zero or return-to-zero waveform, such as with a fixed and/or time-varying pulse duration and/or frequency of the pulses.

Controller 250 can comprise a clamping circuit configured to allow fast charging and/or discharging of the energy storage assembly 270, functional element 260 drivers (e.g. electrode drivers) of controller 250, and/or other components of implantable device 200. The clamping circuit can improve pulse shape by offering additional control and/or configuration of rise and fall times in the shape of the waveform (e.g. to create rapid rise or fall times). In some embodiments, the clamping circuit can be configured to limit the rise and/or fall time to be less than or equal to one-tenth (10%) of the pulse width of an applied stimulation pulse (e.g. less than or equal to 1 μs rise and/or fall time for a 10 μs stimulation pulse).

In some embodiments, controller 250 comprises a matching network configured to match the impedance of a first antenna 240 with the impedance of the receiver 230. In these embodiments, controller 250's matching network can be adjustable. Alternatively or additionally, controller 250 can comprise an adjustable loading impedance to stabilize the load seen at an antenna 240 under different operating conditions. In some embodiments, the adjustable loading impedance is controlled according to the charge rate of the energy storage assembly 270.

Controller 250 and/or any other component of each implantable device 200 can comprise an integrated circuit comprising one or more components selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; energy storage interface; memory register; timing circuit; and combinations of one or more of these.

One or more receivers 230 (singly or collectively receiver 230) can comprise one or more assemblies, such as demodulator 231, rectifier 232 and/or power converter 233 shown in FIG. 1. In some embodiments, receiver 230 can comprise a DC-DC converter such as a boost converter. Receiver 230 can comprise a data receiver, such as a data receiver including an envelope detector and demodulator and/or an envelope averaging circuit. In some embodiments, one more antennas 240 separately connect to one or more receivers 230. In some embodiments, one or more antennas 240 connect to a single receiver 230, such as via a series connection or a parallel connection.

One or more implantable devices 200 can be configured to transmit a data signal to external system 50. In some embodiments, receiver 230 is configured to drive one or more antennas 240 to transmit data to external system 50 (e.g. to an antenna 540 of an external device 500). Alternatively or additionally, implantable device 200 can be configured to transmit a data signal by having receiver 230 adjust a load impedance to backscatter energy, such as a backscattering of energy which can be detected by external system 50. In some embodiments, data transmission is accomplished by receiver 230 manipulating a signal at a tissue interface, such as to transmit a data signal using body conduction.

In some embodiments, receiver 230 comprises a matching network, such as a matching network configured to detune to prevent oversaturation. For example, implantable system 20 can comprise two or more implantable device 200 each of which includes a receiver 230 comprising a matching network. A first implantable device 200's receiver 230's matching network can be configured to detune based on power received by the second implantable device 200's receiver 230.

Demodulator 231 can comprise circuitry that asynchronously recovers signals modulated on the power signal provided by external system 50, and converts the modulated signals into digital signals. In some embodiments, demodulator 231 asynchronously recovers the modulated signal by comparing a dynamically generated moving average with the envelope, outputting a high voltage when the envelope is greater than the moving average and a low voltage when the envelope is less than the moving average. Data can then be extracted from this resulting digital signal from the width and/or amplitude of the pulses in the signal, according to the encoding method used by external system 50. In some embodiments, demodulator 231 recovers a digital signal that can be used as timing information for an implantable device 200, similar to an on-chip clock. The recovered clock signal can also be used to synchronize an on-chip clock generator of controller 250, such as through the use of a frequency and/or phase locked loop (FLL or PLL).

Rectifier 232 can comprise a power signal rectifier, such as to provide power to the energy storage assembly 270 and/or controller 250. In some embodiments, rectifier 232 comprises one or more self-driven synchronous rectifier (SDSR) stages connected in charge-pump configuration, to boost the voltage from input RF amplitude to the rectifier to a higher voltage. The boosted voltage can directly charge energy storage assembly 270, or be further boosted by a DC-DC converter or boost converter. In some embodiments, rectifier 232 can comprise diode-capacitor ladder stages instead of, or in addition to, SDSR stages. On-chip diodes, such as Schottky diodes, or off-chip diodes can be used in one or more rectifier 232 stages. For maximum efficiency, the rectification elements, such as diodes, can be optimized to minimize forward conduction and/or reverse conduction losses by properly sizing the components and selecting appropriate number of stages based on the input RF voltage and load current.

Power converter 233 can comprise one or more voltage conversion elements such as DC-DC converters that boost or otherwise change the voltage to a desired level. In some embodiments, voltage conversion is achieved with a buck-boost converter, a boost converter, a switched capacitor, and/or charge pumps. One or more power converters 233 can interface with energy storage assembly 270 and charge up associated energy storage components to desired voltages. In some embodiments, power converter 233 receives control signals from controller 250, such as to configure voltages, currents, charge/discharge rates, switching frequencies, and/or other operating parameters of power converter 233.

One or more implantable leads 265 (singly or collectively lead 265) can be attached to one or more housings 210, such as a lead 265 comprising one or more functional elements 260. Lead 265 can comprise one or more functional elements 260 configured as a stimulation element (e.g. an electrode configured to deliver electrical energy in monopolar or bipolar mode or an agent delivery element such as an output port fluidly connected to a reservoir within housing 210). Alternatively or additionally, lead 265 can comprise one or more functional elements 260 configured as a physiologic sensor (e.g. an electrode configured to record electrical activity of tissue or other physiologic sensor as described herebelow). Alternatively or additionally, lead 265 can comprise one or more functional elements 260 configured to transmit signals through tissue to external system 50, such as through body conduction.

In some embodiments, lead 265 comprises a removable stylet configured to aid in the implantation of lead 265, such as is described in applicant's co-pending U.S. Provisional Patent Application Ser. No. 62/112,858, titled "Medical Apparatus including an Implantable System and an External System", filed Feb. 6, 2015; the content of which is incorporated herein by reference in its entirety. In some embodiments, implantable system 20 comprises more than one lead 265, comprising one or more functional elements 260 and attached to one or more housings 210 of one or more implantable devices 200. In some embodiments, one or more leads 265 can be attached to a single housing 210.

In some embodiments, lead 265 comprises a diameter between 1 mm and 4 mm, such as a diameter between 1 mm and 2 mm. In some embodiments, lead 265 comprises a length between 3 cm and 60 cm, such as a length between 6 cm and 30 cm. One or more leads 265 can include between 2-64 functional elements 260, such as when a lead 265 comprises between 2 and 64 electrodes, such as between 4 and 32 electrodes. In some embodiments, lead 265 can comprise a paddle lead. In some embodiments, lead 265 comprise a single or multi-lumen catheter, such as when an attached implantable device 200 is configured as an agent delivery apparatus as described herein (e.g. a functional element 260 configured as a catheter comprises at least a portion of lead 265).

One or more functional elements 260 (singly or collectively functional element 260) can comprise one or more sensors, transducers and/or other functional elements. In some embodiments, functional element 260 comprise at least one sensor and/or at least one transducer (e.g. a single functional element 260 or multiple functional elements 260). In some embodiments, functional element 260 comprises a functional element configured to provide a therapy, such as one or more functional elements 260 configured to deliver an agent to tissue (e.g. a needle or catheter), to deliver energy to tissue and/or to otherwise affect tissue. In some embodiments, functional element 260 comprises one or more functional elements 260 configured to record patient information, such as when functional element 260 comprises one or more sensors configured to measure a patient physiologic parameter, as described herebelow. In some embodiments, functional element 260 comprises one or more sensors configured to record an implantable device 200 parameter, also as described herebelow.

One or more functional elements 260 can be positioned on lead 265 as shown in FIG. 1. Alternatively or additionally, one or more functional elements 260 can be positioned on housing 210.

Functional element 260 can comprise one or more functional elements positioned at one or more internal body locations. Functional element 260 can comprise one or more functional elements positioned to interface with (e.g. deliver energy to and/or record a physiologic parameter from) spinal cord tissue, spinal canal tissue, epidural space tissue, spinal root tissue (dorsal or ventral), dorsal root ganglion, nerve tissue (e.g. peripheral nerve tissue, spinal nerve tissue or cranial nerve tissue), brain tissue, ganglia (e.g. sympathetic or parasympathetic) and/or a plexus. In some embodiments, functional element 260 comprises one or more elements positioned proximate and/or within one or more tissue types and/or locations selected from the group consisting of: one or more nerves; one or more locations along, in and/or proximate to the spinal cord; peripheral nerves of the spinal cord including locations around the back; the tibial nerve (and/or sensory fibers that lead to the tibial nerve); the occipital nerve; the sphenopalatine ganglion; the sacral and/or pudendal nerve; brain tissue, such as the thalamus; baroreceptors in a blood vessel wall, such as in the carotid artery; one or more muscles; the medial nerve; the hypoglossal nerve and/or one or more muscles of the tongue; cardiac tissue; the anal sphincter; the dorsal root ganglion; motor nerves; muscle tissue; spine; vagus nerve; renal nerve; organ; heart; liver; kidney; artery; vein; bone; and combinations of one or more of these, such as to stimulate and/or record data from the tissue and/or location in which the functional element 260 is positioned proximate to and/or within.

In some embodiments, functional element 260 comprises one or more sensors configured to record data representing a physiologic parameter of the patient. Functional element 260 can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations of one or more of these.

Apparatus 10 and functional element 260 can be configured to record a patient parameter (e.g. patient physiologic and/or patient environment parameter) selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity; skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

In some embodiments, functional element 260 comprises one or more sensors configured to record data representing a parameter of implantable device 200. In these embodiments, functional element 260 can comprise one or more sensors selected from the group consisting of: an energy sensor; a voltage sensor; a current sensor; a temperature sensor (e.g. a temperature of one or more components of implantable device 200); a contamination detector (e.g. to detect undesired material that has passed through housing 210); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via implantable controller 250, external controller 550 and/or diagnostic assembly 91 described herebelow) the data recorded by functional element 260 to assess one or more of: power transfer; link gain; power use; energy within energy storage assembly 270; performance of energy storage assembly 270; expected life of energy storage assembly 270; discharge rate of energy storage assembly 270; ripple or other variations of energy storage assembly 270; matching of antenna 240 and 540; communication error rate between implantable device 200 and external device 500; integrity of transmission between implantable device 200 and external device 500; and combinations of one or more of these. A functional element 260 can be configured to record temperature, such as when apparatus 10 is configured to deactivate or otherwise modify the performance of an implantable device 500 when the recorded temperature exceeds a threshold.

In some embodiments, one or more functional elements 260 comprise a transducer configured to deliver energy to tissue, such as to treat pain and/or to otherwise stimulate or affect tissue. In some embodiments, functional element 260 comprises a stimulation element, such as one or more transducers selected from the group consisting of: an electrode; an energy delivery element such as an electrical energy delivery element, a light energy delivery element, a laser light energy delivery element, a sound energy delivery element, a subsonic sound energy delivery element and/or an ultrasonic sound delivery element; an electromagnetic field generating element; a magnetic field generating element; a mechanical transducer (e.g. delivering mechanical energy to tissue); a tissue manipulating element; a heat generating element; a cooling (e.g. cryogenic or otherwise heat extracting energy) element; an agent delivery element such as a pharmaceutical drug delivery element; and combinations of one or more of these.

In some embodiments, one or more functional elements 260 comprises a drug or other agent delivery element, such as a needle, port, iontophoretic element, catheter, or other agent delivering element that can be connected to a reservoir of agent positioned within housing 210 (e.g. reservoir 225 described herebelow). In some embodiments, one or more functional elements 260 comprise a drug eluting element configured to improve biocompatibility of implantable system 20.

In some embodiments, one or more functional elements 260 comprise one or more electrodes configured to deliver energy to tissue and/or to sense a patient parameter (e.g. electrical activity of tissue or other patient physiologic parameter). In these embodiments, one or more functional elements 260 can comprise one or more electrodes selected from the group consisting of: microelectrode; cuff electrode; array of electrodes; linear array of electrodes; circular array of electrodes; paddle-shaped array of electrodes; bifurcated electrodes; and combinations of one or more of these.

In some embodiments, apparatus 10 and functional element 260 are configured to both record one or more patient parameters, and also to perform a medical therapy (e.g. stimulation of tissue with energy and/or an agent). In these embodiments, the medical therapy can be performed in a closed-loop fashion, such as when energy and/or agent delivery is modified based on the measured one or more patient physiologic parameters.

In some embodiments, one or more functional elements 260 can comprise one or more electrodes for sensing electrical activity and/or delivering electrical energy. Apparatus 10 can be configured to cause stochastic resonance, and the addition of white noise can enhance the sensitivity of nerves to be stimulated and/or boosts weak signals to be recorded by the one or more functional elements 260.

In some embodiments, apparatus 10 and functional element 260 are configured to perform two functions: record one or more implantable device 200 parameters, and also perform a medical therapy (e.g. stimulation of tissue with energy and/or an agent). In these embodiments, the medical therapy can be performed in a closed-loop fashion, such as when energy and/or agent delivery is modified based on the measured one or more implantable device 200 parameters.

In some embodiments, one or more functional elements 260 comprise an agent delivery element, such as a fluid delivery element (e.g. a catheter, a porous membrane, an iontophoretic element or a needle) in fluid communication with a reservoir of the agent positioned within housing 210, such as reservoir 225 described herebelow.

In some embodiments, apparatus 10 comprises tool 60. Tool 60 can comprise a data logging and/or analysis tool configured to receive data from external system 50 or implantable system 20, such as data comprising: diagnostic information recorded by external system 50 and/or implantable system 20; therapeutic information recorded by external system 50 and/or implantable system 20; patient information (e.g. patient physiologic information) recorded by implantable system 20; patient environment information recorded by implantable system 20; and combinations of one or more of these. Tool 60 can be configured to receive data from wired or wireless (e.g. Bluetooth) means. Tool 60 can comprise a tool selected from the group consisting of: a data logging and/or storage tool; a data analysis tool; a network such as a LAN or the Internet; a cell phone; and combinations of one or more of these.

In some embodiments, tool 60 comprises a battery charging assembly, such as an assembly configured to recharge one or more power supplies 570 comprising a rechargeable battery or capacitor.

In some embodiments, tool 60 comprises an implantation tool, such as an introducer or other implantation tool constructed and arranged to aid in the implantation of housing 210, implantable antenna 240, lead 265 and/or one or more functional elements 260. In some embodiments, tool 60 comprises an implantation tool such as is described herebelow in reference to FIGS. 21 and 22A-D.

In some embodiments, lead 265 comprises a paddle lead or other stimulating lead and tool 60 comprises an introducer (e.g. a needle or an extended-width introducer) configured to deliver at least a distal portion of lead 265 into an epidural space of a patient. Tool 60 can comprise an introducer comprising a Tuohy needle, such as a Tuohy needle of 12 gauge or smaller. Tool 60 can comprise a handle for manipulating lead 265. Tool 60 can be configured to place lead 265 at an entry point above the lumbar spinal column (e.g. between L1 and L2 vertebrae). Tool 60 can include extension tubing used to insert lead 265. Tool 60 can further comprise a tool configured to anchor lead 265, such as when tool 60 comprises sutures, clips, other anchoring elements and/or an anchor securing tool (e.g. a needle or a stapling device), such as to secure lead 265 in subcutaneous tissue. Lead 265 and/or tool 60 can comprise extension tubing used to place lead 265, such as extension tubing that remains in place after removal of an introducer of tool 60. Tool 60 can be configured to place lead 265 against the dura of the spinal cord of the patient.

In some embodiments, tool 60 and/or lead 265 are constructed and arranged to implant lead 265 to stimulate one or more multifidus (MF) muscle fascicles, such as at least three sets of multifidus muscle fascicles. Lead 265 can be secured to a vertebra (e.g. on the transverse process, lamina or vertebral body). Lead 265 can placed via tool 60 such that one or more functional elements 260 (e.g. electrodes) are positioned within the multifidus muscle structures. One or more functional elements 260 can be positioned to deliver electrical energy and/or to otherwise stimulate tissue selected from the group consisting of: muscle motor point(s) or the deep fibers of lumbar multifidus; quadratus lumborum; the erector spinae; psoas major; transverse abdominis; connective tissue such as the annulus or facet capsule; ligaments coupling bony structures of the spine; and combinations of one or more of these. Functional elements 260 can be positioned to: depolarize, hyperpolarize and/or block innervated sections of the muscle that will then propagate an activating and/or inhibiting stimulus along the nerve fibers recruiting muscle tissue remote from the site of stimulation and/or modulate nerve activity (including inhibiting nerve conduction, improving nerve conduction and/or improving muscle activity). In some embodiments, functional elements 260 are positioned to cause transvascular stimulation (e.g. transvascular stimulation from arteries and/or veins in a leg or arm). In some embodiments, functional elements 260 are positioned to stimulate nerve tissue selected from the group consisting of: dorsal ramus nerve; medial branch of dorsal ramus nerve; nervous tissue associated with multifidus muscle; and combinations of one or more of these. In some embodiments, functional elements 260 are configured to deliver stimulation energy to contract the multifidus muscle. In some embodiments, functional elements 260 are configured to stimulate tissue by providing episodic electrical stimulation. In some embodiments, apparatus 10 comprises a tool 60 configured to diagnose a defect in spinal muscle or the motor control system. In some embodiments, apparatus 10 comprises a tool 60 configured to test function of the multifidus muscle, such as when tool comprises an MRI; ultrasound imager; electromyogram; tissue biopsy device; and/or a device configured to test displacement as a function of load for a spine.

In some embodiments, two or more external system 50 components are connected by a connecting filament, such as is described hereabove. Alternatively or additionally, two or more implantable system 20 components are connected by a conduit, such as a connecting filament as described hereabove. Alternatively or additionally, two more external system 50 components and/or two or more implantable system 20 components transmit information and/or power via a wireless transmitter (e.g. an RF transmitter), magnetic coupling, capacitive coupling and/or other wireless transmission means, Apparatus 10 can include one or more devices, such as patient attachment device 70 shown in FIG. 1, that is used to attach one or more portions of external system 50 to a location on or proximate the patient. In some embodiments, patient attachment device 70 is constructed and arranged as described in applicant's co-pending U.S. Provisional Patent Application Ser. No. 62/077,181, titled "Method and Apparatus for Implantable Neuromodulation Systems", filed Nov. 8, 2014, the content of which is incorporated herein by reference in its entirety.

Patient attachment device 70 can comprise one or more elements configured to attach one or more external devices 500 at one or more locations on or proximate the patient's skin, that are relatively close to one or more implantable devices 200 that have been implanted in the patient. Patient attachment device 70 can comprise a component selected from the group consisting of: belt; belt with pockets; belt with adhesive, adhesive; strap; strap with pockets; strap with adhesive shoulder strap; shoulder band; shirt; shirt with pockets; clothing; clothing with pockets; epidural electronics packaging; clip; bracelet; wrist band; wrist watch; anklet; ankle bracelet; knee strap; knee band; thigh strap; thigh band; necklace; hat; headband; collar; glasses; goggles; earpiece; behind-the-earpiece; and combinations of one or more of these. In some embodiments, patient attachment device 70 comprises a belt configured to surround at least one antenna 540 (e.g. at least one antenna 540 mounted to or otherwise positioned on a printed circuit board such as a flexible printed circuit board). Patient attachment device 70 can include one or more pockets, such as one or more pockets configured to collectively surround one or more of: external device 500; one or more antennas 540; power supply 570; controller 550; and combinations of one or more of these. In some embodiments, patient attachment device 70 comprises multiple pockets, such as to allow repositioning of an external antenna 540, external controller 550, external transmitter 530 and/or external power supply 570 to various different locations, such as to improve transmission of power and/or data to one or more implantable devices 200 and/or improve patient comfort. In some embodiments, one or more antennas 540, power supplies 570, and/or transmitters 530 are connected through flexible cables positioned in patient attachment device 70. In some embodiments, the flexible cables are small coax cables that can accommodate the power levels and frequencies of the carried signals. In some embodiments, the one or more antennas 540 are connected to one or more additional components of external device 500 through a single cable with a local power splitting component and/or active matching element that adjusts signal power to each of the one or more antennas 540.

Apparatus 10 can comprise a device configured to operate (e.g. temporarily operate) one or more implantable devices 200, such as trialing interface 80 shown in FIG. 1. Trialing interface 80 can be configured to deliver power to an implantable device 200, deliver data to an implantable device 200, and/or receive data from an implantable device 200. Trialing interface 80 can be configured to interface with one or more implantable devices 200 during an implantation procedure in which one or more implantable device 200 are implanted in a patient (e.g. a sterile clinical procedure). Trialing interface 80 can be configured to be sterilized one or more times. Trialing interface 80 can comprise one or more antennas, such as an antenna similar to antenna 540 of an external device 500. Trial interface 80 can comprise a transmitter, such as a transmitter similar to transmitter 530 of external device 500, and a power supply, such as a power supply similar to power supply 570 of external device 500. In some embodiments, trialing interface is of similar construction and arrangement to the trialing interface described in applicant's co-pending U.S. Provisional Patent Application Ser. No. 62/077,181, titled "Method and Apparatus for Implantable Neuromodulation Systems", filed Nov. 8, 2014, the content of which is incorporated herein by reference in its entirety. In some embodiments, trialing interface 80 includes a housing to be positioned proximate at least a portion of implantable device 200, such as a housing that surrounds an antenna and a transmitter that is configured to operatively couple to (e.g. transmit power and/or data to) one or more antennas 240 of one or more implantable devices 200.

In some embodiments, one or more implantable devices 200 of implantable system 20 can comprise an implantable transmitter configured to transmit data, such as to transmit data (e.g. stimulation information, patient physiologic information, patient environment information, implantable device 200 performance and/or configuration information, and the like) to one or more external devices 500. In these embodiments, receiver 230 can be configured as both a receiver and a transmitter. One or more implantable devices 200 can be configured to transmit data by sending a signal to (i.e. "driving") one or more antennas 240 or another antenna of implantable device 200. An implantable device 200 can be configured to transmit data using one or more of: load modulation; a signal carrier; and/or body conduction. An implantable device 200 can be configured to adjust the transmission, such as to adjust a data transmission parameter selected from the group consisting of: data rate; pulse width; duration of carrier signal; amplitude of carrier signal; frequency of carrier signal; configurable load; and combinations of one or more of these.

In some embodiments, apparatus 10 comprises a diagnostic assembly, diagnostic assembly 91 shown in FIG. 1. In some embodiments, controller 550 and/or implantable controller 250 comprise all or a portion of diagnostic assembly 91. Diagnostic assembly 91 can be configured to assess, monitor, determine and/or otherwise analyze patient information and/or implantable device 200 information, such as when one or more functional elements 260 and/or 560 are configured as a sensor configured to record patient information (e.g. patient physiologic information and/or patient environment information) and/or apparatus 10 information (e.g. implantable device 200 information) as described hereabove. Diagnostic assembly 91 can be configured to analyze communication and/or the power link between an implantable device 200 and an external device 500. In some embodiments, such a communication link analysis can be performed by measuring bit error rate (BER) of a known data stream during communication signal transmission (also referred to as "communication link") measurement phase (e.g. such as during a calibration procedure). The BER can be tracked by the implant controller 250 or external controller 550, such as to monitor and keep track of any trends in the link. This trend can be used to adjust the link and/or provide feedback to an operator of apparatus 10 (e.g. the patient), in case the link cannot be automatically adjusted to compensate for a negative trend (e.g. such that the operator can perform physical re-adjustment of the external system 50). Alternatively or additionally, a power link analysis can be performed by monitoring charge/discharge rate of the implanted energy storage assembly 270. Similar to the communication link, the power link status and/or trending can be monitored and recorded for link adjustment and/or feedback purposes. Diagnostic assembly 91 can be configured to analyze a result of stimulation energy delivered by implantable device 200, such as when a functional element 260 comprises an electrode to record electrical activity of tissue (e.g. in addition to delivering electrical energy to stimulate tissue). A functional element 260 and/or 560 can comprise a sensor configured to record neural activity and/or muscular activity, and the diagnostic assembly configured to analyze the recorded sensor data. In some embodiments, diagnostic assembly 91 can be configured analyze impedance, such as when a functional element 260 and/or 560 comprises a sensor configured to record data related to impedance, such as when implantable device 200 performs a frequency sweep, performs an impulse response and/or compares voltage and current of a stimulation waveform. In some embodiments, diagnostic assembly 91 is configured to assess the impedance of one or more implantable antennas 240 and/or one or more external antennas 540. In these embodiments, impedance can be assessed by performing a function selected from the group consisting of: performing a frequency sweep; performing an impulse response; comparing voltage and current of a waveform; and combinations of one or more of these.

In some embodiments, diagnostic assembly 91 is configured to test or otherwise assess the link between one or more implantable antennas 240 and one or more external antennas 540 (e.g. during a procedure in which one or more implantable devices 200 are implanted in a patient). In these embodiments, diagnostic assembly 91 can be configured to perform a test prior to anchoring housing 210 to tissue (e.g. prior to initial or final suturing into tissue such as the fascia layer). For example, lead 265 can be implanted at a location to stimulate target tissue (e.g. one or more nerves identified to treat pain or another patient condition). Prior to suturing housing 210 in its permanent location, diagnostic assembly 91 can be configured to confirm that one or more external antenna 540 transmission links to one or more implantable antennas 240 are above an efficiency threshold, for example such that sufficient power will be received by the one or more implantable devices 200. Additionally, the procedure can be performed to optimize or otherwise improve the position of the one or more implantable devices 200 to be implanted and subsequently secured to tissue.

In these link testing embodiments, diagnostic assembly 91 can comprise a handheld assembly (e.g. a sterile assembly comprising a wand or other handheld housing). Diagnostic assembly 91 can be configured to send a simple signal to one or more implantable devices 200 (e.g. a diagnostic assembly 91 with similar power and/or data transmission capabilities as an external device 500). Each implantable device 200 can respond (e.g. via data sent via an implantable antenna 240 or other transmitter) with information related to the quality of the transmission link (e.g. information about the power received by the one or more implantable devices 200). Diagnostic assembly 91 could provide a user interface (e.g. a speaker, a text screen and/or a video display) that provides quality or other information (go/no go information, digital or other discrete level information, and/or analog information). Diagnostic assembly 91 could be further configured to provide information confirming detection of one or more implantable devices 200, status of one or more implantable devices 200 (e.g. parameter level and/or fault detection status), and/or self-diagnostic status (i.e. diagnostic assembly 91 status).

Each implantable device 200 can be configured to specifically identify and/or specifically reply to diagnostic assembly 91 (e.g. in a different form than communications with an external device 500). Each implantable device 200 can be configured to provide information related to one or more of: the charge and/or discharge rate of energy storage assembly 270 (e.g. the charge and/or discharge rate of a capacitor or battery of energy storage assembly 270); or the frequency of a voltage-controlled oscillator that is driven by an unregulated voltage of power converter 233. Diagnostic assembly 91 can be configured to perform numerous performance tests (e.g. of one or more implantable devices 200 or implantation locations for one or more implantable devices 200), prior to completion of the implantation procedure (e.g. prior to closing one or more incisions).

In some embodiments, apparatus 10 is configured to provide a therapy by delivering stimulation energy to tissue, such as electrical energy delivered to tissue by one or more functional elements 260 comprising one or more electrodes. Alternatively or additionally, apparatus 10 can be configured as an agent-delivery apparatus (e.g. a pharmaceutical or other agent delivery apparatus). In some embodiments, apparatus 10 comprises one or more reservoirs for storing the agent, such as reservoir 525 of external device 500 and/or reservoir 225 of implantable device 200, each shown in FIG. 1. Reservoirs 525 and/or 225 can be fluidly connected to one or more functional elements 560 and/or 260, respectively (e.g. via one or more tubes). Reservoirs 525 and/or 225 can comprise one or more chambers (e.g. independent chambers configured to separately contain incompatible drugs or otherwise prevent undesired multiple drug interactions). Reservoirs 525 and/or 225 can comprise a volume (e.g. a volume to store one or more agents) between 0.1 ml and 50 ml, such as between 0.1 ml and 3.0 ml, or between 0.1 ml and 1.0 ml. Reservoirs 525 and/or 225 can comprise pressurized reservoirs or otherwise comprise a fluid pumping mechanism (e.g. a peristaltic mechanism, syringe pump or other fluid pump). Reservoirs 525 and/or 225 and can comprise refillable reservoirs (e.g. when reservoir 225 of an implantable device 200 comprises a valved opening such as a silicone septum or a mechanical valve, either accessible via a needle for refilling). The fluidly attached functional elements 560 and/or 260 can comprise a fluid delivery element selected from the group consisting of: a catheter; a porous membrane; an iontophoretic element; a needle; or combinations of one or more of these. Delivered and/or stored (e.g. in a reservoir) agents can comprise an agent selected from the group consisting of: an analgesic agent such as morphine, fentanyl, lidocaine or other agent delivered to treat pain; a chemotherapeutic agent such as a chemotherapeutic agent delivered systemically and/or to a location in or proximate an organ such as the liver or brain to treat cancer; an antibiotic configured to treat or prevent an infection; a hormone such as a hormone delivered intravenously in hormonal therapy; heart medications such as nitroglycerin, a beta blocker or a blood pressure lowing medication; a carbohydrate such as glucose or dextrose delivered to treat a low blood sugar condition; insulin such as to treat a high blood sugar condition; a diabetic medication; a neurological medication; an epilepsy medication; and combinations of one or more of these. In some embodiments, apparatus 10 comprises the one or more agents stored in reservoir 225 and/or 525. In some embodiments, apparatus 10 is constructed and arranged to deliver the agent (e.g. via a catheter-based functional element 560 and/or 260) to a patient location selected from the group consisting of: a vessel; a blood vessel; a vein; an artery; heart; brain; liver; spine; epidural space; intrathecal space; subcutaneous tissue; bone; intraperitoneal space, intraventricular space, and combinations of one or more of these.

In some embodiments, an external device 500 is attached to the patient via a patient attachment device 70 comprising a wrist band, wrist watch, leg band, ankle band or other band configured to position an external device 500 about a limb of the patient (i.e. arm or leg of the patient). In these embodiments, one or more implantable devices 200 are implanted under the skin proximate the intended (limb) location of external device 500 and patient attachment device 70. Apparatus 10 is configured such that external device 500 comprises one or more antennas 540; one or more implantable devices 200 each comprise one or more antennas 240; and each implantable device 200 one or more antennas 240 receive power and/or data from the one or more antennas 540 of the limb-attached external device 500. The limb-attached external device 500 can comprise one or more reservoirs 525 described hereabove and/or one or more functional elements 560 configured as agent delivery elements and/or sensors. The one or more implantable devices 200 can comprise one or more reservoirs 225 described hereabove and/or one or more functional elements 260 configured as agent delivery elements and/or sensors.

In some embodiments, apparatus 10 comprises an agent delivery apparatus and agent is delivered into the patient (e.g. into a blood vessel, muscle or subcutaneous tissue) by an external device 500 functional element 560 (e.g. a needle) based on signals recorded by an implantable device 200 functional element 260 (e.g. a sensor). Alternatively or additionally, agent can be delivered into the patient (e.g. into a blood vessel, muscle or subcutaneous tissue) by an implantable device 500 functional element 260 (e.g. a needle, catheter, porous membrane or iontophoretic delivery element). The amount of agent delivered by functional element 260 can be based on signals recorded by an implantable device 200 functional element 260 (e.g. a sensor) and/or an external device 500 functional element 560 (e.g. a sensor). External device 500 can provide power to one or more implantable devices 200 and/or it can send data (e.g. sensor data from a functional element 560) to implantable device 500, such as to control agent delivery by implantable device 500.

Apparatus 10 can be configured to prevent an electromagnetic field (e.g. an electromagnetic field produced by one or more devices not included in apparatus 10 and/or other present in the patient environment) from adversely affecting and/or otherwise affecting the patient treatment and/or patient information recording (e.g. patient tissue stimulation and/or patient physiologic information gathering) performed by apparatus 10. Electromagnetic fields from one or more apparatus 10 devices and/or otherwise present in the patient environment are essentially potentially interference to apparatus 10. The architecture of the wireless signal transmissions of apparatus 10 can be configured to include certain unique and/or identifiable patterns in the signals transmitted by apparatus 10 to confirm (upon receipt) that the signal originated from a component of apparatus 10. Alternatively or additionally, the stimulation signal produced by an implantable device 200 can be created independent from a power signal received from an external device 500, so that any electromagnetic interference in the wireless link does not affect generation and delivery of the stimulation signal. In some embodiments, each implantable device 200 and/or external device 500 includes unique identification codes that are required to be transmitted prior to any changes in stimulation or other implantable device 200 configuration, ensuring correct operation in the presence of interference. Alternatively or additionally, the communication link can incorporate handshaking protocols, confirmation protocols, data encryption and/or scrambling, coding and other security measures to ensure that interfering signals do not adversely affect the implantable system 20 performance (e.g. stimulation). In some embodiments, external system 50 and/or implantable system 20 can incorporate electromagnetic absorptive and/or reflective materials to minimize external interference from other sources and/or minimize the probability of apparatus 10 interfering with other systems. Alternatively or additionally, apparatus 10 can incorporate error detection and protocols for entering an alarm state (e.g. and shutting down normal operation) and/or otherwise ensuring safe operation.

In some embodiments, implantable system 20 of apparatus 10 is configured to perform magnetic field modulation, such as targeted magnetic field neuromodulation (TMFN), electro-magnetic field neuromodulation, such as targeted electro-magnetic field neuromodulation (TEMFN), transcutaneous magnetic field stimulation (TMS), or any combination of these. Each implantable device 200, via one or more of its functional elements 260 (e.g. electrodes) can be configured to provide localized (e.g. targeted) magnetic and/or electrical stimulation. Combined electrical field stimulation and magnetic field stimulation can be applied by using superposition, and can reduce the overall energy requirement. In some embodiments, implantable apparatus 10 comprises one or more functional elements 260 comprising a magnetic field generating transducer (e.g. microcoils or cuff electrodes positioned to partially surround or otherwise be proximate to one or more target nerves), such as is described herebelow in reference to FIG. 20, 20A, 20B, 21C, 21D or 20E. Functional elements 260 comprising microcoils can be aligned with nerves to minimize affecting non-targeted tissue (e.g. to avoid one or more undesired effects to non-target tissue surrounding or otherwise proximate the target tissue). In some embodiments, the target tissue comprises DRG tissue, and the non-target tissue comprises ventral root tissue (e.g. when the stimulation energy is below a threshold that would result in ventral root tissue stimulation).

In some embodiments, external system 50 of apparatus 10 is configured to provide mechanical external antenna 540 alignment (e.g. mechanically adjustable external antenna 540 alignment). Link gain between one or more external antennas 540 and one or more implantable antennas 240 can degrade over time due to physical misalignment of the antennas, relative orientation change between antennas and/or relative angular misalignment between antennas. In order to compensate for misaligned antennas, electrical beam steering can be included in apparatus 10. Antennas comprising a multi-feed antenna structure and/or an array of antennas can be incorporated (e.g. into external antenna 540, implantable antenna 240 or both) for electrical beam steering. Alternatively or additionally, mechanical antenna steering can be implemented to physically realign one or more external antennas 540 with one or more implanted antennas 240 (or vice versa). A substrate of an implantable antenna 240 and/or an external antenna 540 can be flexible and/or rigid (e.g. a substrate comprising polyamide, polyimide, Rogers, FR4, or a similar material). One or more antennas 540 can be connected to electronics (e.g. a transmitter, receiver or transceiver) using a flexible waveguide or cable (e.g. 50 ohm 0.047" coaxial cable used to provide patient comfort) and/or a flexible PCB substrate transmission line. Mechanical or physical realignment of antennas 240 and/or 540 can be accomplished using one or more of: use of motorized positioners, such as a mechanism including one or more small pulleys and/or tensioners used to translate one or more antennas 240 and/or 540 about one or more axes; an actuator (e.g. a piezoelectric actuator) with directional gears configured to translate one or more antennas 240 and/or 540 about one or more axes; a micro-pump with fluid reservoir (e.g. liquid or gas reservoir) configured to hydraulically and/or pneumatically translate one or more antennas 240 and/or 540 about one or more axes, such as by creating a local pressure difference. In some embodiments, a micro-pump with fluid reservoir can be used to move one or more antennas 240 and/or 540, such as to move an external antenna 540 away from tissue to reduce specific absorption rate (SAR). In these embodiments, external antenna 540 can be positioned in mechanical contact with an expandable reservoir (e.g. a balloon) positioned between external antenna 540 and tissue. The reservoir can be inflated or deflated to control separation distance of the external antenna 540 from the patient's skin surface. In some embodiments, apparatus 10 comprises one or more algorithm positioning algorithms, beam steering functionality and/or mechanical antenna steering as described in applicant's co-pending International PCT Patent Application Serial Number PCT/US2014/043023, titled "Method and Apparatus for Minimally Invasive Implantable Modulators", filed Jun. 18, 2014, or U.S. Provisional Patent Application Ser. No. 62/112,858, titled "Medical Apparatus including an Implantable System and an External System", filed Feb. 6, 2015, the content of each of which is incorporated herein in its entirety.

In some embodiments, implantable system 20 of apparatus 10 is configured to provide paresthesia-enhanced high frequency (e.g. >1 KHz) pain management and rehabilitation therapy. Apparatus 10 can be configured to provide both low frequency (e.g. <1 KHz) stimulation and high frequency stimulation, such as when providing low frequency stimulation to elicit feedback from a patient during intraoperative or other (e.g. post-implantation) stimulation configuration. For example, trialing interface 80 can be used during an intra-operative titration of stimulation configuration using low frequency stimulation (e.g. to position and/or confirm position of one or more functional elements 260, such as to confirm sufficient proximity to target tissue to be stimulated and/or sufficient distance from non-target tissue not to be stimulated). In some embodiments, high frequency stimulation is delivered to reduce pain over extended periods of time, and low frequency stimulation is used in these intra-operative and/or post-implantation titration or other stimulation configuration procedures. Intentional elicitation of paresthesia (e.g. via low frequency stimulation and/or high frequency stimulation) is beneficial during functional element 260 (e.g. electrode) implantation because a patient can provide feedback to the implanting clinician to ensure that the functional elements 260 are positioned close to the target neuromodulation or energy delivery site. This implantation position-optimizing procedure can advantageously reduce the required stimulation energy due to functional elements 260 being closer to target tissue, since a minimum threshold for efficacious stimulation amplitude is proportional to the proximity of functional elements 260 to target tissue (e.g. target nerves). The patient can inform the clinician of the sensation of paresthesia coverage, and the clinician can adjust functional element 260 position to optimize functional element 260 location for efficacious treatment while minimizing unintentional stimulation of non-target tissue (e.g. motor nerves or nerves which are not affected by pain). These paresthesia-inducing techniques (e.g. using low frequency stimulation and/or high frequency stimulation) can be used during or after implantation of one or more implantable systems 200.

In some embodiments, apparatus 10 is configured to deliver low frequency stimulation energy (e.g. electrical energy) to stimulate motor nerves, such as to improve tone and structural support (e.g. physical therapy). In these embodiments, apparatus 10 can be further configured to provide high frequency stimulation, such as to treat pain (e.g. suppress and/or control pain). The combined effect can be used not only for pain management but also muscle strengthening and gradual healing of supportive structures.

As described above, apparatus 10 can be configured for treating numerous disease and disorders, such as neuropathy (e.g. peripheral neuropathy) and/or neuralgia. Apparatus 10 can be configured to treat neuropathy, neuralgia and/or other nerve pain that is related to: surgery; trauma; infection (e.g. a herpetic infection); and/or diabetes (e.g. diabetic neuropathy). One or more functional elements 260 can be configured to deliver stimulation energy (e.g. electrical energy, magnetic energy, light energy and/or sound energy) to nerve tissue such as tissue of the central nervous system and/or peripheral nervous system. One or more leads 265 (each comprising one or more functional elements 260) can be implanted in and/or proximate the spinal cord, the groin and/or a joint such as the hip. For example, apparatus 10 can be configured to treat one or more of: post-surgical neuralgia (e.g. following hernia repair such as a hernia repair including an implanted mesh); headache (e.g. due to occipital neuralgia); post-herpetic neuralgia; chronic pelvic and/or hip pain; knee pain; and combinations of one or more of these.

Knee pain, such as from joint degeneration or join replacement surgery, can be treated via neuromodulation of the nerves innervating the knee and/or via stimulation of the tissue surrounding the knee (peripheral "field" stimulation). In some embodiments, one or more leads 265, such as up to eight leads 265, are placed near and around the knee, such as in proximity to the nerves innervating the knee or within the tissue surrounding the knee. Leads may simply be placed subcutaneously for field stimulation or may be placed directly adjacent to specific nerve targets. In some instances, four leads are placed near and around the knee: medial, lateral, superior and inferior to the knee. It may be appreciated that in some embodiments more or fewer leads may be used. Example nerve targets are as follows:

Medial knee—medial femoral cutaneous or infrapatellar cutaneous branches of saphenous nerve;

Lateral knee—constant articular branches of common peroneal, lateral retinacular nerve;

Anterior knee—lateral, medial, or anterior cutaneous femoral nerve, infrapatellar branch of saphenous nerve, medial or lateral retinacular nerve or articular branches of peroneal nerve;

Posterior knee—obturator, posterior tibial or sciatic nerves.

In addition, the following nerves may be stimulated to treat knee pain:

Arising from the tibial nerve are the superior, middle and inferior genicular nerves.

Arising from the common peroneal are the superior lateral, inferior lateral, and recurrent genicular nerves.

Arising from the obturator nerve is the genicular branch of obturator.

Arising from the femoral nerve is the saphenous.

It may be appreciated that each of these targets may be accessed transvascularly.

To treat pain related to hernia or hernia repair, one or more functional elements 260 (e.g. on a lead 265 and/or on a housing 210) can be positioned to stimulate tissue of the peripheral nervous system and/or the central nervous system. In some embodiments, one or more functional elements 260 are positioned to stimulate the cutaneous branch of the ilioinguinal, inguinal and/or genital branch of the genitofemoral nerves. In some embodiments, one or more functional elements 260 are positioned to stimulate corresponding branches of spinal nerves correlating to one or more dermatomes related to pain associated with at least one of hernia or hernia repair.

Hernia or hernia repair can lead to: inguinal pain; ilioinguinal neuralgia; post-traumatic neuropathic pain; ilioinguinal nerve entrapment; neuropathic pain of ilioinguinal origin; post-surgical inguinal pain; genitofemoral pain; genitofemoral neuralgia; genitofemoral nerve entrapment; neuropathic pain of genitofemoral origin; post-surgical genitofemoral pain; iliohypogastric pain; iliohypogastric neuralgia; iliohypogastric nerve entrapment; neuropathic pain of iliohypogastric origin; post-surgical iliohypogastric pain; testicular pain; scrotal pain; penis pain; groin pain; thigh pain; anal pain; rectal pain; perineal pain; abdominal adhesions; pelvic adhesions; scar pain; diffuse polyneuropathy; and combinations of one or more of these.

The apparatus of the present inventive concepts can be configured to stimulate the ilioinguinal nerve, genitofemoral nerve and/or iliohypogastric nerves, such as to ameliorate pain following hernia repair. One or more leads 265 (e.g. one or more leads 265 comprising one or more electrode-based or otherwise stimulation-based functional elements 260) can be inserted over the inguinal region (which may include the inguinal ring) to stimulate any or all three of these nerves (e.g. in a unilateral or bilateral fashion). Both the ilioinguinal and genital branch of the genitofemoral nerves pass through the inguinal ring. The anterior cutaneous iliohypogastric and femoral branch of the genitofemoral nerve can be stimulated at one or more locations proximate but rostral (iliohypogastric) or lateral (genitofemoral) to the inguinal ring. Leads 265 can comprise one or more functional elements 260 comprising cylindrical, paddle, cuff and/or hemi-cuff electrodes (electrodes placed surgically near and/or around these nerves). The nerves can be localized via ultrasound or other imaging modalities. Contrast can be used to image the vessels nearby (e.g. the testicular and/or ovarian vein and/or artery). The genital branch of the genitofemoral nerve can be stimulated in a transvascular manner through the testicular vein and/or artery. The genitofemoral and/or the ilioinguinal nerves can also be stimulated (e.g. transvascularly stimulated) through the femoral vein and/or artery, or via the superficial or deep external pudendal vein and/or artery, and/or via the superficial epigastric vein and/or artery.

The painful areas innervated by the ilioinguinal nerve, genitofemoral nerve and/or iliohypogastric nerves, can also be treated via spinal cord stimulation provided by apparatus 10 in the L1-L5 region of the spinal cord. In some embodiments, direct stimulation of the L1-L2 dorsal root ganglia is provided in a similar treatment. Leads 265 (e.g. percutaneous or paddle) including stimulation-based functional elements 260 can be placed over the dorsal columns, over the dorsal roots and/or in the dorsal root entry zone, in a unilateral, bilateral and/or midline fashion.

In some embodiments, the ilioinguinal nerve, genitofemoral nerve and/or iliohypogastric nerves are stimulated at low frequencies. In other embodiments, it is preferred to stimulate these nerves at high frequencies (>1 kHz). Both of these forms of stimulation can be accomplished either via subcutaneous field stimulation or by laying the leads adjacent or near these nerves and their branches. It may be appreciated that these nerves may also be stimulated transvascularly with low or high frequencies.

To treat occipital neuralgia, also known as C2 neuralgia, one or more functional elements 260 can be positioned to stimulate peripheral nerve tissue to reduce pain. Occipital neuralgia is a medical condition characterized by chronic pain in the upper neck, back of the head and/or behind the eyes (areas corresponding to the locations of the lesser and greater occipital nerves). In some embodiments, one or more leads 265, each comprising one or more functional elements 260, can be implanted transversely, either unilaterally or bilaterally, at the level of the appropriate target cervical nerve (C1, C2, etc.). The C1, 2, 3 cervical roots include the greater occipital nerve which originates primarily from C2, and the lesser occipital nerves. Relevant trigeminal branches include both the supraorbital and supratrochlear nerves from V1, the infraorbital branches from V2, and the superficial temporal nerves from V3. A partial convergence of these two systems occurs at the Trigemino-Cervical Complex (TCC). In some embodiments, one or more functional elements 260 are positioned to stimulate the trigeminal and/or occipital nerves. One or more leads 265 can be anchored to the fascia proximate the tissue to be stimulated.

To treat post-herpetic neuralgia (e.g. neuralgia associated with shingles), one or more functional elements 260 can be positioned to stimulate corresponding branches of the spinal nerves correlating to one or more dermatomes related to the patient's shingles.

In some embodiments, apparatus 10 is configured to treat pelvic, bladder and/or bowel disorders, such as by stimulating sacral, pudendal and/or tibial nerves. In some embodiments, apparatus 10 is configured to treat pelvic pain by stimulating the tibial nerve.

Apparatus 10 can be configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations of one or more of these.

Apparatus 10 can be configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of these.

Apparatus 10 can be configured to treat one or more of the pelvic disorders, bladder dysfunctions and/or and bowel dysfunctions listed above, by stimulating (e.g. using bilateral and/or unilateral stimulation) one or more of the targets listed below.

In some embodiments, the stimulated targets include the sacral nerves (roots) S2, S3 and/or S4. Stimulation of one or more sacral nerve (roots) S2, S3, S4 can be used to treat a variety of conditions, including overactive bladder, pelvic pain, incontinence, urgency, urgency frequency, fecal incontinence, painful bladder syndrome, and interstitial cystitis, to name a few. One or more leads 265 (e.g. each including one or more stimulation elements 260) can be positioned to stimulate any or all of the three roots, on a single side or both sides, in any bilateral or unilateral combination. The roots can be accessed, with the patient lying in the prone position, by positioning one or more leads 265 (e.g. percutaneously), with or without the use of fluoroscopy, ultrasound or any other imaging modality, into one/any of the sacral foramen (a) from the posterior aspect of the sacrum. One or more leads 265 can be passed through the foramen to the anterior side of the sacrum, and/or one or more leads 265 can remain inside the foramen(a).

In some embodiments, the sacral roots are approached rostrally, via the sacral canal in a retrograde manner. In these embodiments, one or more leads 265 can be passed through the ligamentum flavum, just caudal to L5 or via any of the intervertebral spaces from L5 to T12, into the spinal canal. One or more leads 265 are then threaded, with or without the aid of visualization (fluoroscopy, ultrasound or other imaging modality), in a caudal (retrograde) manner to enter the sacral canal. One or more leads 265 can be placed along the sacral canal, and each root can be stimulated individually and/or each root can be stimulated in concert, via one or more leads 265 positioned along the internal surface of the sacral canal, and spanning one or more foramena.

In some embodiments, one or more leads 265 are threaded from the spinal canal into each and/or all sacral foramen(a), in an anterior direction. The sacral canal can also be accessed caudally by one or more leads 265, via the sacral hiatus in an anterograde manner.

In some embodiments, the sacral roots (S2, S3 and/or S4) are accessed as they enter the spinal cord at the cauda equina. This access can be achieved by inserting the one or more leads 265 through the ligamentum flavum, at a location just caudal to L5, or via any of the intervertebral spaces from L5 to T12, into the spinal canal. The one or more leads 265 can then be threaded, with or without the aid of visualization (fluoroscopy, ultrasound or other imaging modality), up to the cauda equina, where the S2, S3 and/or S4 roots can be stimulated where they enter the spinal cord, and/or the conus medullaris can be stimulated directly (e.g. in the same location). Stimulation of cauda equina and/or conus medullaris can be used to treat a variety of conditions, including overactive bladder, pelvic pain, incontinence, urgency, urgency frequency, fecal incontinence, painful bladder syndrome, and interstitial cystitis, to name a few.

In some embodiments, the pudendal nerve is stimulated through one or more different approaches. The pudendal nerve contains both afferent and efferent fibers carried by S2, S3 and S4 roots. The pudendal fibers exit Alcock's canal near the ischial spine, where they spread out to innervate to the bladder wall, perineum, anus, genitals and urethra. Pelvic and voiding disorders can be treated by stimulating pudendal nerve fibers, along with a variety of conditions including overactive bladder, pelvic pain, incontinence, urgency, urgency frequency, fecal incontinence, painful bladder syndrome, and interstitial cystitis, to name a few. The fibers can be accessed at the Alcock's canal via various approaches. In one embodiment, a transperineal approach is achieved by positioning the patient in the lithotomy position and inserting the lead 265 midpoint between the ischial tuberosity and the anus. A lead 265 is inserted toward the ischial spine, which can be palpated transvaginally or transrectally. The ischial spine can also be visualized through a number of imaging modalities (e.g. fluoroscopy, x-ray, ultrasound, and the like). In another embodiment, a transvaginal approach is achieved by positioning the patient in the lithotomy position and inserting a lead 265 through the vaginal wall, adjacent to the ischial spine (e.g. through the vaginal wall toward the ischial spine). In another embodiment, a posterior approach is achieved by laying the patient in the prone position and inserting a lead 265 just medial to the ischial tuberosity toward the ischial spine. This insertion can be facilitated by rectal palpation of the ischial spine and through visualization via a number of imaging modalities (e.g. fluoroscopy, x-ray, ultrasound, and the like).

In some embodiments, apparatus 10 is configured to stimulate pudendal afferents, such as by stimulating the dorsal genital nerve. These fibers are located just below the skin on the dorsum of the penis or just rostral to the clitoris. In some embodiments, pudendal afferents are stimulated periurethrally. One or more leads 265 can be inserted alongside the urethra to stimulate the pudendal fibers.

In some embodiments, apparatus 10 is configured to stimulate tibial nerve fibers, such as to treat one or more pelvic disorders (e.g. voiding dysfunction, overactive bladder, pelvic pain, incontinence, urgency, urgency frequency, fecal incontinence, painful bladder syndrome, and interstitial cystitis, to name a few). The tibial nerve can be accessed a few mm below the skin surface in the ankle immediately posterior to the medial malleolus. Lead 265 can comprise a cylindrical SCS-type lead, which can be inserted percutaneously in this location. Alternatively or additionally, a direct (surgical) cut-down can be used to insert a cylindrical lead or to apply a cuff electrode directly to the nerve. The tibial nerve can also be accessed approximately half way up the lower leg adjacent to the tibia. One or more leads 265 can be inserted percutaneously in this location. Alternatively or additionally, a direct cut-down can be used to insert lead 265 (e.g. a cylindrical lead or a cuff electrode and/or hemi-cuff electrode applied directly to the nerve in the mid-shin location). Tibial nerve fibers can be accessed in the popliteal fossa behind the knee, for example percutaneously with a lead 265 comprising a cylindrical lead, and/or via a direct cut-down, for example with a lead 265 comprising either a cylindrical or cuff electrode.

In some embodiments, apparatus 10 and one or more leads 265 are constructed and arranged to stimulate the tibial and/or pudendal nerves via a transvascular approach (i.e. stimulation energy delivered from inside a blood vessel to nerve tissue proximate the blood vessel), such as via the femoral vein and/or artery, each of which provide intraluminal access to many other blood vessels (e.g. using standard interventional techniques). The tibial nerve can be transvascularly stimulated by the popliteal vein and/or artery (e.g. by placing one or more functional elements 260 in the popliteal vein and/or artery), at a location behind the knee. The popliteal vein and/or artery can be intraluminally accessed from the femoral artery and vein. The tibial nerve also passes near the small saphenous vein, where it branches off of the popliteal vein. The posterior tibial vein and/or artery are positioned adjacent to the tibial nerve, from the knee to the foot. One or more leads 265 can utilize one or more of these above locations to stimulate the tibial nerve.

In some embodiments, apparatus 10 and one or more leads 265 are constructed and arranged to stimulate the pudendal nerve and/or sacral roots, such as using a lead 265 placed via the femoral vein and/or artery, which in turn provides intraluminal access to many vessels. One or more leads 265 can be configured to utilize any of the following arteries and veins to stimulate the pudendal nerve and/or the sacral roots. One or more leads 265 can be constructed and arranged to stimulate a target site via a blood vessel selected from the group consisting of: the internal pudendal artery or vein (which branch off of common iliac artery or vein, respectively); the inferior and superior gluteal vein and/or artery; middle rectal, pudendal plexus and internal iliac vein and/or artery; medial and lateral sacral vein and/or artery; uterine and obturator vein and/or artery; and combinations of one or more of these.

In some embodiments, apparatus 10 is configured to treat overactive bladder and/or urinary incontinence (singly or collectively "overactive bladder" herein). In some embodiments, apparatus 10 is configured to treat overactive bladder such as to reduce the effects of overactive bladder and/or to decrease use of one or more medications taken by the patient to treat overactive bladder. In some embodiments, one or more functional elements 260 are positioned to stimulate tissue of the central nervous system or tissue and/or tissue of the peripheral nervous system to treat overactive bladder, such as to stimulate one or more nerves that control and/or are otherwise related to bladder function (e.g. to increase bladder capacity, improve bladder emptying, reduce urge incontinence and/or reduce stress incontinence). For example, one or more functional elements 260 can be positioned to stimulate tibial nerve tissue and/or sacral nerve tissue (e.g. at least the S3 nerve root) to treat overactive bladder. In some embodiments, lead 265 is constructed and arranged to be positioned along one or more locations of the tibial nerve, such as a positioning performed using percutaneous technique (e.g. when lead 265 comprises a cylindrical SCS-type lead) and/or surgical (cut-down) techniques (e.g. when lead 265 comprise a cuff electrode and/or hemi-cuff electrode applied directly to the nerve). The tibial nerve branches off of the sciatic nerve just above the knee, and runs along the length of the tibia, medial and lateral to the tibia. The tibial nerve then passes posterior to the medial malleolus prior to innervating the plantar surface of the foot. Lead 265 can be constructed and arranged to access sites proximate the tibial nerve percutaneously and/or through an incision at the back of the knee in the popliteal fossa, along the tibia or behind the medial malleolus. The housing 210 can be placed anywhere in the leg when stimulating the tibial nerve. Lead 265 can be constructed and arranged to stimulate the tibial nerve through a transvascular approach, via the femoral vein and/or artery, each of which provide intraluminal access to many vessels. The tibial nerve can be accessed by the popliteal artery and vein behind the knee, which are intraluminally accessible from the femoral artery and vein, respectively. The tibial nerve also passes near the small saphenous vein, where it branches off of the popliteal vein. The posterior tibial vein and artery travel adjacent to the tibial nerve from the knee to the foot. One or more leads 265 can be constructed and arranged to utilize any of these locations to transvascularly stimulate the tibial nerve (e.g. transvascularly stimulate the tibial nerve via the popliteal artery, popliteal vein, saphenous vein, posterior tibial artery and/or posterior tibial vein via a lead 265 advanced via the femoral vein and/or artery). In these transvascular embodiments, the housing 210 can be placed near the femoral or popliteal access point at locations in the groin, perineum, scrotum, pelvis, hip, thigh, leg, behind the knee, buttocks, abdomen and/or low back. In the case of sacral nerve stimulation, one or more leads 265 can be inserted through an incision(s) made in the lower back, such that one or more functional elements 260 are positioned proximate (e.g. in contact) with the sacral nerve root(s). The housing 210 can be placed anywhere in the groin, perineum, scrotum, pelvis, hip, thigh, leg, behind the knee, buttocks, abdomen and/or low back. Lead 265 (e.g. a lead 265 comprising a lead extension) can be extended underneath the skin (e.g. tunneled) to a second incision (e.g. across the flank to the lower abdomen, across the midline to the buttocks, or low back), and a third incision can be made (e.g. in the abdomen, back or buttocks) where housing 210 can be inserted and connected to lead 265. Alternatively, housing 210 can be inserted at another internal location. If lead 265 is already connected (e.g. attached in manufacturing) to housing 210, lead 265 can be advanced in the opposite direction, such as from the third incision, to the second incision, to the first incision (if three incisions are made), or housing 210 can be advanced under the tissue from incision 1 to incision 2 or from incision 2 to incision 3. In some embodiments, only 1 or 2 incisions are performed. In some embodiments, such as when lead 265 is already connected (e.g. attached in manufacturing) to housing 210, lead 265 and housing 265 are implanted as described herebelow in reference to one or more of FIG. 21 or 22A-D. In some embodiments, a first lead 265 and a first housing 210 (pre-attached or attachable) are utilized in a dose titration or other "trialing procedure", and a second lead 265 and housing 210 (pre-attached or attachable) are implanted in the patient for subsequent treatment of the patient.

In some embodiments, one or more functional elements 260 are positioned to perform posterior tibial nerve stimulation (PTNS), also referred to as percutaneous tibial nerve stimulation, such as to perform an indirect form of neuromodulation to treat bladder voiding dysfunction. The posterior tibial nerve is derived from the lumbar-sacral nerves (L4-S3), which innervate the bladder detrusor and pelvic floor. In some embodiments, one or more functional elements 260 can be positioned to perform retrograde stimulation of the sacral nerve plexus and restore the balance between bladder inhibitory and excitatory control systems of the bladder. One or more functional elements 260 can be positioned above the ankle, proximate and/or into the tibial nerve. Implantable device 200 can deliver stimulation energy to the functional elements 260 comprising low-voltage electrical stimulation configured to produce sensor and/or motor responses. Apparatus 10 can be configured to provide continuous and/or intermittent stimulation to tissue, such as to modulate transmission of excitatory nerve signals to the bladder muscles. In some embodiments, system 20 is configured to deliver a series of repeated stimulation periods, such as a regimen of approximately: weekly thirty minute sessions of stimulation for twelve weeks. In some embodiments, system 20 is configured to provide daily or hourly sessions that deliver stimulation for between 10 minutes and 60 minutes. In some embodiments, apparatus 10 is configured to achieve an approximate 50% reduction in urinary urge incontinence and/or urinary urgency/frequency episodes.

In some embodiments, apparatus 10 is configured to provide temporary stimulation of tissue to treat overactive bladder, such as by using trialing device 80 described hereabove in reference to FIG. 1, such as to provide power and/or date to one or more implantable devices 200 to confirm acceptable improvement of the patient's overactive bladder (e.g. successful stimulation of one or more sacral nerves, tibial nerves or other tissue), before closing an incision or otherwise fully implanting one or more implantable devices 200. In some embodiments, a temporary stimulation is provided for up to one week or up to one month. In some embodiments, one or more implantable devices 200 are left in place if the temporary stimulation period is successful or unsuccessful (e.g. left implanted due to its small size or otherwise minimal impact on the patient).

In some embodiments, apparatus 10 is configured to stimulate a region of the pelvic floor, such as to: change the reflex thresholds of the bladder muscles responsible for bladder emptying, strengthen and/or otherwise improve the condition of the muscles that maintain closure on the bladder outlet; change the state of the neural pathways, musculature and/or bladder during and beyond the period stimulation; and/or otherwise decrease the severity of urinary incontinence. In some embodiments, one or more functional elements 260 are positioned to stimulate periurethral muscles. In some embodiments, one or more functional elements 260 are positioned to stimulate tissue of the vagina or anus. In some embodiments, one or more functional elements 260 are positioned to stimulate sphincter muscles for controlling the bladder, such as two functional elements 260 positioned on either side of the urethral orifice. In these embodiments, housing 210 can be implanted in suprapubic region or in the perineum. In some embodiments, lead 265 comprises (e.g. on a distal portion) a pessary ring comprising two functional elements 260. In some embodiments, functional elements 265 comprise periurethral electrodes configured to stimulate pudendal afferents.

As described above, apparatus 10 can be configured for treating numerous diseases, disorders or other undesirable patient conditions, such as fecal incontinence. Injury of nerves that sense stool in the rectum can lead to fecal incontinence. In some embodiments, one or more functional elements 260 (e.g. one or more electrical, magnetic, light or other energy delivery elements) of one or more leads 265 and/or one or more implantable devices 200 are configured to stimulate tissue to treat fecal incontinence, such as to treat tissue selected from the group consisting of: sacral nerve tissue; tissue whose stimulation strengthens muscles of the bowel and/or rectum; and combinations of one or more of these. In these fecal incontinence applications, leads 265 can be implanted in a location selected from the group consisting of: the pelvic girdle; the sacral foramina; the lower back; the upper buttock; and combinations of one or more of these, such as to stimulate sacral nerve tissue. Leads 265 can be anchored via lead anchors (silicone or other materials), suture, staples, clips, adhesive and the like, such as an attachment to the underlying fascia of target tissue to be stimulated. In some embodiments, apparatus 10 is configured to treat both fecal incontinence and a bladder disorder such as overactive bladder, such as when one or more functional elements 260 are configured to deliver energy to sacral nerve or other tissue.

In some embodiments, apparatus 10 is configured to treat fecal incontinence, overactive bladder (i.e. overactive bladder and/or urinary incontinence), and/or pelvic disorders, and implantable device 200: comprises between 2 and 6 functional elements 260, such as four electrodes; delivers electrical stimulation energy at a range of approximately between 10 Hz and 15 Hz (or a range of between 5 Hz and 25 Hz); delivers electrical stimulation energy with a pulse width of approximately between 180 μsec and 240 μsec (or between 10 µsec and 200 µsec); provides electrical stimulation energy with an amplitude of approximately 0.1V to 8.5V (e.g. providing a current between 0.1 mA to 10 mA), such as an amplitude between 0.4V and 2.0V; delivers continuous electrical stimulation energy; delivers intermittent electrical stimulation energy, such as with a period between 8 seconds and 24 seconds and/or an on time between 8 seconds and 16 seconds; delivers monopolar electrical energy; delivers bipolar electrical energy; and combinations of one or more of these.

In some embodiments, apparatus 10 is configured to treat an occipital neuralgia, such as migraine headache, headache and/or cluster headache, and one or more functional elements 260 (e.g. small column paddle electrodes, standard paddle electrodes or other electrodes) are positioned to stimulate nerve tissue selected from the group consisting of: occipital; supraorbital; infraorbital; greater occipital nerve (GON); lesser occipital nerve (LON); both supraorbital and GON; supratroclear; sphenopalantine (SPG); and combinations of one or more of these.

In some embodiments, apparatus 10 is configured to treat neuralgia, such as a neuralgia resulting from surgery (e.g. groin, shoulder, lung and/or amputation), trauma and/or phantom pain, and one or more functional elements 260 are positioned to stimulate nerve tissue.

In some embodiments, apparatus 10 is configured to treat neuralgia, such as a neuralgia resulting from groin surgery (e.g. hernia or other groin surgery), and one or more functional elements 260 are positioned to stimulate nerve tissue selected from the group consisting of: ilioinguinal; genitofemoral; iliohypogastric; and combinations of one or more of these.

In some embodiments, apparatus 10 is configured to treat neuralgia, such as a neuralgia resulting from shoulder surgery, and one or more functional elements 260 are positioned to stimulate axial nerve tissue (e.g. one or more functional elements 260 positioned on a lead 265 implanted in a suprascapular location).

In some embodiments, apparatus 10 is configured to treat neuralgia, such as a neuralgia resulting from lung surgery, and one or more functional elements 260 are positioned to stimulate intercostal nerve tissue.

In some embodiments, apparatus 10 is configured to treat neuralgia, such as a neuralgia associated with carpal tunnel syndrome, and one or more functional elements 260 are positioned to stimulate median nerve tissue.

In some embodiments, apparatus 10 is configured to treat neuralgia, such as a neuralgia associated with temporomandibular joint disorder (TMJ), and one or more functional elements 260 are positioned to stimulate V2 of trigeminal nerve tissue.

In some embodiments, apparatus 10 is configured to treat neuralgia, such as a facial neuralgia, and one or more functional elements 260 are positioned to stimulate trigeminal nerve tissue.

In some embodiments, apparatus 10 is configured to treat neuralgia, such as a leg (sciatic) neuralgia, and one or more functional elements 260 are positioned to stimulate nerve tissue proximal a contributing lesion.

In some embodiments, apparatus 10 is configured to treat pelvic pain, such as interstitial cystitis and/or bladder pain, and one or more functional elements 260 are positioned to stimulate peripheral nervous system tissue (e.g. pudendal tissue and/or S-2, S-3 and/or S-4 roots) and/or central nervous system tissue (e.g. lower spinal cord and/or S3 neural foramen).

In some embodiments, apparatus 10 is configured to treat pelvic pain, such as anal pain, and one or more functional elements 260 are positioned to stimulate peripheral nerve tissue such as pudendal tissue and/or S-2, S-3 and/or S-4 roots.

In some embodiments, apparatus 10 is configured to treat subcutaneous pain, and one or more functional elements 260 (e.g. paddle electrodes) are positioned to stimulate nerve tissue.

In some embodiments, apparatus 10 is configured to treat diabetic neuropathy, such as painful diabetic neuropathy, and one or more functional elements 260 are positioned proximate the lower spinal cord (e.g. to stimulate S3 nerves) or other body location to stimulate nerve tissue.

In some embodiments, apparatus 10 is configured to treat visceral pain, angina and/or other pain, and one or more functional elements 260 are positioned to stimulate the vagus nerve.

In some embodiments, apparatus 10 is configured to treat peripheral vascular disease, diabetic neuropathy and/or other conditions associated with diabetes, such as to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations of one or more of these. In these embodiments, lead 265 can be positioned proximate a nerve in the foot, leg, arm and/or sacrum (e.g. such that one or more functional elements 260 are positioned proximate the nerve to be stimulated). In some embodiments, lead 265 is positioned to stimulate the dorsal root ganglia to treat diabetic neuropathy (e.g. diabetic neuropathy of the hand and/or foot). Lead 265 can be implanted percutaneously and/or surgically as described herein. Lead 265 and/or one or more functional elements 260 can comprise a paddle electrode, such as one or more paddle electrodes implanted in the foot, leg and/or arm. Lead 265 and/or one or more functional elements 265 can comprise a cuff or hemi-cuff electrode surgically implanted around a nerve in the foot, leg and/or arm. Apparatus 10 can be configured to provide spinal cord stimulation, either through percutaneous insertion of one or more leads 265 in the epidural space or surgical implantation of a lead 265 comprising a paddle lead positioned in the epidural space. Apparatus 10 can be configured to provide transvascular stimulation of nerves in the foot, leg and/or arm, (e.g. to treat diabetic neuropathy) such as when one or more leads 265 are interventionally advanced into the venous or arterial system. Leads 265 can be positioned using percutaneous transforaminal placement in the sacral foramina, such as for treatment of foot or leg disorders. Leads 265 can be constructed and arranged for cephalocaudal insertion (retrograde) into the epidural space or sacral canal, such as for treatment of foot or leg disorders. Leads 265 can be constructed and arranged to provide dorsal root ganglion stimulation, such as for treatment of foot, leg, arm and/or hand disorders.

One or more leads 265 (e.g. each including one or more functional elements 260) can be constructed and arranged to stimulate tibial nerve fibers, such as to treat diabetic neuropathy and/or diabetic related maladies of the foot. The tibial nerve can be accessed as described herein.

One or more leads 265 can be configured to stimulate the peroneal nerve or saphenous nerve, such as at one or more locations described herebelow. The peroneal nerve can be accessed percutaneously or surgically behind the knee in the popliteal fossa where it branches off of the sciatic nerve. It can also be accessed as it wraps around the lateral aspect of the knee just prior to diving under the fibularis longus and extensor digitorum longus muscles. The deep fibular nerve (a branch of the peroneal nerve) innervates top medial foot, whereas the superficial fibrular (peroneal) innervates top of both medial and lateral foot. In some embodiments, functional element 260 comprises one or more electrodes positioned in the anterior tibial vein and/or artery to transvascularly stimulate the deep fibular nerve. The saphenous nerve comes off the femoral nerve deep in the thigh. It passes around the medial aspect of the knee medial to the patella. It then runs down the medial shin adjacent to the tibia, gastrocnemius and soleus muscles where it can be accessed surgically or percutaneously. It then surfaces just as it warps around the anterior aspect of the medial malleolus where it supplies the medial posterior foot in front of heel. The medial sural cutaneous nerve comes off of the tibial at the popliteal fossa, then runs down the back of the calf (over the gastrocnemius) and wraps around the posterior aspect of the lateral malleolus before innervating the lateral aspect of the sole and heel. In some embodiments, the saphenous nerve is transvascularly stimulated by positioning one or more functional elements 260 in a blood vessel selected from the group consisting of: femoral vein; femoral artery; great saphenous vein; great saphenous artery; and combinations of one or more of these. In some embodiments, the sural nerve is stimulated. In these embodiments, the sural nerve can be transvascularly stimulated by positioning one or more functional elements 260 in the saphenous vein.

One or more leads 265 can be configured to stimulate the median nerve, ulnar nerve and/or radial nerve. The median nerve can be accessed percutaneously in the upper arm lateral to the brachial vein and/or artery, but medial to the biceps muscle, whereas the ulnar nerve runs medial to the brachial artery in the upper arm. The median nerve passes through the anterior aspect of the elbow under the bicipital aponeurosis. The ulnar nerve runs medial and posterior to the medial epicondyle of the humerus. The median nerve can also be accessed in the wrist just proximal to the palm and the palmar carpal ligament. The ulnar nerve can be accessed just proximal to the palmar carpal ligament adjacent to the pisiform. The radial nerve can be accessed percutaneously just as it passes anterior to the lateral epicondyle. In some embodiments, apparatus 10 can be configured to transvascularly stimulate at least one of a median nerve, an ulnar nerve or a radial nerve, and functional element 260 can comprise one or more electrodes positioned in a vessel selected from the group consisting of: brachial vein; brachial artery; basilic vein; basilic artery; deep vein of the arm; deep artery of the arm; and combinations thereof. In some embodiments, apparatus 10 can be configured to transvascularly stimulate at least one of a median nerve or an ulnar nerve, and functional element 260 can comprise one or more electrodes positioned in a vessel selected from the group consisting of: brachial vein; brachial artery; and combinations thereof. In some embodiments, apparatus 10 can be configured to transvascularly stimulate the radial nerve, and functional element 260 can comprise one or more electrodes positioned in a vessel selected from the group consisting of: deep vein of arm; deep artery of arm; basilic vein; radial collateral vein; radial collateral artery; medial collateral vein; medial collateral artery; radial vein; radial artery; and combinations thereof. In some embodiments, apparatus 10 can be configured to transvascularly stimulate the medial cutaneous nerve, and functional element 260 can comprise one or more electrodes positioned in the basilic vein. In some embodiments, apparatus 10 is configured to transvascularly stimulate the ulnar nerve, and functional element 260 can comprise one or more electrodes positioned in a vessel selected from the group consisting of: ulnar collateral vein; ulnar collateral artery; ulnar vein; ulnar artery; and combinations thereof. In some embodiments, apparatus 10 is configured to transvascularly stimulate the median nerve, and functional element 260 can comprise one or more electrodes positioned in a vessel selected from the group consisting of: brachial vein; brachial artery; ulnar vein; ulnar artery; and combinations thereof.

As described herein, one or more leads 265 can be positioned to stimulate the spinal cord, such as via percutaneous insertion of a lead 265 in the epidural space or surgical implantation of the lead 265 (e.g. a paddle lead) in the epidural space. A lead 265 can be placed such that one or more functional elements 260 (e.g. one or more electrodes) are positioned from T5-S5, such as to capture the area of pain or reduced circulation of the leg or foot, or treat a variety of conditions, including overactive bladder, pelvic pain, incontinence, urgency, urgency frequency, fecal incontinence, painful bladder syndrome, and interstitial cystitis, to name a few. One or more functional elements 260 of one or more leads 265 can be positioned from C2 to T8, such as to capture the area of pain or reduced circulation of the arm or hand. One or more leads 265 can be placed along the midline, unilaterally and/or bilaterally over the dorsal columns, in the gutter (over dorsal roots) and/or in the dorsal root entry zone. Leads 265 can span several vertebral levels or they can be positioned to span a single level.

One or more functional elements 260 (e.g. one or more electrodes attached to one or more leads 265) can be positioned to transvascularly stimulate one or more nerves, such as one or more nerves in the foot, leg and/or arm, such as when the one or more functional elements 260 are implanted within one or more blood vessels of the venous and/or arterial system.

In the leg, the tibial nerve, sacral roots and/or deep fibular nerve can be stimulated, such as when a lead 265 accesses the tissue to be stimulated through a transvascular approach, such as via the femoral vein and/or artery, as described herein. The deep fibular nerve can be stimulated by one or more functional elements 260 positioned in the anterior tibial vein and/or the anterior tibial artery. In the arm, the median nerve, ulnar nerve, superior ulnar nerve, medial cutaneous nerve and/or radial nerve can be stimulated, such as when lead 265 accesses the tissue to be stimulated through a transvascular approach, such as via the brachial vein and/or artery, the basilic vein and/or artery, and/or the deep vein and/or artery.

One or more functional elements 260 (e.g. one or more electrodes attached to one or more leads 265) can be positioned to stimulate one or more dorsal root ganglia. Examples include dorsal root ganglia that supply the following nerves (e.g. to treat the leg and/or foot): common peroneal (L4-S2); tibial (L4-S3); femoral (L2-L4); and combinations of one or more of these. One or more functional elements 260 (e.g. one or more electrodes attached to one or more leads 265) can be positioned to stimulate dorsal root ganglia that supply the following nerves (e.g. to treat the hand and/or arm): radial (C5-T1); median (C5-T1); ulnar (C7-T1); and combinations of one or more of these. In these embodiments, one or more leads 265 can be passed through the intervertebral foramina, either unilaterally or bilaterally, at a single vertebral level or at multiple vertebral levels. Stimulation of various dorsal root ganglions can be used to treat a variety of conditions, including overactive bladder, pelvic pain, incontinence, urgency, urgency frequency, fecal incontinence, painful bladder syndrome, and interstitial cystitis, to name a few.

In some embodiments, apparatus 10 is configured to treat post-amputation pain, such as to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations of one or more of these. Apparatus 10 can be configured to treat the conditions associated with post-amputation pain (i.e., stump pain), such as by using a high frequency alternating current (HFAC) block approaches. In these embodiments, one or more leads 265 can be implanted such that one or more functional elements 260 stimulate one or more nerves in the leg, arm and/or sacrum. One or more leads 265 can be surgically implanted, such as when lead 265 comprises a paddle electrode positioned near a nerve in the foot, leg or arm and/or a cuff electrode or hemi-cuff electrode positioned to at least partially surround a nerve in the foot, leg or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg or arm, such as when one or more functional elements 260 are implanted within a vein or artery. One or more leads 265 can be implanted using percutaneous transforaminal placement in the sacral foramina, such as for treatment of leg stump pain. One or more leads 265 can be implanted using cephalocaudal insertion (retrograde) into the epidural space or sacral canal, such as for treatment of leg stump pain. One or more leads 265 can be positioned to perform dorsal root ganglion stimulation and/or block, such as for treatment of leg and/or arm stump pain.

In some embodiments, apparatus 10 is configured to treat occipital and/or headache (HA) pain, such as when apparatus 10 is configured to treat a disease or disorder selected from the group consisting of: occipital neuralgia; cervicogenic headache; tension headache; chronic and episodic migraine headache; tension headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations of one or more of these.

Apparatus 10 can be configured to treat the conditions associated with headache pain and/or occipital neuralgia by stimulating one or more nerves in the head, such as one or more nerves selected from the group consisting of: greater and/or lesser occipital nerve (e.g. which arise from C2 and C3); the greater and/or lesser auricular nerves (e.g. which also arise from C2/C3); the third (least) occipital nerve (e.g. which arises from C3); and combinations of one or more of these. The infraorbital or supraorbital nerves can be access subcutaneously below and above the eye, respectively. Apparatus 10 can be configured to stimulate auriculotemporal, supratrochlear and/or sub-occipital nerves. To stimulate any of these nerves, lead 265 (e.g. a cylindrical SCS-type lead) can be inserted percutaneously either subcutaneously or under the muscle. Alternatively, surgical (e.g. direct cut-down) can be performed to insert lead 265 (e.g. a cylindrical lead, a paddle lead, a cuff or hemi-cuff electrode) proximate, one and/or around these nerves. Alternatively or additionally, the nerves can be accessed transvascularly as described herein (e.g. when one or more functional elements 260 are implanted in a blood vessel). Housing 210 can be implanted anywhere in the head under the skin, including: behind the ear, back of the head, the neck, in the face, and the like, where an one or more external devices 500 can be positioned in, on and/or within a hat, headband, glasses, goggles, earpiece, necklace, patch, and the like. Apparatus 10 can be configured to treat headache pain and/or occipital neuralgia by stimulating tissue in the cervical spinal cord (C2-C3), for example proximate the location the nerve enters the cord from the foramen. One or more leads 265 can be placed over the dorsal columns, in the gutter, over the dorsal root entry zone and/or out in the foramen at the dorsal root ganglion. In some embodiments, the trigeminal and pterygopalatine ganglia are accessed by inserting one or more leads 265 through the face or the roof of the mouth. In these embodiments, housing 210 can be placed anywhere in the head under the skin, as described hereabove.

In some embodiments, apparatus 10 is configured to treat post-herpetic neuralgia, such as to treat a disease or disorder selected from the group consisting of: shingles; herpes zoster; zoster; zona; varicella zoster virus infection; zoster sine herpete; fever blisters; herpes zoster blisters; herpes zoster rash; and combinations of one or more of these. In some embodiments, apparatus 10 is configured to treat post-herpetic neuralgia using high frequency alternating current (HFAC) block approaches. In these embodiments, one or more leads 265 can be implanted such that one or more functional elements 260 stimulate one or more nerves in the leg, arm, torso and/or sacrum. One or more leads 265 can be surgically implanted, such as when lead 265 comprises a paddle electrode positioned near a nerve in the foot, leg, torso and/or arm and/or a cuff electrode or hemi-cuff electrode positioned to at least partially surround a nerve in the foot, leg, torso or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg, torso and/or arm, such as when one or more functional elements 260 are implanted within a vein or artery. One or more leads 265 can be implanted using percutaneous transforaminal placement in the sacral foramina, such as for treatment of leg or foot pain. One or more leads 265 can be implanted using cephalocaudal insertion (retrograde) into the epidural space or sacral canal, such as for treatment of leg or foot pain. One or more leads 265 can be positioned to perform dorsal root ganglion stimulation and/or block, such as for treatment of leg, torso and/or arm pain.

In some embodiments, apparatus 10 is configured to treat angina, such as to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations of one or more of these.

In some embodiments, apparatus 10 is configured to treat carpal tunnel syndrome, such as to treat a disease or disorder selected from the group consisting of: median nerve entrapment; tingling and/or numbness in fingers or hand; median nerve irritation or compression; narrowing of the carpal tunnel; and combinations of one or more of these.

In some embodiments, apparatus 10 is configured to treat erectile dysfunction (ED), such as to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED; and combinations of one or more of these.

In some embodiments, apparatus 10 is configured to treat complex regional pain syndrome (CRPS), such as to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations thereof.

Figure 2:
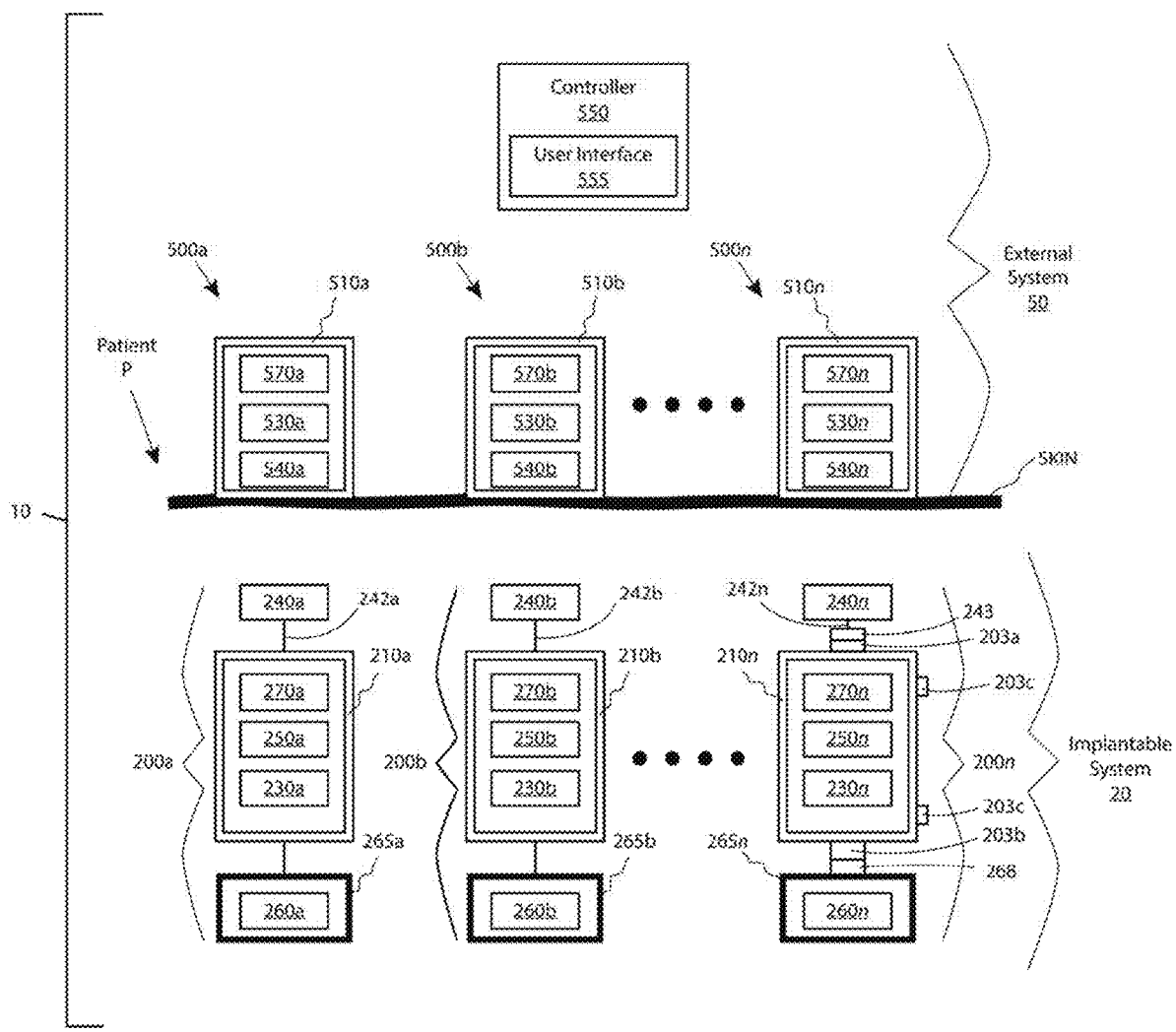
FIG. 2 is a schematic anatomical view of a medical apparatus comprising multiple external devices and multiple implantable devices, consistent with the present inventive concepts.

Referring now to FIG. 2, a schematic anatomical view of an apparatus for treating and/or diagnosing a patient comprising multiple implantable devices is illustrated, consistent with the present inventive concepts. Apparatus 10 comprises implantable system 20 and external system 50. Implantable system 20 can comprise two or more implantable devices, such as implantable devices 200a and 200b, up to 200n (singly or collectively implantable device 200) shown in FIG. 2. Each implantable device 200 is shown implanted beneath the skin of patient P. External system 50 can comprise one or more external devices 500, such as external devices 500a, 500b up to 500n (singly or collectively external device 500) shown in FIG. 2. Apparatus 10 of FIG. 2 can comprise tool 60, patient attachment device 70, trialing interface 80 and/or diagnostic assembly 91, not shown but such as is described hereabove in reference to FIG. 1.

Each external device 500 is configured to transmit power and/or data to one or more implantable devices 200. In some embodiments, one or more external devices 500 are configured to transmit both power and data (e.g. simultaneously and/or sequentially) to one or more implantable devices 200. In some embodiments, one or more external devices 500 are further configured to receive data from one or more implantable devices 200. Each external device 500 can comprise housing 510, power supply 570, transmitter 530 and/or antenna 540, any or all of which can be of similar construction and arrangement to the similar components of external device 500 described hereabove in reference to FIG. 1.

External system 50 can further comprise controller 550, which can comprise a user interface, such as user interface 555 and can be of similar construction and arrangement to controller 550 described hereabove in reference to FIG. 1. Controller 550 is configured to control one or more external devices 500, such as external devices 500a, 500b through 500n shown in FIG. 2. Controller 550 can send commands to an external device 500 via a wireless and/or wired connection (wired connection not shown but such as a connection comprising one or more insulated conductive wires). In some embodiments, one or more external devices 500 comprise controller 550, such as when user interface 555 is integrated into a housing 510 of an external device 500.

In some embodiments, a first external device 500a is positioned proximate a first implantable device 200a, and a second external device 500b is positioned proximate a second implantable device 200b, as shown in FIG. 2. In some embodiments, one or more external devices define a radiation footprint, as described hereabove. The radiation footprint can be expanded by incorporating an array of antennas 540 into external system 50 and/or an array of antennas 240 into implantable system 20. External system 50 can activate one or more antennas 540 within the array based on power link and/or data link monitoring information that controller 550 receives from one or more implantable devices 200. The acceptable range of depths between external antenna 540 and implantable antenna 240 can vary (e.g. vary between applications and/or patient geometry), such as an acceptable depth range between 0.3 cm and 7 cm, between 0.5 cm and 5 cm, or between 1 cm and 3 cm. Lateral and/or angular misalignment can be compensated for by utilizing controllable polarizations and activation of one or more antennas 540 in an antenna array and/or by using orthogonal implantable antennas 240. Alternatively or additionally, two or more implantable antennas 240 can be oriented in different planes with respect to each other and/or implantable antennas 240 can comprise combinations of dipole and loop antennas. In some embodiments, lateral misalignment tolerance can be between 0.1 cm and 10 cm, such as between 0.1 cm and 5 cm, or between 0.1 cm and 3 cm.

Each implantable device 200 is configured to receive power and/or data from one or more external devices 500. Each implantable device 200 comprises an implantable antenna 240, comprising one or more implantable antennas positioned within or outside of housing 210. In the embodiment shown in FIG. 2, each implantable antenna 240 is positioned outside of housing 210, and operatively connected to housing 210 (e.g. electrically connected to one or more components within housing 210) by connecting filament 242. Connecting filament 242 can comprise one or more wires configured to electrically connect one or more antennas 240 to housing 210. Alternatively or additionally, filament 242 can comprise one or more connecting filaments as defined herein. In some embodiments, one or more implantable devices 200 are configured to receive both power and data (e.g. simultaneously and/or sequentially) from one or more external devices 500. In some embodiments, a single external device 500 sends power and/or data to multiple implantable devices 200. Alternatively or additionally, two or more external devices 500 can send power and/or data to a single implantable device 200.

In some embodiments, one or more implantable devices 200 are further configured to transmit data to one or more external devices 500. Each implantable device 200 can comprise housing 210, energy storage assembly 270, receiver 230, demodulator 231, rectifier 232, power converter 233, antenna 240, controller 250 and/or lead 265, any or all of which can be of similar construction and arrangement to the similar components of implantable device 200 described hereabove in reference to FIG. 1.

Each lead 265a, 265b through 265n (singly or collectively lead 265) can each comprise one or more functional elements 260, such as functional element 260a, 260b through 260n, respectively. Each functional element 260 can comprise one or more functional elements, such as one or more functional elements 260 described hereabove in reference to FIG. 1. Each functional element 260 can comprise a sensor, a transducer and/or other functional elements. In some embodiments, one or more functional elements 260 comprise a sensor such as a sensor configured to record data representing a patient parameter or an implantable device

200 parameter. In some embodiments, one or more functional elements 260 comprise an electrode or other element configured to deliver energy to tissue, such as to treat pain and/or to stimulate tissue.

In some embodiments, one or more components of external system 50 (e.g. one or more power supplies 570, antennas 540, and the like) can comprise swappable, replaceable, and/or position-adjustable components. One or more portions of external system 50 can be positioned on, in and/or within an elastic belt with multiple pockets to surround one or more components of the external system 50 (e.g. for patient comfort and/or ease of use). The patient can choose the placement of the supported components depending on physical activity and/or comfort preference (e.g. patients who prefer sleeping on their back can choose to position a power supply 570 in a pocket on a side or front body position of the belt). Power supply 570 (e.g. a rechargeable battery) can be disconnected and replaced with a different power supply 570. The discharged battery can be placed in a recharging dock (e.g. a tool 60 described hereabove in reference to FIG. 1 configured as a power supply 570 recharging assembly). Swappable power supplies 570 can be beneficial for patients, such as by avoiding a recharge protocol which requires spending time by a recharge unit and/or carrying a recharge unit with them.

In some embodiments, a flexible cable, such as a flexible coaxial cable of thin diameter (for comfort of a patient), can be used to connect one or more antennas 540 to external transmitter 530. Alternatively or additionally, one or more flexible or semi-rigid cables can be used for low frequency control or DC connections, such as between a swappable and/or position-adjustable power supply 570, external transmitter 530, and/or one or more external controllers 550.

Two implantable device 200s, or two discrete components of a single implantable device 200 (e.g. two components comprising or positioned in different housings), can be attached to each other by a connecting filament as defined hereabove. A connecting filament can comprise a user-attachable connector on one or both ends. The filament connector is configured to operably attach to a mating connector on a component (e.g. a housing) of an implantable device 200. For example, as shown in FIG. 2, filament 242*n* comprises filament connector 243 which is configured to allow a user to operably attach antenna 240*n* to housing 210*n* via connector 203*a*. Alternatively or additionally, lead 265*n* can comprise connector 268 which is configured to allow a user to operably attach lead 265 to housing 210*n* via a second connector 203*b*, also as shown in FIG. 2. Similarly, two external devices 500, or two discrete components of a single external device 500 (e.g. two components comprising or positioned in different housings), can be attached to each other by a connecting filament.

Each implantable device 200 can comprise a connector 203, such as connectors 203*a*, 203*b*, 203*c* and/or 203*d* shown in FIG. 2 and attached to housing 210*n* of implantable device 200*n*. Connectors 203*a* and 203*b* are described hereabove. Connectors 203*c* and/or 203*d* can be included for operable attachment (e.g. electrical attachment, optical attachment, fluid attachment and/or mechanical attachment) to one or more leads 265 (e.g. when an implantable device 200 comprises multiple leads 265), implantable antennas 240 (e.g. when an implantable device 200 comprises multiple antennas 240 positioned outside of housing 210), and/or other component of implantable system 20. In some embodiments, connectors 203*c* and/or 203*d* attach to a mating connector of a lead 265 (e.g. similar to connector 268 of lead 265*n*), such as to electrically, optically, fluidly and/or mechanically connect with one or more functional elements 260 of lead 265, such as one or more functional elements 260 comprising one or more of: an electrode, an optical element (e.g. a lens or prism), a drug delivery element (e.g. a needle, exit port or catheter), a magnetic energy delivery element and/or a mechanical transducer.

Figure 3A:
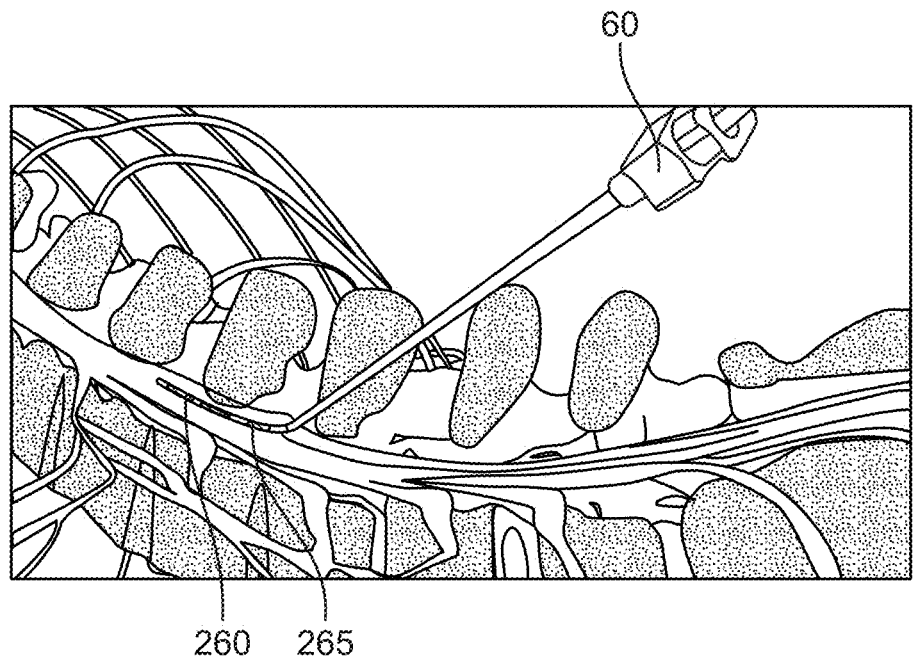
FIGS. 3A, 3B and 3C are an anatomical schematic of a human spine, a sectional anatomical view of a lead being inserted into the epidural space of a spine, and a sectional anatomical view of a lead inserted into the epidural space of a spine, respectively, consistent with the present inventive concepts.
Figure 3B:
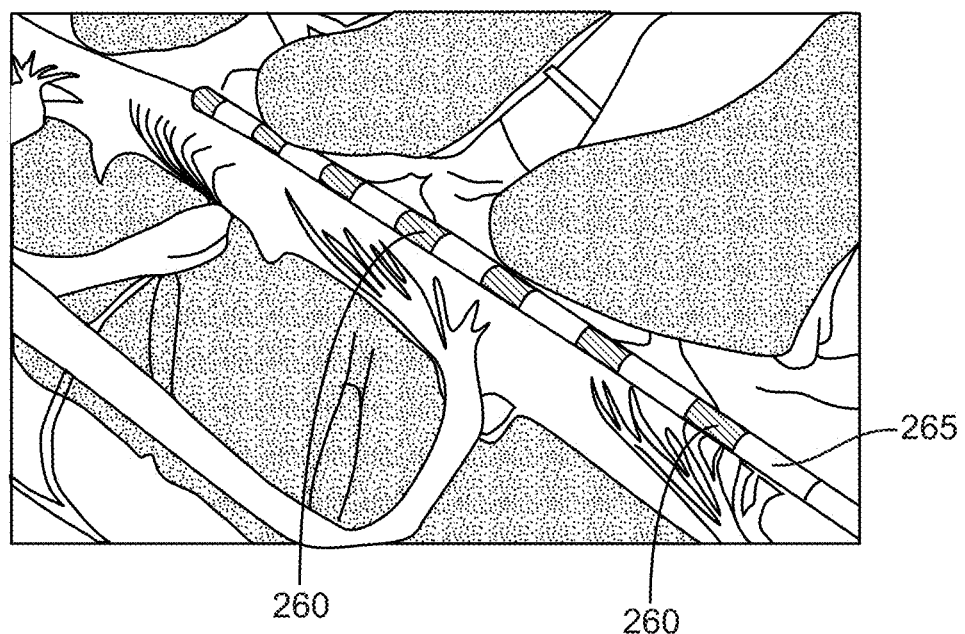
Figure 3C:
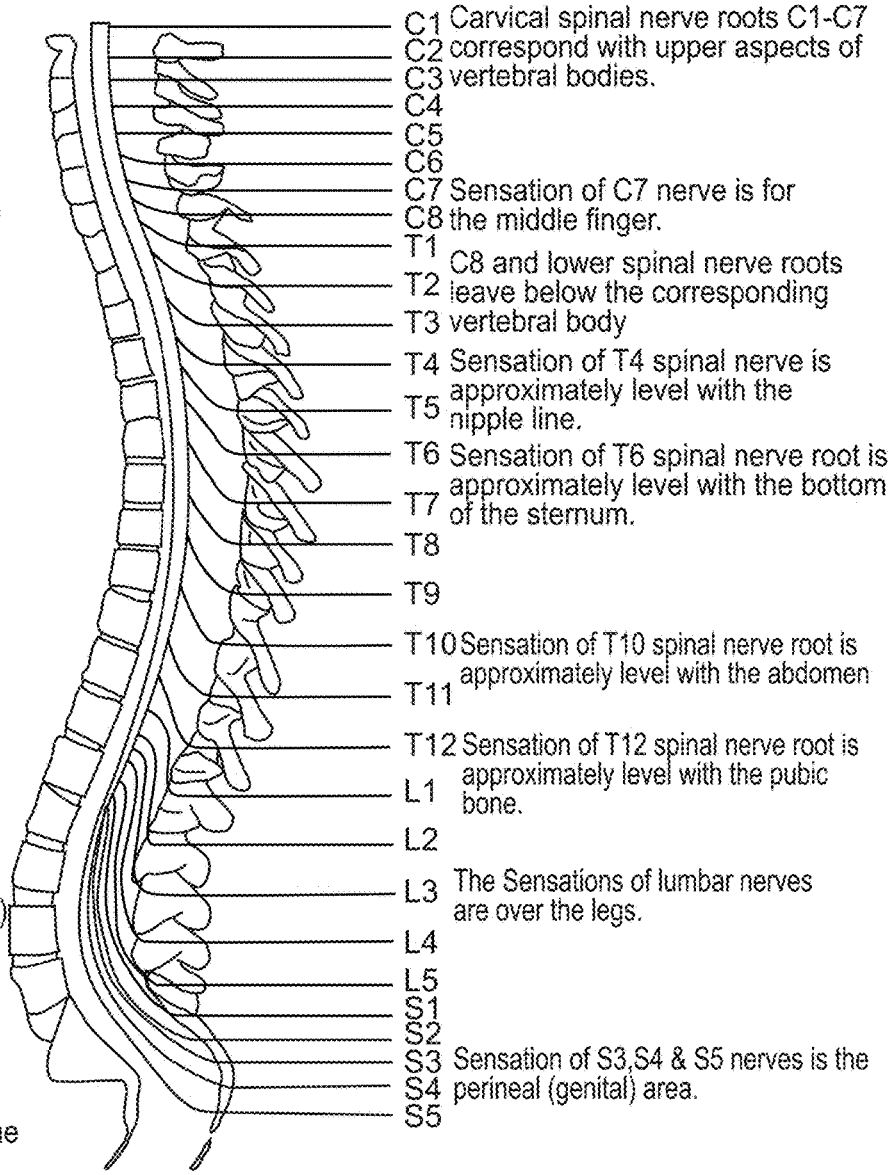

Referring now to FIGS. 3A, 3B and 3C, an anatomical schematic of a human spine, a sectional anatomical view of a lead being inserted into the epidural space of a spine, and a sectional anatomical view of a lead inserted into the epidural space of a spine, respectively, are illustrated, consistent with the present inventive concepts. A lead 265 can be inserted into the epidural space via a tool 60 (e.g. a needle, an introducer, or other lead delivery tool). Lead 265 comprises one or more functional elements 260 (e.g. one or more electrodes, sensors, drug delivery elements, energy delivery elements). In some embodiments, lead 265, one or more functional elements 260 and/or tool 60 can be of similar construction and arrangement to the similar components described hereabove in reference to FIG. 1 or 2.

Lead 265 can be positioned within the epidural space of the spine. In some embodiments, lead 265 is positioned within the intrathecal space. In other embodiments, lead 265 is positioned outside of the dura in the epidural space, but proximate the spine. One or more leads 265 can be positioned in one or more of these implanted locations such that one or more functional elements 260 can deliver energy to nerves, muscles or other tissue of the spine and/or sense electrical or other physiologic parameters present in tissue of the spine.

In some embodiments, lead 265 is implanted at a location (e.g. within the epidural space) such that one or more functional elements 260 (e.g. electrodes) can deliver stimulation energy in the area of one or more vertebrae between T9 and T12 (e.g. to treat back pain). In some embodiments, lead 265 is implanted at a location (e.g. within the epidural space) such that one or more functional elements 260 can deliver stimulation energy in the area of one or more vertebrae between L5 and T5 (e.g. to stimulate peripheral nerves). In some embodiments, lead 265 is implanted at a location (e.g. between fascia and fat layers of tissue) such that one or more functional elements 260 can deliver stimulation energy to stimulate peripheral nerves. In some embodiments, lead 265 is implanted at a location (e.g. within the epidural space) such that one or more functional elements 260 can deliver stimulation energy in the area of one or more vertebrae between C5 and T1 or between C3 and T5 (e.g. to treat upper limb pain). In some embodiments, lead 265 is implanted at a location (e.g. within the epidural space) such that one or more functional elements 260 can deliver stimulation energy in the area of one or more vertebrae between T9 and T11 or between T5 an L5 (e.g. to treat lower limb pain). In some embodiments, lead 265 is implanted at a location (e.g. within the epidural space) such that one or more functional elements 260 can deliver stimulation energy in the area of one or more vertebrae between C7 and T1 or between C5 and T5 (e.g. to treat angina).

An imaging device (e.g. a fluoroscope or ultrasound imaging device) can be used to visualize the pedicles of the vertebral bodies at an intended implantation site. During this visualization, an optimized level for midline epidural entry can be determined. This site is typically in the dorsal midline at the level that the spinal cord becomes the conus medullaris, where lumbosacral nerve roots disperse laterally to form the cauda equina, such as at the level above or below L1. Anterior-posterior (AP) imaging (e.g. fluoroscopic imaging) of the working site can be first optimized by aligning the image so that the spinous processes bisect the pedicles. Subsequently, the imaging device (e.g. a C-arm) can be adjusted in a cephalad or caudal direction to "square-off" the vertebral end plates. The skin entry point can be paramedian, such as 2 levels below the desired midline epidural entrance, adjacent the medial border of the ipsilateral pedicle. A shallow angle of entry can facilitate lead advancement. For dual lead 265 placement, pedicles can be marked for 2 consecutive levels or on the contralateral side. Following application of an agent such as 1% lidocaine (e.g. without epinephrine or preservative), skin and subcutaneous analgesia is achieved. Subsequently, an epidural access needle can be used to identify the epidural space, such as by using a loss of resistance syringe or a hanging drop technique. The cervical epidural space extends from the dura of the foramen magnum to the inferior border of C7. The thoracic epidural space begins at C7 and extends to the upper margin of the L1 vertebrae. The lumbosacral epidural space extends from the upper margin of the L1 vertebra. The size of epidural space, as measured by the distance between the ligamentum flavum and the dura, varies with location in the spinal column. The largest distance is typically at L2, where it can measure up to 5 mm-6 mm. However, in the thoracic spine, the distance is typically reduced to approximately 3 mm-4 mm, and at C7 the distance is typically only 1.5 mm-2 mm. In approximately 40% of patients, the anatomic (vertebral) and physiologic (spinal cord) midlines may differ by as much as 2 mm at all spinal cord levels. For these reasons, a first lead 265 can be tested as a suitable site for providing paresthesia, such as before a second lead 265 is placed. To cover a desired dermatomal area with paresthesia, electrodes (e.g. functional elements 260) can be placed over the dorsal columns of several segments cephalad to that level. In some embodiments, lead 265 is placed slightly offset from the midline between C2 and C4, such as to deliver stimulation to alleviate or at least reduce shoulder pain. When coverage that encompasses the entire upper extremity is desirable, leads 265 can be placed offset from the physiologic midline between C3 and C4. For stimulation of the more medial forearm and hand, leads 265 can be placed more in a more inferior location. Placing two leads 265, each slightly offset from the physiologic midline, to the right and left between C4 and C6, can provide bilateral upper extremity stimulation. Lateral imaging (e.g. fluoroscopy) allows the operator to position and/or document lead 265 placement in the dorsal epidural space. Stimulation of the back and both lower extremities is often intended following failed lumbar surgery for treatment of lower torso and extremity neuropathic pain. Most patients can achieve stimulation coverage when the leads 265 are placed in the midline between T8 and T9. A single midline lead 265 can be implanted for treatment of lower back pain; however, multiple leads 265 can alternatively be implanted (e.g. such that paresthesia coverage can be achieved such as via reprogramming that can be performed in cases when lead 265 migration occurs). Placing two leads 265 slightly offset from the physiologic midline to the right and left between T8 and T10 can provide for both lower back and lower extremity stimulation. Coverage of midline low back pain with current steering systems can be achieved with leads 265 that are less than 4 mm apart, such that delivered current can be directed to the midline to obtain low back stimulation. Often unilateral lower extremity stimulation can be produced by lead 265 placement slightly offset from the midline between T9 and T11. Distal lower extremity stimulation (e.g. the foot) can be achieved with leads 265 placed as low as T12 and L1, usually 1-4 mm offset from the midline. Retrograde lead 265 placement is sometimes necessary to achieve foot or pelvic stimulation. Numerous, often more complex techniques that require retrograde lead 265 placement for lumbosacral nerve root stimulation are sometimes performed when attempting pain coverage for rectal, perineal, or coccygeal pain.

After implantation of a lead 265, the implantable device 200 can be attached to the lead 265 (e.g. if it includes a connector as described herein), and lead 265 can be sutured to tissue. Prior to suturing or anchoring implantable device 200, a test device, such as trialing interface 80 described hereabove, can be placed outside the body to evaluate the quality of the link to one or more implantable antennas 240. Trialing interface 80 can include basic power transfer and telemetry in a simple form factor that is suitable for an operating room environment. Once the link has been confirmed to be acceptable, the implantable device 200 can be sutured or anchored in place.

Figure 4:
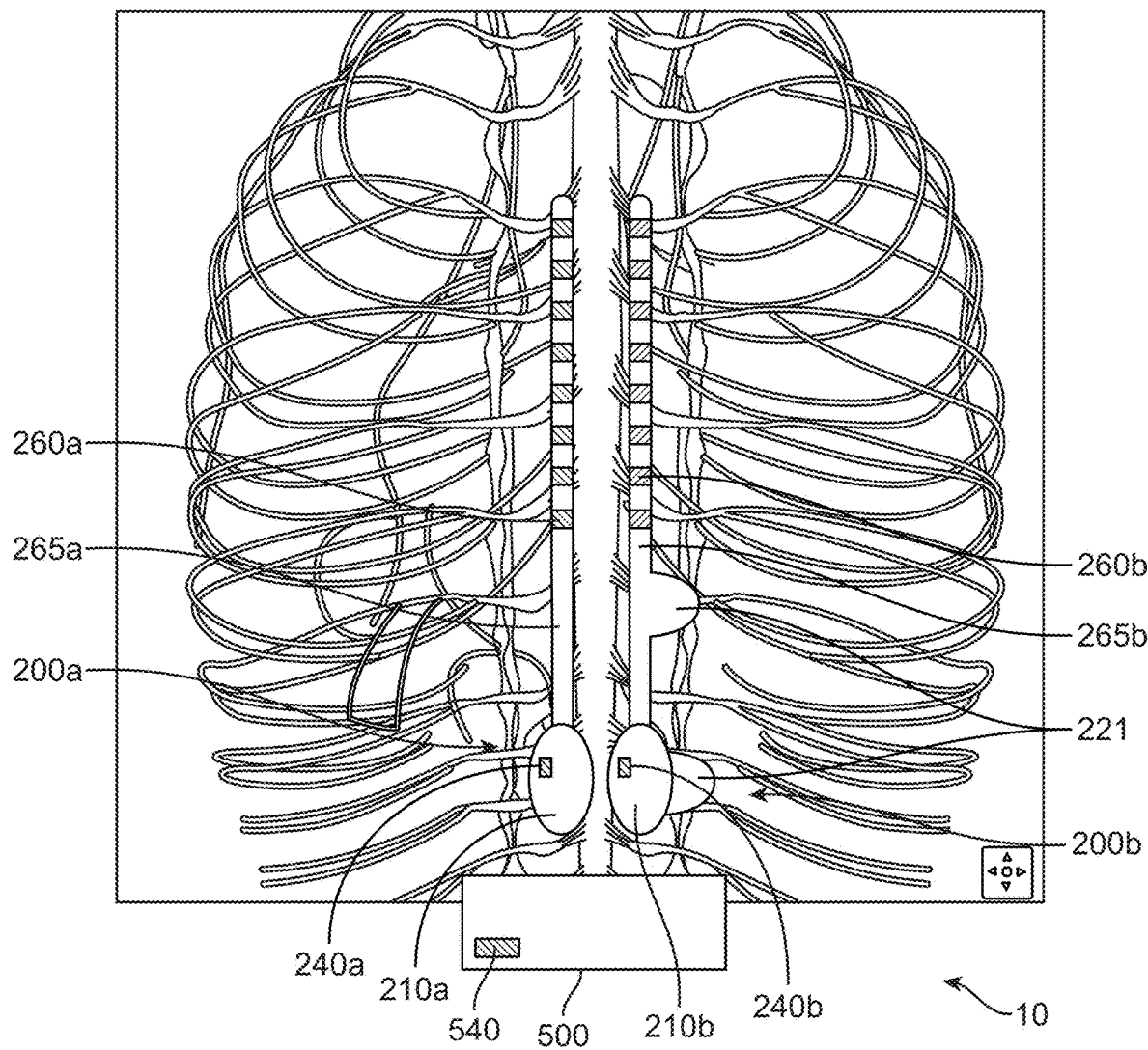
FIG. 4 is an anatomical view of a medical apparatus comprising an external device and two implantable devices, each implantable device including a lead implanted along a portion of a spine, consistent with the present inventive concepts.

Referring now to FIG. 4, an anatomical view of a medical apparatus comprising an external device and two implantable devices, each implantable device including a lead implanted along a portion of a spine, is illustrated, consistent with the present inventive concepts. Apparatus 10 of FIG. 4 comprises an external system comprising external device 500 and an internal system comprising two implantable devices 200a and 200b. Each implantable device 200 comprises a lead 265, which is attached to a housing 210. Each lead 265 comprises multiple functional elements 260 (e.g. eight functional elements 260 on each lead as shown). Each functional element 260 can comprise a transducer (e.g. an electrode configured to deliver electrical energy or other energy delivery element) and/or a sensor (e.g. an electrode configured to record electrical activity of tissue or other sensor). The two leads 265 have been inserted into the epidural space or other location proximate the spine, such as has been described hereabove in reference to FIG. 1, 2, or 3. Leads 265 have been positioned at similar but opposite lateral offsets from the center of the spine, with the sets of functional elements 260 relatively aligned along the length of the spine (i.e. vertically aligned with respect to the page). In alternative embodiments, functional elements 260a are implanted in a staggered orientation with respect to functional elements 265b, such as is described herebelow in reference to FIG. 6. Apparatus 10, external device 500, external antenna 540, implantable devices 200a and 200b, housings 210a and 210b, implantable antennas 240a and 240b, leads 265a and 265b and/or functional elements 260a and 260b can be of similar construction and arrangement to the similar components described hereabove in reference to FIG. 1 or 2.

Housings 210a and/or 210b (singly or collectively housing 210) can surround one or more components, such as implantable antenna 240 as shown. Alternatively or additionally, one or more implantable antennas 240 can be positioned outside of a housing 210, such as when an implantable antenna 240 is operatively connected to a housing 210 via a connecting filament as described herein (e.g. connecting filament 242a described hereabove in reference to FIG. 2). In the embodiment of FIG. 4, a single external device 500 (e.g. comprising one or more external antennas, such as external antenna 540 described herein) is positioned proximate the patient's skin to transmit power and/or data to implantable device 100a (e.g. via its implantable antenna 240) and implantable device 100b (e.g. via its implantable antenna 240). External device 500 can be positioned at a skin location close to (e.g. directly over) an implantable antenna 240 or at a skin location proximate a geometric center of multiple implantable antennas 240 (e.g. to transmit power and/or data to multiple antennas 240 simultaneously or sequentially). In other embodiments, external device 500 comprises a first external device 500a which transmits power and/or data to implantable device 200a and a second external device 500b which transmits power and/or data to implantable device 200b (e.g. as described hereabove in reference to FIG. 2). During use (e.g. during stimulation, recording or other operation requiring transmission of power and/or data), each external antennas 540 can be maintained in proximity to the patient's skin (e.g. at a location proximate one or more associated implantable devices 200) via adhesive or a mechanical attachment device, such as patient attachment device 70 described hereabove in reference to FIG. 1.

In some embodiments, one or more housings 210 and/or leads 265 comprise an anchor element, such as anchor element 221 shown projecting from housing 210b or anchor element 221 shown projecting from lead 265b. Anchor element 221 can be configured to receive a suture, such as to secure housing 210 and/or lead 265 to a fascia layer and/or other tissue. Anchor element 221 can comprise a penetrable portion (e.g. an elastomeric portion) and/or it can include a ring or other open structure, each configured to allow a suture, clip, staple or other tissue securing element to pass therethrough.

Figure 5:
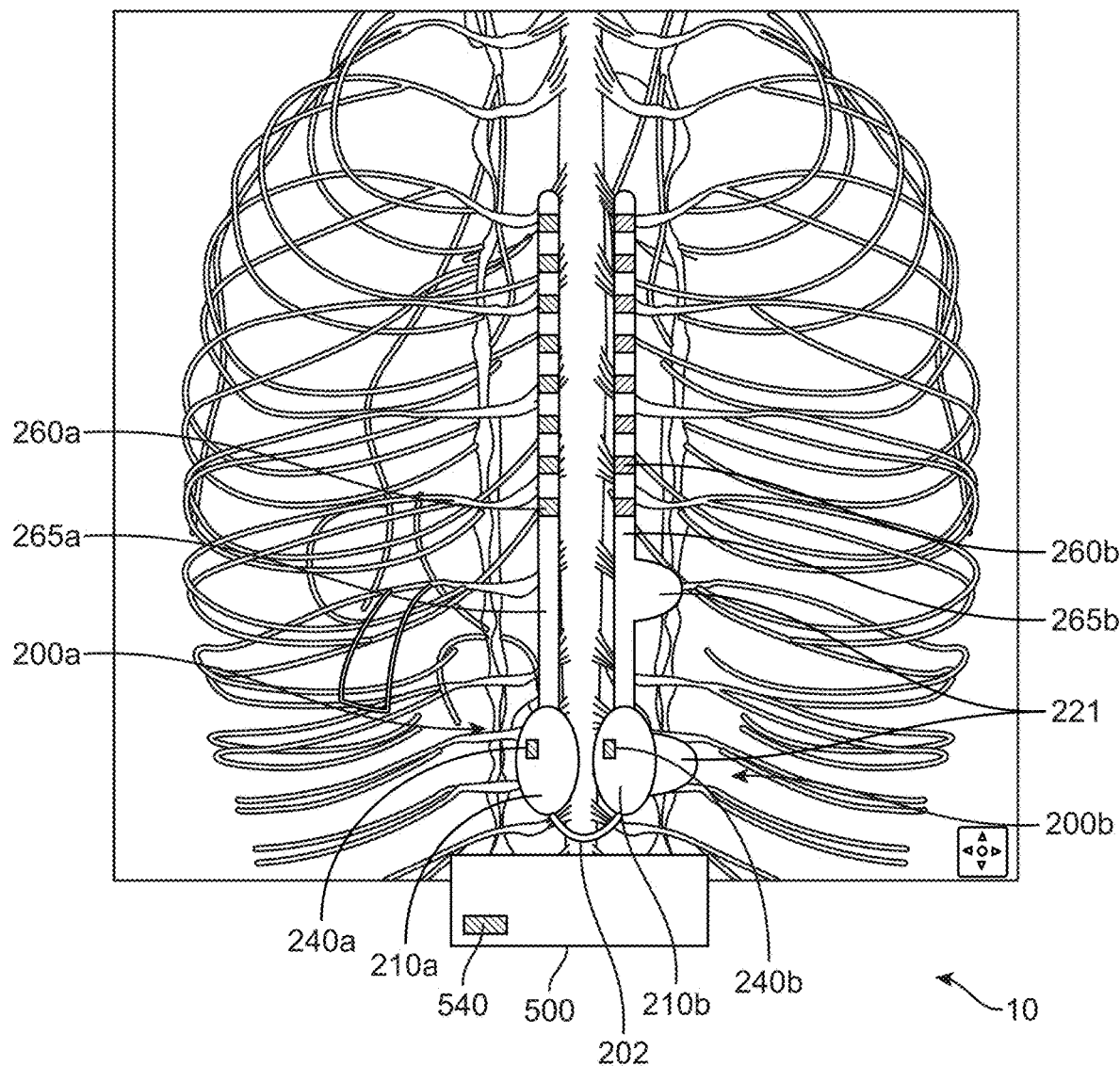
FIG. 5 is an anatomical view of a medical apparatus comprising an external device and two operatively connected implantable devices, each implantable device including a lead implanted along a portion of a spine, consistent with the present inventive concepts.

Referring now to FIG. 5, an anatomical view of a medical apparatus comprising an external device and two operatively connected implantable devices, each implantable device including a lead implanted along a portion of a spine, is illustrated, consistent with the present inventive concepts. Apparatus 10 of FIG. 5 comprises similar components to apparatus 10 of FIG. 4, with the addition of connecting filament 202 which operatively connects implantable device 200a and implantable device 200b. Connecting filament 202 can comprise one or more wires, optical fibers or other connecting filaments as defined herein. In some embodiments, connecting filament 202 comprises a connector (e.g. connector 212 as described hereabove in reference to FIG. 2) on either or both ends, and housings 210a and/or 210b comprise a mating connector (e.g. connector 205 as described hereabove in reference to FIG. 2), such that a user can attach lead 265a and/or lead 265b to housing 210a and/or 210b, respectively. Leads 265a and 265b have been implanted in a similar fashion to the leads 265a and 265b of FIG. 4, with the sets of functional elements 260ha and 265b vertically aligned as displayed on the page. Connecting filament 202 mechanically connects to housing 210a of implantable device 200a and to housing 210b of implantable device 200b. Connecting filament 202 can comprise one or more connecting filaments as described herein. Connecting filament 202 can comprise a flexible filament or can contain flexible and/or rotating portions.

Implantable devices 200a and 200b and flexible filament 202 can be configured to include an electrical signal connection (e.g. common signal path) between implantable devices 200a and 200b (e.g. between electronic circuitry of each), such as to cause current to flow from one or more electrode-based functional elements 260a and one or more functional elements 260b (e.g. by applying an electrostatic potential between an electrode-based functional element 260a and an electrode-based functional element 260b). Current flow between one or more functional elements 260a of lead 265a and one or more functional elements 260b of lead 265b can be enabled by an electrical connection between implantable device 200a and implantable device 200b that provided by one or more conductors of filament 202. This configuration of current flow between two leads 265 can stimulate different tissue that would be stimulated by delivering current between two or more functional elements 260 of a single lead 265. This configuration of current flow between two leads 265 can be arranged to "steer" current in tissue.

Alternatively or additionally, implantable devices 200a and 200b and flexible filament 202 can be configured to allow: transfer of fluids; transfer of mechanical energy (e.g. via a linkage) or other energy transfer; transfer of light signals or light energy; and combinations of one or more of these, between implantable device 200a and implantable device 200b. In some embodiments, apparatus 10 comprises three or more implantable devices 200, and one or more connecting filaments 202 operatively connect the three or more implantable devices 200.

During use, external device 500 can be positioned (e.g. one or more external antennas 540 of external device 500) on the patient's skin in close proximity to one or more implantable antennas 240, such as is described hereabove in reference to FIG. 2 or 4. Alternatively, multiple external antennas 540 (of one or more external devices 500) can each be positioned proximate one or more implantable antennas 240, such as is also described hereabove in reference to FIG. 2 or 4.

In some embodiments, housing 210a and housing 210b comprise a single housing surrounding the components described hereabove as positioned collectively within housing 210a and 210b and/or other components of an implantable system 20, such as a single housing 210 that is attachable and/or attached to both lead 265a and lead 265b. Housing 210a and/or housing 210b can be physically (e.g. via a connecting filament as described herein) and/or wirelessly connected to another implanted component, such as to transfer power and/or data to that implanted component.

Figure 6:
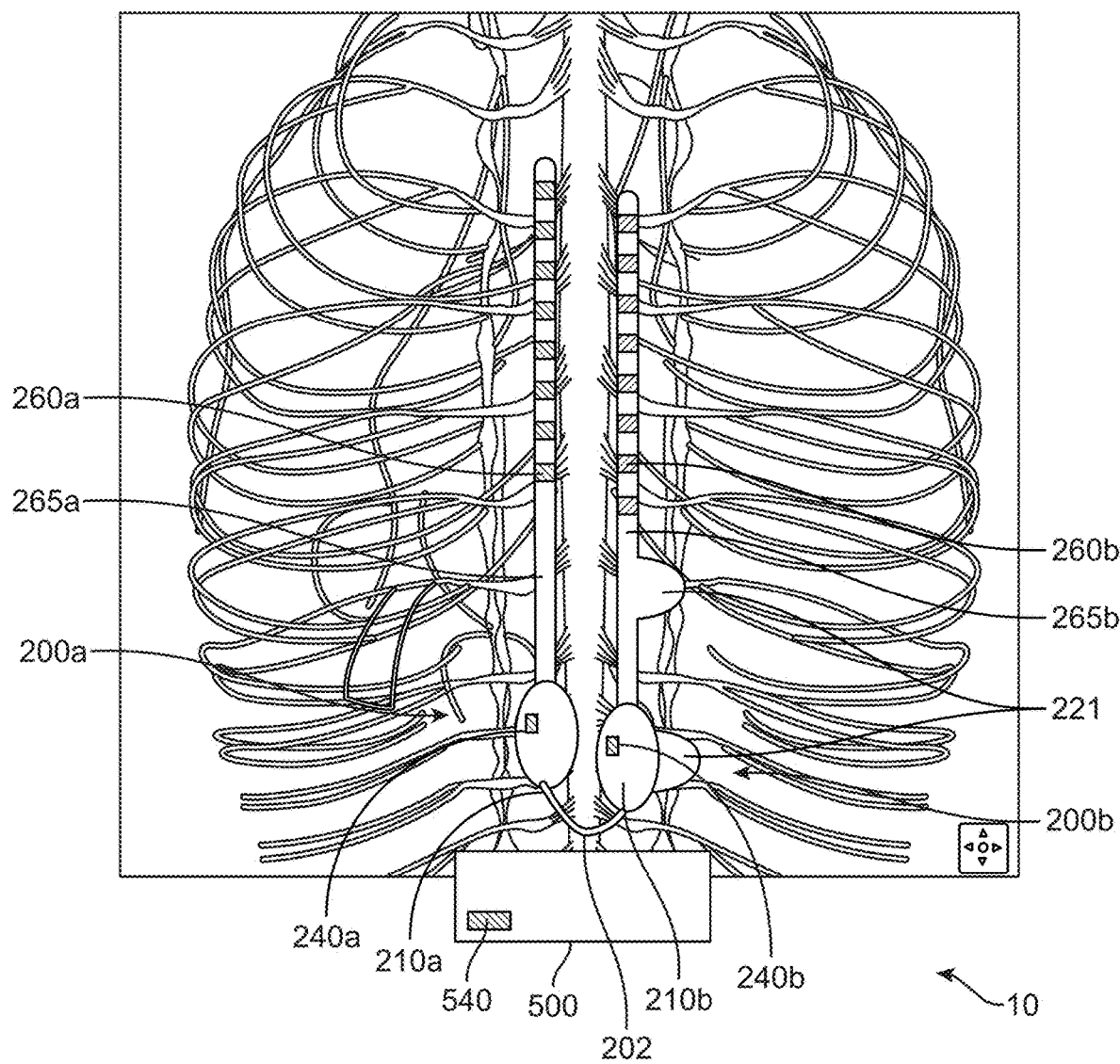
FIG. 6 is an anatomical view of a medical apparatus comprising an external device and two implantable devices, each implantable device including a lead implanted in a staggered arrangement along a portion of a spine, consistent with the present inventive concepts.

Referring now to FIG. 6, an anatomical view of a medical apparatus comprising an external device and two implantable devices, each implantable device including a lead implanted in a staggered arrangement along a portion of a spine, is illustrated, consistent with the present inventive concepts. Apparatus 10 of FIG. 6 comprises similar components to apparatus 10 of FIG. 4. In some embodiments, apparatus 10 of FIG. 6 further includes connecting filament 202, which operatively connects implantable device 200a and implantable device 200b as described hereabove in reference to FIG. 5. Leads 265a and 265b have been implanted such that functional elements 260a and 260b are vertically offset as displayed on the page. In an alternative embodiment, lead 265a and lead 265b have functional elements 260 positioned at different locations (e.g. at different axial locations along the length of each lead 265) such that each lead 265 can be positioned at the same relative vertical position of the spine and the sets of functional elements 260 will be at different vertical positions. This configuration of staggered functional elements 260 can be arranged to stimulate additional and/or different tissue than would be stimulated in a non-staggered configuration.

In some embodiments, housings 210a and 210b comprise a single housing 210 which attaches to each of leads 265a and 265b.

Figure 7:
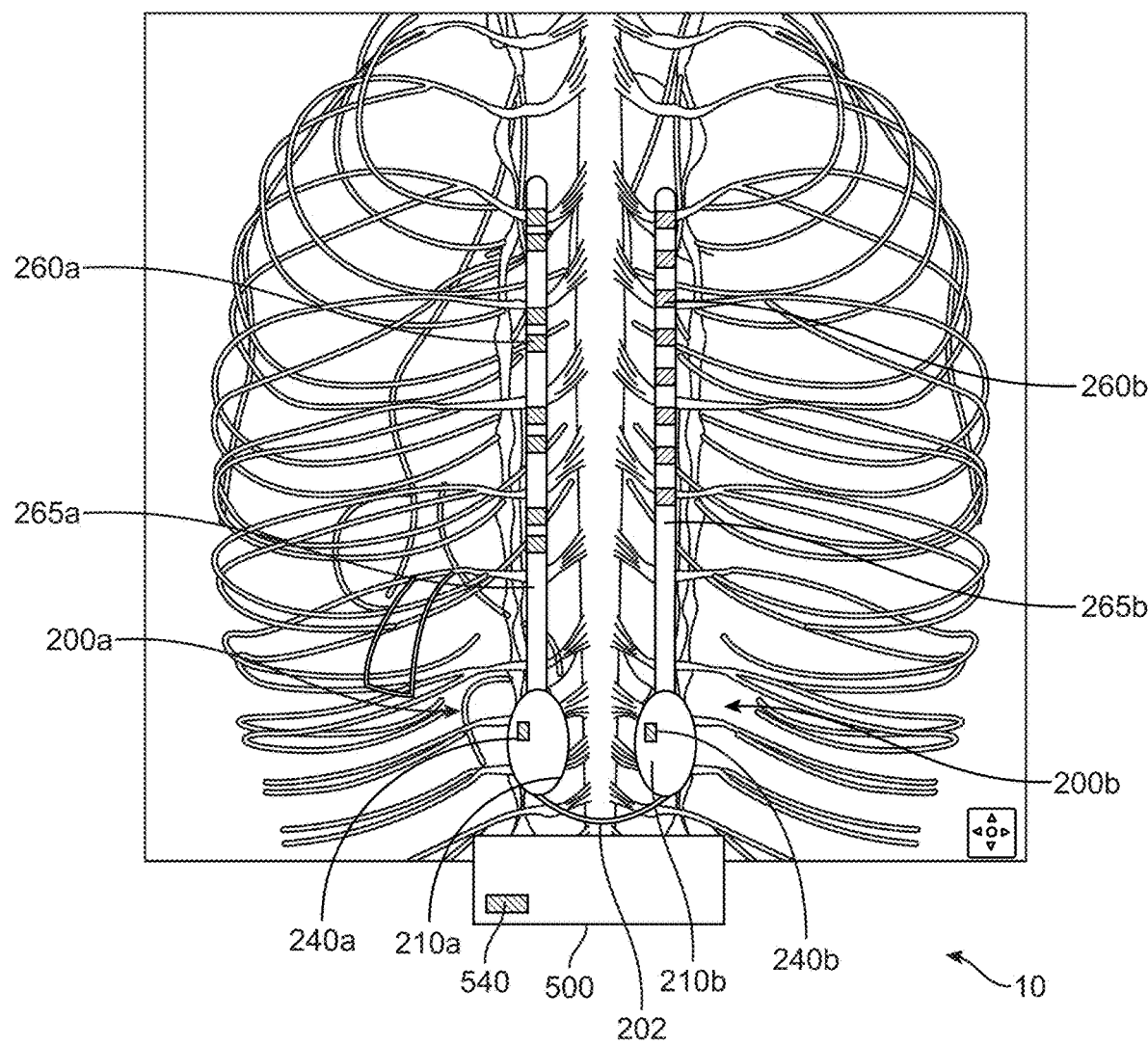
FIG. 7 is an anatomical view of a medical apparatus comprising an external device and two implantable devices, each implantable device including a lead implanted to stimulate dorsal root ganglia, consistent with the present inventive concepts.

Referring now to FIG. 7, an anatomical view of a medical apparatus comprising an external device and two implantable devices, each implantable device including a lead implanted to stimulate dorsal root ganglia, is illustrated, consistent with the present inventive concepts. Apparatus 10 of FIG. 7 comprises similar components to apparatus 10 of FIG. 4. In some embodiments, apparatus 10 of FIG. 7 further includes connecting filament 202, which operatively connects implantable device 200a and implantable device 200b as described hereabove in reference to FIG. 5. Leads 265a and 265b have been implanted such that functional elements 260a and 260b are positioned to stimulate dorsal root ganglia (DRG) of the spine (e.g. at a greater lateral offset from the center of the spine than the positioning illustrated in FIGS. 4, 5 and 6 such that functional elements 260 are in closer proximity to dorsal root ganglion). In some embodiments, lead 265 is implanted in relative proximity to the DRG and outside of the epidural space. In some embodiments, lead 265 comprises multiple functional elements 260 (e.g. multiple electrodes) configured to stimulate (e.g. electrically stimulate) multiple dorsal root ganglia, simultaneously or sequentially. Functional elements 260a and 260b can be vertically aligned (as described hereabove in reference to FIG. 4 or 5) and/or they can be vertically offset (as described hereabove in reference to FIG. 6). Apparatus 10 can comprise additional (i.e. three or more), implantable devices 200 and/or additional leads 265 (e.g. when one or more implantable devices 200 includes multiple leads 265 as described herebelow), such as to simplify placement, to improve simulation of DRG or other tissue and/or to reduce adverse effects that might be caused due to leads 265 migration.

In some embodiments, housings 210a and 210b comprise a single housing 210 which attaches to each of leads 265a and 265b.

Figure 8:
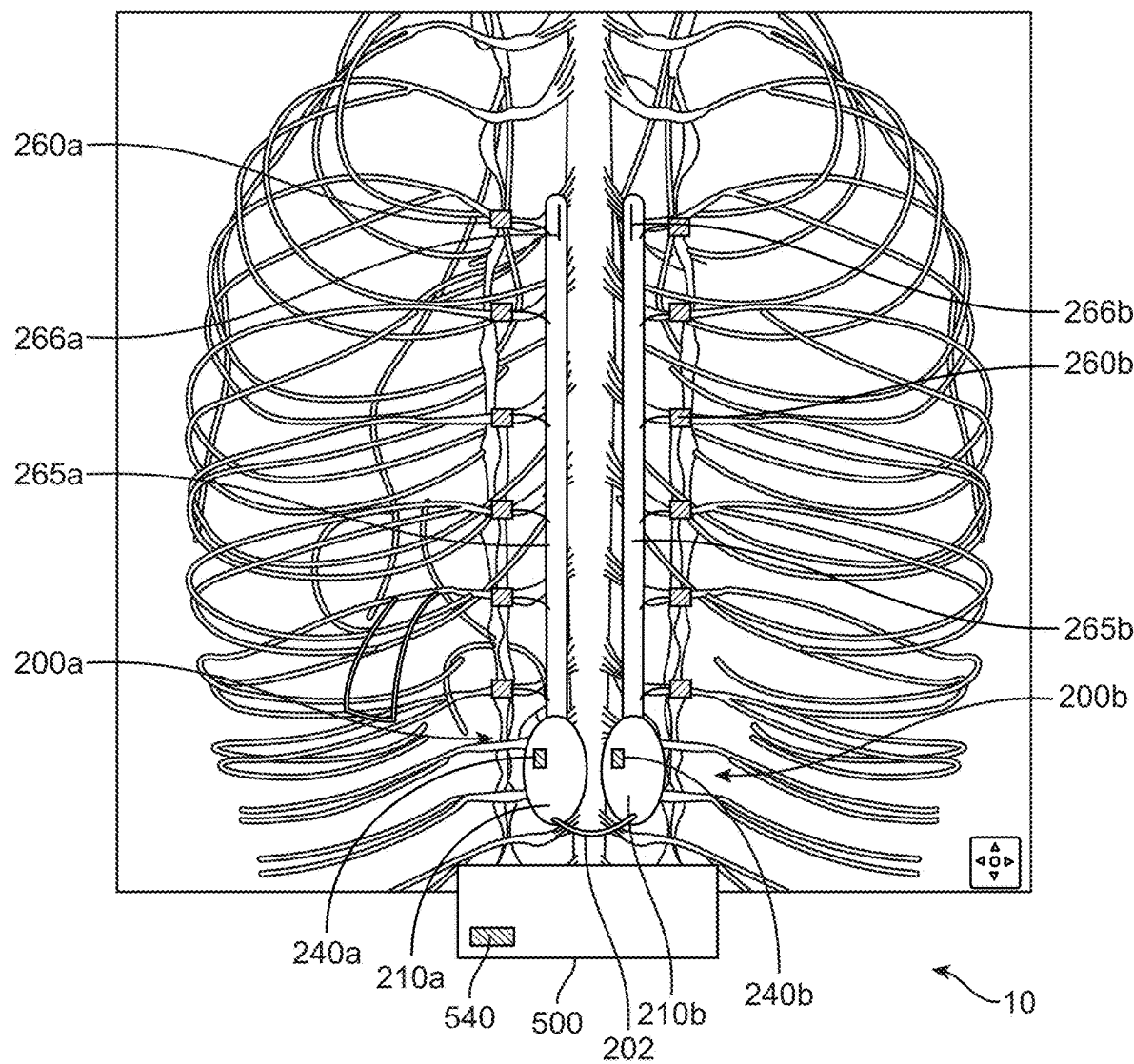
FIG. 8 is an anatomical view of a medical apparatus comprising an external device and two implantable devices, each implantable device including a lead comprising advanceable functional elements, consistent with the present inventive concepts.

Referring now to FIG. 8, an anatomical view of a medical apparatus comprising an external device and two implantable devices, each implantable device including a lead comprising advanceable functional elements is illustrated, consistent with the present inventive concepts. Apparatus 10 of FIG. 8 comprises similar components to apparatus 10 of FIG. 4. In some embodiments, apparatus 10 of FIG. 8 further includes connecting filament 202, which operatively connects implantable device 200a and implantable device 200b as described hereabove in reference to FIG. 5. Leads 265a and 265b have been implanted at a location medial to dorsal root ganglia (i.e. towards the center of the spine). Leads 265 can comprise functional elements 260 that are configured to be advanced (e.g. laterally advanced), from the associated lead 265. In some embodiments, a lead 265 comprises one or more advanceable functional elements 260 and one or more functional elements 260 that are in a fixed position relative to lead 265 (i.e. non-advanceable).

In some embodiments, each lead 265 comprises one or more lumens 266, such as one or more lumens 266a and 266b shown. Each lumen 266 can be constructed and arranged to allow one or more functional elements to slidingly translate within the lumen 266, and to exit (i.e. laterally deploy from) an opening in the outer surface of lead 265 in communication with the lumen 266. In these embodiments, each functional element 260 (e.g. an electrode) can be attached to and/or otherwise advanced via a mechanical linkage, fluid drive, magnetic drive and/or other driving means that is accessible via or otherwise controlled by lead 265 and/or housing 210 (e.g. via a port attached to housing 210 and/or lead 265 that is in communication with one or more lumens 266. In some embodiments, a lead 265 comprises a single lumen 266 and multiple functional elements 260 are sequentially advanced out of different openings of lead 265 using one or more steering or other advancement techniques (e.g. a technique in which a first functional element 260 is advanced out of a most distal opening of lead 265, and a second functional element 260 is advanced out of a second most distal opening, and so on). In an alternative embodiment, lead 265 comprises multiple lumens 266, each in communication with a single opening of lead 265, and each including a linkage or other mechanism configured to individually advance an associated functional element 260 out of lead 265, such as to position one or more functional elements 260 at a location offset from lead 265 (e.g. a location not directly available for lead 265 implantation).

In some embodiments, leads 265 are implanted and functional elements 260 are advanced, such that the functional elements 260 are positioned to stimulate dorsal root ganglia (DRG) of the spine. Alternatively or additionally, a lead 265 can be implanted and one or more functional elements 260 can be advanced toward any nerve, muscle or other tissue (e.g. as described herein), such as when positioning of lead 265 closer to a target stimulation site is difficult or otherwise undesirable. After advancement, functional elements 260a and 260b can be vertically aligned (as described hereabove in reference to FIG. 4 or 5) and/or they can be vertically offset (as described hereabove in reference to FIG. 6). Apparatus 10 can comprise additional (i.e. three or more), implantable devices 200 and/or additional leads 265 (e.g. when one or more implantable devices 200 includes multiple leads 265 as described herebelow), such as to simplify placement, to improve simulation of DRG or other tissue and/or to reduce adverse effects that might be caused due to lead 265 and/or functional element 260 migration.

In some embodiments, housings 210a and 210b comprise a single housing 210 which attaches to each of leads 265a and 265b. Leads 265a and/or 265b can be placed in the epidural space (e.g. on either side over the dorsal columns), and the functional elements 260 advanced towards the DRG (e.g. and optionally anchored in place). In some embodiments, leads 265a and/or 265b comprise multiple functional elements 260 (e.g. electrodes), such that multiple dorsal root ganglia can be stimulated (e.g. simultaneously or sequentially).

Figure 9:
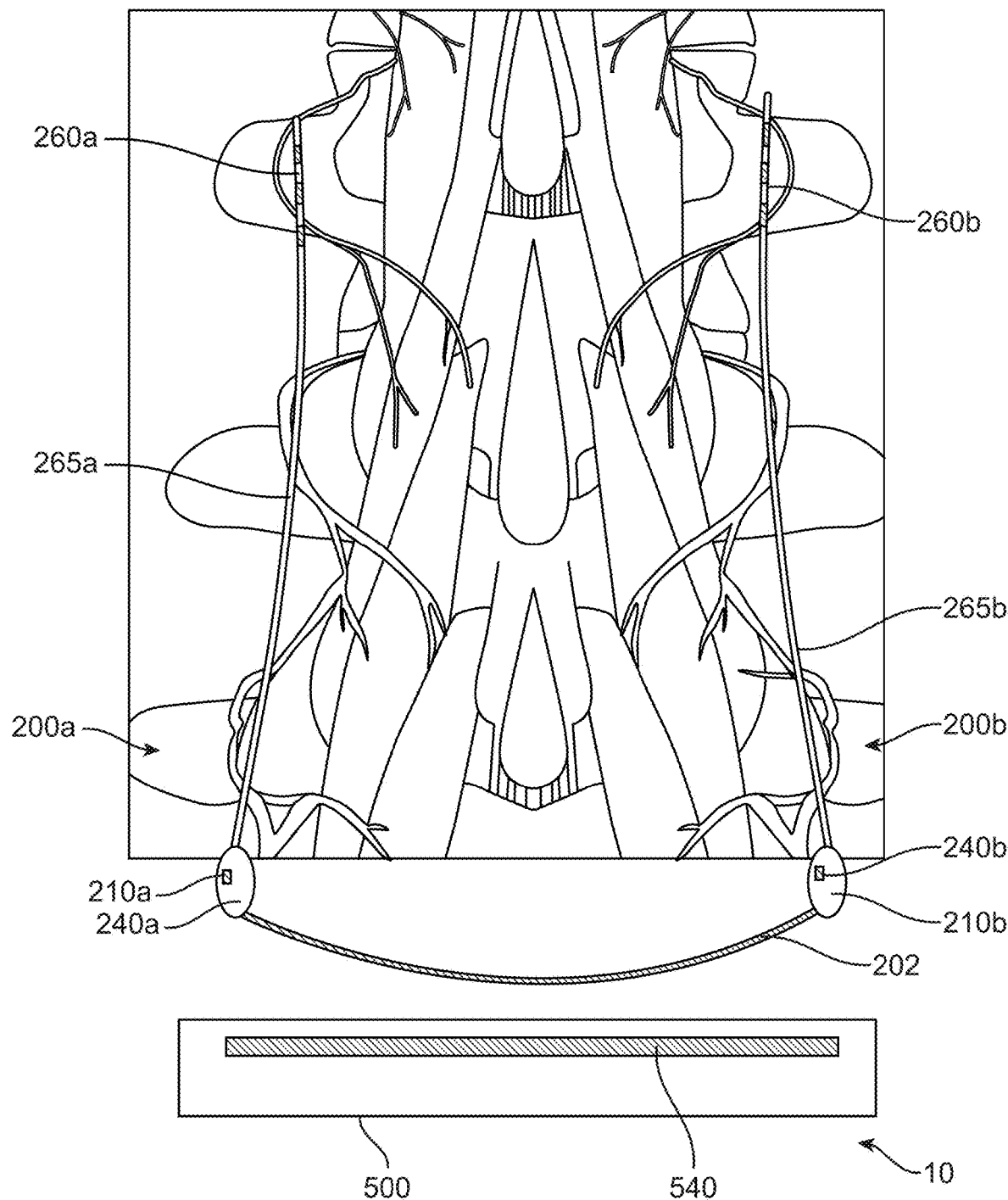
FIG. 9 is an anatomical view of a medical apparatus comprising an external device and two implantable devices, each implantable device including a lead implanted to stimulate muscle tissue of the spine, consistent with the present inventive concepts.

Referring now to FIG. 9, an anatomical view of a medical apparatus comprising an external device and two implantable devices, each implantable device including a lead implanted to stimulate muscle tissue of the spine, is illustrated, consistent with the present inventive concepts. Apparatus 10 of FIG. 9 comprises similar components to apparatus 10 of FIG. 4. In some embodiments, apparatus 10 of FIG. 9 further includes connecting filament 202, which operatively connects implantable device 200a and implantable device 200b as described hereabove in reference to FIG. 5. Leads 265a and 265b have been implanted such that functional elements 260a and 260b are positioned to stimulate muscle tissue of the spine, such as multifidus muscle tissue of the spine, such as to improve spinal stability. In some embodiments, one or more functional elements 260 are positioned to stimulate tissue selected from the group consisting of: multifidus tissue; transverse abdominus tissue; quadratus lumborum tissue; psoas major tissue; internus abdominus tissue; obliquus externus abdominus tissue; erector spinae tissue; and combinations of one or more of these.

Functional elements 260a and 260b can be vertically aligned (as described hereabove in reference to FIG. 4 or 5) and/or they can be vertically offset (as described hereabove in reference to FIG. 6). Apparatus 10 can comprise additional (i.e. three or more), implantable devices 200 and/or additional leads 265 (e.g. when one or more implantable devices 200 includes multiple leads 265 as described herebelow), such as to simplify placement, to improve simulation of DRG or other tissue and/or to reduce adverse effects that might be caused due to lead 265 migration.

In some embodiments, housings 210a and 210b comprise a single housing 210 which attaches to each of leads 265a and 265b.

Figure 10:
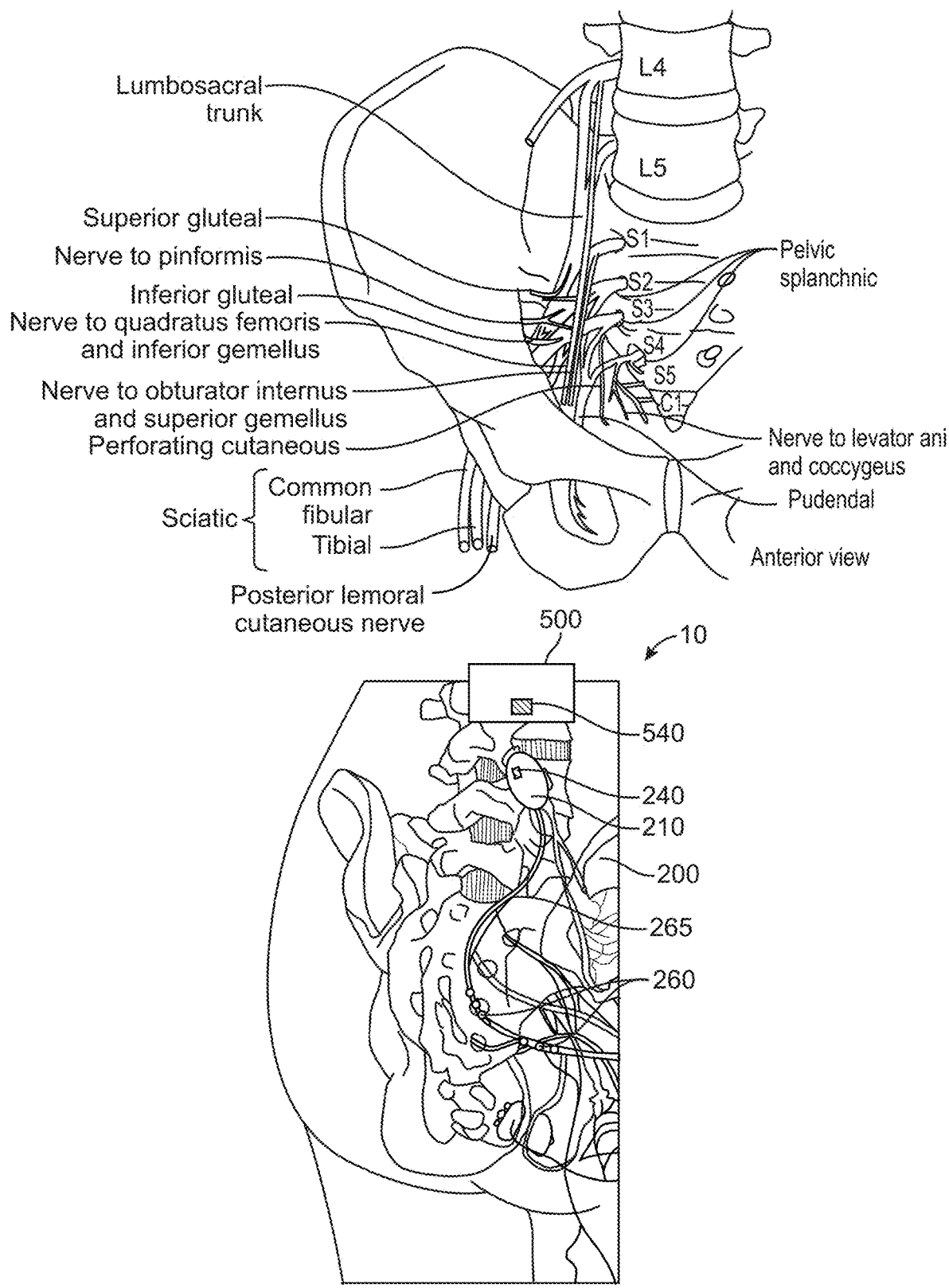
FIG. 10 is an anatomical schematic of a human pelvis and an anatomical view of a medical apparatus for treating pelvic pain and comprising an external device and an implantable device, consistent with the present inventive concepts.

Referring now to FIG. 10, an anatomical schematic of a human pelvis and an anatomical view of a medical apparatus for treating pelvic pain and comprising an external device and an implantable device is illustrated, consistent with the present inventive concepts. Apparatus 10 of FIG. 10 comprises similar components to apparatus 10 of FIG. 4, with the exception of a single implantable device 200. In some embodiments, apparatus 10 comprises two or more implantable devices 200, such as to stimulate multiple stimulation sites and/or to communicate with one or more external devices 500 to be positioned at various skin locations, as is described in detail herein. Lead 265 has been implanted such that functional elements 260 are positioned to stimulate tissue to treat pelvic pain, such as one or more functional elements 260 (e.g. electrodes) positioned to stimulate sacral nerve tissue.

In some embodiments, lead 265 and housing 210 of implantable device 200 is constructed and arranged (e.g. of sufficiently small size) to be implanted while avoiding tunneling through bone. An imaging device (e.g. a portable c-arm fluoroscope) can be used to identify the midline of the spine and level of the S3 foramen. The skin can be marked and the area infiltrated with local anesthetic. Under fluoroscopic or other imaging guidance, Foramen needles can then be inserted into the S3 foramen on each side at approximately a 60° angle relative to the skin. A lateral image can be used to confirm the location and depth in the foramen. The needles can receive stimulation energy to confirm appropriate positioning. If the needles are in the correct position during stimulation, there will be bellows contraction of the pelvic floor due to contraction of the levator muscles and plantar flexion of the great toe. The patient, if awake, will be able to confirm correct positioning by noticing contraction and/or tingling of the pelvic floor muscles. If the needles are in the S2 foramen, plantar flexion of the whole foot with lateral rotation will occur with the stimulation. If the needles are in the S4 foramen, there will be no lower extremity movement despite bellows response. Once correct positioning of the needles has been confirmed, a lead 265 can be advanced through each of the foramen needles, and the needles subsequently removed carefully to prevent dislodgement of the leads 265. Implantable device 200 can be configured to be implanted outside of bone, at a location in the lower back of the patient or directly over the sacrum.

In some embodiments, one or more leads 265 can be positioned to stimulate (e.g. electrically stimulate) sacral nerves, such as to treat overactive bladder syndrome, incontinence, fecal incontinence, interstitial cystitis and/or pelvic disorders. One or more leads 265 can also be placed such that the sacral roots are stimulated within the foramen, rather than anterior to the sacrum. To facilitate stimulation within the foramen, apparatus 10 can be configured to deliver very short stimulus pulse-widths (e.g. 5 or 10 microsecond). One or more leads 265 can include tines, barbs and/or other fixation means to aid in the anchoring within the foramen. The leads 265 can be left implanted in the patient provided they have a successful (e.g. safe and efficacious) trial.

Figure 11:
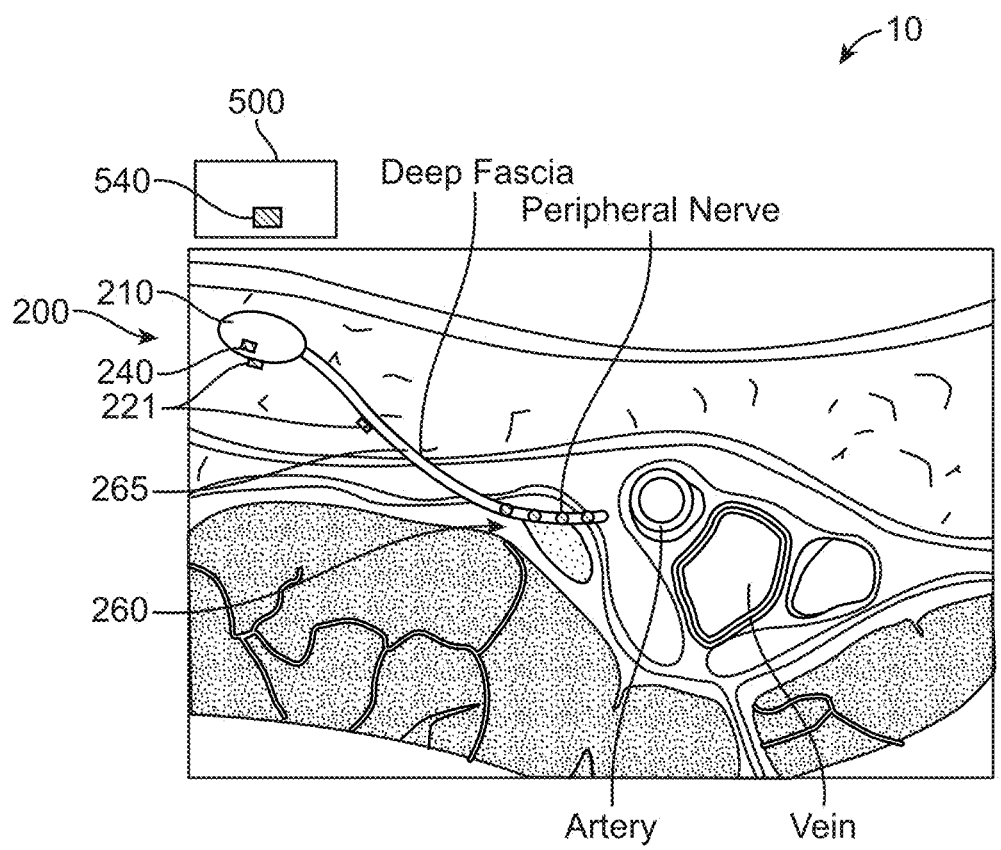
FIG. 11 is an anatomical view of a medical apparatus for stimulating peripheral nerves and comprising an external device and an implantable device, consistent with the present inventive concepts.

Referring now to FIG. 11, an anatomical view of a medical apparatus for stimulating peripheral nerves and comprising an external device and an implantable device is illustrated, consistent with the present inventive concepts. Apparatus 10 of FIG. 11 comprises similar components to apparatus 10 of FIG. 4, with the exception of a single implantable device 200. In some embodiments, apparatus 10 comprises two or more implantable devices 200, such as to stimulate multiple stimulation sites and/or to communicate with one or more external devices 500 to be positioned at various skin locations, as is described in detail herein. Lead 265 has been implanted such that functional elements 260 are positioned to stimulate one or more peripheral nerves. In some embodiments, functional elements 260 are positioned to stimulate tibial nerve tissue. In some embodiments, functional elements 260 are positioned such that stimulation energy treats one or more of: back pain, diabetic neuropathy; angina; incontinence, overactive bladder; fecal incontinence; and combinations of one or more of these. In some embodiments, functional elements 260 are positioned such that stimulation energy improves physical therapy, such as when functional elements 260 are positioned to stimulate a peripheral nerve at least during a physical therapy treatment. In these embodiments, apparatus 10 can be configured such that one or more functional elements 260 deliver stimulation energy only during a physical therapy treatment.

In some embodiments, housing 210 and/or lead 265 comprise an anchor element 221, such as has been described hereabove, such as to anchor housing 210 and/or lead 265 to deep fascial tissue. Anchor element 221 can be configured to be anchored to tissue with suture, clips or staples as described hereabove. In some embodiments, one of housing 210 or lead 265 is anchored via anchor element 221, and the other of housing 210 or lead 265 is unanchored (i.e. allowed to move in tissue).

Figure 12:
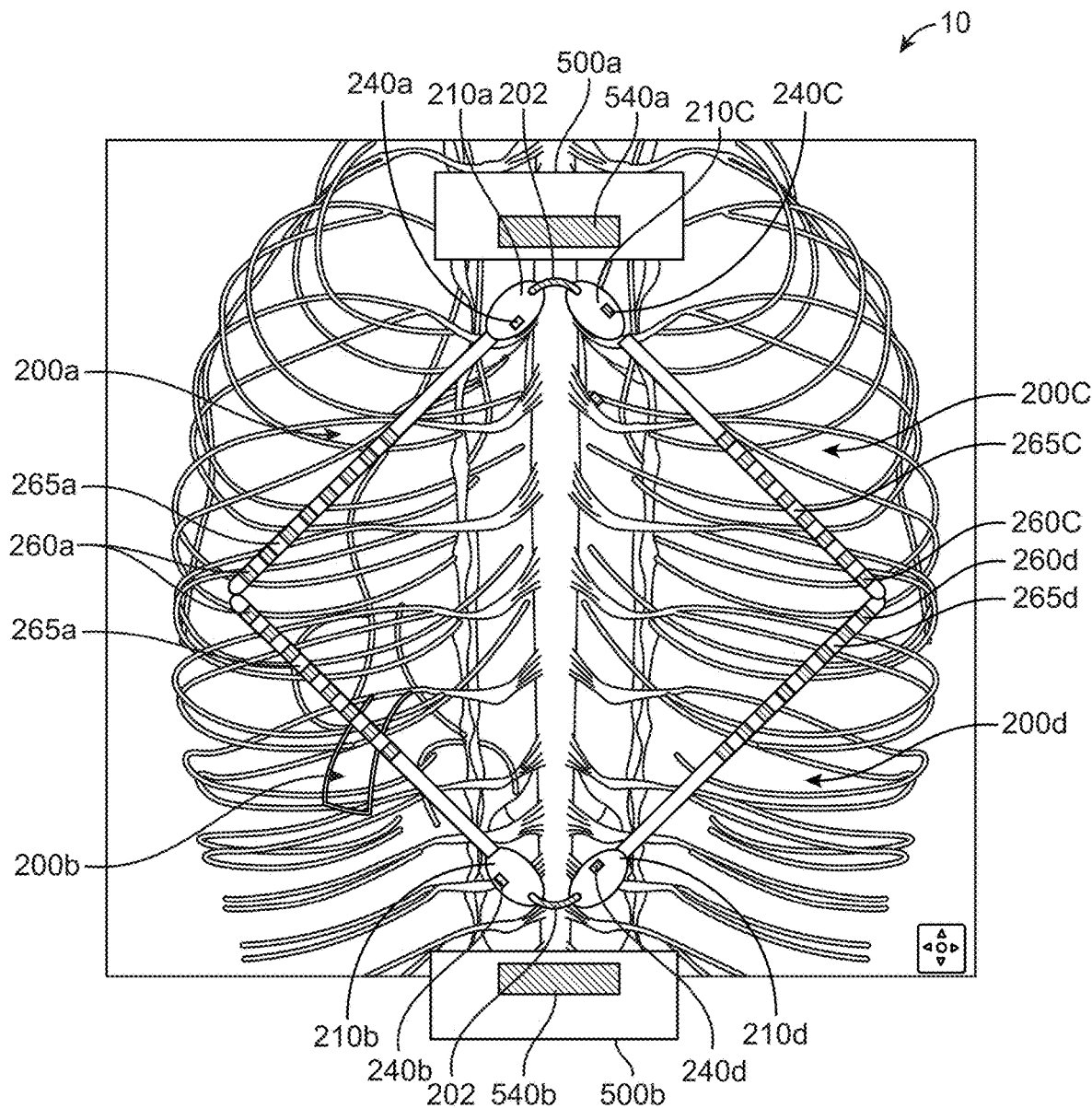
FIG. 12 is an anatomical view of a medical apparatus comprising multiple external devices and multiple implantable devices, each implantable device including a lead implanted as part of a pre-determined lead pattern, consistent with the present inventive concepts.

Referring now to FIG. 12, an anatomical view of a medical apparatus comprising multiple external devices and multiple implantable devices, each implantable device including a lead implanted as part of a pre-determined lead pattern, is illustrated, consistent with the present inventive concepts. Apparatus 10 of FIG. 12 comprises similar components to apparatus 10 of FIG. 4, and includes two external devices 500a and 500b, each including an external antenna 540 which can comprise one or more antennas as described herein. In some embodiments, apparatus 10 of FIG. 12 further includes one or more connecting filaments 202 (two shown), each of which configured to operatively connect two implantable devices 200, such as is described hereabove in reference to FIG. 5. Implantable devices 200a and 200b have been connected via a connecting filament 202 and leads 265a and 265b have been implanted such that any of functional elements 260a and/or 260b can transmit current between each other (i.e. between two functional elements 260a, between two functional elements 260b and/or between a functional element 260a and a functional element 260b). Similarly, implantable devices 200c and 200d have been connected via a connecting filament 202 and leads 265c and 265d have been implanted such that any of functional elements 260c and/or 260d can transmit current between each other. Each of functional elements 260a, 260b, 260c and 260d can be configured to stimulate tissue, such as tissue of the spine, such as nerve, muscle and other tissue in and/or proximate the spine. Leads 265a-d and their associated functional elements 260a-d can be arranged in one or more pre-determined patterns, such as the diamond pattern shown in FIG. 12. Numerous patterns of functional elements 260 can be accomplished, such as when apparatus 10 comprises one or more leads 265, connected to one or more implantable devices 200. While the leads 265 are shown in a relatively linear placement, curvilinear placements can be accomplished as well, such as a curvilinear trajectory of one or more leads 265 in two or three dimensions.

In some embodiments, leads 265a and 265b include mating connectors (e.g. at their distal ends) configured to allow operative connection (e.g. electrical connection) of leads 265a to 265b prior to, during or after implantation of leads 265a and 265b. Similarly, leads 265c and 265d can be configured for connection to each other, such as to allow current to pass between any of the functional elements 260 on any of the leads 265.

In some embodiments, housings 210a and 210b comprise a single housing 210 which attaches to each of leads 265a and 265b.

Figure 13:
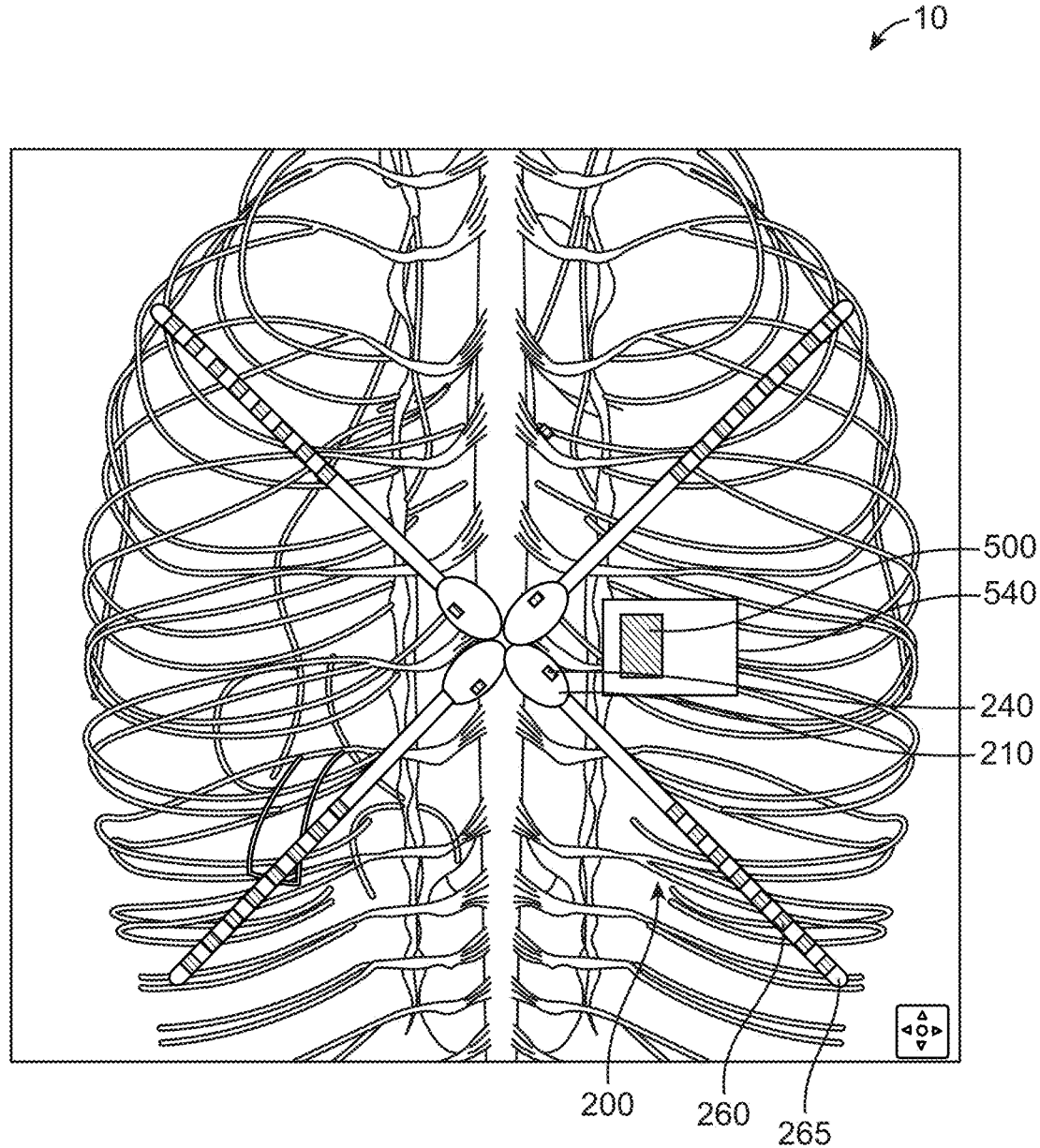
FIG. 13 is an anatomical view of a medical apparatus comprising a single external device and multiple implantable devices, each implantable device including a lead implanted as part of a pre-determined lead pattern, consistent with the present inventive concepts.

Referring now to FIG. 13, an anatomical view of a medical apparatus comprising a single external device and multiple implantable devices, each implantable device including a lead implanted as part of a pre-determined lead pattern, is illustrated, consistent with the present inventive concepts. Apparatus 10 of FIG. 13 comprises similar components to apparatus 10 of FIG. 4, and includes multiple implantable devices 200 (four shown), each comprising a lead 265 comprising one or more functional elements 260 (e.g. the eight electrodes shown on each lead 265). In some embodiments, apparatus 10 of FIG. 12 further includes one or more connecting filaments 202 (none shown), each of which can be configured to operatively connect two or more implantable devices 200, such as is described hereabove in reference to FIG. 5. Connection of two or more implantable devices 200 can allow transmission of current between one or more functional elements 260 on a first lead 265 to one or more functional elements 260 on one or more different leads 265 (in addition to current that can flow between functional elements 260 on the same lead 265). Each of functional elements 260 can be configured to stimulate tissue, such as tissue of the spine, such as nerve, muscle and other tissue in and/or proximate the spine. Leads 265 and their associated functional elements 260 can be arranged in one or more pre-determined patterns, such as the "X" pattern shown in FIG. 13. Numerous patterns of functional elements 260 can be accomplished, such as when apparatus 10 comprises one or more leads 265, connected to one or more implantable devices 200. While the leads 265 are shown in a relatively linear placement, curvilinear placements can be accomplished as well, such as a curvilinear trajectory of one or more leads 265 in two or three dimensions.

In some embodiments, housings 210a and 210b comprise a single housing 210 which attaches to each of leads 265a and 265b.

FIGS. 14-19D illustrate various configurations of implantable devices 200 of the present inventive concept. In some embodiments, an implantable device 200 of FIGS. 14-20 is of similar construction and arrangement to implantable device 200 of FIG. 1 or 2. Alternatively or additionally, an implantable device 200 of FIGS. 14-19D is of similar construction and arrangement to one or more of the implantable devices described in applicant's co-pending U.S. Provisional Patent Application Ser. No. 62/112,858, titled "Medical Apparatus including an Implantable System and an External System", filed Feb. 6, 2015, the content of which is incorporated herein by reference in its entirety. Each implantable device 200 comprises at least one housing 210 which surrounds one or more power and/or or data handling components, stimulation components, drug delivery components and/or sensing components as described herein. Housing 210 can surround one or more components described hereabove in reference to FIG. 1 or 2, such as: energy storage assembly 270, controller 250, reservoir 225 and/or receiver 230. In some embodiments, housing 210 surrounds an implantable antenna 240 comprising one or more implantable antennas 240 (e.g. two orthogonal antennas). Alternatively or additionally, an implantable antenna 240 is attached to housing 210 via a connecting filament, such as connecting filament 242 described herein. In some embodiments, two or more implantable antennas 240 are connected (e.g. electrically connected) to housing 210 via a corresponding two or more connecting filaments 242. Housing 210 can be operatively connected (e.g. electrically, fluidly, optically or mechanically connected) to one or more leads 265, and each lead 265 can comprise one or more functional elements 260 (e.g. electrodes configured to deliver electrical energy; electrodes configured to sense electrical activity; light delivery elements, drug or other agent delivery elements; ultrasound delivery elements; energy delivery elements; sensors; and combinations of one or more of these). Housing 210 can comprise one or more portions and/or one or more materials that are transmissive to radiofrequency transmissions, such as at least a portion of housing 210 that comprises glass and/or ceramic. Housing 210 can comprise a covering, such as an atraumatic covering which includes at least a portion transmissive to radiofrequency signals, such as covering 218 described herebelow in reference to FIG. 15. Housing 210, lead 265 and/or another component of implantable device 200 can comprise one or more anchor elements 221, such as is described hereabove in reference to FIG. 1.

Referring now to FIGS. 14A and 14B, an exploded view and an assembled view of an implantable device comprising an implantable housing surrounding multiple antennas and various electrical components is illustrated, consistent with the present inventive concepts. Implantable device 200 of FIGS. 14A-B comprises a three piece housing 210 comprising housing portions 210a, 210b and 210c as shown, which can be attached (e.g. sealed) to each other during assembly of each implantable device 200. Attachment of one housing 210 portion to another housing 210 portion can be performed using epoxy or another adhesive. Alternatively or additionally, attachment of one housing 210 portion to another housing 210 portion can be performed using a bonding method (e.g. solvent bonding and/or ultrasonically-activated agent bonding), welding (e.g. laser welding or ultrasonic welding) and/or mechanical fixation (e.g. swaging). Implantable device 200 comprises substrate 211 (e.g. a foldable printed circuit board or other foldable substrate), onto which components 216 are operably attached (e.g. soldered or crimped), and implantable antenna 240 comprising one or more antennas such as antennas 240a and 240b shown. Components 216 can comprise an ASIC, such as an ASIC wire-bonded and/or flip-chip bonded to substrate 211. Substrate 211, components 216 and antennas 240a and 240b are constructed and arranged to fit within housings 210a-c when assembled.

In some embodiments, one or more functional elements (not shown but such as functional elements 260 described herein) are positioned on housing 210 (e.g. and electrically connected to one or more components 216). In some embodiments, housing 210 comprises a connector for attachment to a lead 265. Alternatively or additionally, implantable device 200 further comprises feedthroughs 213, for attachment to lead 265 or other component external to an assembled housing 210. Feedthroughs 213 can comprise a high-density array of feedthroughs or other feedthrough array configured to allow wires to pass through housing 210 and/or to allow wires inside of housing 210 to be electrically connected to wires outside of housing 210 (e.g. connections made at each feedthrough of feedthroughs 213). In some embodiments, feedthroughs 213 are configured to attach (e.g. electrically attach) a lead (e.g. lead 265 comprising one or more functional elements 260) to substrate 211 and/or components 216.

In some embodiments, feedthroughs 213 are positioned away from antenna 240 (e.g. proximate substrate 211 and/or components 216 as shown), such as to avoid destructive interference with coupling of the power and/or data link transmitted between external system 50 and antenna 240. Feedthroughs 213 can be positioned in any of housings 210a (as shown), 210b and/or 210c.

In some embodiments, one or more conductors (e.g. conductive pads or posts) of feedthroughs 213 are electrically connected to one or more wires electrically connected to components 216 and/or functional elements 260, the electrical connection created by one or more of: soldering; crimping; wire bonding; welding such as laser welding or ultrasonic welding; tab bonding; applying a conductive adhesive such as a conductive epoxy; tab welding (e.g. welding a folded flap with mating metal pads); and combinations of one or more of these. In some embodiments, one or more electrical connections are made at or via feedthroughs 213, such as via a wire (e.g. a platinum wire) that is crimped to a conductive ribbon (e.g. a fold ribbon). The ribbon can be welded to one or more feedthroughs (e.g. a post) of feedthroughs 213.

In some embodiments, housing 210 comprises a two-piece housing (e.g. constructed of two discrete housing portions), such as when housings 210a and 210b comprise a single housing, or housings 210b and 210c comprise a single housing. Housing 210 can comprise one or more materials, such as glass, ceramic and/or a plastic (e.g. urethane). In some embodiments, housing 210 comprises a metal such as titanium, such as when one or more housing 210 portions are brazed together and antenna 240 is positioned outside of housing 210.

In some embodiments, housing 210 comprises a major axis less than or equal to 50 mm, such as a major axis less than or equal to 25 mm, 20 mm, 15 mm, 12 mm or 10 mm. In some embodiments, housing 210 comprises a minor axis less than or equal to 20 mm, such as a minor axis less than or equal to 10 mm, 8 mm, 6 mm or 5 mm. Housing 210 can comprise a wall thickness between 0.2 mm and 2.0 mm, such as a wall thickness between 0.2 mm and 0.5 mm, 0.2 mm and 1.0 mm, 0.5 mm and 1.5 mm, or approximately 1.3 mm or 0.3 mm. Implantable device 200 further comprises antennas 240, such as the two antennas 240a and 240b shown positioned on relatively orthogonal planes of a portion of substrate 211 (e.g. a foldable portion of substrate 211). Implantable device 200 further comprises components 216, which have been positioned on substrate 211, such as when substrate 211 comprises a printed circuit board (e.g. a flexible printed circuit board) comprising one or more electrical traces electrically connecting one or more components 216 and/or one or more of antennas 240. Components 216 can be configured to function as one or more assemblies of implantable device 200, such as receiver 230, controller 250, functional element 260 and/or energy storage assembly 270 as described hereabove in reference to FIG. 1. In some embodiments, implantable device 200 further comprises a lead comprising one or more functional elements 260 (e.g. one or more electrodes or other sensors and/or transducers as described herein), not shown but such as lead 265 described hereabove in reference to FIG. 1, 2, 3, 4 or 10 which passes through housing 210 and operably connects (e.g. electrically, fluidly, optically and/or mechanically) to one or more of components 216. Alternatively or additionally, one or more functional elements 260 can be positioned in, on and/or within housing 210 (e.g. obviating the need for a lead such as lead 265).

In some embodiments, one or more components of components 216 are positioned on a surface of a housing 210, such as an inner surface of housing 210. For example, components 216 can comprise one or more passive electrical components (e.g. a capacitor). One or more components 216 (e.g. one or more capacitors or other passive components) can be attached to an interior or exterior surface of a housing 210. In some embodiments, antenna 240 can comprise an antenna electrically patterned on the surface of housing 210 (e.g. an inner or outer surface comprising glass) and electrically connected to components 216. For example, antenna 240 comprising two orthogonal antennas can be patterned on two orthogonal surfaces of one or more housings 210. Antenna 240 comprising one or more patterned antennas can include meandering lines, such as to control the effective electrical length of the antennas 240. Antenna 240 can comprise one or more patterned antennas configured as a loop antenna, electric dipole antenna and/or patch antenna. In some embodiments, antenna 240 comprises one or more insulated wires (e.g. braided wires) that can be attached (e.g. adhesively attached) to a surface of a housing 210 (e.g. connected to an outer surface and electrically connected to components 216 via feedthroughs 211).

In some embodiments, components 216 comprise a desiccant or other moisture-absorbing material, such as to absorb small amounts of fluid that are present within and/or enter into the area within a sealed housing 210 (e.g. prior to and/or after implantation).

In some embodiments, housing 210b (e.g. a glass or ceramic housing) is attached (e.g. bonded, welded and/or adhesively attached as described hereabove) to housing 210a (e.g. a glass or ceramic housing). Subsequently, substrate 211 and components 216 can be positioned within the fixedly attached assembly (e.g. after folding of substrate 211). In embodiments where feedthroughs 213 are included, wires can be passed through the feedthroughs and/or electrical attachment to the feedthroughs (e.g. attachment of one or more wires of a lead 265) can be performed (as described hereabove). Subsequently, housing 210c (e.g. a glass or ceramic housing) can be attached (e.g. bonded, welded and/or adhesively attached) to the housing 210b portion of the assembly.

In a first manufacturing method, substrate 211 (e.g. in a folded state) is attached (e.g. electrically attached) to feedthroughs 213, such as when housing 210a is already attached to housing 210b or prior to attachment of housing 210a to housing 210b. After attachment of substrate 211 to feedthroughs 213 and attachment of housing 210a to housing 210b, housing 210b can be attached to housing 210c (e.g. with all components 216 and optionally antenna 240 positioned within the assembled housing 210). Alternatively, substrate 211 (e.g. in a folded state) can be attached (e.g. electrically attached) to feedthroughs 213 of housing 210a. Housing 210b can be attached to housing 210c, and subsequently housing 210b can be attached to housing 210a (e.g. with all components 216 and optionally antenna 240 positioned within the assembled housing 210).

In a second manufacturing method, a pattern for pass-thru holes of feedthroughs 213 is made in housing 210a. A pattern of attachment pads can be positioned at each of the pass-thru hole locations. Housing 210a can be attached (e.g. welded) to housing 210b. A conductive epoxy can be deposited to attach the feedthroughs 213 either inside the package to substrate 211 or outside to the interconnects of lead 265.

An assembly comprising substrate 211, one or more components 216 and optionally antenna 240 can be positioned within housing 210b (which is attached to housing 210a). A curing process can subsequently be performed. A fill material can be applied, such as to fill any gaps present between and/or within components, such as to enhance distribution of mechanical force, provide a seal and/or otherwise improve the construction of each implantable device 200. An additional curing process can subsequently be performed. Housing 210c can then be attached to housing 210b. Lead 265 can be operably attached (e.g. electrically attached) to feedthroughs 213. A covering can be applied to surround at least housing 210, such as a covering 218 as described herein (e.g. applied in an overmolding or dipping process).

In some embodiments, one or more locations within housing 210 are filled with potting material (e.g. low density and/or low expansion coefficient RF-transparent epoxy), such as to provide a stabilizing force to and/or between antenna 240, substrate 211 and/or components 216. In some embodiments, a forming fixture is used to place and stabilize antenna 240 during assembly of implantable device 200.

In some embodiments, housing 210 is surrounded by a covering (e.g. covering 218 described herein), such as via a dipping or overmolding process, such as a covering applied after assembly of all housing 210 portions and connection of a lead 265 to feedthroughs 213.

FIG. 14C illustrates a perspective view of the implantable device 200 of FIGS. 14A and 14B is illustrated, further comprising a lead 265, consistent with the present inventive concepts. Lead 265 comprises one or more functional elements 260, such as functional elements 260a-d shown. Functional elements 260a-d can comprise one or more sensors and/or transducers (e.g. electrodes) such as are described hereabove. One or more wires, tubes, optical fibers or other filaments of lead 265 pass through housing 210 at feedthroughs 213 (e.g. via a sealed passageway) and/or operably attaches (e.g. electrically attaches) to feedthroughs 213, such as to operably connect (e.g. electrically connect) lead 265 to one or more components within housing 210 (e.g. components 216 and/or antenna 240).

Figure 15:
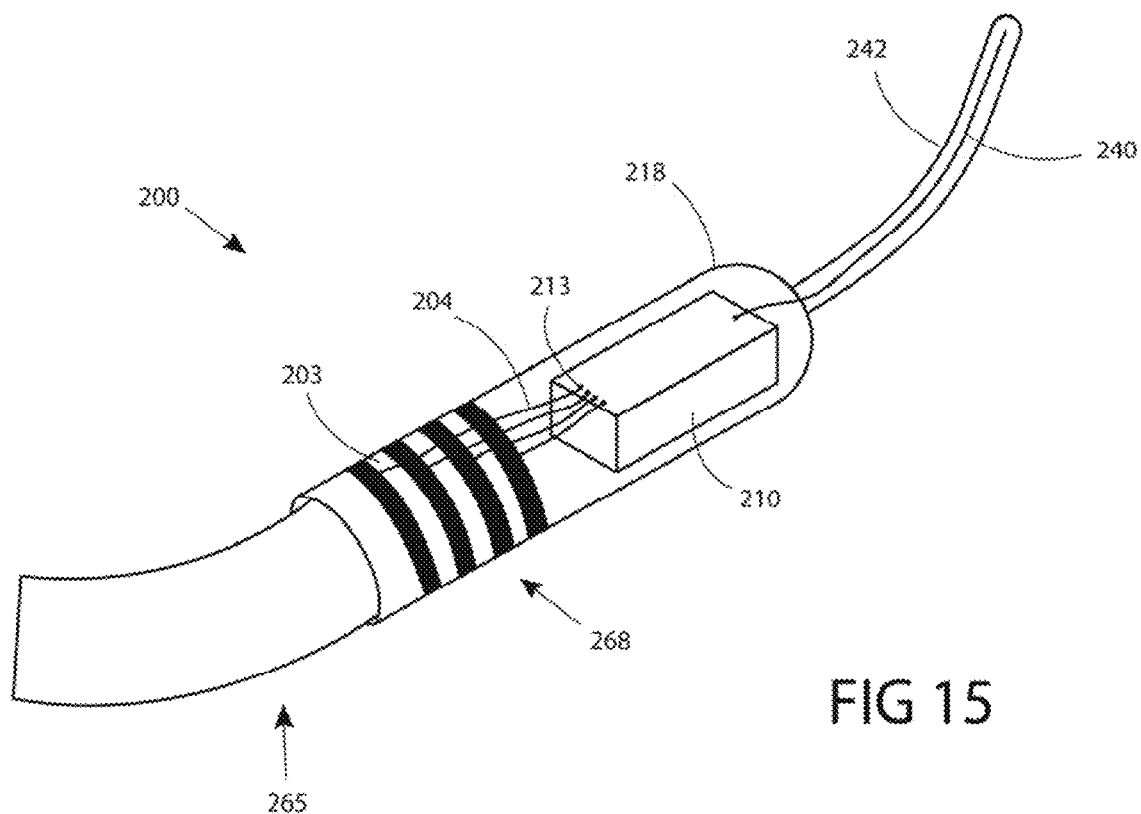
FIG. 15 is a perspective view of an implantable device comprising a housing, from which extend a lead and an antenna, consistent with the present inventive concepts.

Referring now to FIG. 15, a perspective view of an implantable device comprising a housing, from which extend a lead and an antenna, is illustrated, consistent with the present inventive concepts. Implantable device 200 comprises housing 210, which can be of similar construction and arrangement (e.g. surround similar components) as housing 210 of FIG. 14. Extending from a first end of housing 210 is filament 242, which contains antenna 240. Extending from the other end of housing 210 is lead 265, which can comprise one or more functional elements 260 (not shown but such as two to sixteen electrodes). In some embodiments, lead 265 comprises a connecting filament which attaches to a second housing 210, such as a second housing 210 surrounding similar or dissimilar components to the first housing 210. Lead 265 and/or filament 242 can be positioned at different locations of housing 210, such as when one or both extend from a side of housing 210.

In some embodiments, antenna 240 comprises a dipole antenna. In some embodiments, antenna 240 comprises a meander dipole antenna and/or a reactively loaded dipole antenna. Antenna 240 can comprise a length that is longer than a major axis of housing 210 (i.e. antenna 240 would not fit within housing 210 in a linear condition). Antenna can be positioned outside of housing 210 to physically separate the antenna 240 from any conductive materials inside or within the housing 210. In some embodiments, antenna 240 comprises a dipole antenna with a length of at least 2 mm. such as a dipole antenna with a length between 5 mm and 50 mm, such as a length between 10 mm and 30 mm or between 15 mm and 30 mm. In some embodiments, at least a portion of antenna 240 extends into housing 210. In some embodiments, one or more additional antennas 240 is positioned within housing 210 and/or within a second filament 242. In some embodiments, antenna 240 comprises a dipole antenna and an associated external device (e.g. external device 500 described herein) provides external antenna polarization to improve transmission coupling between the external device and the dipole antenna-based antenna 240 (e.g. to compensate for the transmission alignment requirements of a dipole antenna and/or to compensate for the lack of an orthogonal dipole antenna prevented by space constraints).

Implantable device 200 of FIG. 15 can comprise an atraumatic or other implantable covering, such as covering 218 shown surrounding housing 210. Covering 218 can comprise a flexible material (e.g. silicone, a thermoplastic elastomer or other elastomer) positioned around all or a portion of housing 210. Covering 218 can be applied in an overmolding process, a dipping process, and the like. Covering 218 can comprise a material or at least a portion that is transmissive to radiofrequency transmissions, such as an elastomeric material or portion free of conductive materials.

In some embodiments, lead 265 or filament 242 comprising a user (e.g. clinician) attachable component, such as is shown in FIG. 15 for lead 265 in which lead 265 comprises connector 268 which can be operatively (e.g. electrically) connected to connector 203 (e.g. during an implantation procedure for implantable device 200). Connector 203 attaches to conduits 204 (e.g. wires) which operatively attach to housing 210 via feedthroughs 213.

Figure 16:
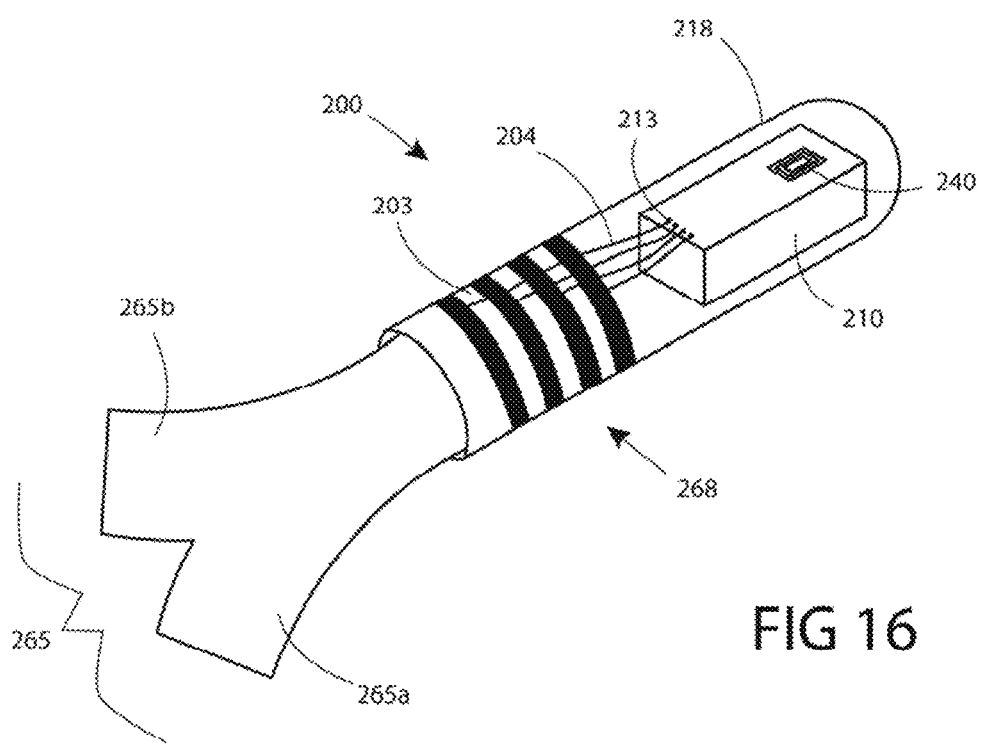
FIG. 16 is a perspective view of an implantable device comprising a housing, from which extends a bifurcated lead, consistent with the present inventive concepts.

Referring now to FIG. 16, a perspective view of an implantable device comprising a housing, from which extends a bifurcated lead, is illustrated, consistent with the present inventive concepts. Implantable device 200 comprises housing 210, which can be of similar construction and arrangement (e.g. surround similar components) as housing 210 of FIG. 14. Implantable device 200 can comprise covering 218 that surrounds at least a portion of housing 210 and/or one or more other components of implantable device 200, such as covering 218 described hereabove in reference to FIG. 15. Positioned within housing 210 is implantable antenna 240, comprising one or more antennas (e.g. two orthogonal antennas). Lead 265 can comprise a user-attachable lead, such as when lead 265 comprises connector 268 which is operably connectable (e.g. electrically connectable) to connector 203, which in turn operably connects to housing 210 via conduits 204 and feedthroughs 213 (as shown and described hereabove in reference to FIG. 15).

Extending from one end of housing 210 is lead 265, which comprises bifurcated leads 265a and 265b. Each of leads 265a and 265b can comprise one or more functional elements 260 (not shown, but such as two to sixteen electrodes). Bifurcation of lead 265 into leads 265a and 265b allows implantation of each lead 265 (each including one or more functional elements 260) in different trajectories, each extending from housing 210. Lead 265 can be attachable at different locations of housing 210, such as when connector 203 extends from a side of housing 210.

In some embodiments, leads 265a and 265b each comprise a connectorized end, such as to individually connect to connector 203 (e.g. when connector 203 comprises a single-connection connector or dual-connection connector), or to connect to a separate joining connector that connects to each of leads 265a and 265b on a first end, and to connector 203 on a second end.

Figure 17:
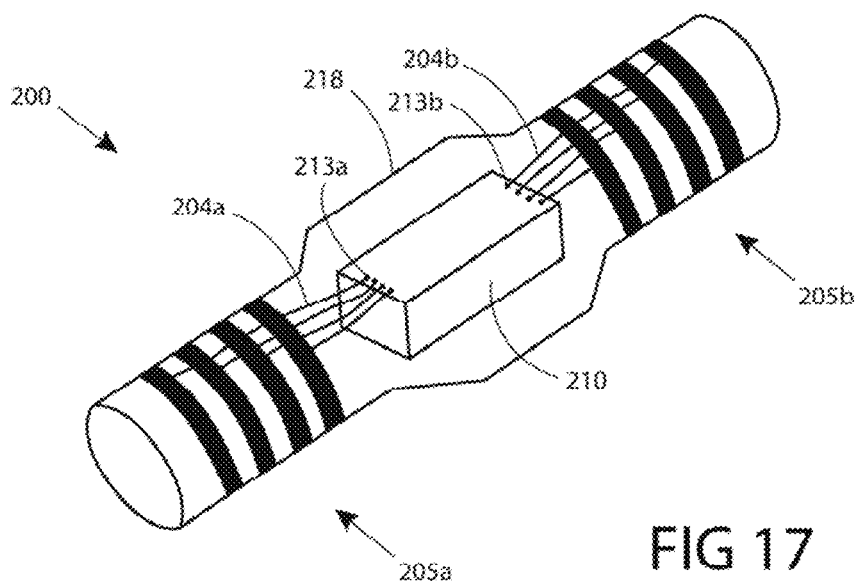
FIG. 17 is a perspective view of an implantable device comprising a housing including two connectors, consistent with the present inventive concepts.

Referring now to FIG. 17, a perspective view of an implantable device comprising a housing including two connectors is illustrated, consistent with the present inventive concepts. Implantable device 200 comprises housing 210, which can be of similar construction and arrangement (e.g. surround similar components) as housing 210 of FIG. 14. Implantable device 200 can comprise covering 218 that surrounds at least a portion of housing 210 and/or one or more other components of implantable device 200, such as covering 218 described hereabove in reference to FIG. 15.

Implantable device 200 can comprise connector 205a and/or 205b (singly or collectively connector 205). Each connector 205 operatively connects to housing 210 (e.g. electrically, optically, fluidly and/or mechanically connects to one or more components within housing 210), via conduits 204 and feedthroughs 213. In some embodiments, a connector 205 is configured to allow a user (e.g. during an implantation procedure) to operably attach housing 210 to a lead 265 comprising one or more functional elements 260 as described herein. Alternatively or additionally, a connector 205 can be configured to allow a user to operably attach housing 210 to an implantable antenna 240 such as via a connecting filament 202, also as described herein. In some embodiments, a single connector 205 comprises a "universal" connector configured to allow a user to attach to either a lead 265 or an implantable antenna 240, such as when connector 205 comprises differentiating connection points and/or circuitry of housing 210 automatically detects the type of component attached to the connector 205, such as is described in applicant's co-pending U.S. Provisional Patent Application Ser. No. 62/077,181, titled "Method and Apparatus for Implantable Neuromodulation Systems", filed Nov. 8, 2014; the content of which is incorporated herein by reference in its entirety.

Figure 18:
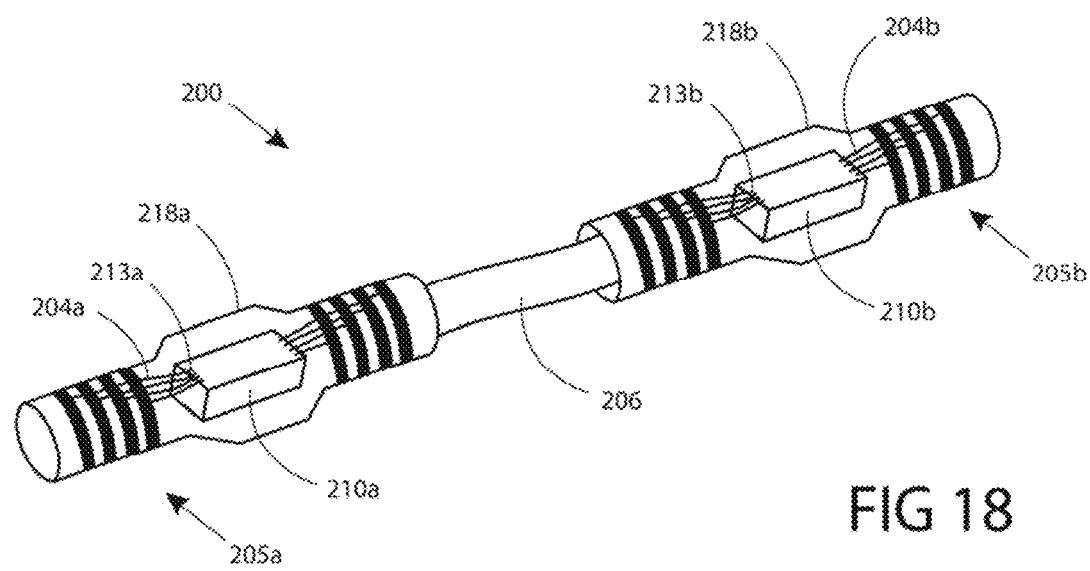
FIG. 18 is a perspective view of an implantable device comprising two housings connected by a connecting filament, consistent with the present inventive concepts.

Referring now to FIG. 18, a perspective view of an implantable device comprising two housings connected by a connecting filament is illustrated, consistent with the present inventive concepts. Implantable device 200 comprises housings 210a and 210b, each of which can be of similar construction and arrangement (e.g. surround similar components) as housing 210 of FIG. 14. Implantable device 200 can comprise coverings 218a and/or 218b that surround at least a portion of housings 210a and/or 210b, respectively, such as covering 218 described hereabove in reference to FIG. 15.

Housing 210a is operatively connecting to housing 210b via connecting filament 206 (e.g. a connecting filament as defined herein), such that electrical power or signals; optical signals or energy; fluidic agents, hydraulic fluids or pneumatic fluids; or mechanical energy or motion; can be transferred between housing 210a and 210b. Filament 206 can comprise rigid filament, a flexible filament or it can comprise one or more flexible portions. Filament 206 can comprise a length between 1 cm and 30 cm, such as a length between 2 cm and 15 cm. Implantable system 200 of FIG. 18 allows current to be steered from one or more functional elements 260 (e.g. electrodes) of a first lead 265a (not shown) connected to connector 205a to one or more functional elements 260 of a second lead 265b (not shown) connected to connector 205b, as described hereabove in reference to FIG. 5 or 6. Current can be controllably steered (controllably direct current) between any electrodes of corresponding leads 264 (or within a single lead 265). Components within housings 210a and 210b can share power received from external system 50 (not shown). For example, if components within housing 210a receive less power than components within housing 210b receive and/or if the components within housing 210a simply need more power, a transfer of power can be performed (e.g. via connecting filament 206). Components of a first housing 210a can communicate with components of second housing 210b via connecting filament 206, such as to create a communication interface that can be used as a low-wire count and/or low power data link interface, such as SPI, JTAG, I2C, and/or another similar communication interface. While the embodiment of implantable device 200 of FIG. 18 shows two housings "daisy-chained" together, three or more housings 210 can be connected, such as to increase the number of stimulation sites (e.g. stimulation electrodes), to increase available power and/or to decrease each housing 210 volume by distributed components among them.

Implantable device 200 can comprise connector 205a operatively attached to housing 210a, and/or connector 205b operative attached to housing 210b. Connectors 205a and/or 205b (singly or collectively connector 205), can be of similar construction and arrangement to connectors 205 described hereabove in reference to FIG. 17, such as to allow user attachment to a lead 265 and/or an implantable antenna 240. Each connector 205 is operatively connected to a housing 210 (e.g. electrically, optically, fluidly and/or mechanically connected to one or more components within housing 210), via conduits 204 and feedthroughs 213 as shown.

In some embodiments, one or both ends of connecting filament 206 comprises a connector configured to attach to housing 210a and/or 210b, such as when either or both housings 210 include an additional connector similar to connectors 205a and/or 205b.

Referring now to FIGS. 19A-D, a set of configurations for implantable devices comprising a housing including an extending flap is illustrated, consistent with the present inventive concepts. Each of the embodiments of FIGS. 19A-D includes an implantable device 200 comprising a housing 210. Housing 210 can be of similar construction and arrangement (e.g. surround similar components) as housing 210 of FIG. 14. Implantable device 200 can comprise a covering surrounding housing 210, such as covering 218 described hereabove in reference to FIG. 15. Housing 210 can be operatively attached to one or more leads 265 and/or one or more implantable antennas 240 (e.g. via a connecting filament 242). Alternatively or additionally, housing 210 can include a connector, such as connectors 203 or 205 described hereabove.

Implantable device 200 can comprise one or more flanges 207. Each flange 207 can be flexible, rigid or include flexible portions. Flange 207 can be constructed and arranged to be folded, such as to allow minimally invasive implantation of housing 210 (e.g. through a needle or small diameter introducer). In some embodiments, flange 207 is configured as or includes an anchor element, such as anchor element 221 described hereabove. In these embodiments, flange 207 can comprise an opening and/or a portion configured to be penetrated by a needle, suture, clip and/or staple, such as to anchor housing 210 to tissue during an implantation procedure (e.g. to prevent migration of one or more portions of implantable device 200). Alternatively or additionally, in some embodiments flange 207 comprises one or more components of implantable device 200, such as: an implantable antenna 240; a conductive sheet, conductive surface and/or other conductive element; capacitor (e.g. a supercapacitor) or other energy storage element, and/or other components.

Figure 19A:
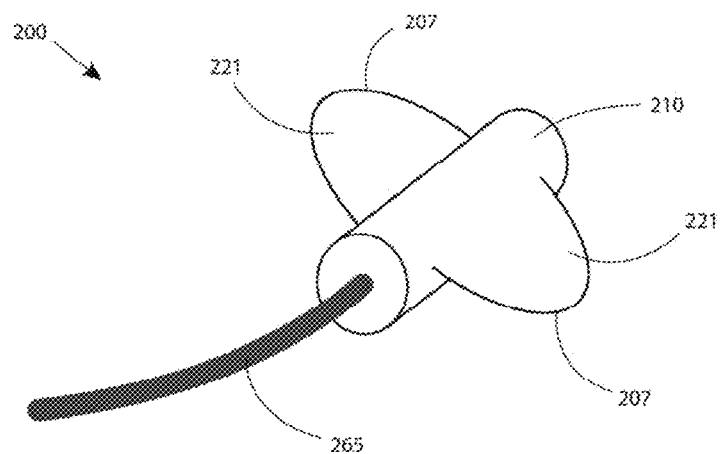
FIGS. 19A-D is a set of configurations for implantable devices comprising a housing including an extending flap, consistent with the present inventive concepts.

In FIG. 19A, a perspective view of an implantable device 200 is illustrated, consistent with the present inventive concepts. Housing 210 comprises two flanges 207 that extend from housing 210. Either or both flanges 207 can be configured as or otherwise include anchor element 221. Extending from housing 210 is lead 265, which can be a pre-attached or connectable lead 265 as described hereabove.

Figure 19B:
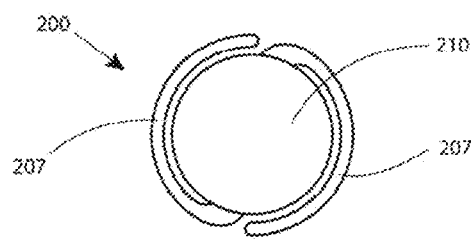

In FIG. 19B, an end view of an implantable device 200 is illustrated, consistent with the present inventive concepts. Housing 210 comprises two flanges 207 that have been folded around a tubular shaped housing 210 such as to allow for minimally invasive implantation of implantable device 200.

Figure 19C:
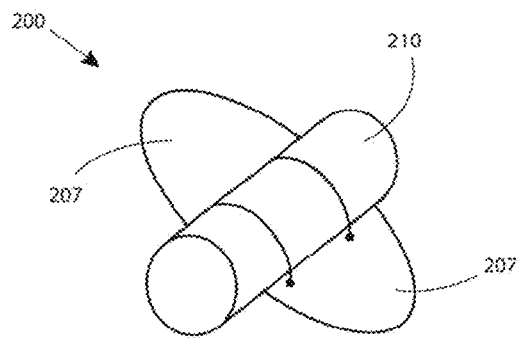

In FIG. 19C, a perspective view of an implantable device 200 is illustrated, consistent with the present inventive concepts. Housing 210 comprises two projecting flaps 207. Housing 210 has been secured to tissue (tissue not shown), via suture that passes through flaps 207.

Figure 19D:
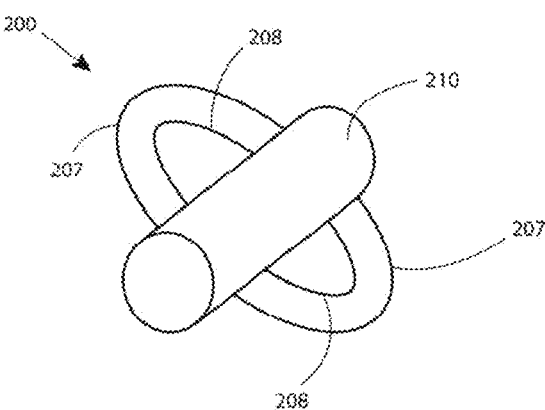

In FIG. 19D, a perspective view of an implantable device 200 is illustrated, consistent with the present inventive concepts. Housing 210 comprises two projecting flaps 207. Positioned within one or more flaps 207 is element 208. In some embodiments, element 208 is configured as an implantable antenna 240 of the present inventive concepts. In some embodiments, element 208 comprises a conductive sheet, conductive surface and/or other conductive element. In some embodiments, element 208 comprises a capacitor or other energy storage element. In some embodiments, element 208 comprises an electrical conductor or other component configured to improve coupling with an external device (e.g. improve transmission of power and/or data from an external device 500 or improve transmission of data to an external device 500). In these embodiments, element 208 can be configured as a "passive relay" configured to provide passive amplification of signals (e.g. signals received and/or transmitted by an implantable antenna within housing 210). Element 208 can comprise a conductor that is not connected to any component (e.g. not electrically or physically connected to any component within housing 210), yet is configured to electromagnetically couple to implantable antenna 240. Alternatively or additionally, element 208 can be configured as an antenna that is not physically connected (e.g. via a connecting filament 242) to one or more antennas 240 within housing 210 (e.g. configured as a passive antenna gain element such as a reflector, resonator, and/or relay coil). Some of the advantages of a passively coupled antenna is that it is electrically isolated from electronics inside the housing 210; it increases the effective coupling to one or more external antennas 540 without necessarily requiring a larger antenna 240 within housing 210; and it functionally increase the effective size of implantable antenna 240 inside housing 210 without increasing its physical dimensions. Element 208 can comprise a conductive material such as a gold-coated wire. Element 208 can comprise a visualizable material, such as a radiopaque and/or ultrasonically reflective material. Element 208 can be positioned in, on and/or within flange 207 (as shown), or in, on and/or within another covering or extension of housing 210 (e.g. covering 218 described herein). Element 208 can be constructed and arranged to provide rigidity (e.g. after deployment of flange 207), such as to stabilize implantable device 200 within tissue and/or to prevent unfolding of flange 207.

Flanges 207 can be attached to housing 210 and/or to a covering surrounding at least a portion of housing 210, such as covering 218 described herein. Flanges 207 and/or covering 218 can be attached to housing t210 during an implantation procedure.

Figure 20:
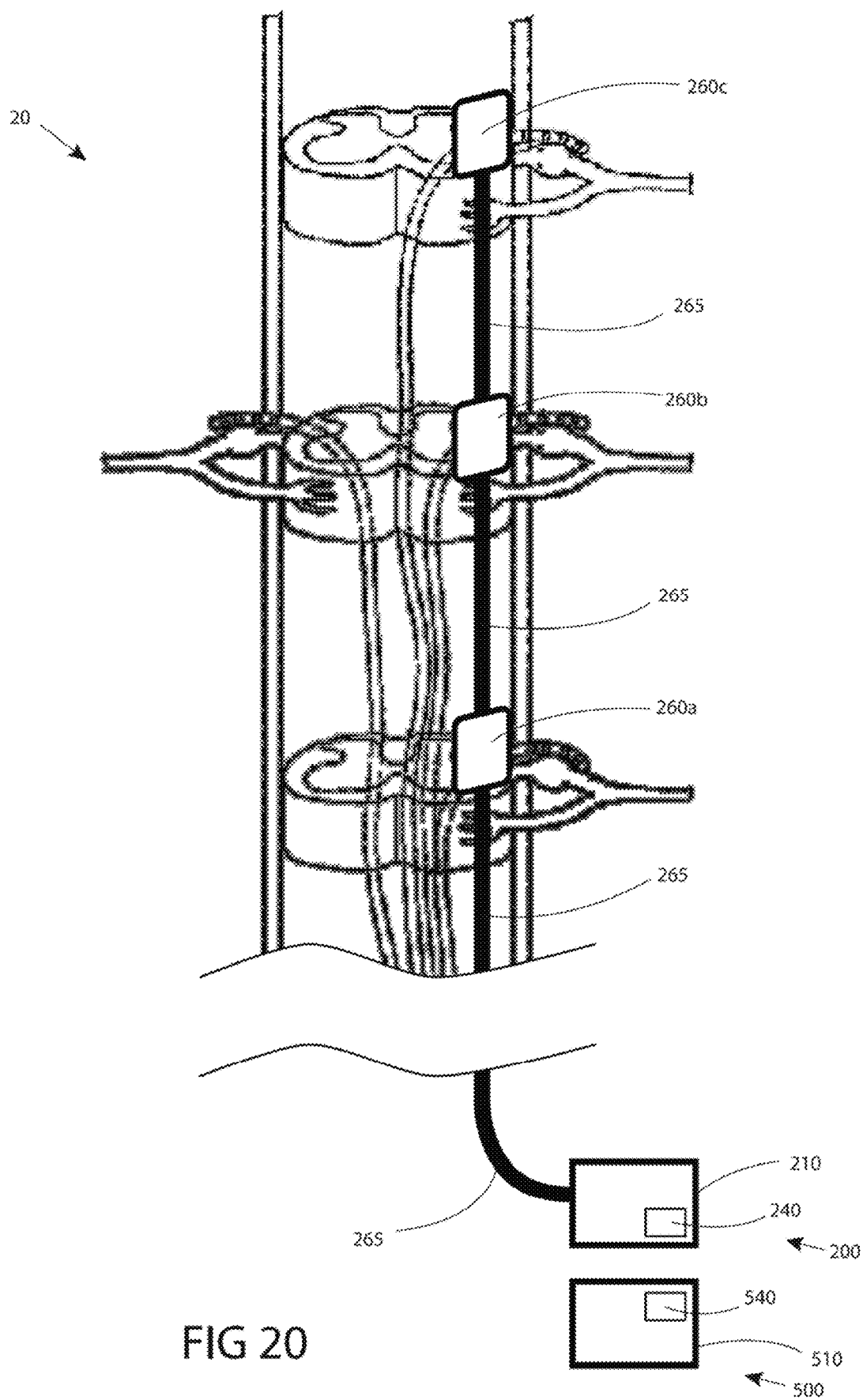
FIG. 20 is an anatomical view of a medical apparatus comprising an external device and an implantable device, the implantable device configured to perform magnetic stimulation of tissue, consistent with the present inventive concepts.

Referring now to FIG. 20, an anatomical view of a medical apparatus comprising an external device and an implantable device, the implantable device configured to perform magnetic stimulation of tissue and/or to generate magnetic fields that induce the application of mechanical energy to tissue, is illustrated, consistent with the present inventive concepts. Apparatus 10 of FIG. 20 can comprise similar components to apparatus 10 of FIG. 1 or FIG. 2, such as one or more implantable devices 200, each comprising housing 210, implantable antenna 240 and lead 265, and one or more external devices 500, each comprising housing 510 and external antenna 540. Implantable device 200 is implanted and external device 500 is positioned proximate the patient's skin such that power and/or data can be transferred from external device 500 to implanted device 200. Implantable device 200 comprises lead 265 which includes one or more multiple functional elements 260 (e.g. functional elements 260a, 260b and 260c shown in FIG. 20). Each functional element 260 is configured to at least deliver magnetic stimulation to tissue, such as tissue of and/or proximate to the spine as shown by the functional element 260 implantation location of FIG. 20. In some embodiments, one or more functional elements 260 are implanted in relative proximity to the DRG, to one or more peripheral nerves, and/or to other tissue. Functional elements 260a, 260b and/or 260c can be vertically aligned (as described hereabove in reference to FIG. 4 or 5) and/or they can be vertically offset (as described hereabove in reference to FIG. 6). Apparatus 10 can comprise additional (i.e. two or more), implantable devices 200 and/or additional leads 265 (e.g. when one or more implantable devices 200 includes multiple leads 265 as described hereabove), such as to simplify placement, to improve simulation of DRG, peripheral nerves and/or other tissue and/or to reduce adverse effects that might be caused due to leads 265 migration. In some embodiments, a first lead 265 is positioned as shown in FIG. 20, and a second lead 265 is positioned on the other side of the spine (e.g. a second lead 265 attached to the same implantable device 200 and/or a second implantable device 200).

Functional elements 260 of FIG. 20 can be configured to provide magnetic stimulation to tissue to treat pain. Implantable device 200 can be configured to provide single pulses of stimulation, pairs of stimuli separated by variable intervals (in same or different tissue areas), and/or as trains of repetitive stimuli at various frequencies. Single stimuli can depolarize neurons and evoke measurable effects. Trains of stimuli can modify excitability of the cerebral cortex at the stimulated site and also at remote areas along functional anatomical connections. In some embodiments, functional elements 260a, 260b and/or 260c comprise an array of multiple electrodes, such as is described herebelow in reference to FIG. 20A. In some embodiments, functional elements 260a, 260b and/or 260c comprise one or more microcoils, such as is described herebelow in reference to FIG. 20B. In some embodiments, functional elements 260a, 260b and/or 260c comprise one or more magnetic field generating elements configured to at least partially surround a cylindrical volume of tissue (e.g. to at least partially surround DRG tissue), such as is described herebelow in reference to FIG. 20C, 20D or 20E. For example, one or more functional elements 260 can comprise a cuff electrode or other curved electrode assembly configured to at least partially surround target tissue, such as DRG tissue, and to avoid stimulation to non-target tissue positioned outside of the radius of curvature of the functional element 260. In some embodiments, one or more functional elements 260 are configured be manipulated (e.g. shaped by a clinician) to at least partially surround target tissue to be stimulated.

In some embodiments, one or more functional elements 260 are configured to allow steering of delivered current and/or steering of a generated magnetic field. In some embodiments, one or more functional elements 260 comprise a tissue "grabbing" (e.g. anchoring) feature. In some embodiments, one or more functional elements 260 or other component of apparatus 10 are of similar construction and arrangement (e.g. similarly configured to anchor in tissue and/or to provide steering of delivered electrical and/or magnetic energy) as one or more components described in applicant's co-pending U.S. Provisional Patent Application Ser. No. 62/015,392, titled "Method and Apparatus for Neuromodulation Treatments of Pain and Other Conditions", filed Jun. 21, 2014; the content of which is incorporated herein by reference in its entirety.

Referring now to FIG. 20A, a perspective view of a functional element comprising an array of electrodes is illustrated, consistent with the present inventive concepts. Functional element 260' of FIG. 20A can be configured to deliver electrical and/or magnetic stimulation to tissue (e.g. nerve tissue). Implantable systems 200 incorporating one or more functional elements 260' of FIG. 20A can be configured to utilize field steering and/or current steering to stimulate target tissue (e.g. DRG tissue) without affecting non-target tissue (e.g. ventral root tissue), such as to reduce the amount of precision required in the placement of lead 265 and/or its functional elements 260.

Referring now to FIG. 20B, a side view of a functional element comprising a coil is illustrated, consistent with the present inventive concepts. Functional element 260" can be configured to deliver magnetic stimulation to tissue (e.g. nerve tissue). Functional element 260" of FIG. 20B can comprise one or more coils (e.g. one or more micro-coils). Functional element 260" can comprise laminar spiral microcoil. Functional element 260" can comprise one or more coils electroplated onto a substrate (e.g. platinum-iridium alloy, gold and/or platinum deposited onto glass or silicon). Functional element 260" can comprise a coil that is no more than 500 μm long by 500 μm wide. Functional element 260" can comprise a coil that is no more than 100 μm thick. Functional element 260" can comprise a coil with conductors that are approximately 10 μm to 20 μm wide and/or are spaced apart at a distance of approximately 10 μm to 20 μm.

Referring now to FIG. 20C, a side view of a functional element comprising a solenoid coil is illustrated, consistent with the present inventive concepts. Functional element 260''' comprises a solenoid coil configured to deliver a constant and/or varying magnetic field to target tissue. In some embodiments, functional element 260''' is configured to allow a clinician to wrap functional element 260''' around target tissue.

Referring now to FIG. 20D, a side view of a functional element comprising a toroid coil is illustrated, consistent with the present inventive concepts. Functional element 260'''' comprises a toroid coil configured to deliver a constant and/or varying magnetic field to target tissue. In some embodiments, functional element 260'''' is configured to allow a clinician to wrap functional element 260'''' around target tissue (e.g. functional element 260'''' is configured to be opened and/or closed to surround target tissue).

Referring now to FIG. 20E, a side view of a functional element comprising a broken toroid coil is illustrated, consistent with the present inventive concepts. Functional element 260''''' comprises a broken toroid coil configured to deliver a constant and/or varying magnetic field to target tissue. In some embodiments, functional element 260''''' is configured to be positioned around target tissue, without having to manipulate the geometry of functional element 260''''' (e.g. not having to open or close its geometry).

Referring now to FIG. 21, a schematic view of an apparatus comprising an external device, an implantable device and a tool for implanting the implantable device is illustrated, consistent with the present inventive concepts. Apparatus 10 can comprise an apparatus configured to deliver stimulation energy to tissue, and comprises at least one implantable device 200 and at least one external device 500. Apparatus 10, implantable device 200 and/or external device 500 can comprise one or more devices or components of similar construction and arrangement to those described hereabove in reference to FIG. 1 or 2. Implantable device 200 comprises housing 210, lead 265 and at least one functional element 260 (e.g. the eight shown positioned on a distal portion of lead 265 in FIG. 21). In some embodiments, functional element 260 comprises between 1 and 24 electrodes. Implantable device 200 can be constructed and arranged to be implanted beneath the skin of the patient using tool 60. Tool 60 comprises a penetrating element 61 configured to penetrate the patient's tissue. Tool 60 further comprises a cannula 62, such as a peel-apart cannula constructed and arranged to surround (e.g. at least partially circumferentially surround) an elongate member (e.g. lead 265) and to subsequently be peeled apart to facilitate removal from the elongate member. Penetrating element 61 and cannula 62 can each comprise a lumen from their proximal end to their distal end. Tool 60 can further comprise a stiffening element 64. Tool 60 can further comprise a stylet 67, such as a stylet constructed and arranged to be positioned within lead 265 during its advancement through tissue. Cannula 62 is configured to slidingly receive (e.g. via an internal lumen) penetrating element 61 and stiffening element 64 (e.g. sequentially). Penetrating element 61 can also be constructed and arranged to slidingly receive (e.g. via an internal lumen) stiffening element 64. Any component of tool 60 (e.g. penetrating element 61, cannula 62, stiffening element 64 and/or stylet 67) can comprise one or more markers, such as marker 66 shown positioned on stiffening element 64. Marker 66 or another marker of tool 60 can comprise a marker selected from the group consisting of: radiopaque marker; ultrasonically reflective marker; magnetic marker; and combinations thereof.

Penetrating element 61 can comprise a Tuohy needle, an epidural needle or other needle. Penetrating element 61 can comprise a material selected from the group consisting of: stainless steel; titanium; metal; plastic; and combinations of one or more of these. Penetrating element 61 can comprise a needle with a diameter between 10 and 20 gauge. Penetrating element 61 can comprise a shaft with a length between 1" and 8". Cannula 62 can comprise a material such as nylon, Teflon or other rigid plastic material. Cannula 62 can comprise a tapered, beveled and/or chamfered distal end. Cannula 62 can comprise a diameter between 10 and 20 gauge. Cannula 62 can comprise a tear-away portion 63, such as a reduced thickness and/or perforated axial segment along the full length of cannula 62. In some embodiments, tear-away portion 63 comprises two axial segments on either side of cannula 62 (e.g. approximately 180° apart). Stiffening element 64 can comprise a metal or plastic material, and can comprise a guidewire (e.g. wound coil) construction. Stiffening element 64 can comprise at least a malleable portion configured to allow an operator (e.g. an implanting clinician) to create and/or adjust a desired trajectory for implantation (e.g. advancement through tissue) of lead 265 of implantable device 200. Stiffening element 64 may have radio opaque markers at the distal tip that correspond to the locations of the contacts (260) contained on the device (265).

Figure 22A:
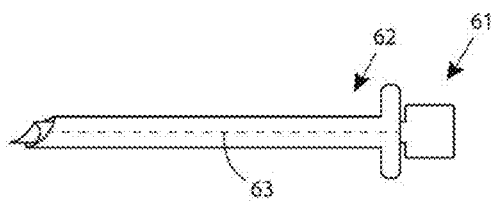
FIGS. 22A-22E are a series of side views of a method of implanting an implantable device using a kit of implantation tools including a peel-away introducer, consistent with the present inventive concepts.

Referring now to FIGS. 22A-D, a series of steps of implanting the implantable device 200 of FIG. 21 are illustrated, consistent with the present inventive concepts. The implantation method described in FIGS. 22A-D are shown with the patient tissue removed for illustrative clarity. In FIG. 22A, penetrating element 61 has been inserted into cannula 62. Cannula 62 and penetrating element 61 are then percutaneously inserted through the patient's skin, such as to a location relatively proximate to patient tissue to be treated (e.g. stimulated) and/or diagnosed. In some embodiments, penetrating element 61 and cannula 62 are inserted such that in subsequent steps, one or more functional elements 260 of implantable device 200 are implanted proximate nerve tissue. In some embodiments, penetrating element 61 and cannula 62 are inserted such that in subsequent steps, one or more functional elements 260 of implantable device 200 are implanted within a blood vessel (e.g. to transvascularly stimulate nerve tissue). In some embodiments, penetrating element 61 and cannula 62 are inserted into the epidural space of a patient. In some embodiments, an implanting clinician inserts penetrating element 61 and cannula 62 by using one or more anatomical landmarks, such as spinal level T9 during an epidural insertion.

Figure 22B:
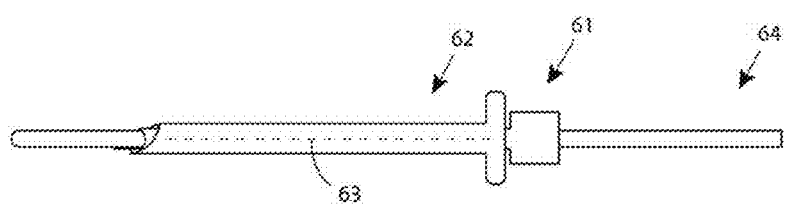

In FIG. 22B, stiffening element 64 has been inserted into penetrating element 61, such that the distal portion of stiffening element 64 advanced beyond the distal end of penetrating element 61 and cannula 62. In some embodiments, the distal portion of stiffening element 64 is positioned in the epidural space. In some embodiments, stiffening element 64 is not used, such as when lead 265 of implantable system 200 is positioned in one or more blood vessels (e.g. to perform transvascular stimulation) or other easy-to-navigate locations.

Figure 22C:
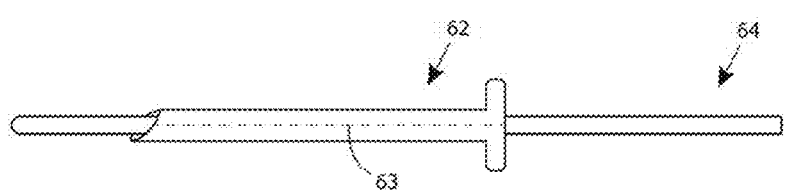

In FIG. 22C, penetrating element 61 has been removed, leaving stiffening element 64 to reside within a lumen of cannula 62.

Figure 22D:
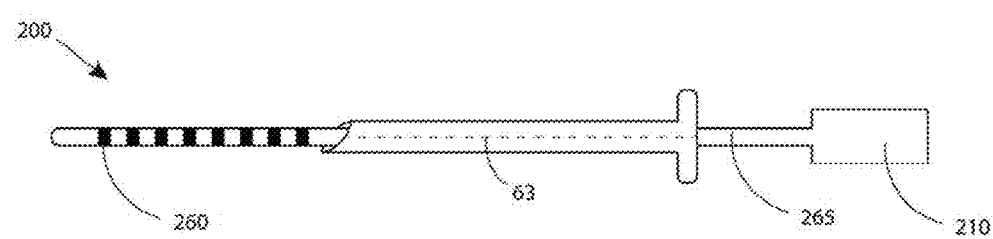

In FIG. 22D, stiffening element 64 has been removed, and lead 265 of implantable device 200 has been inserted into cannula 62 such that its distal portion (including one or more electrodes or other functional elements 260) is positioned proximate one or more nerves or other tissue to be stimulated. In some embodiments, functional elements 260 are positioned at one or more desired spinal levels.

In some embodiments, the configuration shown in FIG. 22D is used to titrate, confirm, modify or otherwise assess the placement of functional elements 260, such as when external device 200 and/or a trialing interface, such as trialing interface 80 described hereabove in reference to FIG. 1) transmits power and/or data to the implantable device 200. During transmission of the power and/or data to implantable device 200, one or more functional elements 260 are activated (e.g. deliver stimulation energy to tissue and/or record a physiologic parameter of the tissue), and proper placement of functional elements 260 is confirmed and/or modified (e.g. the patient confirms a sufficient and/or non-excessive amount of stimulation energy is being delivered, and/or a sufficient amount of pain relief is being achieved). Once proper placement is confirmed, cannula 62 is removed as described herebelow in reference to FIG. 22E.

Figure 22E:
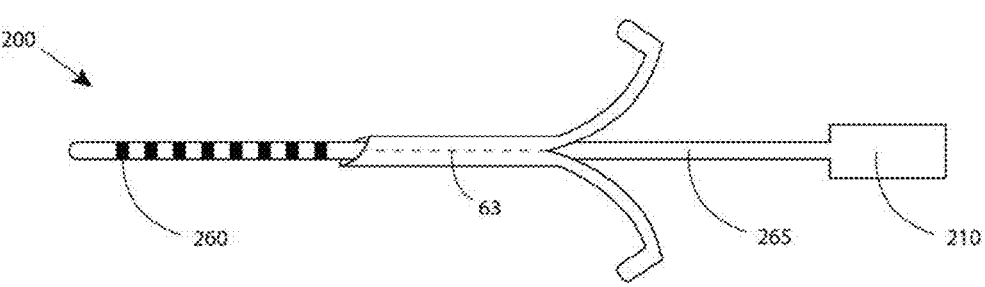

In FIG. 22E, cannula 62 is being laterally separated (e.g. by the implanting clinician) at tear-away portion 63, such that cannula 62 can be removed from about implantable device 200. Subsequently, housing 210 can be implanted under the patient's skin, such as in a subcutaneous pocket formed with blunt dissection (e.g. via the implanting clinician's finger). Housing 210 can be affixed to tissue, as described hereabove. All incisions can be closed using standard techniques, and percutaneous entry sites may be compressed and/or covered.

Figure 23A:
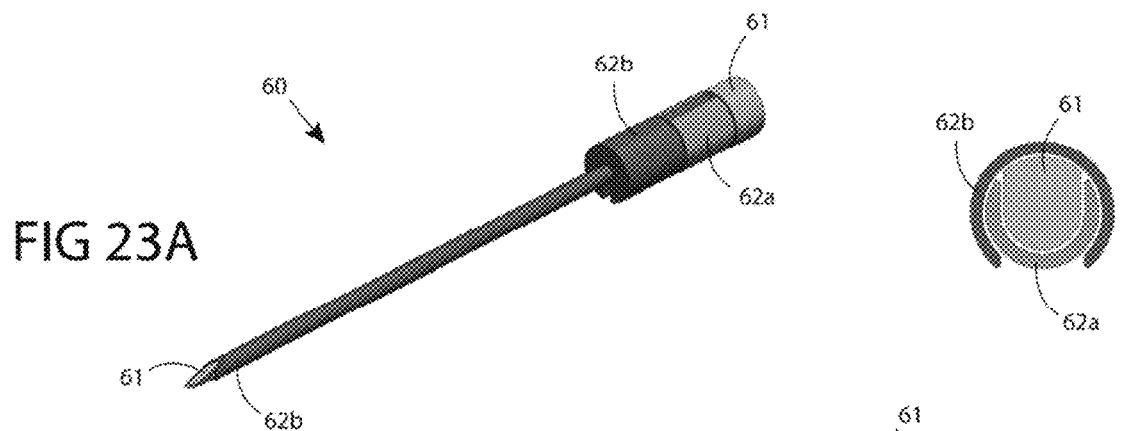
FIGS. 23A-23E are a series of perspective and end sectional views of a method of implanting an implantable device using a kit of implantation tools including a cannula with an inner and outer portion, consistent with the present inventive concepts.
Figure 23B:
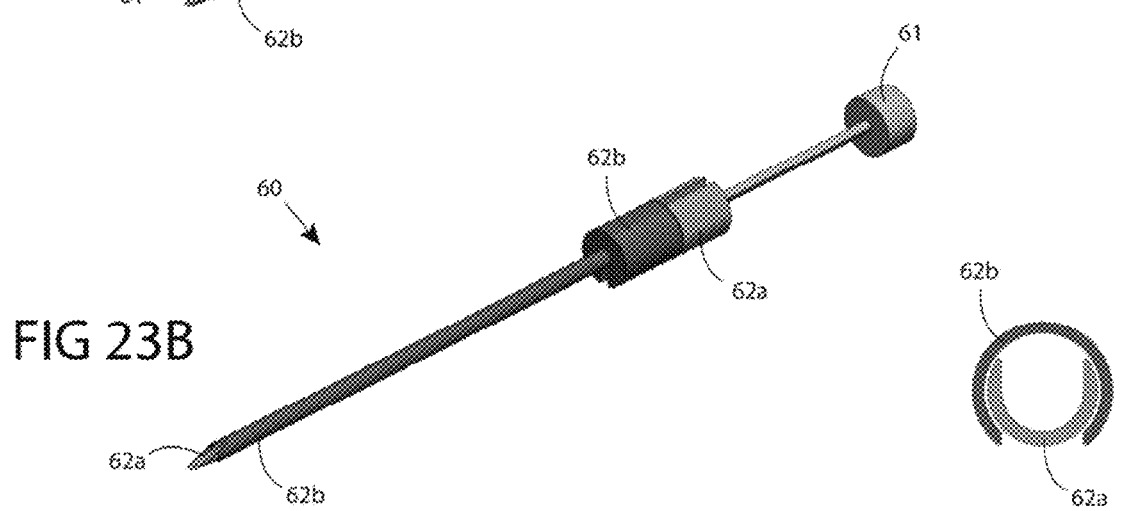
Figure 23C:
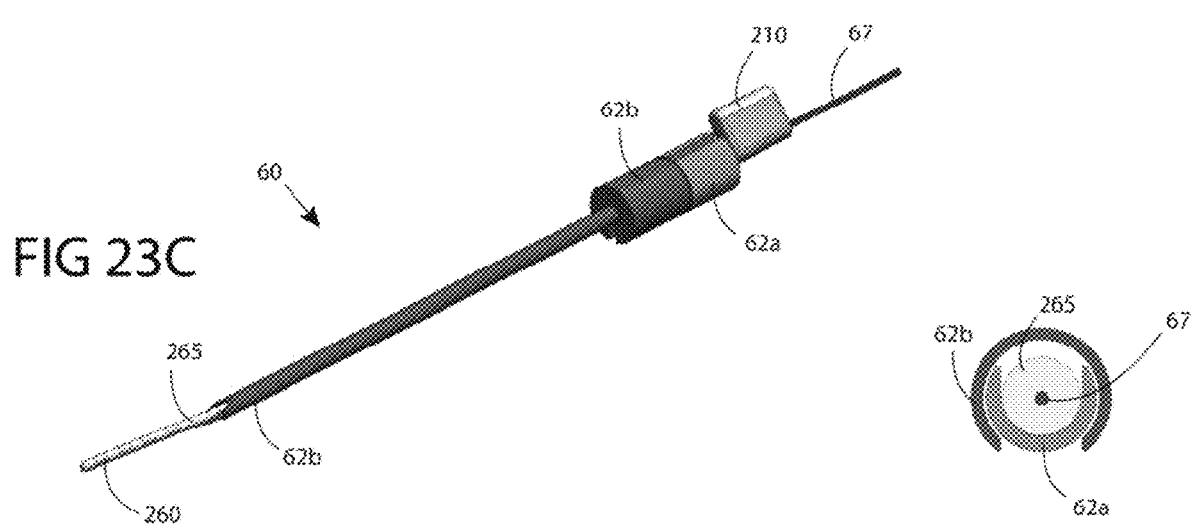
Figure 23D:
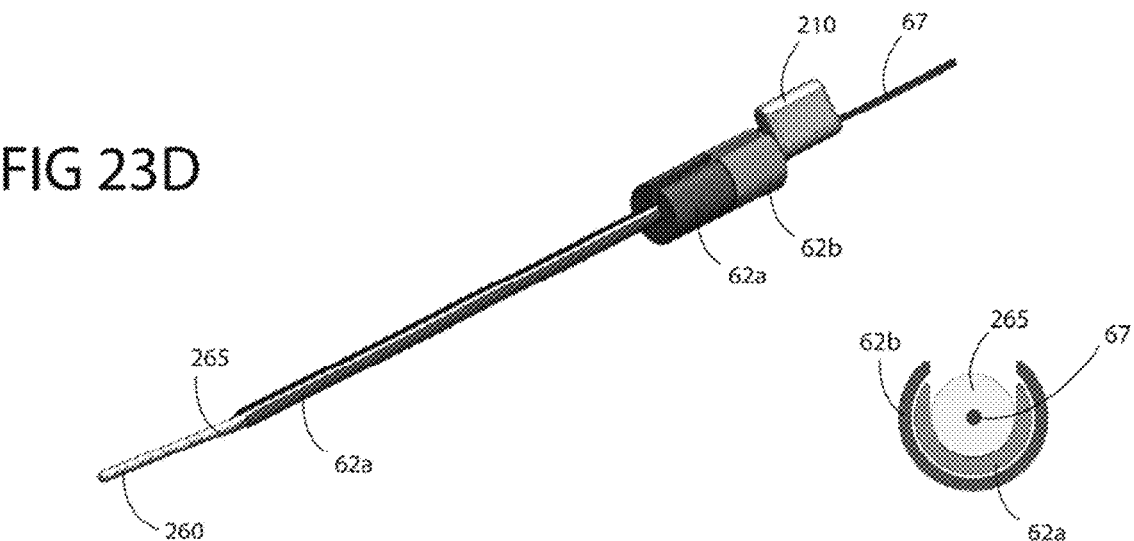
Figure 23E:
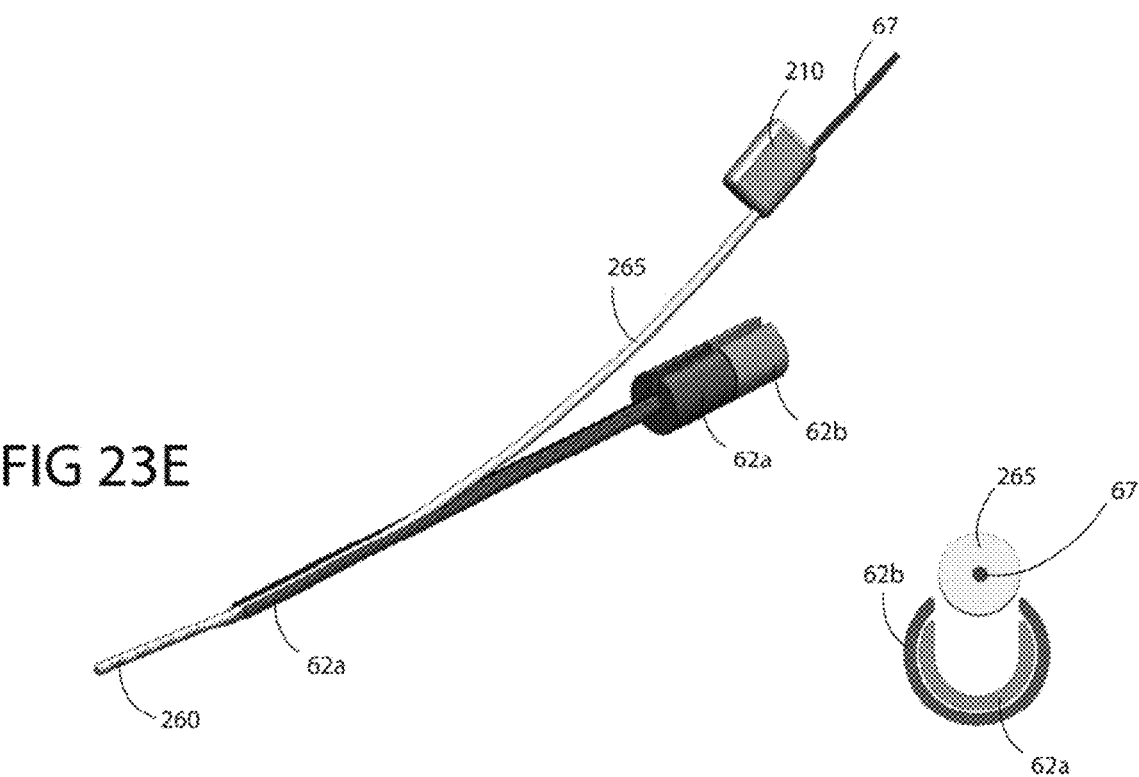

Referring now to FIGS. 23A-E, a series of steps of implanting an implantable lead 265 are illustrated (including sets of perspective and end sectional views), consistent with the present inventive concepts. Lead 265 comprises one or more functional elements 260 (e.g. one or more electrodes) configured to deliver energy to tissue such as nerve tissue. Lead 265 can be a component of a stimulation apparatus, such as apparatus 10 described herein comprising at least one implantable device 200 and at least one external device 500. Apparatus 10, implantable device 200 and/or external device 500 can comprise one or more devices or components of similar construction and arrangement to those described hereabove in reference to FIG. 1 or 2. An implantable housing 210 (as shown in FIGS. 23C, 23D and 23E) can be positioned on the proximal end of lead 265. Alternatively, housing 210 can be operatively attached to lead 265 (e.g. after lead 265 is implanted in the patient).

Lead 265 can be constructed and arranged to be implanted beneath the skin of the patient using tool 60. Tool 60 comprises a penetrating element 61 configured to penetrate the patient's tissue. Tool 60 further comprises a cannula, comprising inner cannula 62*a* and an outer cannula 62*b* (collectively cannula 62), which can also be configured to penetrate the patient's tissue. Inner cannula 62*a* and outer cannula 62*b* each comprise an elongate structure with a partial circumferential (e.g. less than 360°) cross sectional profile, each comprising an "open portion" along their length. Outer cannula 62*b* comprises a larger radius of curvature than inner cannula 62, and inner cannula 62*a* is shown slidingly positioned within outer cannula 62*b*. Inner cannula 62*a* and outer cannula 62*b* are rotatable relative to each other. Cannula 62 comprises a lumen from its proximal end to their distal end. Tool 60 can further comprise a stylet 67, such as a stylet constructed and arranged to be positioned within lead 265 during its advancement through tissue (e.g. styled 67 shown in FIGS. 23C, 23D and 23E). Cannula 62 is configured to slidingly receive (e.g. via an internal lumen) penetrating element 61. Any component of tool 60 (e.g. penetrating element 61, cannula 62, and/or stylet 67) can comprise one or more markers, such as marker 66 shown positioned on stiffening element 64 of FIG. 21 described hereabove.

The implantation method described in FIGS. 23A-E are shown with the patient tissue removed for illustrative clarity. In FIG. 23A, penetrating element 61 has been inserted into cannula 62. Inner cannula 62*a* and outer cannula 62*b* are rotationally oriented such that the open portion of inner cannula 62*a* is oriented toward a closed portion (i.e. not the open portion) of outer cannula 62*b*, collectively creating a closed tubular structure surrounding penetrating element 61. Cannula 62 and penetrating element 61 are then percutaneously inserted through the patient's skin, such as to a location relatively proximate to patient tissue to be treated (e.g. stimulated) and/or diagnosed. In some embodiments, penetrating element 61 and cannula 62 are inserted such that in subsequent steps, one or more functional elements 260 of implantable device 200 are implanted proximate nerve tissue. In some embodiments, penetrating element 61 and cannula 62 are inserted such that in subsequent steps, one or more functional elements 260 are implanted within a blood vessel (e.g. to transvascularly stimulate nerve tissue). In some embodiments, penetrating element 61 and cannula 62 are inserted into the epidural space of a patient. In some embodiments, an implanting clinician inserts penetrating element 61 and cannula 62 by using one or more anatomical landmarks, such as spinal level T9 during an epidural insertion.

In FIG. 23B, penetrating element 61 is being removed and is shown in a partially retracted state.

In FIG. 23C, penetrating element 61 has been removed, and lead 265 has been inserted through cannula 62 and into the patient such that functional elements 260 have extended beyond the distal end of cannula 62 (e.g. functional elements 260 are positioned proximate one or more nerves or other tissue to be stimulated). Housing 210 is positioned proximate the proximal end of cannula 62. In certain embodiments, lead 265 is advanced with stylet 67 in place.

In some embodiments, the configuration shown in FIG. 23C is used to titrate, confirm, modify or otherwise assess the placement of functional elements 260, such as when external device 500 and/or a trialing interface (e.g. trialing interface 80 described hereabove in reference to FIG. 1) transmits power and/or data to the implantable device 200. During transmission of the power and/or data to implantable device 200, one or more functional elements 260 are activated (e.g. deliver stimulation energy to tissue and/or record a physiologic parameter of the tissue), and proper placement of functional elements 260 is confirmed and/or modified (e.g. the patient confirms a sufficient and/or non-excessive amount of stimulation energy is being delivered, and/or a sufficient amount of pain relief is being achieved). Once proper placement is confirmed, cannula 62 is removed as described herebelow in reference to FIGS. 23D and 23E.

In FIG. 23D, inner cannula 62*a* and outer cannula 62*b* have been rotated relative to each other such that the open portion of inner cannula 62*a* is aligned with the open portion of outer cannula 62*b* as shown.

In FIG. 23E, lead 265 exits the aligned open portions of inner cannula 62*a* and outer cannula 62*b* such that cannula 62 can be laterally removed (e.g. with housing 210 attached to the end of lead 265). Subsequently, housing 210 can be implanted under the patient's skin, such as in a subcutaneous pocket formed with blunt dissection (e.g. via the implanting clinician's finger). Housing 210 can be affixed to tissue, as described hereabove. All incisions can be closed using standard techniques, and percutaneous entry sites may be compressed and/or covered.

Figure 24:
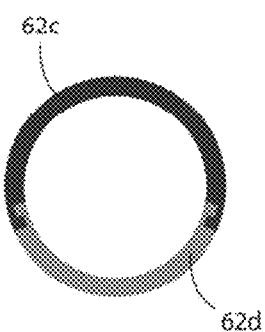
FIG. 24 is an end sectional view of an alternatively embodiment of the cannula of FIGS. 23A-E.

Referring now to FIG. 24, an alternative embodiment of cannula 62 is shown, comprising cannula first portion 62*c* and cannula second portion 62*d*. In this embodiment, cannula first portion 62*c* and cannula second portion 62*d* each comprise the same radius of curvature, and comprise complementary segments of a full circle. Cannula first portion 62*c* and cannula second portion 62*d* mechanically engage (e.g. slidingly, frictionally, magnetically, adhesively or otherwise engage) such as to perform the implantation steps shown in FIGS. 23A through 23C hereabove. When used in the steps shown in FIGS. 23D and 23E, cannula first portion 62*c* disengages from cannula second portion 62*d* (similar to that shown in FIG. 23D), such as to create an opening to allow lead 265 to laterally be removed from the remaining portion of cannula 62 (as shown in FIG. 23E).

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A medical apparatus for providing spinal cord stimulation to a patient, the medical apparatus comprising:
    (a) an external system configured to transmit one or more transmission signals, each transmission signal comprising at least power or data; and
    (b) an implantable system configured to receive the one or more transmission signals from the external system;
    wherein the external system comprises a first external device comprising:
        (i) at least one external antenna configured to transmit a first transmission signal to the implantable system, the first transmission signal comprising at least power or data;
        (ii) an external transmitter configured to drive the at least one external antenna;
        (iii) an external power supply configured to provide power to at least the external transmitter; and
        (iv) an external controller configured to control the external transmitter; and
    wherein the implantable system comprises a first implantable device comprising:
        (i) at least one implantable antenna configured to receive the first transmission signal from the first external device;
        (ii) an implantable receiver configured to receive the first transmission signal from the at least one implantable antenna;
        (iii) at least one implantable functional element configured to be placed at least partially within an epidural space of the patient to interface with the patient;
        (iv) an implantable controller configured to control the at least one implantable functional element;
        (v) an implantable energy storage assembly configured to provide power to an element selected from the group consisting of: the at least one implantable functional element; the implantable controller; the implantable receiver; and combinations thereof; and
        (vi) an implantable housing surrounding at least the implantable controller and the implantable receiver;
    wherein the implantable controller is configured to produce a stimulation signal comprising a mix and/or modulation of a high frequency signal and a low frequency signal,
    wherein the high frequency signal is at or above 1 kHz and configured to treat pain of the patient,
    wherein the low frequency signal is below 1 kHz and configured to stimulate motor nerve tissue of the patient, and
    wherein the implantable controller is operatively coupled to the at least one functional element to deliver the mix and/or modulation of the high frequency signal and the low frequency signal to the patient.

2. The medical apparatus according to claim 1, wherein the at least one functional element is further configured to deliver electrical energy at frequencies below 1 kHz during a trialing procedure.

3. The medical apparatus according to claim 1, wherein the at least one functional element comprises an array of electrodes.

4. The medical apparatus according to claim 3, wherein the array of electrodes is configured to utilize field steering and/or current steering to stimulate target tissue without affecting non-target tissue.

5. The medical apparatus according to claim 4, wherein the target tissue comprises DRG tissue, and wherein the non-target tissue comprises ventral root tissue.

6. The medical apparatus according to claim 1, wherein the implantable controller is configured to control a parameter selected from the group consisting of: a direct current (DC) parameter such as amplitude of voltage and/or current; amplitude; frequency; pulse width; inter-pulse interval (e.g. random, varied or constant); an amplitude modulation parameter; a frequency modulation parameter; anode/cathode configuration; voltage; current; pulse shape; a duty cycle parameter such as frequency, pulse width or off time; polarity; drive impedance; energy storage capacity; and combinations thereof.

7. The medical apparatus according to claim 1, wherein the implantable controller is configured to provide a stimulation signal comprising a duty cycle between 0.1% and 25%.

8. The medical apparatus according to claim 1, wherein the implantable controller is configured to provide a stimulation signal comprising a duty cycle between 1% and 10%.

9. The medical apparatus according to claim 1, wherein the implantable controller is configured to provide a frequency modulated stimulation waveform comprising a frequency component between 1 kHz and 20 kHz.

10. The medical apparatus according to claim 1, wherein the low frequency signal comprises one or more signals between 1 Hz and 1000 Hz, and wherein the high frequency signal comprises one or more signals between 1 kHz and 50 kHz.

11. The medical apparatus according to claim 1, wherein the implantable controller is configured to produce a stimulation signal comprising a train of high frequency signals and bursts of low frequency signals.

12. The medical apparatus according to claim 1, wherein the implantable controller is configured to produce a stimulation signal comprising a train of low frequency signals and bursts of high frequency signals.

13. The medical apparatus according to claim 1, wherein the implantable controller is configured to produce a stimulation signal comprising one or more high frequency signals modulated with one or more low frequency signals.

14. The medical apparatus according to claim 13, wherein the implantable controller modulates the high frequency signal via frequency modulation, amplitude modulation, phase modulation, and/or pulse width modulation.

15. The medical apparatus according to claim 1, wherein the implantable controller is configured to produce a stimulation signal comprising a pseudo random binary sequence non-return to zero or return to zero waveform.

16. The medical apparatus according to claim 15, wherein the stimulation signal comprises fixed pulse duration and/or fixed frequency of stimulation pulses.

17. The medical apparatus according to claim 15, wherein the stimulation signal comprises time-varying pulse duration and/or time-varying frequency of stimulation pulses.

18. The medical apparatus according to claim 1, wherein the at least one implantable functional element is configured to deliver a high frequency alternating current block.

19. The medical apparatus according to claim 1, wherein the at least one implantable functional element is configured to deliver a stimulation signal comprising a waveform selected from the group consisting of: square wave; sine wave; sawtooth; triangle wave; trapezoidal; ramp; waveform with exponential increase; waveform with exponential decrease; pulse shape which minimizes power consumption; Gaussian pulse shape; pulse train; root-raised cosine; bipolar pulses; and combinations thereof.

20. The medical apparatus according to claim 1, further comprising a second implantable device comprising: at least one implantable functional element configured to interface with the patient.

21. The medical apparatus according to claim 1, wherein the at least one implantable functional element is implanted to at least partially surround tissue to be stimulated.

22. The medical apparatus according to claim 1, wherein the at least one implantable antenna is positioned within the implantable housing.

23. The medical apparatus according to claim 1, wherein the at least one implantable antenna is positioned outside the implantable housing.

24. The medical apparatus according to claim 1, wherein the implantable housing comprises a major axis less than or equal to 20 mm in length.

25. The medical apparatus according to claim 1, wherein the implantable housing comprises a minor axis with a length less than or equal to 8 mm.

* * * * *